United States Patent
Oguro et al.

(10) Patent No.: US 8,691,828 B2
(45) Date of Patent: Apr. 8, 2014

(54) THIENOPYRIMIDINE AS CDC7 KINASE INHIBITORS

(75) Inventors: Yuya Oguro, Kanagawa (JP); Osamu Kurasawa, Kanagawa (JP)

(73) Assignee: Takeda Pharmaceutical Company Limited, Osaka-shi (JP)

( * ) Notice: Subject to any disclaimer, the term of this patent is extended or adjusted under 35 U.S.C. 154(b) by 234 days.

(21) Appl. No.: 13/254,551

(22) PCT Filed: Mar. 4, 2010

(86) PCT No.: PCT/JP2010/054073
§ 371 (c)(1),
(2), (4) Date: Oct. 25, 2011

(87) PCT Pub. No.: WO2010/101302
PCT Pub. Date: Sep. 10, 2010

(65) Prior Publication Data
US 2012/0040981 A1      Feb. 16, 2012

Related U.S. Application Data

(60) Provisional application No. 61/157,760, filed on Mar. 5, 2009, provisional application No. 61/294,991, filed on Jan. 14, 2010, provisional application No. 61/298,338, filed on Jan. 26, 2010.

(51) Int. Cl.
*C07D 495/04* (2006.01)
*A61K 31/519* (2006.01)
*A61P 35/00* (2006.01)

(52) U.S. Cl.
USPC ........................ 514/260.1; 544/278

(58) Field of Classification Search
USPC ........................ 544/278; 514/260.1
See application file for complete search history.

(56) References Cited

U.S. PATENT DOCUMENTS

| | | |
|---|---|---|
| 2005/0043323 A1 | 2/2005 | Vanotti |
| 2007/0142414 A1 | 6/2007 | Vanotti |
| 2008/0255120 A1 | 10/2008 | Lin |

FOREIGN PATENT DOCUMENTS

| | | |
|---|---|---|
| WO | 2005014572 | 2/2005 |
| WO | 2005095386 A1 | 10/2005 |
| WO | 2007068728 A2 | 6/2007 |

OTHER PUBLICATIONS

International Search Report for PCT/JP2010/054073, date of mailing, Jun. 16, 2010.
Menichincheri, M. et al., 2009, First Cdc7 Kinase Inhibitors: Pyrrolopyridinones as Potent and Orally Active Antitumor Agents. 2. Lead Discovery, J. Med. Chem., 52, 293-307.
Molecular Target and Cancer Therapeutics 2007, Poster Session A224.
Vanotti, E, 2008, Cdc7 Kinase Inhibitors: Pyrrolopyridinones as Potential Antitumor Agents. I. Synthesis and Structure-Activity Relationships, J. Med. Chem., 51, 487-501.
Print-out of search results from CHEMCATS (13 returns) [6 pages], (2002-2006).
Shah, M., 2002, Synthesis and biological evaluation of thienopyrimidine derivatives, Oriental J. Chem., 18(1), 159-161 [only Chemical structure—1 page].

*Primary Examiner* — Susanna Moore
(74) *Attorney, Agent, or Firm* — Hogan Lovells US LLP

(57) ABSTRACT

The present invention relates to a compound represented by the formula (I):

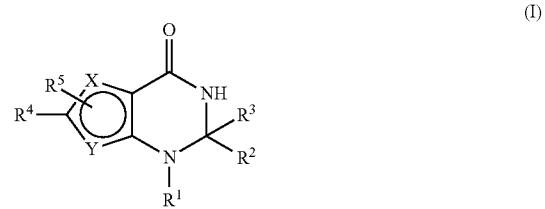

wherein each symbol is as defined in the specification, or a salt thereof, or a prodrug thereof, which is useful for the prophylaxis or treatment of cancer.

15 Claims, No Drawings

SEQUENCE LISTING

<160> NUMBER OF SEQ ID NOS: 4

<210> SEQ ID NO 1
<211> LENGTH: 51
<212> TYPE: DNA
<213> ORGANISM: Artificial
<220> FEATURE:
<223> OTHER INFORMATION: synthetic DNA for His Tag

<400> SEQUENCE: 1
tatgcatcat catcatcatc acggatccca tcatcatcat catcactgag c    51

<210> SEQ ID NO 2
<211> LENGTH: 53
<212> TYPE: DNA

```
<213> ORGANISM: Artificial
<220> FEATURE:
<223> OTHER INFORMATION: synthetic DNA for His Tag

<400> SEQUENCE: 2
ggccgctcag tgatgatgat gatgatggga tccgtgatga tgatgatgat gca        53

<210> SEQ ID NO 3
<211> LENGTH: 29
<212> TYPE: DNA
<213> ORGANISM: Artificial
<220> FEATURE:
<223> OTHER INFORMATION: primer

<400> SEQUENCE: 3
cgcggatcca tggcatccag cccggccca                                    29

<210> SEQ ID NO 4
<211> LENGTH: 39
<212> TYPE: DNA
<213> ORGANISM: Artificial
<220> FEATURE:
<223> OTHER INFORMATION: primer

<400> SEQUENCE: 4
attcttatgc ggccgctcac agctcctcca ccagaggca                         39
```

THIENOPYRIMIDINE AS CDC7 KINASE INHIBITORS

This application is a U.S. National Phase under 35 U.S.C. §371 of International Application PCT/JP2010/054073, filed on Mar. 4, 2010, which claims priority upon U.S. provisional application Ser. No. 61/157,760, filed on Mar. 5, 2009; U.S. provisional application Ser. No. 61/294,991, filed on Jan. 14, 2010; and U.S. provisional application Ser. No. 61/298,338, filed on Jan. 26, 2010; the contents of which are all herein incorporated by this reference in their entireties. All publications, patents, patent applications, databases and other references cited in this application, all related applications referenced herein, and all references cited therein, are incorporated by reference in their entirety as if restated herein in full and as if each individual publication, patent, patent application, database or other reference were specifically and individually indicated to be incorporated by reference.

TECHNICAL FIELD

The present invention relates to heterocyclic compounds and use thereof. More particularly, the present invention relates to fused heterocyclic compounds having a strong cell division cycle 7 (cdc7) inhibitory activity, which is useful for the prophylaxis or treatment of cancer, and the like, and use thereof.

BACKGROUND OF THE INVENTION

Cancer is characterized as un-controlled proliferative disease. Most cancer cells proliferate more rapidly than their normal counter-partners. In the cell cycle division, chromosome duplication is essential and replication of DNA in S phase is tightly regulated. Inhibition of DNA replication is proved therapy for cancer treatment and inhibitors are widely used in clinic, for example, gemcitabine, active metabolites of 5-fluorouracil and Hydroxyurea (HU).

Cdc7 is evolutionally conserved serine/threonine kinase and plays important roles in initiation of DNA replication (Jiang W et al., EMBO J. 1999 Oct. 15; 18(20):5703-13). The kinase activity of cdc7 is regulated by binding with its activating partner. During the late G1 phase and the S phase, cdc7 forms a complex with Dbf4 (also known as ASK) and controls transition from the G1 phase to the S phase by phosphorylating its substrates (Masai H et al., J Cell Physiol. 2002 March; 190(3):287-96). Furthermore, recent studies report that cdc7 plays important roles in both DNA replication and DNA damage signaling pathways (Kim J M et al., Oncogene. 2008 May 29; 27(24):3475-82).

Recently, cdc7 kinase is getting a lot of attention as an attractive target for cancer therapy. Over-expression of cdc7 kinase is observed in multiple cancer cell lines and primary breast, colon, lung and other tumors (Bonte D et al., Neoplasia. 2008 Sep.; 10(9):920-31). Copy number of Dbf4 increases in some cell lines. In primary breast cancer, increased expressions of cdc7 and Dbf4 are highly correlated with loss of p53 activity. Interestingly, depletion of cdc7 kinase by siRNA results in different response between cancer cells and untransformed fibroblast cells. Depletion of cdc7 by siRNA causes the S-phase arrest and apoptosis in cancer cells, while normal fibroblast cells are arrested in G1 phase dependently on p53 activity (Montagnoli A et al., Cancer Res. 2004 Oct. 1; 64(19):7110-6.). Inhibition of DNA licensing checkpoint also causes similar phenotype to cdc7 inhibition (Shreeram S et. al., Oncogene. 2002 Sep. 26; 21(43):6624-32). Furthermore, cdc7 is activated in the cells under replication stress and depletion of cdc7 increased apoptosis induced by hydroxyurea or etoposide (Tenca P et al., J Biol. Chem. 2007 Jan. 5; 282(1):208-15.). Thus, inhibitor of cdc7 has utility in the cancer selective treatment, as either a single agent or in combination with other chemotherapeutic agents.

The following compounds are known as a compound having a cdc7 inhibitory action, whose structure is similar to those of the compound of the present invention.

1) Patent document 1 discloses the following compounds having cdc7, PKA and Akt inhibitory actions.

146

147

2) Patent document 2 discloses the following compound having cdc2 and cdc7 inhibitory actions.

wherein R is a hydrogen atom, amino, arylamino or the like;

$R_1$ and $R_2$ are each independently a hydrogen atom, a halogen atom, $C_{1-6}$ alkyl, amino, arylamino or the like;

$R_3$, $R_3'$, $R_4$ and $R_4'$ are each independently a hydrogen atom, $C_{1-6}$ alkyl, $C_{3-6}$ cycloalkyl, a heterocyclic group or the like; and $R_5$ is a hydrogen atom, a halogen atom, $C_{1-6}$ alkyl or the like.

REFERENCES

Patent Documents

Patent Document 1 WO 2005/095386
Patent Document 2 WO 2005/014572

SUMMARY OF THE INVENTION

Problems to be Solved by the Invention

A cdc7 inhibitor superior in the efficacy expression, pharmacokinetics, solubility, interaction with other pharmaceutical products, safety and stability is expected to show a therapeutically superior effect. Accordingly, it is an object of the present invention to provide a low-toxic compound having a cdc7 inhibitory activity and sufficiently satisfactory as a pharmaceutical product.

Means of Solving the Problems

The present inventors have found that the following compound represented by the formula (I) has a superior cdc7 inhibitory action, and conducted further studies and completed the present invention. Accordingly, the present invention relates to (1) a compound represented by the formula

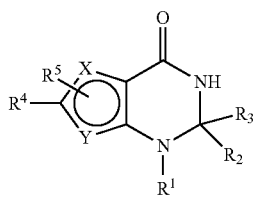

(I)

wherein
as X and Y,
(1) X is a sulfur atom, and Y is a carbon atom, or
(2) X is a carbon atom, and Y is a sulfur atom;
$R^1$ is a hydrogen atom, a hydrocarbon group optionally having substituent(s) or a heterocyclic group optionally having substituent(s),
$R^2$ is a hydrogen atom, a halogen atom, a hydrocarbon group optionally having substituent(s), a heterocyclic group optionally having substituent(s), or acyl,
$R^3$ is a hydrogen atom, a halogen atom, a hydrocarbon group optionally having substituent(s), a heterocyclic group optionally having substituent(s), or acyl, or
$R^1$ and $R^2$ are optionally bonded to form a nitrogen-containing heterocycle optionally having substituent(s), or $R^2$ and $R^3$ are optionally bonded to form a ring optionally having substituent(s);
$R^4$ is a heterocyclic group optionally having substituent(s); and
$R^5$ is a hydrogen atom, a halogen atom or a hydrocarbon group optionally having substituent(s),
or a salt thereof (in the present specification, sometimes to be abbreviated as "compound (I)");
(2) the compound of the above-mentioned (1), wherein X is a sulfur atom, and Y is a carbon atom;
(3) the compound of the above-mentioned (1) or (2), wherein $R^1$ is a hydrogen atom or a $C_{1-6}$ alkyl group optionally having substituent(s);
(4) the compound of any one of the above-mentioned (1) to (3), wherein $R^2$ is a $C_{1-6}$ alkyl group optionally having substituent(s) or a $C_{6-14}$ aryl group optionally having substituent(s);
(5) the compound of any one of the above-mentioned (1) to (4), wherein $R^3$ is a hydrogen atom or a $C_{1-6}$ alkyl group optionally having substituent(s);
(6) the compound of any one of the above-mentioned (1) to (3), wherein $R^2$ and $R^3$ are optionally bonded to form a $C_{3-8}$ cycloalkane optionally condensed with a benzene ring, which optionally has substituent(s), or a 5- or 6-membered non-aromatic heterocycle optionally crosslinked, which optionally has substituent(s);

(7) the compound of any one of the above-mentioned (1) to (6), wherein $R^4$ is an aromatic heterocyclic group optionally having substituent(s);
(8) the compound of any one of the above-mentioned (1) to (7), wherein $R^5$ is a hydrogen atom;
(9) the compound of any one of the above-mentioned (1) to (8), wherein
X is a sulfur atom;
Y is a carbon atom;
$R^1$ is
(1) a hydrogen atom; or
(2) a $C_{1-6}$ alkyl group optionally substituted by 1 to 3 substituents selected from
(a) a halogen atom,
(b) a hydroxy group,
(c) a $C_{1-6}$ alkoxy-carbonyl group,
(d) a $C_{6-14}$ aryl group optionally substituted by 1 to 3 substituents selected from
(i) an amino group, and
(ii) a nitro group,
(e) an aromatic heterocyclic group, and
(f) a non-aromatic heterocyclylcarbonyl group;
$R^2$ is
(1) a $C_{1-6}$ alkyl group optionally substituted by 1 to 3 substituents selected from
(a) a halogen atom,
(b) a $C_{1-6}$ alkoxy-carbonyl group, and
(c) a carbamoyl group optionally mono- or di-substituted by $C_{1-6}$ alkyl group(s); or
(2) a $C_{6-14}$ aryl group;
$R^3$ is
(1) a hydrogen atom;
(2) a $C_{1-6}$ alkyl group optionally substituted by 1 to 3 substituents selected from
(a) a halogen atom,
(b) a $C_{1-6}$ alkoxy-carbonyl group, and
(c) a carbamoyl group optionally mono- or di-substituted by $C_{1-6}$ alkyl group(s); or
(3) —CO—$OR^{41}$ (wherein $R^{41}$ is a hydrogen atom or a $C_{1-6}$ alkyl group); or
$R^2$ and $R^3$ are optionally bonded to form
(1) a $C_{3-8}$ cycloalkane optionally condensed with a benzene ring, which is optionally substituted by 1 to 3 substituents selected from
(a) a halogen atom,
(b) a hydroxy group,
(c) an oxo group,
(d) a $C_{1-6}$ alkoxy-carbonyl group,
(e) a $C_{6-14}$ aryl group optionally substituted by 1 to 3 halogen atoms,
(f) a $C_{3-10}$ cycloalkyl group, and
(g) an amino group optionally mono- or di-substituted by substituent(s) selected from
(i) a $C_{6-14}$ aryl group, and
(ii) a $C_{1-6}$ alkoxy-carbonyl group optionally substituted by 1 to 3 $C_{6-14}$ aryl groups; or
(2) a 5- or 6-membered non-aromatic heterocycle optionally crosslinked, which is optionally substituted by 1 to 3 substituents selected from
(a) a $C_{1-6}$ alkyl group optionally substituted by 1 to 3 substituents selected from
(i) a $C_{6-14}$ aryl group,
(ii) a $C_{1-6}$ alkoxy-carbonyl group,
(iii) a $C_{3-10}$ cycloalkyl-carbonyl group,
(iv) an aromatic heterocyclic group optionally substituted by 1 to 3 $C_{1-6}$ alkyl groups, (b) a $C_{6-14}$ aryl group optionally substituted by 1 to 3 halogen atoms,
(c) an aromatic heterocyclic group,
(d) a $C_{1-6}$ alkyl-carbonyl group optionally substituted by 1 to 3 substituents selected from
  (i) a halogen atom,
  (ii) a $C_{1-6}$ alkoxy group,
  (ii) a $C_{1-6}$ alkoxy-carbonyl group,
  (iii) a $C_{6-14}$ aryl group,
  (iv) an aromatic heterocyclic group, and
  (v) an amino group optionally mono- or di-substituted by substituent(s) selected from a $C_{1-6}$ alkyl-carbonyl group and a $C_{1-6}$ alkoxy-carbonyl group,
(e) a $C_{1-6}$ alkoxy-carbonyl group optionally substituted by 1 to 3 $C_{6-14}$ aryl groups,
(f) a $C_{6-14}$ aryl-carbonyl group,
(g) a $C_{6-14}$ aryloxy-carbonyl group,
(h) a $C_{3-10}$ cycloalkyl-carbonyl group optionally substituted by 1 to 3 $C_{6-14}$ aryl groups,
(i) an aromatic heterocyclylcarbonyl group,
(j) a non-aromatic heterocyclylcarbonyl group, and
(k) a carbamoyl group optionally mono- or di-substituted by $C_{1-6}$ alkyl group(s);

$R^4$ is a 5- or 6-membered aromatic heterocyclic group optionally condensed with a benzene ring or a 5- or 6-membered aromatic heterocycle, which is optionally substituted by 1 to 3 substituents selected from
(a) a halogen atom,
(b) an amino group,
(c) a $C_{1-6}$ alkyl group optionally substituted by amino group(s) optionally mono- or di-substituted by $C_{7-13}$ aralkyl group(s), and
(d) a sulfamoyl group optionally mono- or di-substituted by $C_{1-6}$ alkyl group(s); and $R^5$ is a hydrogen atom, a halogen atom or a $C_{1-6}$ alkyl group;

(10) 1'-ethyl-6'-(pyridin-4-yl)-1'H-spiro[cyclopentane-1,2'-thieno[3,2-d]pyrimidin]-4'(3'H)-one, or a salt thereof;

(11) 1,2-dimethyl-6-(5-methyl-1H-pyrazol-4-yl)-2-(2,2,2-trifluoroethyl)-2,3-dihydrothieno[3,2-d]pyrimidin-4(1H)-one, or a salt thereof;

(12) 2-fluoro-6'-(5-methyl-1H-pyrazol-4-yl)-1'H-spiro[cyclohexane-1,2'-thieno[3,2-d]pyrimidin]-4'(3'H)-one, or a salt thereof;

(13) a prodrug of compound (I);

(14) a medicament comprising compound (I) or a prodrug thereof;

(15) the medicament of the above-mentioned (14), which is a cell division cycle 7 inhibitor;

(16) the medicament of the above-mentioned (14), which is an agent for the prophylaxis or treatment of cancer;

(17) a method of inhibiting a cell division cycle 7 in a mammal, which comprises administering an effective amount of compound (I) or a prodrug thereof to the mammal;

(18) a method for the prophylaxis or treatment of cancer in a mammal, which comprises administering an effective amount of compound (I) or a prodrug thereof to the mammal;

(19) use of compound (I) or a prodrug thereof for the production of a cell division cycle 7 inhibitor;

(20) use of compound (I) or a prodrug thereof for the production of an agent for the prophylaxis or treatment of cancer; and the like.

Effect of the Invention

The compound of the present invention has a low toxicity and a strong cdc7 inhibitory action. Accordingly, the present invention can provide a clinically useful agent for the prophylaxis or treatment of cancer, cancer growth inhibitor and cancer metastasis suppressive agent.

DETAILED DESCRIPTION OF THE INVENTION

The present invention is explained in detail in the following.

Unless otherwise specified, the "halogen atom" in the present specification means a fluorine atom, a chlorine atom, a bromine atom or an iodine atom.

Examples of the "$C_{1-6}$ alkyl (group)" in the present specification include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

Examples of the "$C_{1-10}$ alkyl (group)" in the present specification include heptyl, octyl, nonyl and decyl, besides groups exemplified as the above-mentioned $C_{1-6}$ alkyl (group).

Examples of the "$C_{2-10}$ alkenyl (group)" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl and 1-octenyl.

Examples of the "$C_{2-10}$ alkynyl (group)" in the present specification include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl and 1-octynyl.

Examples of the "$C_{3-10}$ cycloalkyl (group)" in the present specification include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and adamantyl.

Examples of the "$C_{3-10}$ cycloalkenyl (group)" in the present specification include 2-cyclopenten-1-yl, 3-cyclopenten-1-yl, 2-cyclohexen-1-yl and 3-cyclohexen-1-yl.

Examples of the "$C_{4-10}$ cycloalkadienyl (group)" in the present specification include 2,4-cyclopentadien-1-yl, 2,4-cyclohexadien-1-yl and 2,5-cyclohexadien-1-yl.

Examples of the "$C_{6-14}$ aryl (group)" in the present specification include phenyl, naphthyl, anthryl, phenanthryl, acenaphthyl and biphenylyl.

Examples of the "$C_{1-7-13}$ aralkyl (group)" in the present specification include benzyl, phenethyl, phenylpropyl, naphthylmethyl and biphenylylmethyl.

Examples of the "$C_{1-6}$ alkoxy (group)" in the present specification include methoxy, ethoxy, propoxy, isopropoxy, butoxy, isobutoxy, sec-butoxy and tert-butoxy.

Examples of the "$C_{1-6}$ alkoxy-carbonyl (group)" in the present specification include methoxycarbonyl, ethoxycarbonyl, propoxycarbonyl and tert-butoxycarbonyl.

Examples of the "$C_{1-6}$ alkyl-carbonyl (group)" in the present specification include acetyl, propanoyl, butanoyl, isobutanoyl, pentanoyl, isopentanoyl and hexanoyl.

Examples of the "heterocyclic group" in the present specification include an aromatic heterocyclic group and a non-aromatic heterocyclic group.

Examples of the "aromatic heterocyclic group" in the present specification include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (the sulfur atom is optionally oxidized) and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed.

Preferable examples of the aromatic heterocyclic group include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; and fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Examples of the "non-aromatic heterocyclic group" in the present specification include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom (the sulfur atom is optionally oxidized) and a nitrogen atom, and a fused non-aromatic heterocyclic group. Examples of the fused non-aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, and a group wherein the above-mentioned group is partially saturated. In addition, the non-aromatic heterocyclic group is optionally crosslinked. Examples of the crosslinked non-aromatic heterocyclic group include azabicyclo[3.2.1]octane.

Preferable examples of the non-aromatic heterocyclic group include monocyclic non-aromatic heterocyclic groups such as oxetanyl (e.g., 2-oxetanyl, 3-oxetanyl), pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), 2-thioxo-1,3-oxazolidin-5-yl, pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1, 2,3-triazol-1-yl), azepanyl (e.g., azepane-3-yl) and the like; and fused non-aromatic heterocyclic groups such as dihydroindolyl (e.g., 2,3-dihydro-1H-isoindol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like.

When compound (I) has a tautomer, each isomer is also encompassed in compound (I).

For example, a compound wherein the partial structure of compound (I) represented by the formula

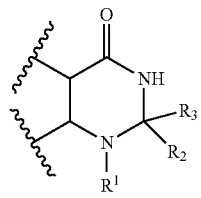

wherein each symbol is as defined above, is a formula

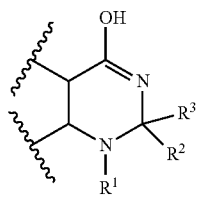

wherein each symbol is as defined above, is also encompassed in compound (I).

In addition, when compound (I) has a 4-pyrazolyl group as its partial structure, the 4-pyrazolyl group may be

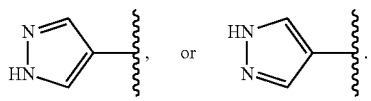

$R^1$ is a hydrogen atom, a hydrocarbon group optionally having substituent(s) or a heterocyclic group optionally having substituent(s), $R^2$ is a hydrogen atom, a halogen atom, a hydrocarbon group optionally having substituent(s), a heterocyclic group optionally having substituent(s), or acyl, or $R^1$ and $R^2$ are optionally bonded to form a nitrogen-containing heterocycle optionally having substituent(s), $R^3$ is a hydrogen atom, a halogen atom, a hydrocarbon group optionally having substituent(s), a heterocyclic group optionally having substituent(s), or acyl, or $R^2$ and $R^3$ are optionally bonded to form a ring optionally having substituent(s).

Examples of the "hydrocarbon group" of the "hydrocarbon group optionally having substituent(s)" for $R^1$, $R^2$ or $R^3$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group and a $C_{6-14}$ aryl group.

The aforementioned $C_{3-10}$ cycloalkyl group, $C_{3-10}$ cycloalkenyl group and $C_{4-10}$ cycloalkadienyl group are each optionally condensed with a benzene ring to form a fused ring group. Examples of the fused ring group include indanyl, dihydronaphthyl, tetrahydronaphthyl and fluorenyl. In addition, a cross-linked hydrocarbon group such as norbornanyl, adamantyl and the like is also encompassed in the aforementioned hydrocarbon group.

The aforementioned $C_{1-10}$ alkyl group, $C_{2-10}$ alkenyl group and $C_{2-10}$ alkynyl group exemplified as the aforementioned "hydrocarbon group" optionally have 1 to 5 (preferably 1 to 3) substituents at substitutable positions.

Examples of the substituent include the following Group Substituent A. When the number of the substituents is not less than 2, respective substituents may be the same or different.

Group Substituent A (1) a $C_{3-10}$ cycloalkyl group (e.g., cyclopropyl, cyclohexyl);

(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom,
  (e) an amino group, and
  (f) a nitro group;

(3) an aromatic heterocyclic group (e.g., thienyl, furyl, pyridyl, pyrazolyl, imidazolyl, tetrazolyl, oxazolyl, thiazolyl, oxadiazolyl, thiadiazolyl, pyrimidinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;

(4) a non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;

(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 halogen atoms,
  (c) a $C_{1-6}$ alkoxy-carbonyl group optionally substituted by 1 to 3 substituents selected from a halogen atom and a $C_{6-14}$ aryl group (e.g., phenyl),
  (d) a $C_{1-6}$ alkylsulfonyl group (e.g., methylsulfonyl) optionally substituted by 1 to 3 halogen atoms,
  (e) a carbamoyl group optionally mono- or di-substituted by $C_{1-6}$ alkyl group(s) optionally substituted by 1 to 3 halogen atoms,
  (f) a $C_{6-14}$ aryl group (e.g., phenyl), and
  (g) an aromatic heterocyclic group (e.g., thienyl, furyl, pyridyl, pyrazolyl, imidazolyl, tetrazolyl, oxazolyl, thiazolyl, oxadiazolyl, thiadiazolyl);

(6) a $C_{1-6}$ alkyl-carbonyl group optionally substituted by 1 to 3 substituents selected from
  (a) a halogen atom,
  (b) a $C_{1-6}$ alkoxy group,
  (c) a $C_{1-6}$ alkoxy-carbonyl group,
  (d) a $C_{6-14}$ aryl group (e.g., phenyl),
  (e) an aromatic heterocyclic group (e.g., indolyl), and
  (f) an amino group optionally mono- or di-substituted by substituent(s) selected from a $C_{1-6}$ alkyl-carbonyl group and a $C_{1-6}$ alkoxy-carbonyl group;

(7) a $C_{1-6}$ alkoxy-carbonyl group optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);

(8) a $C_{1-6}$ alkylsulfonyl group (e.g., methylsulfonyl, ethylsulfonyl, isopropylsulfonyl) optionally substituted by 1 to 3 halogen atoms;

(9) a carbamoyl group optionally mono- or di-substituted by $C_{1-6}$ alkyl group(s) optionally substituted by 1 to 3 halogen atoms;

(10) a thiocarbamoyl group optionally mono- or di-substituted by $C_{1-6}$ alkyl group(s) optionally substituted by 1 to 3 halogen atoms;

(11) a sulfamoyl group optionally mono- or di-substituted by $C_{1-6}$ alkyl group(s) optionally substituted by 1 to 3 halogen atoms;

(12) a carboxy group;
(13) a hydroxy group;
(14) a $C_{1-6}$ alkoxy group optionally substituted by 1 to 3 substituents selected from
  (a) a halogen atom,
  (b) a carboxy group,
  (c) a $C_{1-6}$ alkoxy group,
  (d) a $C_{1-6}$ alkoxy-carbonyl group (e.g., phenyl) optionally substituted by 1 to 3 $C_{6-24}$ aryl groups,
  (e) an amino group optionally mono- or di-substituted by substituent(s) selected from a $C_{1-6}$ alkyl group and a $C_{1-6}$ alkoxy-carbonyl group,
  (f) a heterocyclic group (e.g., tetrahydrofuryl), and
  (g) a $C_{3-20}$ cycloalkyl group;
(15) a $C_{1-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-24}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
  (a) a halogen atom, and
  (b) a $C_{1-6}$ alkyl group optionally substituted by 1 to 3 halogen atoms;
(20) a $C_{3-10}$ cycloalkyl-carbonyl group (e.g., cyclopropylcarbonyl) optionally substituted by 1 to 3 $C_{6-14}$ aryl groups (e.g., phenyl);
(21) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(22) a non-aromatic heterocyclylcarbonyl group (e.g., pyrrolidinylcarbonyl, morpholinylcarbonyl, tetrahydrofurylcarbonyl) optionally substituted by 1 to 3 substituents selected from a $C_{1-6}$ alkyl group optionally substituted by 1 to 3 halogen atoms;
(23) a $C_{6-14}$ aryloxy-carbonyl group (e.g., phenoxycarbonyl);
(24) a $C_{7-13}$ aralkyloxy-carbonyl group (e.g., benzyloxycarbonyl);
(25) a mercapto group;
(26) a $C_{1-6}$ alkylthio group (e.g., methylthio, ethylthio) optionally substituted by 1 to 3 substituents selected from
  (a) a halogen atom, and
  (b) a $C_{1-6}$ alkoxy-carbonyl group;
(27) a $C_{7-13}$ aralkylthio group (e.g., benzylthio);
(28) a $C_{6-14}$ arylthio group (e.g., phenylthio, naphthylthio);
(29) a cyano group;
(30) a nitro group;
(31) a halogen atom;
(32) a $C_{1-3}$ alkyleneoxy group (e.g., methyleneoxy, ethyleneoxy);
(33) a $C_{1-3}$ alkylenedioxy group; and
(34) a $C_{3-10}$ cycloalkyloxy group (e.g., cyclopropyloxy, cyclopentyloxy) optionally substituted by 1 to 3 substituents selected from
  (a) a halogen atom (e.g., a fluorine atom), and
  (b) a $C_{1-6}$ alkoxy group (e.g., methoxy).

The aforementioned $C_{3-10}$ cycloalkyl group, $C_{3-10}$ cycloalkenyl group, $C_{4-10}$ cycloalkadienyl group and $C_{6-14}$ aryl group exemplified as the aforementioned "hydrocarbon group" optionally have 1 to 5 (preferably 1 to 3) substituents at substitutable positions.

Examples of the substituent include the following Group Substituent B. When the number of the substituents is not less than 2, respective substituents may be the same or different.
Group Substituent B
(1) groups exemplified as the aforementioned Group Substituent A;
(2) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group,
  (f) an amino group optionally mono- or di-substituted by $C_{1-6}$ alkyl group(s),
  (g) a $C_{3-20}$ cycloalkyl-carbonyl group (e.g., cyclohexylcarbonyl), and
  (h) an aromatic heterocyclic group (e.g., pyridyl, pyrrolyl) optionally substituted by 1 to 3 $C_{1-6}$ alkyl groups;
(3) a $C_{2-6}$ alkenyl group (e.g., ethenyl, 1-propenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by $C_{1-6}$ alkyl group(s); and
(4) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group,
  (d) a halogen atom,
  (e) an amino group, and
  (f) a nitro group.

Examples of the "heterocyclic group" of the "heterocyclic group optionally having substituent(s)" for $R^1$, $R^2$ or $R^3$ include an aromatic heterocyclic group and an non-aromatic heterocyclic group.

The "heterocyclic group" of the aforementioned "heterocyclic group optionally having substituent(s)" optionally has 1 to 5 (preferably 1 to 3) substituents at substitutable positions. Examples of the substituent include those similar to the group exemplified as the aforementioned Group Substituent B. In addition, when the heterocyclic group is a non-aromatic heterocyclic group, examples of the substituent further include an oxo group. When the number of the substituents is not less than 2, respective substituents may be the same or different.

Examples of the "nitrogen-containing heterocycle" of the "nitrogen-containing heterocycle optionally having substituent(s)" formed by $R^1$ and $R^2$ bonded to each other include a 5- to 7-membered nitrogen-containing heterocycle containing, as a ring constituting atom besides carbon atom, at least one nitrogen atom and optionally further containing 1 or 2 hetero atoms selected from an oxygen atom, a sulfur atom and a nitrogen atom. Specific examples of the nitrogen-containing heterocycle include pyrrolidine, imidazolidine, pyrazolidine, piperidine, piperazine, morpholine and thiomorpholine.

The "nitrogen-containing heterocycle" optionally has 1 to 5 (preferably 1 to 3) substituents at substitutable positions. Examples of the substituent include those similar to the group exemplified as the aforementioned Group Substituent B. In addition, when the nitrogen-containing heterocycle is a non-aromatic nitrogen-containing heterocycle, examples of the substituent further include an oxo group. When the number of the substituents is not less than 2, respective substituents may be the same or different.

Examples of the "acyl" for $R^2$ or $R^3$ include a group represented by formula: —$COR^{A1}$, —CO—$OR^{A1}$, —$SO_3R^{A1}$, —$SO_2R^{A1}$, —$SOR^{A1}$, —CO—$NR^{A2}R^{B2}$ or —$SO_2NR^{A2}R^{B2}$ wherein $R^{A1}$ is a hydrogen atom, a hydrocarbon group optionally having substituent(s) or a heterocyclic group optionally having substituent(s), and $R^{A2}$ and $R^{B2}$ are each independently a hydrogen atom, a hydrocarbon group optionally having substituent(s) or a heterocyclic group optionally having substituent(s), or $R^{A2}$ and $R^{B2}$ form, together with the adjacent nitrogen atom, a nitrogen-containing heterocycle optionally having substituent(s).

Examples of the "hydrocarbon group" of the "hydrocarbon group optionally having substituent(s)" for $R^{A1}$, $R^{A2}$ or $R^{B2}$ include those similar to the "hydrocarbon group" of the "hydrocarbon group optionally having substituent(s)" for $R^1$, $R^2$ or $R^3$.

The "hydrocarbon group" of the "hydrocarbon group optionally having substituent(s)" for $R^{A1}$, $R^{A2}$ or $R^{B2}$ optionally has 1 to 5 (preferably 1 to 3) substituents at substitutable positions. Examples of the substituent include those similar to the substituent that the "hydrocarbon group" of the "hydrocarbon group optionally having substituent(s)" for $R^1$, $R^2$ or $R^3$ optionally has. When the number of the substituents is not less than 2, respective substituents may be the same or different.

Examples of the "heterocyclic group" of the "heterocyclic group optionally having substituent(s)" for $R^{A1}$, $R^{A2}$ or $R^{B2}$ include those similar to the "heterocyclic group" of the "heterocyclic group optionally having substituent(s)" for $R^1$, $R^2$ or $R^3$.

The "heterocyclic group" of the "heterocyclic group optionally having substituent(s)" for $R^{A1}$, $R^{A2}$ or $R^{B2}$ optionally has 1 to 5 (preferably 1 to 3) substituents at substitutable positions. Examples of the substituent include those similar to the group exemplified as the aforementioned Group Substituent B. In addition, when the heterocyclic group is a non-aromatic heterocyclic group, examples of the substituent further include an oxo group. When the number of the substituents is not less than 2, respective substituents may be the same or different.

Examples of the "nitrogen-containing heterocycle" of the "nitrogen-containing heterocycle optionally having substituent(s)" formed by $R^{A2}$ and $R^{B2}$ together with the adjacent nitrogen atom include those similar to the "nitrogen-containing heterocycle" of the "nitrogen-containing heterocycle optionally having substituent(s)" formed by $R^1$ and $R^2$ bonded to each other.

The "nitrogen-containing heterocycle" of the "nitrogen-containing heterocycle optionally having substituent(s)" formed by $R^{A2}$ and $R^{B2}$ together with the adjacent nitrogen atom optionally has 1 to 5 (preferably 1 to 3) substituents at substitutable positions. Examples of the substituent include those similar to the group exemplified as the aforementioned Group Substituent B. In addition, when the nitrogen-containing heterocycle is a non-aromatic nitrogen-containing heterocycle, examples of the substituent further include an oxo group. When the number of the substituents is not less than 2, respective substituents may be the same or different.

The "acyl" for $R^2$ or $R^3$ is preferably
(1) a formyl group;
(2) a carboxy group;
(3) a $C_{1-6}$ alkyl-carbonyl group optionally substituted by 1 to 3 substituents selected from
  (i) a halogen atom,
  (ii) an amino group,
  (iii) a carboxy group,
  (iv) a $C_{1-6}$ alkoxy-carbonyl group,
  (v) a $C_{6-14}$ aryl group (e.g., phenyl), and
  (vi) a $C_{1-6}$ alkoxy group;
(4) a $C_{1-6}$ alkoxy-carbonyl group optionally substituted by 1 to 3 substituents selected from
  (i) a halogen atom,
  (ii) a $C_{6-14}$ aryl group (e.g., phenyl),
  (iii) a $C_{1-6}$ alkoxy group, and
  (iv) a heterocyclic group (e.g., tetrahydrofuryl);
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl) optionally substituted by 1 to 3 halogen atoms;
(7) a carbamoyl group optionally mono- or di-substituted by substituent(s) selected from
  (i) a $C_{1-6}$ alkyl group optionally substituted by 1 to 3 substituents selected from
    (a) a halogen atom,
    (b) a $C_{1-6}$ alkoxy-carbonyl group,
    (c) a $C_{6-14}$ aryl group (e.g., phenyl),
    (d) a $C_{1-6}$ alkoxy group, and
    (e) an aromatic heterocyclic group (e.g., furyl),
  (ii) a $C_{3-10}$ cycloalkyl group (e.g., cyclopentyl, cyclohexyl),
  (iii) a $C_{6-14}$ aryl group (e.g., phenyl) optionally substituted by 1 to 3 substituents selected from
    (a) a halogen atom,
    (b) a $C_{1-6}$ alkyl group optionally substituted by 1 to 3 halogen atoms, and
    (c) a $C_{1-6}$ alkoxy group,
  (iv) a $C_{1-6}$ alkylsulfonyl group (e.g., methylsulfonyl), and
  (v) an aromatic heterocyclic group (e.g., pyridyl) optionally substituted by 1 to 3 $C_{1-6}$ alkyl groups;
(8) a $C_{1-6}$ alkylsulfonyl group (e.g., methylsulfonyl, ethylsulfonyl, isopropylsulfonyl) optionally substituted by 1 to 3 substituents selected from
  (i) a halogen atom, and
  (ii) a $C_{6-14}$ aryl group (e.g., phenyl);
(9) a $C_{6-14}$ arylsulfonyl group (e.g., benzenesulfonyl) optionally substituted by 1 to 3 substituents selected from
  (i) a halogen atom, and
  (ii) a $C_{1-6}$ alkyl group;
(10) a $C_{3-10}$ cycloalkylsulfonyl group (e.g., cyclopropylsulfonyl);
(11) a sulfamoyl group optionally mono- or di-substituted by substituent(s) selected from
  (i) a $C_{1-6}$ alkyl group optionally substituted by 1 to 3 substituents selected from
    (a) a halogen atom, and
    (b) a non-aromatic heterocyclic group (e.g., pyrrolidinyl) optionally substituted by an oxo group;
(12) a thiocarbamoyl group optionally mono- or di-substituted by substituent(s) selected from a $C_{1-6}$ alkyl group optionally substituted by 1 to 3 halogen atoms;
(13) an aromatic heterocyclylcarbonyl group (e.g., furylcarbonyl, thienylcarbonyl, pyrazolylcarbonyl, pyridylcarbonyl, isooxazolylcarbonyl, thiazolylcarbonyl) optionally substituted by 1 to 3 substituents selected from a $C_{1-6}$ alkyl group optionally substituted by 1 to 3 halogen atoms; and
(14) a non-aromatic heterocyclylcarbonyl group (e.g., tetrahydrofurylcarbonyl, tetrahydropyranylcarbonyl) optionally substituted by 1 to 3 substituents selected from a $C_{1-6}$ alkyl group optionally substituted by 1 to 3 halogen atoms.

Examples of the "ring" of the "ring optionally having substituent(s)" formed by $R^2$ and $R^3$ bonded to each other include a $C_{3-10}$ cycloalkane, a $C_{3-10}$ cycloalkene, a $C_{4-10}$ cycloalkadiene, a $C_{6-14}$ aromatic hydrocarbon and a heterocycle.

Examples of the $C_{3-10}$ cycloalkane, $C_{3-10}$ cycloalkene and $C_{4-10}$ cycloalkadiene include a ring corresponding to the $C_{3-10}$ cycloalkyl group, $C_{3-10}$ cycloalkenyl group and $C_{4-10}$ cycloalkadienyl group exemplified as the "hydrocarbon group" of the "hydrocarbon group optionally having substituent(s)" for $R^1$, $R^2$ or $R^3$.

Examples of the $C_{6-14}$ aromatic hydrocarbon include a ring corresponding to the $C_{6-14}$ aryl group exemplified as the "hydrocarbon group" of the "hydrocarbon group optionally having substituent(s)" for $R^1$, $R^2$ or $R^3$.

Examples of the heterocycle include a ring corresponding to the aromatic heterocyclic group and non-aromatic heterocyclic group exemplified as the "heterocyclic group" of the "heterocyclic group optionally having substituent(s)" for $R^1$, $R^2$ or $R^3$.

The "ring" of the "ring optionally having substituent(s)" formed by $R^2$ and $R^3$ bonded to each other optionally has 1 to 5 (preferably 1 to 3) substituents at substitutable positions. Examples of the substituent include those similar to the group exemplified as the aforementioned Group Substituent B. In addition, when the ring is a non-aromatic heterocycle, examples of the substituent further include an oxo group. When the number of the substituents is not less than 2, respective substituents may be the same or different.

$R^1$ is preferably a hydrogen atom, a $C_{1-6}$ alkyl group optionally having substituent(s), a $C_{6-14}$ aryl group optionally having substituent(s), a heterocyclic group optionally having substituent(s), or the like, more preferably a hydrogen atom, a $C_{1-6}$ alkyl group optionally having substituent(s), or the like.

$R^1$ is further more preferably
(1) a hydrogen atom;
(2) a $C_{1-6}$ alkyl group (e.g., methyl, ethyl, propyl, butyl) optionally substituted by 1 to 3 $C_{6-14}$ aryl groups (e.g., phenyl);
or the like.

In another embodiment, $R^1$ is further more preferably
(1) a hydrogen atom;
(2) a $C_{1-6}$ alkyl group (e.g., methyl, ethyl, propyl, isopropyl, butyl) optionally substituted by 1 to 3 substituents selected from
  (a) a halogen atom (e.g., a fluorine atom),
  (b) a hydroxy group,
  (c) a $C_{1-6}$ alkoxy-carbonyl group (e.g., ethoxycarbonyl)
  (d) a $C_{6-14}$ aryl group (e.g., phenyl) optionally substituted by 1 to 3 substituents selected from
    (i) an amino group, and
    (ii) a nitro group,
  (e) an aromatic heterocyclic group (e.g., pyridyl), and
  (f) a non-aromatic heterocyclylcarbonyl group (e.g., morpholinylcarbonyl);
or the like.

$R^2$ is preferably a halogen atom, a $C_{1-6}$ alkyl group optionally having substituent(s), a $C_{6-14}$ aryl group optionally having substituent(s), or the like, more preferably a $C_{1-6}$ alkyl group optionally having substituent(s), a $C_{6-14}$ aryl group optionally having substituent(s), or the like.

$R^2$ is further more preferably
(1) a $C_{1-6}$ alkyl group (e.g., methyl, ethyl, propyl, isopropyl, butyl) optionally substituted by 1 to 3 halogen atoms (e.g., a fluorine atom);
(2) a $C_{6-14}$ aryl group (e.g., phenyl);
or the like.

In another embodiment, $R^2$ is further more preferably
(1) a $C_{1-6}$ alkyl group (e.g., methyl, ethyl, propyl, isopropyl, butyl) optionally substituted by 1 to 3 substituents selected from
  (a) a halogen atom (e.g., a fluorine atom),
  (b) a $C_{1-6}$ alkoxy-carbonyl group (e.g., methoxycarbonyl), and
  (c) a carbamoyl group optionally mono- or di-substituted by $C_{1-6}$ alkyl group(s) (e.g., methyl);
(2) a $C_{6-14}$ aryl group (e.g., phenyl);
or the like.

$R^3$ is preferably a hydrogen atom, a halogen atom, a $C_{1-6}$ alkyl group optionally having substituent(s), an aromatic heterocyclic group optionally having substituent(s), —$COR^{A1}$, —CO—$OR^{A1}$, —$SO_3R^{A1}$, —$SO_2R^{A1}$, —$SOR^{A1}$, —CO—$NR^{A2}R^{B2}$ (wherein each symbol is as defined above), or the like, more preferably a hydrogen atom, a $C_{1-6}$ alkyl group optionally having substituent(s), —CO—$OR^{A1}$ (wherein $R^{A1}$ is as defined above), or the like, further more preferably a hydrogen atom, a $C_{1-6}$ alkyl group optionally having substituent(s), or the like.

$R^3$ is particularly preferably
(1) a hydrogen atom;
(2) a $C_{1-6}$ alkyl group (e.g., methyl, ethyl, propyl, isopropyl, butyl) optionally substituted by 1 to 3 halogen atoms (e.g., a fluorine atom); or the like.

In another embodiment, $R^3$ is particularly preferably
(1) a hydrogen atom;
(2) a $C_{1-6}$ alkyl group (e.g., methyl, ethyl, propyl, isopropyl, butyl) optionally substituted by 1 to 3 substituents selected from
  (a) a halogen atom (e.g., a fluorine atom),
  (b) a $C_{1-6}$ alkoxy-carbonyl group (e.g., methoxycarbonyl), and
  (c) a carbamoyl group optionally mono- or di-substituted by $C_{1-6}$ alkyl group(s) (e.g., methyl);
(3) —CO—$OR^{A1}$ (wherein $R^{A1}$ is a hydrogen atom or a $C_{1-6}$ alkyl group) (e.g., methoxycarbonyl); or the like.

Alternatively, preferably, $R^2$ and $R^3$ are bonded to form a $C_{3-10}$ cycloalkane (preferably a $C_{3-8}$ cycloalkane) optionally condensed with a benzene ring, which optionally has substituent(s); a heterocycle (preferably a non-aromatic heterocycle) optionally crosslinked, which optionally has substituent(s); or the like.

More preferably, $R^2$ and $R^3$ are bonded to form a $C_{3-10}$ cycloalkane (preferably a $C_{3-8}$ cycloalkane) optionally condensed with a benzene ring, which optionally has substituent(s); a non-aromatic heterocycle (preferably a 5- or 6-membered non-aromatic heterocycle) optionally crosslinked, which optionally has substituent(s); or the like.

Further more preferably, $R^2$ and $R^3$ are bonded to form
(1) a $C_{3-8}$ cycloalkane (e.g., cyclopentane, cyclohexane, cycloheptane);
(2) a 5- or 6-membered non-aromatic heterocycle (e.g., tetrahydropyran, tetrahydrofuran, piperidine) optionally substituted by 1 to 3 $C_{7-13}$ aralkyloxy-carbonyl groups (e.g., benzyloxycarbonyl);
or the like.

In another embodiment, further more preferably, $R^2$ and $R^3$ are bonded to form
(1) a $C_{3-8}$ cycloalkane optionally condensed with a benzene ring (e.g., cyclobutane, cyclopentane, cyclohexane, cycloheptane, indane), which is optionally substituted by 1 to 3 substituents selected from
  (a) a halogen atom (e.g., a fluorine atom),
  (b) a hydroxy group,
  (c) an oxo group,
  (d) a $C_{1-6}$ alkoxy-carbonyl group (e.g., ethoxycarbonyl), (e) a C$_{6-14}$ aryl group (e.g., phenyl) optionally substituted by 1 to 3 halogen atoms (e.g., a fluorine atom),
(f) a C$_{3-10}$ cycloalkyl group (e.g., cyclohexyl), and
(g) an amino group optionally mono- or di-substituted by substituent(s) selected from
  (i) a C$_{6-14}$ aryl group (e.g., phenyl), and
  (ii) a C$_{1-6}$ alkoxy-carbonyl group (e.g., methoxycarbonyl, tert-butoxycarbonyl) optionally substituted by 1 to 3 C$_{6-14}$ aryl groups (e.g., phenyl);
(2) a 5- or 6-membered non-aromatic heterocycle optionally crosslinked (e.g., tetrahydropyran, tetrahydrofuran, piperidine, pyrrolidine, tetrahydrothiopyran, 1-oxidotetrahydrothiopyran, 1,1-dioxidotetrahydrothiopyran, azabicyclo[3.2.1]octane), which is optionally substituted by 1 to 3 substituents selected from
  (a) a C$_{1-6}$ alkyl group (e.g., methyl, ethyl) optionally substituted by 1 to 3 substituents selected from
    (i) a C$_{6-14}$ aryl group (e.g., phenyl),
    (ii) a C$_{1-6}$ alkoxy-carbonyl group (e.g., ethoxycarbonyl),
    (iii) a C$_{3-10}$ cycloalkyl-carbonyl group (e.g., cyclohexylcarbonyl),
    (iv) an aromatic heterocyclic group (e.g., pyridyl, pyrrolyl) optionally substituted by 1 to 3 C$_{1-6}$ alkyl groups (e.g., methyl),
  (b) a C$_{6-14}$ aryl group (e.g., phenyl) optionally substituted by 1 to 3 halogen atoms (e.g., a fluorine atom),
  (c) an aromatic heterocyclic group (e.g., pyridyl, pyrimidinyl),
  (d) a C$_{1-6}$ alkyl-carbonyl group (e.g., acetyl, propionyl) optionally substituted by 1 to 3 substituents selected from
    (i) a halogen atom (e.g., a fluorine atom),
    (ii) a C$_{1-6}$ alkoxy group (e.g., methoxy),
    (ii) a C$_{1-6}$ alkoxy-carbonyl group (e.g., methoxycarbonyl),
    (iii) a C$_{6-14}$ aryl group (e.g., phenyl),
    (iv) an aromatic heterocyclic group (e.g., indolyl), and
    (v) an amino group optionally mono- or di-substituted by substituent(s) selected from a C$_{1-6}$ alkyl-carbonyl group (e.g., acetyl) and a C$_{1-6}$ alkoxy-carbonyl group (e.g., tert-butoxycarbonyl),
  (e) a C$_{1-6}$ alkoxy-carbonyl group (e.g., methoxycarbonyl, tert-butoxycarbonyl) optionally substituted by 1 to 3 C$_{6-14}$ aryl groups (e.g., phenyl),
  (f) a C$_{6-14}$ aryl-carbonyl group (e.g., benzoyl),
  (g) a C$_{6-14}$ aryloxy-carbonyl group (e.g., phenoxycarbonyl),
  (h) a C$_{3-10}$ cycloalkyl-carbonyl group (e.g., cyclopropylcarbonyl) optionally substituted by 1 to 3 C$_{6-14}$ aryl groups (e.g., phenyl),
  (i) an aromatic heterocyclylcarbonyl group (e.g., pyridylcarbonyl),
  (j) a non-aromatic heterocyclylcarbonyl group (e.g., tetrahydrofurylcarbonyl), and
  (k) a carbamoyl group optionally mono- or di-substituted by C$_{1-6}$ alkyl group(s) (e.g., methyl);
or the like.

R$^4$ is a heterocyclic group optionally having substituent(s).
Examples of the "heterocyclic group" of the "heterocyclic group optionally having substituent(s)" for R$^4$ include those similar to the "heterocyclic group" of the "heterocyclic group optionally having substituent(s)" for R$^1$, R$^2$ or R$^3$.
The "heterocyclic group" of the "heterocyclic group optionally having substituent(s)" for R$^4$ optionally has 1 to 5 (preferably 1 to 3) substituents at substitutable positions. Examples of the substituent include those similar to the group exemplified as the aforementioned Group Substituent B. In addition, when the heterocyclic group is a non-aromatic heterocyclic group, examples of the substituent further include an oxo group. When the number of the substituents is not less than 2, respective substituents may be the same or different.

R$^4$ is preferably an aromatic heterocyclic group optionally having substituent(s), or the like, more preferably a 5- or 6-membered aromatic heterocyclic group optionally condensed with a benzene ring or a 5- or 6-membered aromatic heterocycle (preferably pyridyl, pyrazolyl, pyrimidinyl, oxazolyl, imidazolyl, pyrrolopyridyl, quinolyl), which optionally has substituent(s), or the like, further more preferably a 5- or 6-membered aromatic heterocyclic group optionally condensed with a benzene ring or a 5- or 6-membered aromatic heterocycle (preferably pyridyl, pyrazolyl, pyrimidinyl, oxazolyl, imidazolyl, pyrrolopyridyl, quinolyl), which is optionally substituted by 1 to 3 substituents selected from
(a) a halogen atom (e.g., a fluorine atom),
(b) an amino group,
(c) a C$_{1-6}$ alkyl group (e.g., methyl, ethyl) optionally substituted by amino group(s) optionally mono- or di-substituted by C$_{7-13}$ aralkyl group(s) (e.g., 2-phenylethyl), and
(d) a sulfamoyl group optionally mono- or di-substituted by C$_{1-6}$ alkyl group(s) (e.g., methyl) or the like.

R$^5$ is a hydrogen atom, a halogen atom or a hydrocarbon group optionally having substituent(s).

Examples of the "hydrocarbon group" of the "hydrocarbon group optionally having substituent(s)" for R$^5$ include those similar to the "hydrocarbon group" of the "hydrocarbon group optionally having substituent(s)" for R$^1$, R$^2$ or R$^3$.

The "hydrocarbon group" of the "hydrocarbon group optionally having substituent(s)" for R$^5$ optionally has 1 to 5 (preferably 1 to 3) substituents at substitutable positions. Examples of the substituent include those similar to the substituent that the "hydrocarbon group" of the "hydrocarbon group optionally having substituent(s)" for R$^1$, R$^2$ or R$^3$ optionally has. When the number of the substituents is not less than 2, respective substituents may be the same or different.

R$^5$ is preferably a hydrogen atom, a halogen atom (e.g., a bromine atom), a C$_{1-6}$ alkyl group (e.g., methyl) optionally having substituent(s), or the like, more preferably a hydrogen atom, a halogen atom (e.g., a bromine atom), a C$_{1-6}$ alkyl group (e.g., methyl), or the like, particularly preferably a hydrogen atom.

As X and Y,
(1) X is a sulfur atom, and Y is a carbon atom, or
(2) X is a carbon atom, and Y is a sulfur atom.
That is, the formula (I) is

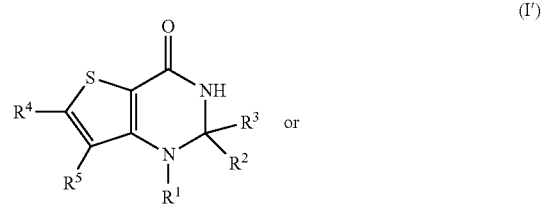

(I')

or

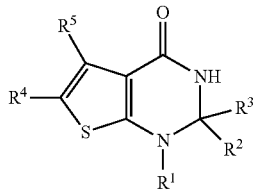

(I″)

As X and Y, preferably, X is a sulfur atom, and Y is a carbon atom.

Preferable examples of compound (I) include the following compounds.

Compound A-1
Compound (I) wherein
X is a sulfur atom;
Y is a carbon atom;
$R^1$ is a hydrogen atom, a $C_{1-6}$ alkyl group optionally having substituent(s), a $C_{6-14}$ aryl group optionally having substituent(s) or a heterocyclic group optionally having substituent(s),
$R^2$ is a halogen atom, a $C_{1-6}$ alkyl group optionally having substituent(s) or a $C_{6-14}$ aryl group optionally having substituent(s), or
$R^1$ and $R^2$ are optionally bonded to form a nitrogen-containing heterocycle optionally having substituent(s),
$R^3$ is a hydrogen atom, a halogen atom, a $C_{1-6}$ alkyl group optionally having substituent(s), an aromatic heterocyclic group optionally having substituent(s), —$COR^{A1}$, —CO—$OR^{A1}$, —$SO_3R^{A1}$, —$SO_2R^{A1}$, —$SOR^{A1}$ or —CO—$NR^{A2}R^{B2}$ (wherein each symbol is as defined above), or
$R^2$ and $R^3$ are optionally bonded to form a $C_{3-10}$ cycloalkane optionally having substituent(s) or a heterocycle optionally having substituent(s);
$R^4$ is a heterocyclic group optionally having substituent(s); and
$R^5$ is a hydrogen atom, a halogen atom or a $C_{1-6}$ alkyl group optionally having substituent(s).

Compound B-1
Compound (I) wherein
X is a sulfur atom;
Y is a carbon atom;
$R^1$ is a hydrogen atom or a $C_{1-6}$ alkyl group optionally having substituent(s),
$R^2$ is a $C_{1-6}$ alkyl group optionally having substituent(s) or a $C_{6-14}$ aryl group optionally having substituent(s),
$R^3$ is a hydrogen atom or a $C_{1-6}$ alkyl group optionally having substituent(s), or
$R^2$ and $R^3$ are optionally bonded to form a $C_{3-10}$ cycloalkane (preferably a $C_{3-8}$ cycloalkane) optionally having substituent(s) or a non-aromatic heterocycle (preferably a 5- or 6-membered non-aromatic heterocycle) optionally having substituent(s);
$R^4$ is an aromatic heterocyclic group (preferably a 5- or 6-membered aromatic heterocyclic group) optionally having substituent(s); and
$R^5$ is a hydrogen atom.

Compound C-1
Compound (I) wherein
X is a sulfur atom;
Y is a carbon atom;
$R^1$ is
(1) a hydrogen atom; or
(2) a $C_{1-6}$ alkyl group (e.g., methyl, ethyl, propyl, butyl) optionally substituted by 1 to 3 $C_{6-14}$ aryl groups (e.g., phenyl);
$R^2$ is
(1) a $C_{1-6}$ alkyl group (e.g., methyl, ethyl, propyl, isopropyl, butyl) optionally substituted by 1 to 3 halogen atoms (e.g., a fluorine atom); or
(2) a $C_{6-14}$ aryl group (e.g., phenyl);
$R^3$ is
(1) a hydrogen atom; or
(2) a $C_{1-6}$ alkyl group (e.g., methyl, ethyl, propyl, isopropyl, butyl) optionally substituted by 1 to 3 halogen atoms (e.g., a fluorine atom); or
$R^2$ and $R^3$ are optionally bonded to form
(1) a $C_{3-8}$ cycloalkane (e.g., cyclopentane, cyclohexane, cycloheptane); or
(2) a 5- or 6-membered non-aromatic heterocycle (e.g., tetrahydropyran, tetrahydrofuran, piperidine) optionally substituted by 1 to 3 $C_{7-13}$ aralkyloxy-carbonyl groups (e.g., benzyloxycarbonyl);
$R^4$ is a 5- or 6-membered aromatic heterocyclic group (preferably pyridyl, pyrazolyl); and
$R^5$ is a hydrogen atom.

Compound A-2
Compound (I) wherein
X is a sulfur atom;
Y is a carbon atom;
$R^1$ is a hydrogen atom, a $C_{1-6}$ alkyl group optionally having substituent(s), a $C_{6-14}$ aryl group optionally having substituent(s) or a heterocyclic group optionally having substituent(s),
$R^2$ is a halogen atom, a $C_{1-6}$ alkyl group optionally having substituent(s) or a $C_{6-14}$ aryl group optionally having substituent(s), or
$R^1$ and $R^2$ are optionally bonded to form a nitrogen-containing heterocycle optionally having substituent(s),
$R^3$ is a hydrogen atom, a halogen atom, a $C_{1-6}$ alkyl group optionally having substituent(s), an aromatic heterocyclic group optionally having substituent(s), —$COR^{A1}$, —CO—$OR^{A1}$, —$SO_3R^{A1}$, —$SO^2R^{A1}$, —$SOR^{A1}$ or —CO—$NR^{A2}R^{B2}$ (wherein each symbol is as defined above), or
$R^2$ and $R^3$ are optionally bonded to form a $C_{3-10}$ cycloalkane optionally condensed with a benzene ring, which optionally has substituent(s), or a heterocycle optionally crosslinked, which optionally has substituent(s);
$R^4$ is a heterocyclic group optionally having substituent(s); and
$R^5$ is a hydrogen atom, a halogen atom or a $C_{1-6}$ alkyl group optionally having substituent(s).

Compound B-2
Compound (I) wherein
X is a sulfur atom;
Y is a carbon atom;
$R^1$ is a hydrogen atom or a $C_{1-6}$ alkyl group optionally having substituent(s),
$R^2$ is a $C_{1-6}$ alkyl group optionally having substituent(s) or a $C_{6-14}$ aryl group optionally having substituent(s),
$R^3$ is a hydrogen atom, a $C_{1-6}$ alkyl group optionally having substituent(s), or —CO—$OR^{A1}$ (wherein $R^{A1}$ is as defined above), or
$R^2$ and $R^3$ are optionally bonded to form a $C_{3-10}$ cycloalkane (preferably a $C_{3-8}$ cycloalkane) optionally condensed with a benzene ring, which optionally has substituent(s), or a non-aromatic heterocycle (preferably a 5- or 6-membered non-aromatic heterocycle) optionally crosslinked, which optionally has substituent(s);

$R^4$ is an aromatic heterocyclic group (preferably a 5- or 6-membered aromatic heterocyclic group optionally condensed with a benzene ring or a 5- or 6-membered aromatic heterocycle), which optionally has substituent(s); and $R^5$ is a hydrogen atom, a halogen atom or a $C_{1-6}$ alkyl group.

Compound C-2

Compound (I) wherein

X is a sulfur atom;

Y is a carbon atom;

$R^1$ is (1) a hydrogen atom; or (2) a $C_{1-6}$ alkyl group (e.g., methyl, ethyl, propyl, isopropyl, butyl) optionally substituted by 1 to 3 substituents selected from
(a) a halogen atom (e.g., a fluorine atom),
(b) a hydroxy group,
(c) a $C_{1-6}$ alkoxy-carbonyl group (e.g., ethoxycarbonyl),
(d) a $C_{6-14}$ aryl group (e.g., phenyl) optionally substituted by 1 to 3 substituents selected from
(i) an amino group, and
(ii) a nitro group,
(e) an aromatic heterocyclic group (e.g., pyridyl), and
(f) a non-aromatic heterocyclylcarbonyl group (e.g., morpholinylcarbonyl);

$R^2$ is (1) a $C_{1-6}$ alkyl group (e.g., methyl, ethyl, propyl, isopropyl, butyl) optionally substituted by 1 to 3 substituents selected from
(a) a halogen atom (e.g., a fluorine atom),
(b) a $C_{1-6}$ alkoxy-carbonyl group (e.g., methoxycarbonyl), and
(c) a carbamoyl group optionally mono- or di-substituted by $C_{1-6}$ alkyl group(s) (e.g., methyl); or (2) a $C_{6-14}$ aryl group (e.g., phenyl);

$R^3$ is (1) a hydrogen atom;

(2) a $C_{1-6}$ alkyl group (e.g., methyl, ethyl, propyl, isopropyl, butyl) optionally substituted by 1 to 3 substituents selected from
(a) a halogen atom (e.g., a fluorine atom),
(b) a $C_{1-6}$ alkoxy-carbonyl group (e.g., methoxycarbonyl), and
(c) a carbamoyl group optionally mono- or di-substituted by $C_{1-6}$ alkyl group(s) (e.g., methyl); or (3) —CO—$OR^{41}$ (wherein $R^{41}$ is a hydrogen atom or a $C_{1-6}$ alkyl group) (e.g., methoxycarbonyl); or $R^2$ and $R^3$ are optionally bonded to form (1) a $C_{3-8}$ cycloalkane optionally condensed with a benzene ring (e.g., cyclobutane, cyclopentane, cyclohexane, cycloheptane, indane), which is optionally substituted by 1 to 3 substituents selected from
(a) a halogen atom (e.g., a fluorine atom),
(b) a hydroxy group,
(c) an oxo group,
(d) a $C_{1-6}$ alkoxy-carbonyl group (e.g., ethoxycarbonyl),
(e) a $C_{6-14}$ aryl group (e.g., phenyl) optionally substituted by 1 to 3 halogen atoms (e.g., a fluorine atom),
(f) a $C_{3-10}$ cycloalkyl group (e.g., cyclohexyl), and
(g) an amino group optionally mono- or di-substituted by substituent(s) selected from
(i) a $C_{6-14}$ aryl group (e.g., phenyl), and
(ii) a $C_{1-6}$ alkoxy-carbonyl group (e.g., methoxycarbonyl, tert-butoxycarbonyl) optionally substituted by 1 to 3 $C_{6-14}$ aryl groups (e.g., phenyl); or (2) a 5- or 6-membered non-aromatic heterocycle optionally crosslinked (e.g., tetrahydropyran, tetrahydrofuran, piperidine, pyrrolidine, tetrahydrothiopyran, 1-oxidotetrahydrothiopyran, 1,1-dioxidotetrahydrothiopyran, azabicyclo[3.2.1]octane), which is optionally substituted by 1 to 3 substituents selected from
(a) a $C_{1-6}$ alkyl group (e.g., methyl, ethyl) optionally substituted by 1 to 3 substituents selected from
(i) a $C_{6-14}$ aryl group (e.g., phenyl),
(ii) a $C_{1-6}$ alkoxy-carbonyl group (e.g., ethoxycarbonyl),
(iii) a $C_{3-10}$ cycloalkyl-carbonyl group (e.g., cyclohexylcarbonyl),
(iv) an aromatic heterocyclic group (e.g., pyridyl, pyrrolyl) optionally substituted by 1 to 3 $C_{1-6}$ alkyl groups (e.g., methyl),
(b) a $C_{6-14}$ aryl group (e.g., phenyl) optionally substituted by 1 to 3 halogen atoms (e.g., a fluorine atom),
(c) an aromatic heterocyclic group (e.g., pyridyl, pyrimidinyl),
(d) a $C_{1-6}$ alkyl-carbonyl group (e.g., acetyl, propionyl) optionally substituted by 1 to 3 substituents selected from
(i) a halogen atom (e.g., a fluorine atom),
(ii) a $C_{1-6}$ alkoxy group (e.g., methoxy),
(ii) a $C_{1-6}$ alkoxy-carbonyl group (e.g., methoxycarbonyl),
(iii) a $C_{6-14}$ aryl group (e.g., phenyl),
(iv) an aromatic heterocyclic group (e.g., indolyl), and
(v) an amino group optionally mono- or di-substituted by substituent(s) selected from a $C_{1-6}$ alkyl-carbonyl group (e.g., acetyl) and a $C_{1-6}$ alkoxy-carbonyl group (e.g., tert-butoxycarbonyl),
(e) a $C_{1-6}$ alkoxy-carbonyl group (e.g., methoxycarbonyl, tert-butoxycarbonyl) optionally substituted by 1 to 3 $C_{6-14}$ aryl groups (e.g., phenyl),
(f) a $C_{6-14}$ aryl-carbonyl group (e.g., benzoyl),
(g) a $C_{6-14}$ aryloxy-carbonyl group (e.g., phenoxycarbonyl),
(h) a $C_{3-10}$ cycloalkyl-carbonyl group (e.g., cyclopropylcarbonyl) optionally substituted by 1 to 3 $C_{6-14}$ aryl groups (e.g., phenyl),
(i) an aromatic heterocyclylcarbonyl group (e.g., pyridylcarbonyl),
(j) a non-aromatic heterocyclylcarbonyl group (e.g., tetrahydrofurylcarbonyl), and
(k) a carbamoyl group optionally mono- or di-substituted by $C_{1-6}$ alkyl group(s) (e.g., methyl);

$R^4$ is a 5- or 6-membered aromatic heterocyclic group optionally condensed with a benzene ring or a 5- or 6-membered aromatic heterocycle (preferably pyridyl, pyrazolyl, pyrimidinyl, oxazolyl, imidazolyl, pyrrolopyridyl, quinolyl), which is optionally substituted by 1 to 3 substituents selected from
(a) a halogen atom (e.g., a fluorine atom),
(b) an amino group,
(c) a $C_{1-6}$ alkyl group (e.g., methyl, ethyl) optionally substituted by amino group(s) optionally mono- or di-substituted by $C_{7-13}$ aralkyl group(s) (e.g., 2-phenylethyl), and
(d) a sulfamoyl group optionally mono- or di-substituted by $C_{1-6}$ alkyl group(s) (e.g., methyl); and $R^5$ is a hydrogen atom, a halogen atom or a $C_{1-6}$ alkyl group.

Compound D

1'-ethyl-6'-(pyridin-4-yl)-1'H-spiro[cyclopentane-1,2'-thieno[3,2-d]pyrimidin]-4'(3'H)-one (Example 27), or a salt thereof;

1,2-dimethyl-6-(5-methyl-1H-pyrazol-4-yl)-2-(2,2,2-trifluoroethyl)-2,3-dihydrothieno[3,2-d]pyrimidin-4(1H)-one (Example 104), or a salt thereof; and 2-fluoro-6'-(5-methyl-1H-pyrazol-4-yl)-1'H-spiro[cyclohexane-1,2'-thieno[3,2-d]pyrimidin]-4'(3'H)-one (Example 122), or a salt thereof;

The salt of compound (I) is preferably a pharmacologically acceptable salt, and examples thereof include salts with inorganic bases, salts with organic bases, salts with inorganic acids, salts with organic acids, and salts with basic or acidic amino acids.

Preferable examples of the salt with inorganic base include alkali metal salts such as a sodium salt, a potassium salt and the like; alkaline earth metal salts such as a calcium salt, a magnesium salt and the like; an aluminum salt and an ammonium salt.

Preferable examples of the salt with organic base include a salt with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine or N,N-dibenzylethylenediamine.

Preferable examples of the salt with inorganic acid include a salt with hydrochloric acid, hydrobromic acid, nitric acid, sulfuric acid or phosphoric acid.

Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid.

Preferable examples of the salt with basic amino acid include a salt with arginine, lysine or ornithine.

Preferable examples of the salt with acidic amino acid include a salt with aspartic acid or glutamic acid.

The production methods of compound (I) are explained in the following.

The compounds in the following reaction schemes may form salts, and examples of such salt include those similar to the salts of compound (I).

While the compounds obtained in respective steps can be used for the next reaction in the form of a reaction mixture as a crude product, they can also be isolated from the reaction mixture by a known separation means such as recrystallization, distillation, chromatography and the like.

Compound (I) can be obtained, for example, according to the method shown in following reaction scheme, or a method analogous thereto.

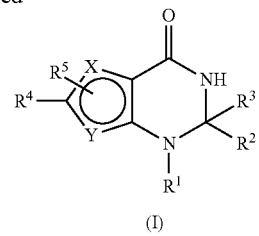

wherein G is —CO— or —C(OR$^{101}$)$_2$— (R$^{101}$ is a C$_{1-6}$ alkyl group (preferably methyl, ethyl)), and the other symbols are as defined above.

In this reaction, compound (I) can be produced by reacting compound (II) with compound (III).

Compound (III) may be a hydrate.

The amount of compound (III) to be used in this reaction is generally 1 to 1000 equivalents, preferably 3 to 100 equivalents, relative to compound (II).

The reaction is preferably carried out in a solvent. In addition, in this reaction, an acid such as p-toluenesulfonic acid, concentrated hydrochloric acid, concentrated sulfuric acid and the like can be used in an amount of about 0.01 to 1 equivalents, preferably 0.05 to 0.2 equivalents, relative to compound (II).

Examples of the solvent used for the reaction include aromatic hydrocarbons (e.g., benzene, toluene, xylene), lower organic acids (e.g., acetic acid), dioxane, alcohols (e.g., ethanol), amides (e.g., N,N-dimethylformamide, N,N-dimethylacetamide, N-methylpyrrolidone) and a mixed solvent thereof.

The reaction can be carried out under heating (about 40 to 200° C., preferably about 60 to 150° C.). The reaction time is generally about 15 min to 72 hr, preferably about 1 to 20 hr.

Compound (III) may be a commercially available product, or can be produced according to a method known per se.

Compound (II) can be obtained, for example, according to the method shown in following reaction scheme.

Reaction scheme 2

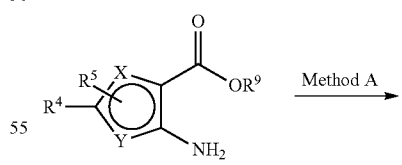

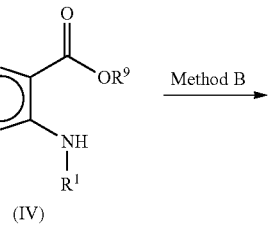

Reaction scheme 1

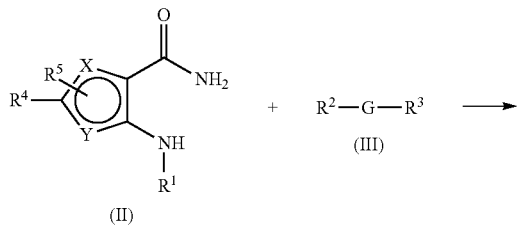

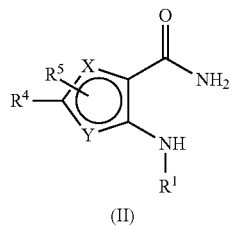

(II)

wherein $R^9$ is a $C_{1-6}$ alkyl group (e.g., methyl, ethyl), and the other symbols are as defined above.

Method A

Compound (1V) can be produced by reacting compound (V) with a halide corresponding to $R^1$.

Examples of the halide include alkyl halides such as methyl iodide, ethyl iodide and the like; and aryl halides such as bromobenzene, 4-chloropyridine and the like. The amount of the halide to be used is, for example, about 1 to 10 equivalents, relative to compound (V).

The reaction is preferably carried out in the presence of a base. Examples of the base include cesium carbonate, sodium hydride and tert-butoxy potassium. The amount of the base to be used is, for example, about 1 to 10 equivalents, relative to compound (V).

Examples of the solvent used for the reaction include ethers (e.g., tetrahydrofuran, dioxane, 1,2-dimethoxyethane) and amides (e.g., N,N-dimethylformamide, N,N-dimethylacetamide, N-methylpyrrolidone).

The reaction can be carried out under cooling (about 0 to 10° C.), at room temperature (about 15 to 30° C.), or under heating (about 40 to 60° C.). The reaction time is generally about 1 to 48 hr, preferably about 1 to 10 hr.

When an aryl halide is used as a halide, a condition using a palladium complex as a catalyst, which is so-called the Buchwald reaction, can be employed. Examples of the palladium complex include a combination of palladium acetate and Xantphos or BINAP.

The amount of the catalyst to be used is, for example, about 0.01 to 1 equivalents, relative to compound (V).

The reaction can be carried out at room temperature (about 15 to 30° C.) or under heating (about 40 to 180° C.). The reaction time is generally about 1 to 48 hr, preferably about 1 to 10 hr.

Alternatively, compound (1V) can also be produced by subjecting compound (V) to a reductive amination reaction using an aldehyde corresponding to $R^1$ or an equivalent thereof and a reducing agent.

Examples of the aldehyde include benzaldehyde and the like. The amount of the aldehyde to be used is, for example, about 2 to 20 equivalents, relative to compound (V). Examples of the equivalent of the aldehyde include 2-methoxypropene. The amount of the equivalent of the aldehyde to be used is, for example, about 2 to 20 equivalents, relative to compound (V).

Examples of the reducing agent include sodium triacetoxyborohydride and sodium cyanoborohydride. The amount of the reducing agent to be used is, for example, about 2 to 10 equivalents, relative to compound (V).

Examples of the solvent used for the reaction include ethers such as tetrahydrofuran, dioxane, 1,2-dimethoxyethane and the like; halogen solvents such as dichloromethane and the like; and N,N-dimethylformamide.

The reaction can be carried out at room temperature (about 15 to 30° C.). The reaction time is generally about 2-72 hr, preferably about 2 to 24 hr.

Compound (V) can be produced according to a method known per se.

Method B

In Method B, compound (II) can be produced by subjecting compound (1V) to hydrolysis, and subjecting the obtained carboxylic acid to a condensation reaction with ammonia.

An alkali metal hydroxide such as sodium hydroxide, lithium hydroxide, potassium hydroxide, barium hydroxide and the like is used for the hydrolysis. The amount of the alkali metal hydroxide to be used is, for example, about 1 to 10 equivalents, relative to compound (1V).

Examples of the solvent used for the reaction include a mixed solvent of water and an organic solvent such as an alcohol (e.g., methanol, ethanol); an ether (e.g., tetrahydrofuran, dioxane, 1,2-dimethoxyethane) and the like.

The reaction can be carried out at room temperature (about 15 to 30° C.) or under heating (about 40 to 100° C.). The reaction time is generally about 1 to 20 hr, preferably about 1 to 10 hr.

Compound (II) can be produced by reacting the obtained carboxylic acid or a salt thereof (e.g., a sodium salt) in a known condensation reaction condition, for example, with ammonium chloride, triethylamine, 1-hydroxybenzotriazole and EDC (1-ethyl-3-(3-dimethylaminopropyl)carbodiimide) in N,N-dimethylformamide.

Alternatively, compound (I) can also be produced according to the method shown in the following reaction scheme.

Reaction scheme 3

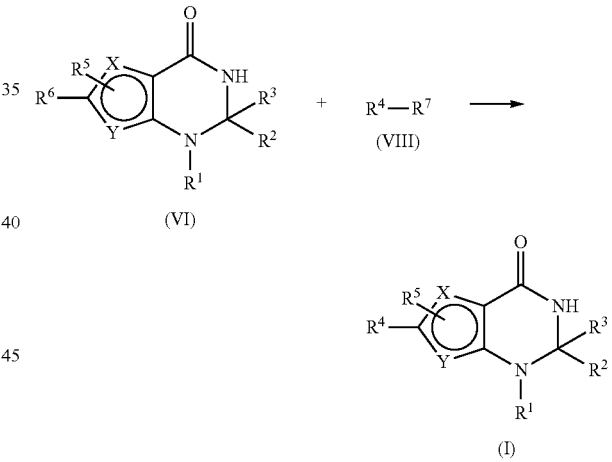

wherein $R^6$ is Br, Cl or I, $R^7$ is a boric acid group, a borate group (e.g., 4,4,5,5-tetramethyl-1,3,2-dioxaborolan-2-yl), a trifluoromethanesulfonyl group, or a stannyl group having substituent(s) (e.g., tributylstannyl), and the other symbols are as defined above.

In this reaction, compound (I) can be produced by subjecting compound (VI) to a reaction generally known as the Suzuki reaction or Stille reaction, or a reaction analogous thereto.

In this reaction, compound (VI) is generally reacted with compound (VIII) in the presence of a palladium catalyst.

The amount of compound (VIII) to be used is about 1 to 3 equivalents, relative to compound (VI).

This reaction can be carried out in the presence of a base. Examples of the base include sodium carbonate, potassium carbonate and cesium carbonate. The amount of the base to be used is about 2 to 20 equivalents, relative to compound (VI).

Examples of the palladium catalyst include [1,1'-bis (diphenylphosphino)ferrocene]dichloropalladium(II) dichloromethane complex and tetrakis(triphenylphosphine)palladium(0). The amount of the palladium catalyst to be used is about 0.01 to 1 equivalents, relative to compound (VI).

Examples of the solvent used for the reaction include aromatic hydrocarbons (e.g., benzene, toluene, xylene), ethers (e.g., tetrahydrofuran, dioxane, 1,2-dimethoxyethane), acetone, acetonitrile, ethyl acetate, N,N-dimethylformamide, N,N-dimethylacetamide, 1-methyl-2-pyrrolidone, dimethyl sulfoxide, water and a mixed solvent thereof.

The reaction can be carried out at room temperature (about 15 to 30° C.) or under heating (about 40 to 150° C.). The reaction time is generally about 1 to 50 hr, preferably about 1 to 20 hr.

Alternatively, compound (I) can also be produced by converting compound (VI) to a boric acid derivative using a bis(pinacolato)diboron and the like, and reacting the boric acid derivative with a halide (e.g., 4-chloropyridine) or a triflate in the aforementioned condition.

Compound (VIII) can be produced according to a method known per se.

Compound (VI) can be produced, for example, according to the method shown in the following reaction scheme.

Reaction scheme 4

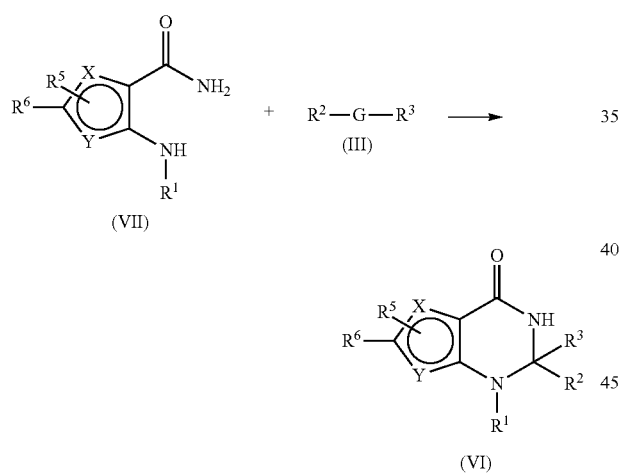

wherein each symbol is as defined above.

In this reaction, compound (VI) can be produced by reacting compound (VII) with compound (III) in the same manner as in the aforementioned Reaction scheme 1. The amount of compound (III) to be used is generally 1 to 1000 equivalents, preferably 3 to 100 equivalents, relative to compound (VII). The reaction can be carried out under heating (about 40 to 200° C., preferably about 60 to 150° C.). The reaction time is generally about 15 min to 72 hr, preferably about 1 to 20 hr.

Compound (III) may be a commercially available product, or can be produced according to a method known per se.

Compound (VII) can be produced, for example, according to the method shown in the following reaction scheme.

Reaction scheme 5

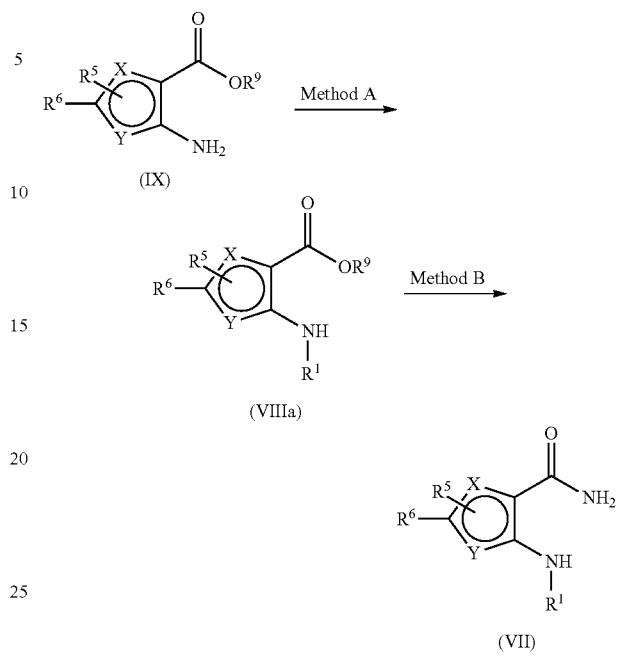

wherein each symbol is as defined above.

Method A

Compound (VIIIa) can be produced from compound (IX) in the same manner as in Method A of the aforementioned Reaction scheme 2.

Method B

Compound (VII) can be produced from compound (VIIIa) in the same manner as in Method B of the aforementioned Reaction scheme 2.

Compound (IX) can be produced according to a method known per se.

Compound (Ia), which is compound (I) wherein $R^4$ is thiazolyl optionally having substituent(s), can be produced according to the method shown in the following reaction scheme.

Reaction scheme 6

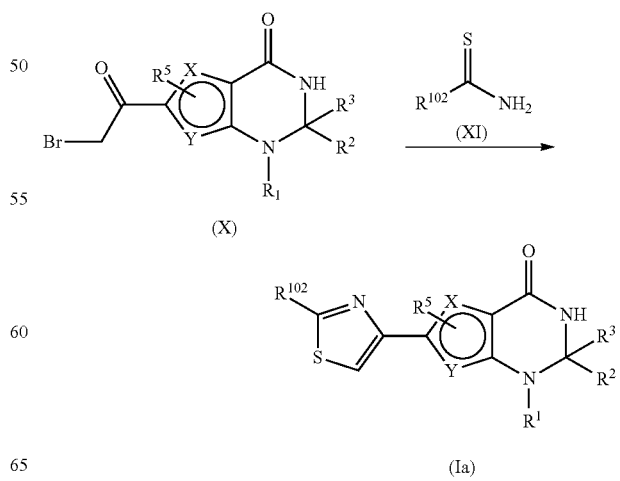

wherein $R^{102}$ is a substituent, and the other symbols are as defined above.

Examples of the substituent for $R^{102}$ include those similar to the substituent that the "heterocyclic group optionally having substituent(s)" for $R^4$ optionally has.

Compound (Ia) can be produced by reacting compound (X) with compound (XI)

The amount of compound (XI) to be used is, for example, about 0.5 to 2 equivalents, relative to compound (X).

Examples of the solvent used for the reaction include ethanol and N,N-dimethylformamide.

The reaction can be carried out at about 20 to 100° C., preferably about 20 to 80° C. The reaction time is generally about 0.5 to 24 hr, preferably about 2 to 16 hr.

Compound (X) and (XI) can be produced according to a method known per se.

Compound (Ib), which is compound (I) wherein $R^4$ is pyrazolyl, can be produced according to the method shown in the following reaction scheme.

Reaction scheme 7

(XII)

(Ib)

wherein each symbol is as defined above.

Compound (Ib) can be produced by reacting by compound (XII) with N,N-dimethylformamidedimethylacetal (DMFDMA) and then hydrazine.

The amount of the DMFDMA to be used is, for example, about 2 to 50 equivalents, relative to compound (XII).

The amount of the hydrazine to be used is, for example, about 1 to 10 equivalents, relative to compound (XII).

The step of the reaction with DMFDMA is generally carried out without a solvent. In the step of the reaction with hydrazine, examples of the solvent used for the reaction include ethanol, acetic acid and N,N-dimethylformamide.

The reaction can be carried out about 40 to 120° C., preferably about 40 to 80° C. The reaction time is generally about 1 to 24 hr, preferably about 2 to 8 hr.

Compound (XII) can be produced according to a method known per se.

Compound (VII) can also be produced according to a method shown in the following reaction scheme.

Reaction scheme 8

(IX)

(XIII)

(XIV)

(XV)

(VII)

wherein PG is a protecting group, and the other symbols are as defined above.

Method A

Compound (XIII) can be produced by subjecting compound (IX) to hydrolysis, and subjecting the obtained compound to a condensation reaction with an amine having a protecting group (PG).

Examples of the protecting group include 4-methoxybenzyl group, 2,4-dimethoxybenzyl group and the like.

An alkali metal hydroxide such as sodium hydroxide, lithium hydroxide, potassium hydroxide, barium hydroxide and the like is used for the hydrolysis.

Examples of the solvent used for the reaction include a mixed solvent of water and an organic solvent such as an alcohol (e.g., methanol, ethanol), an ether (e.g., tetrahydrofuran, dioxane, 1,2-dimethoxyethane) and the like.

The reaction can be carried out at room temperature (about 15 to 30° C.) or under heating (about 40 to 100° C.). The reaction time is generally about 1 to 20 hr, preferably about 1 to 10 hr.

Compound (XIII) can be produced by reacting the obtained carboxylic acid or a salt thereof (e.g., a sodium salt) in a known condensation reaction condition, for example, with 4-methoxybenzylamine, 1-hydroxybenzotriazole and EDC (1-ethyl-3-(3-dimethylaminopropyl)carbodiimide) in N,N-dimethylformamide.

Method B

In this reaction, compound (XIV) can be produced by reacting compound (XIII) with compound (III) in the same manner as in the aforementioned Reaction scheme 1.

Method C

Compound (XV) can be produced from compound (XIV) in the same manner as in Method A of the aforementioned Reaction scheme 2.

Method D

Compound (VII) can be produced by reacting compound (XV) with an acid.

An acid such as trifluoroacetic acid, hydrochloric acid and the like is used for the reaction. The amount of the acid to be used is generally 5 to 1000 equivalents, preferably 10 to 1000 equivalents, relative to compound (XV).

The reaction can be carried out at room temperature (about 15 to 30° C.) or under heating (about 40 to 100° C.). The reaction time is generally about 1 to 20 hr, preferably about 1 to 10 hr.

A compound within the scope of the present invention can be also produced by applying means known per se to compound (I) for conversion of substituent (i.e., introduction of substituent and conversion of functional group).

For conversion of substituent, a known conventional method can be used. Examples thereof include conversion to carboxy group by hydrolysis of ester, conversion to carbamoyl group by amidation of carboxy group, conversion to hydroxymethyl group by reduction of carboxy group, conversion to alcohol compound by reduction or alkylation of carbonyl group, reductive amination of carbonyl group, oximation of carbonyl group, acylation of amino group, ureation of amino group, sulfonylation of amino group, alkylation of amino group, substitution and amination of active halogen by amine, alkylation of hydroxy group, substitution and amination of hydroxy group and the like.

When a reactive moiety that causes non-objective reaction is present during the introduction of substituents and conversion of functional groups, a protecting group is introduced in advance as necessary into the reactive moiety by a means known per se, and the protecting group is removed by a means known per se after the objective reaction, whereby the compound within the scope of the present invention can be also produced.

For example, when the starting material compound or the intermediate has an amino group, a carboxyl group or a hydroxy group as a substituent, these groups may be protected by a protecting group generally used in the peptide chemistry and the like. In this case, the object compound can be obtained by eliminating the protecting group as necessary after the reaction.

Examples of the amino-protecting group include a formyl group; a $C_{1-6}$ alkyl-carbonyl group, a $C_{1-6}$ alkoxy-carbonyl group, a benzoyl group, a $C_{7-13}$ aralkyl-carbonyl group (e.g., benzylcarbonyl), a $C_{7-13}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl) and a $C_{1-6}$ alkenyl group (e.g., 1-allyl). These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-20}$ aralkyl group (e.g., benzyl), a phenyl group, a trityl, a substituted silyl group (e.g., trimethylsilyl, triethylsilyl, dimethylphenylsilyl, tert-butyldimethylsilyl, tert-butyldiethylsilyl) and a $C_{1-6}$ alkenyl group (e.g., 1-allyl). These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-13}$ aralkyl group (e.g., benzyl), a formyl group, a $C_{1-6}$ alkyl-carbonyl group, a benzoyl group, a $C_{7-13}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl) and a $C_{2-6}$ alkenyl group (e.g., 1-allyl). These groups are optionally substituted by 1 to 3 substituents selected from a halogen atom, a $C_{1-6}$ alkyl group, a $C_{1-6}$ alkoxy group and a nitro group.

For elimination of the above-mentioned protecting group, a method known per se, for example, a method described in Protective Groups in Organic Synthesis, John Wiley and Sons (1980) and the like can be employed. For example, employed is a method using acid, base, UV light, hydrazine, phenyl hydrazine, sodium N-methyldithiocarbamate, tetrabutylammonium fluoride, palladium acetate, trialkylsilyl halide (e.g., trimethylsilyl iodide, trimethylsilyl bromide and the like) and the like, reduction and the like.

Depending on the kind of the substituent of the starting compound, a starting compound having a different substituent can be produced by the aforementioned conversion of substituent from, as a starting material, a compound produced by the aforementioned production method.

Compound (I), which is a product of the reaction, may be produced as a single compound or as a mixture.

Thus-obtained compound (I) can be isolated and purified by a separation means known per se, such as concentration, concentration under reduced pressure, solvent extraction, crystallization, recrystallization, phase transfer, chromatography and the like.

When compound (I) is obtained as a free form, it can be converted to a desired salt by a method known per se or a method analogous thereof; conversely, when compound (I) is obtained as a salt, it can be converted to a free form or other desired salt by a method known per se or a method analogous thereof.

When compound (I) has an isomer such as an optical isomer, a stereoisomer, a positional isomer, a rotational isomer and the like, such isomer and a mixture thereof are also encompassed in compound (I). For example, when compound (I) has an optical isomer, an optical isomer resolved from a racemate is also encompassed in compound (I). These isomers can be obtained as single products by synthesis techniques and separation techniques known per se (e.g., concentration, solvent extraction, column chromatography, recrystallization).

Compound (I) may be in the form of a crystal, and the crystal form of the crystal may be single or plural, both of which are encompassed in the compound (I). The crystal can be produced by a crystallization method known per se.

In addition, compound (I) may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion, hygroscopicity and stability) at room temperature. The cocrystal and cocrystal salt can be produced according to a cocrystallization method known per se.

Compound (I) may be a solvate (e.g., hydrate) or a non-solvate, both of which are encompassed in the compound (I).

Compound (I) may be labeled with an isotope (e.g., $^3$H, $^{14}$C, $^{35}$S, $^{125}$I etc.) and the like, which is also encompassed in the compound (I).

A prodrug of the compound (I) of the present invention means a compound which is converted to compound (I) by a reaction due to an enzyme, gastric acid, etc. under the physiological conditions in the living body, that is, a compound which is converted to compound (I) by oxidation, reduction, hydrolysis, etc. according to an enzyme; a compound which is converted to compound (I) by hydrolysis etc. due to gastric acid, etc. A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any of these compounds can be produced from compound (I) by a method known per se.

A prodrug of compound (I) may also be one which is converted to compound (I) under physiological conditions, such as those described in IYAKUHIN no KAIHATSU (Development of Pharmaceuticals), Vol. 7, Design of Molecules, pp. 163-198, Published by HIROKAWA SHOTEN (1990).

Compound (I) or a prodrug thereof (in the specification, sometimes to be abbreviated as "the compound of the present invention") possesses a cdc7 inhibitory activity, which is clinically useful for an agent for the prophylaxis or treatment of cancer, a cancer growth inhibitor and a cancer metastasis suppressive agent.

Since the compound of the present invention shows a strong inhibitory activity on cdc7, and is also superior in the efficacy expression, pharmacokinetics (e.g., absorption, distribution, metabolism, excretion), solubility (e.g., water-solubility), interaction with other pharmaceutical products (e.g., drug-metabolizing enzyme (e.g., CYP3A4) inhibitory action), safety (acute toxicity, chronic toxicity, genetic toxicity, reproductive toxicity, cardiotoxicity, carcinogenicity) and stability (chemical stability, stability to enzyme etc.), it is useful as a medicament.

Accordingly, the compound of the present invention can be used for inhibiting excessive (abnormal) cdc7 action on mammals (for example, mouse, rat, hamster, rabbit, cat, dog, bovine, sheep, monkey, human).

The compound of the present invention is used as a medicament such as an agent for the prophylaxis or treatment of diseases possibly influenced by cdc7, for example, cancer [for example, colorectal cancer (e.g., colon cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), cancer of pharynx, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., infiltrating intraductal carcinoma, noninfiltrating intraductal carcinoma, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer), liver cancer (e.g., hepatocyte cancer, primary liver cancer, Extrahepatic Bile Duct Cancer), thyroid cancer (e.g., medullary thyroid carcinoma), kidney cancer (e.g., renal cell carcinoma, transitional cell carcinoma of renal pelvis and urinary duct), uterus cancer (e.g., cervical cancer, cancer of uterine body, uterus sarcoma), brain tumor (e.g., medulloblastoma, glioma, pineal astrocytoma, pilocytic astrocytoma, diffuse astrocytoma, anaplastic astrocytoma, pituitary adenoma), retinoblastoma, skin cancer (e.g., basal cell tumor, malignant melanoma), sarcoma (e.g., rhabdomyosarcoma, leiomyosarcoma, soft tissue sarcoma), malignant bone tumor, urinary bladder cancer, blood cancer (e.g., multiple myeloma, leukemia, malignant lymphoma, Hodgkin's disease, chronic bone marrow proliferative disease), unknown primary cancer], a cancer growth inhibitor, a cancer metastasis suppressive agent and the like.

Particularly, the compound of the present invention is effective for blood cancer, breast cancer, colorectal cancer, lung cancer, pancreatic cancer and the like.

The compound of the present invention can be administered, as a medicament, orally or parenterally as it is or in a mixture with a pharmacologically acceptable carrier to the aforementioned mammal.

The medicament comprising the compound of the present invention (sometimes to be abbreviated as "the medicament of the present invention") is explained in detail in the following.

Examples of the dosage form of the medicament of the present invention for oral administration of the compound of the present invention include oral preparations such as tablet (including sugar-coated tablet, film-coated tablet, sublingual tablet, buccal tablet, mouth cavity quick-integrating tablet), pill, granule, powder, capsule (including soft capsule, microcapsule), syrup, emulsion, suspension and films (e.g., mouth cavity mucous membrane adhesion film). Examples of the dosage form of the medicament of the present invention for parenteral administration include injection, injecting agent, instillation and suppository. In addition, it is effective to make a sustained release preparation by combining the compound with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester).

As a method for preparing the compound of the present invention into the above-mentioned dosage form (a method for preparing the medicament of the present invention), a known production method (e.g., the method described in the Japanese Pharmacopoeia) generally used in the pertinent field can be employed. When the compound of the present invention is prepared into the above-mentioned dosage form, suitable amounts of additives such as excipient, binder, disintegrant, lubricant, sweetening agent, surfactant, suspending agent, emulsifier and the like, generally used in the preparation field, are appropriately added as necessary for production.

When the compound of the present invention is prepared into a tablet, for example, it can be prepared by adding an excipient, a binder, a disintegrant, a lubricant and the like, and when a pill or a granule is to be prepared, it can be prepared by adding an excipient, a binder or a disintegrant. When a powder or a capsule is to be prepared, it can be prepared by adding an excipient and the like, when a syrup is to be prepared, it can be prepared by adding a sweetener and the like, and when an emulsion or a suspension is to be prepared, it can be prepared by adding a suspending agent, a surfactant, an emulsifier and the like.

Examples of the excipient include lactose, sucrose, glucose, starch, sucrose, microcrystalline cellulose, powdered glycyrrhiza, mannitol, sodium hydrogen carbonate, calcium phosphate and calcium sulfate.

Examples of the binder include 5-10 wt % starch liquid paste, 10-20 wt % gum arabic solution or gelatin solution, 1-5 wt % tragacanth solution, carboxymethyl cellulose solution, sodium alginate solution and glycerin.

Examples of the disintegrant include starch and calcium carbonate.

Examples of the lubricant include magnesium stearate, stearic acid, calcium stearate and purified talc.

Examples of the sweetener include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, sodium carboxymethyl cellulose, methyl cellulose and bentonite.

Examples of the emulsifier include gum arabic, tragacanth, gelatin, polysorbate 80 and the like.

Furthermore, when the compound of the present invention is prepared into the above-mentioned dosage form, a suitable amount of a colorant, a preservative, an aromatic, a corrigent, a stabilizer, a thickening agent and the like typically used in the field of preparation can be added on demand.

Examples of the injection include intravenous injection as well as subcutaneous injection, intracutaneous injection, intramuscular injection, instillation and the like. Examples of the sustained release preparation include an iontophoresis transdermal agent and the like.

Such injections are prepared by methods known per se, or by dissolving, suspending or emulsifying the compound of the present invention in a sterilized aqueous or oily liquid. Examples of the aqueous liquid for injection include physiological saline, isotonic solutions containing glucose or other auxiliary drugs (e.g., D-sorbitol, D-mannitol, sodium chloride and the like) and the like, and they can be used in combination with suitable solubilizing agents such as alcohols (e.g., ethanol), polyalcohols (e.g., propylene glycol, polyethylene glycol) and nonionic surfactants (e.g., polysorbate 80, HCO-50). Examples of the oily liquid include sesame oil, soybean oil and the like and they can be used in combination with solubilizing agents such as benzyl benzoate and benzyl alcohol. In addition, buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol) and the like can be blended. A prepared injection is generally filled in an ampoule.

While the content of the compound of the present invention in the medicament of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the medicament of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 1 to 1000 mg, preferably about 3 to 300 mg, more preferably about 10 to 200 mg, as an active ingredient (the compound of the present invention), which can be given in a single administration or administered in 2 or 3 portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg body weight, which is preferably given by intravenous injection.

The compound of the present invention can be used concurrently with other drugs. To be specific, the compound of the present invention can be used together with medicaments such as hormonal therapeutic agents, chemotherapeutic agents, immunotherapeutic agents, drugs inhibiting the action of cell proliferation factors or receptors thereof, and the like. In the following, the drugs that can be used in combination with the compound of the present invention are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testrolactone, aminoglutethimide, LH-RH agonists (e.g., goserelin acetate, buserelin, leuprorelin), droloxifene, epitiostanol, ethinylestradiol sulfonate, aromatase inhibitors (e.g., fadrozole hydrochloride, anastrozole, retrozole, exemestane, vorozole, formestane), anti-androgens (e.g., flutamide, bicartamide, nilutamide), 5α-reductase inhibitors (e.g., finasteride, epristeride), adrenocorticohormone drugs (e.g., dexamethasone, prednisolone, betamethasone, triamcinolone), androgen synthesis inhibitors (e.g., abiraterone), retinoid and drugs that retard retinoid metabolism (e.g., liarozole), thyroid gland hormone, and DDS (Drug Delivery System) preparations thereof.

Examples of the "chemotherapeutic agents" include alkylating agents, antimetabolites, anticancer antibiotics, and plant-derived anticancer agents.

Examples of the "alkylating agents" include nitrogen mustard, nitrogen mustard N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and DDS preparations thereof.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine), aminopterine, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, bendamustine, and DDS preparations thereof.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and DDS preparations thereof.

Examples of the "plant-derived anticancer agents" include etoposide, etoposide phosphate, vinblastine sulfate, vincristine sulfate, vindesine sulfate, teniposide, paclitaxel, docetaxel, vinorelbine, and DDS preparations thereof.

Examples of the "immunotherapeutic agents" include picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole and anti-CTLA4 antibody.

Examples of the "cell growth factor" in the "drugs inhibiting the action of cell proliferation factors or receptors thereof" include any substances that promote cell proliferation, which are normally peptides having a molecular weight of not more than 20,000 that are capable of exhibiting their activity at low concentrations by binding to a receptor, and specific examples thereof include (1) EGF (epidermal growth factor) or substances possessing substantially the same activity as it [e.g., TGF-α], (2) insulin or substances possessing substantially the same activity as it [e.g., insulin, IGF (insulin-like growth factor)-1, IGF-2], (3) FGF (fibroblast growth factor) or substances possessing substantially the same activity as it [e.g., acidic FGF, basic FGF, KGF (keratinocyte growth factor), FGF-10], and (4) other cell growth factors [e.g., CSF (colony stimulating factor), EPO (erythropoietin), IL-2 (interleukin-2), NGF (nerve growth factor), PDGF (platelet-derived growth factor), TGF β (transforming growth factor β), HGF (hepatocyte growth factor), VEGF (vascular endothelial growth factor), heregulin, angiopoietin].

Examples of the "cell proliferation factor receptors" include any receptors capable of binding to the aforementioned cell proliferation factors, and specific thereof include EGF receptor, heregulin receptor (HER3, etc.), insulin receptor, IGF receptor-1, IGF receptor-2, FGF receptor-1 or FGF receptor-2, VEGF receptor, angiopoietin receptor (Tie2 etc.), PDGF receptor, and the like.

Examples of the "drugs inhibiting the action of cell proliferation factors or receptors thereof" include EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER0 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, Aurora inhibitor, PLK inhibitor, MEK(MEK1/2) inhibitor, MET inhibitor, CDK inhibitor, Akt inhibitor, ERK inhibitor and the like. Specific examples thereof include anti-VEGF antibody (e.g., Bevacizumab), anti-HER2 antibody (e.g., Trastuzumab, Pertuzumab), anti-EGFR antibody (e.g., Cetuximab, Panitumumab, Matuzumab, Nimotuzumab), anti-VEGFR antibody, anti-HGF antibody, Imatinib mesylate, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino) pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino) pyrimidin-2-ylsulfanyl]phenyl]cyclopropanecarboxamide (VX-680), 2-[N-[3-[4-[5-[N-(3-fluorophenyl)carbamoylmethyl]-1H-pyrazol-3-ylamino]quinazoline-7-yloxy]propyl]-N-ethylamino]ethyl phosphate (AZD-1152), 4-[9-chloro-7-(2,6-difluorophenyl)-5H-primido[5,4-d][2]benzazepin-2-ylamino]benzoic acid (MLN-8054), N-[2-methoxy-5-[(E)-2-(2,4,6-trimethoxyphenyl) vinylsulfonylmethyl]phenyl] glycine sodium salt (ON-1910Na), 4-[8-cyclopentyl-7(R)-ethyl-5-methyl-6-oxo-5,6,7,8-tetrahydropteridine-2-ylamino]-3-methoxy-N-(1-methylpiperidin-4-yl)benzamide (BI-2536), 2-hydroxyethyl 5-(4-bromo-2-chlorophenylamino)-4-fluoro-1-methyl-1H-benzimidazole-6-carbohydroxamate (AZD-6244), N-[2(R),3-dihydroxypropoxy]-3,4-difluoro-2-(2-fluoro-4-iodophenylamino)benzamide (PD-0325901), everolimus (RAD001) and the like.

In addition to the aforementioned drugs, L-asparaginase, aceglatone, procarbazine hydrochloride, protoporphyrin-cobalt complex salt, mercuric hematoporphyrin-sodium, topoisomerase I inhibitor (e.g., irinotecan, topotecan), topoisomerase II inhibitor (e.g., sobuzoxane), differentiation inducer (e.g., retinoid, vitamin D), other angiogenesis inhibitor (e.g., fumagillin, shark extract, COX-2 inhibitor), a-blocker (e.g., tamsulosin hydrochloride), bisphosphonic acid (e.g., pamidronate, zoledronate), thalidomide, 5-azacytidine, decitabine, proteasome inhibitor (e.g., bortezomib), antitumor antibody such as anti-CD20 antibody and the like, toxin labeled antibody and the like can be used.

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer, (4) a sustained treatment effect can be designed, (5) a synergistic effect can be afforded by a combined use of the compound of the present invention and a concomitant drug, and the like, can be achieved.

Hereinafter, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to the administration subject simultaneously, or may be administered at different times. The dosage of the concomitant drug may be determined according to the administration amount clinically used, and can be appropriately selected depending on the administration subject, administration route, disease, combination and the like.

Examples of the administration mode of the compound of the present invention and the concomitant drug include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug is appropriately determined in accordance with its clinical dose. The ratio of the compound of the present invention and the concomitant drug is appropriately determined depending on the administration subject, administration route, target disease, symptom, combination, and the like. For example, when the administration subject is human, the concomitant drug is used in 0.01 to 100 (parts by weight), relative to 1 part by weight of the compound of the present invention.

The combination drug of the present invention is low toxic and can be safely administered orally or parenterally (e.g., topical, rectal, intravenous administration), for example, after admixing the compound of the present invention and/or the aforementioned concomitant drug with a pharmacologically acceptable carrier to give a pharmaceutical composition such as tablets (including sugar-coated tablets and film-coated tablets), powders, granules, capsules (including soft capsules), liquids, injections, suppositories and sustained-release agents, according to a method known per se, to a mammal (e.g., mouse, rat, hamster, rabbit, cat, dog, bovine, sheep, monkey, human). Injection can be administered by intravenous, intramuscular, subcutaneous or intraorgan administration or directly to the lesion.

Examples of the pharmacologically acceptable carrier which may be used for preparing the combination agent of the present invention include those similar to the aforementioned pharmacologically acceptable carriers that can be used for the preparation of the medicament of the present invention. Where necessary, the aforementioned additives that can be used for the preparation of the medicament of the present invention, such as preservatives, antioxidants, colorants, sweetening agents, adsorbents, wetting agents and the like can also be appropriately used in appropriate amounts.

The mixing ratio of the compound of the present invention and the concomitant drug in the combination drug of the present invention can be appropriately determined according to the subject of administration, administration route, disease and the like.

For example, the content of the compound of the present invention in the combination drug of the present invention varies depending on the form of preparation, and is usually from about 0.01% by weight to 100% by weight, preferably from about 0.1% by weight to 50% by weight, more preferably from about 0.5% by weight to 20% by weight, relative to the total of the preparation.

The content of the concomitant drug in the combination drug of the present invention varies depending on the form of preparation, and is usually from about 0.01% by weight to 90% by weight, preferably from about 0.1% by weight to 50% by weight, more preferably from about 0.5% by weight to 20% by weight, relative to the total of the preparation.

The content of additive in the combination drug of the present invention varies depending on the form of preparation, and is usually from about 1% by weight to 99.99% by weight, preferably from about 10% by weight to 90% by weight, to the total of the preparation.

When the compound of the present invention and the concomitant drug are formulated separately, the same contents may be adopted.

The combination agent of the present invention can be prepared by a per se known method commonly used in the pharmaceutical manufacturing process.

For example, the compound of the present invention and the concomitant drug can be made as an injection such as an aqueous injection together with a dispersing agent (e.g., Tween 80 (manufactured by Atlas Powder, US), HCO 60 (manufactured by Nikko Chemicals Co., Ltd.), polyethylene glycol, carboxymethyl cellulose, sodium alginate, hydroxypropylmethyl cellulose, dextrin), a stabilizer (e.g., ascorbic acid, sodium pyrosulfite), a surfactant (e.g., Polysorbate 80, macrogol), a solubilizer (e.g., glycerin, ethanol), a buffer (e.g., phosphoric acid and alkali metal salt thereof, citric acid and alkali metal salt thereof), an isotonizing agent (e.g., sodium chloride, potassium chloride, mannitol, sorbitol, glucose), a pH regulator (e.g., hydrochloric acid, sodium hydroxide), an antiseptic (e.g., ethyl paraoxybenzoate, benzoic acid, methylparaben, propylparaben, benzyl alcohol), a dissolving agent (e.g., conc. glycerin, meglumine), a solubilizing agent (e.g., propylene glycol, sucrose), a soothing agent (e.g., glucose, benzyl alcohol) and the like, or an oily injection by dissolving, suspending or emulsifying them in a vegetable oil such as olive oil, sesame oil, cotton seed oil, corn oil and the like, or a solubilizing agent such as propylene glycol.

In addition, an excipient (e.g., lactose, sucrose, starch), a disintegrating agent (e.g., starch, calcium carbonate), a binder (e.g., starch, gum arabic, carboxymethylcellulose, polyvinylpyrrolidone, hydroxypropylcellulose) and a lubricant (e.g., talc, magnesium stearate, polyethylene glycol 6000) may be added to the compound of the present invention or the concomitant drug, and the mixture can be compression-molded, according to a method known per se then if desirable, the molded product can be coated by a method known per se for the purpose of masking of taste, enteric property or durability, to give a preparation for oral administration. Examples of the coating agent include hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid acrylic acid copolymer, manufactured by Rohm, Del.) and pigment (e.g., iron oxide red, titanium dioxide). The preparation for oral administration may be any of an immediate-release preparation and a sustained release preparation.

Moreover, the compound of the present invention and the concomitant drug can be made into an oily or aqueous solid, semisolid or liquid suppository according to a method known per se, by mixing them with an oily substrate, aqueous substrate or aqueous gel substrate. Examples of the above-mentioned oily substrate include glycerides of higher fatty acid [e.g., cacao butter, Witepsols (manufactured by Dynamit Nobel, Germany)], glycerides of medium chain fatty acid [e.g., Miglyols (manufactured by Dynamit Nobel, Germany)] and vegetable oils (e.g., sesame oil, soybean oil, cotton seed oil). Furthermore, examples of the aqueous substrate include polyethylene glycol and propylene glycol. Examples of the aqueous gel substrate include natural gums, cellulose derivatives, vinyl polymers and acrylic acid polymers.

Examples of the above-mentioned sustained release preparation include sustained release microcapsules. The sustained release microcapsule can be produced by a method known per se, for example, a method shown in the following [2].

The compound of the present invention is preferably molded into an oral administration preparation such as a solid preparation (e.g., powder, granule, tablet, capsule) and the like, or molded into a rectal administration preparation such as a suppository. Particularly, an oral administration preparation is preferable.

The concomitant drug can be made into the above-mentioned drug form depending on the kind of the drug.

In the following, there will be shown specifically [1] an injection of the compound of the present invention or the concomitant drug and preparation thereof, [2] a rapid release preparation or sustained release preparation of the compound of the present invention or the concomitant drug and preparation thereof and [3] a sublingual tablet, a buccal or an intraoral quick integrating agent of the compound of the present invention or the concomitant drug and preparation thereof.

[1] Injection and Preparation Thereof

It is preferred that an injection is prepared by dissolving the compound of the present invention or the concomitant drug in water. This injection may be allowed to contain a benzoate and/or a salicylate.

The injection is obtained by dissolving the compound of the present invention or the concomitant drug, and if desired, a benzoate and/or a salicylate, into water.

The above-mentioned salts of benzoic acid and salicylic acid include, for example, salts of alkali metals such as sodium, potassium etc., salts of alkaline earth metals such as calcium, magnesium etc., ammonium salts, meglumine salts and salts with organic base such as tromethamol.

The concentration of the compound of the present invention or the concomitant drug in an injection is from 0.5 w/v % to 50 w/v %, preferably from about 3 w/v % to about 20 w/v %. The concentration of a salt of benzoic acid or/and a salt of salicylic acid is from 0.5 w/v % to 50 w/v %, preferably from 3 w/v % to 20 w/v %.

Conventional additives to be used in an injection may be appropriately added in an injection of the present invention. Examples of the additives include a stabilizer (e.g., ascorbic acid, sodium pyrosulfite), a surfactant (e.g., Polysorbate 80, macrogol), a solubilizer (e.g., glycerin, ethanol), a buffer (e.g., phosphoric acid and alkali metal salt thereof, citric acid and alkali metal salt thereof), an isotonizing agent (e.g., sodium chloride, potassium chloride), a dispersing agent (e.g., hydroxypropylmethyl cellulose, dextrin), a pH regulator (e.g., hydrochloric acid, sodium hydroxide), an antiseptic (e.g., ethyl paraoxybenzoate, benzoic acid), a dissolving agent (e.g., conc. glycerin, meglumine), a solubilizing agent (e.g., propylene glycol, sucrose), a soothing agent (e.g., glucose, benzyl alcohol). These additives are blended in a usual proportion generally employed in an injection.

It is advantageous that the pH of the injection is controlled from pH 2 to 12, preferably from pH 2.5 to 8.0 by addition of a pH regulator.

An injection is obtained by dissolving the compound of the present invention or the concomitant drug and if desired, a salt of benzoic acid and/or a salt of salicylic acid, and if necessary, the above-mentioned additives into water. These may be dissolved in any order, and can be appropriately dissolved in the same manner as in a conventional method of producing an injection.

An aqueous solution for injection may be advantageously heated, alternatively, for example, filter sterilization, high pressure heat sterilization, etc. can be conducted in the same manner as those for a usual injection, to provide an injection.

It may be advantageous that an aqueous solution for injection is subjected to high pressure heat sterilization at 100° C. to 121° C. for 5 minutes to 30 minutes.

Further, a preparation endowed with the antibacterial property of a solution may also be produced so that it can be used as a preparation which is divided and administered multiple-times.

[2] Sustained Release Preparation or Rapid Release Preparation, and Preparation Thereof.

Preferred is a sustained release preparation which is obtained, by coating a core containing the compound of the present invention or the concomitant drug with a film forming agent such as a water-insoluble substance, swellable polymer, etc., if desired. For example, a sustained release preparation for oral once-a-day administration is preferable.

The water insoluble substance used in a film forming agent includes, for example, a cellulose ether such as ethyl cellulose, butyl cellulose, etc.; a cellulose ester such as cellulose acetate, cellulose propionate, etc.; a polyvinyl ester such as polyvinyl acetate, polyvinyl butyrate, etc.; an acrylic acid polymer such as acrylic acid/methacrylic acid copolymer, methylmethacrylate copolymer, ethoxyethyl methacrylate/ cinnamoethylmethacrylate/aminoalkyl methacrylate copolymer, polyacrylic acid, polymethacrylic acid, methacrylic acid alkyl amide copolymer, poly(methyl methacrylate), polymethacrylate, polymethacryl amide, amino alkyl methacrylate copolymer, poly(methacrylic acid anhydride), glycidyl methacrylate copolymer, specially an Eudragit (manufactured by Rohm Pharma) such as Eudragit RS-100, RL-100, RS-30D, RL-30D, RL-PO, RS-PO (copolymer of ethyl acylate/methyl methacrylate/trimethyl chloride methacrylate/ ammonium ethyl), Eudragit NE-30D (copolymer of methyl methacrylate/ethyl acrylate), etc., a hydrogenated oil such as hardened caster oil (e.g., Lubri wax (Freund Corporation)), etc.; a wax such as carnauba wax, fatty acid glycerin ester, paraffin, etc.; polyglycerin fatty acid ester.

The swellable polymer is preferably a polymer having acidic dissociating group and pH-dependent swelling property, and a polymer having acidic dissociating group which swells little in an acidic area such as stomach and swells greatly in a neutral area such as the small intestine or the large intestine.

The polymer having acidic dissociating group and pH-dependent swelling property includes, for example, crosslinkable polyacrylic polymer such as Carbomer 934P, 940, 941, 974P, 980, 1342 etc., polycarbophil, calcium polycarbophil (all are manufactured by BF Goodrich.), Hibiswako 103, 104, 105, 304 (all are manufactured by Wako Pure Chemical Industries, Ltd.), etc.

The film forming agent used in a sustained release preparation may further contain a hydrophilic substance.

The hydrophilic substance includes, for example, a polysaccharide optionally having sulfuric acid group such as pullulans, dextrin, arginic acid alkali metal salt, etc.; a polysaccharide having hydroxyalkyl or carboxyalkyl such as hydroxypropyl cellulose, hydroxypropyl methyl cellulose, sodium carboxymethyl cellulose, etc.; methyl cellulose; polyvinyl pyrrolidone; polyvinyl alcohol; polyethylene glycol.

The content of water-insoluble substance in the film forming agent of sustained release preparation is about 30% (w/w) to about 90% (w/w), preferably about 35% (w/w) to about 80% (w/w), and more preferably about 40% (w/w) to about 75% (w/w). The content of swellable polymer is about 3% (w/w) to about 30% (w/w), preferably about 3% (w/w) to about 15% (w/w). The film forming agent may further contain a hydrophilic substance, in this case, the content of the hydrophilic substance in the film forming agent is about 50% (w/w) or less, preferably about 5% (w/w) to about 40% (w/w), and more preferably about 5% (w/w) to about 35% (w/w). This % (w/w) indicates % by weight based on a film forming agent composition which is obtained by removing a solvent (e.g., water, lower alcohols such as methanol, ethanol etc.) from a film forming agent liquid.

The sustained release preparation is manufactured by preparing a core containing drug, then, coating the resultant core with a film forming agent liquid prepared by heating and dissolving a water-insoluble substance, swellable polymer, etc. or by dissolving or dispersing it in a solvent as exemplified below.

I. Preparation of Core Containing a Drug

The form of a core containing a drug to be coated with a film forming agent (hereinafter, sometimes simply referred to as the core) is not particularly limited, and preferably the core is formed into particles such as granules or fine particles.

When the core is composed of granules or fine particles, the average particle size thereof is preferably from about 150 to about 2,000 µm, further preferably from about 500 µm to about 1,400 µm.

Preparation of the core can be conducted by a usual preparation method. For example, it can be prepared by mixing a suitable excipient, binding agent, disintegrating agent, lubricant, stabilizer, etc. with a drug, and subjecting the mixture to wet-extrusion granulating method or fluidized bed granulating method.

The content of drugs in a core is from about 0.5% (w/w) to about 95% (w/w), preferably from about 5.0% (w/w) to about 80% (w/w), further preferably from about 30% (w/w) to about 70% (w/w).

The excipient contained in the core includes, for example, saccharides such as sucrose, lactose, mannitol, glucose etc., starch, crystalline cellulose, calcium phosphate, corn starch. Among them, crystalline cellulose, corn starch are preferable.

The binders include, for example, polyvinyl alcohol, hydroxypropyl cellulose, polyethylene glycol, polyvinyl pyrrolidone, Pluronic F68, gum arabic, gelatin, starch. The disintegrant include, for example, carboxymethyl cellulose calcium (ECG505), croscarmellose sodium (Ac-Di-Sol), crosslinkable polyvinyl pyrrolidone (crospovidone), low-substituted hydroxypropyl cellulose (L-HPC). Among these, hydroxypropyl cellulose, polyvinyl pyrrolidone and low-substituted hydroxypropyl cellulose are preferable. The lubricants or the aggregation inhibitor includes, for example, talc, magnesium stearate and an inorganic salt thereof. The lubricant includes a polyethylene glycol. The stabilizing agent includes an acid such as tartaric acid, citric acid, succinic acid, fumaric acid, maleic acid, etc.

In addition to the above-mentioned production method, the core can also be prepared by, for example, a rolling granulation method in which a drug or a mixture of the drug with an excipient, lubricant, etc. is added portionwise onto an inert carrier particle which is the core of the core while spraying a binder dissolved in a suitable solvent such as water, lower alcohol (e.g., methanol, ethanol, etc.) etc., a pan coating method, a fluidized bed coating method or a melt granulating method. The inert carrier particle includes, for example, those made of sucrose, lactose, starch, crystalline cellulose or waxes, and the average particle size thereof is preferably from about 100 µm to about 1,500 µm.

For the purpose of separating the drug contained in the core from the film forming agent, the surface of the core may be coated with a protective agent. The protective agent includes, for example, the above-mentioned hydrophilic substances, water-insoluble substances. The protective agent includes, preferably polyethylene glycol, and polysaccharides having hydroxyalkyl or carboxyalkyl, more preferably hydroxypropylmethyl cellulose and hydroxypropyl cellulose. The protective agent may contain a stabilizer such as acids such as tartaric acid, citric acid, succinic acid, fumaric acid, maleic acid etc., and a lubricant such as talc etc. When the protective agent is used, the coating amount is from about 1% (w/w) to about 15% (w/w), preferably from about 1% (w/w) to about 10% (w/w), further preferably from about 2% (w/w) to about 8% (w/w), based on the core.

The coating of the protective agent can be carried out by a usual coating method, and specifically, the coating can be carried out by spraying the protective agent onto a core by a fluidized bed coating method, pan coating method.

II. Coating of Core with a Film Forming Agent

A core obtained in the above-mentioned step 1 is coated with a film forming agent liquid obtained by heating and dissolving the above-mentioned water-insoluble substance and pH-dependent swellable polymer, and a hydrophilic substance, or by dissolving or dispersing them in a solvent, to give a sustained release preparation.

The method for coating a core with a film forming agent liquid includes, for example, a spray coating method.

The composition ratio of a water-insoluble substance, swellable polymer and hydrophilic substance in a film forming agent liquid is appropriately selected so that the contents of these components in a coated film are the above-mentioned contents, respectively.

The coating amount of a film forming agent is from about 1% (w/w) to about 90% (w/w), preferably from about 5% (w/w) to about 50% (w/w), further preferably from about 5% (w/w) to 35% (w/w), based on a core (exclusive of the coating amount of the protective agent).

The solvent in the film forming agent liquid includes water or an organic solvent, alone or in admixture thereof. In the case of use in admixture, the mixing ratio of water to an organic solvent (water/organic solvent:weight ratio) can be varied in the range from 1 to 100%, and preferably from 1% to about 30%. The organic solvent is not particularly limited as long as it dissolves a water-insoluble substance, and for example, it includes lower alcohols such as methyl alcohol, ethyl alcohol, isopropyl alcohol, n-butyl alcohol, etc., lower alkanones such as acetone, etc., acetonitrile, chloroform, methylene chloride. Among them, lower alcohols are preferable, and ethyl alcohol and isopropyl alcohol are particularly preferable. Water, and a mixture of water and an organic solvent are preferably used as a solvent for a film forming agent. In this case, if necessary, an acid such as tartaric acid, citric acid, succinic acid, fumaric acid, maleic acid, etc. may also be added into a film forming agent liquid for stabilizing the film forming agent liquid.

An operation of coating by spray coating can be conducted by a usual coating method, and specifically, it can be conducted by spray-coating a film forming agent liquid onto a core, for example, by a fluidized bed coating method, pan coating method. In this case, if necessary, talc, titanium oxide, magnesium stearate, calcium stearate, light anhydrous silicic acid etc. may also be added as a lubricant, and glycerin fatty acid ester, hydrogenated castor oil, triethyl citrate, cetyl alcohol, stearyl alcohol etc. may also be added as a plasticizer.

After coating with a film forming agent, if necessary, an antistatic agent such as talc etc. may be mixed.

The rapid release preparation may be liquid (solution, suspension, emulsion etc.) or solid (particle, pill, tablet etc.). It may be oral agents or parenteral agents such as an injection, etc., and preferably oral agents.

The rapid release preparation, usually, may contain, in addition to an active component drug, also carriers, additives and excipients conventionally used in the field of formulation (hereinafter, sometimes abbreviated as the excipient). The excipient used is not particularly limited as long as it is an excipient ordinarily used as a preparation excipient. For example, the excipient for an oral solid preparation includes lactose, starch, corn starch, crystalline cellulose (Avicel PH101, manufactured by Asahi Kasei Corporation, etc.), powder sugar, granulated sugar, mannitol, light anhydrous silicic acid, magnesium carbonate, calcium carbonate, L-cysteine, and preferably corn starch and mannitol, etc. These excipients can be used alone or in combination of two or more. The content of the excipient is, for example, from about 4.5 w/w % to about 99.4 w/w %, preferably from about 20 w/w % to about 98.5 w/w %, further preferably from about 30 w/w % to about 97 w/w %, based on the total amount of the rapid release preparation.

The content of a drug in the rapid release preparation can be appropriately selected in the range from about 0.5% to about 95 w/w %, preferably from about 1% to about 60 w/w % based on the total amount of the rapid release preparation.

When the rapid release preparation is an oral solid preparation, it usually contains a disintegrating agent in addition to the above-mentioned components. The disintegrating agent includes, for example, carboxymethyl cellulose calcium (ECG-505, manufactured by GOTOKU CHEMICAL COMPANY LTD.), croscarmellose sodium (e.g., acjizol, manufactured by Asahi Kasei Corporation), crospovidone (e.g., colidone CL, manufactured by BASF), low-substituted hydroxypropyl cellulose (manufactured by Shin-Etsu Chemical Co., Ltd.), carboxymethylstarch (manufactured by Matsutani Chemical Industry Co., Ltd.), carboxymethylstarch sodium (Exprotab, manufactured by Kimura Sangyo), partially α-starch (PCS, manufactured by Asahi Kasei Corporation), and for example, includes those which disintegrate a granule by absorbing water in contact with water, causing swelling, or making a channel between an effective ingredient constituting the core and an excipient. These disintegrating agents can be used alone or in combinations of two or more. The amount of the disintegrating agent used is appropriately selected depending on the kind and blending amount of a drug used, formulation design for release property, etc., and for example, from about 0.05 w/w % to about 30 w/w %, preferably from about 0.5 w/w % to about 15 w/w %, based on the total amount of the rapid release preparation.

When the rapid release preparation is an oral solid preparation, it may further contain if desired, additives conventional in solid preparations in addition to the above-mentioned composition. Such an additive includes, for example, a binder (e.g., sucrose, gelatin, arabic gum powder, methyl cellulose, hydroxypropyl cellulose, hydroxypropylmethyl cellulose, carboxylmethyl cellulose, polyvinylpyrrolidone, pullulans, dextrin), a lubricant (e.g., polyethylene glycol, magnesium stearate, talc, light anhydrous silicic acid (e.g., aerosil (Nippon Aerosil))), a surfactant (e.g., anionic surfactants such as sodium alkylsulfate, etc., nonionic surfactants such as polyoxyethylene fatty acid ester and polyoxyethylene sorbitan fatty acid ester, polyoxyethylene castor oil derivatives, etc.), a colorant (e.g., tar coloring matter, caramel, iron oxide red, titanium oxide, riboflavine), if necessary, a corrigent (e.g., sweetening agent, flavor), an adsorbent, an antiseptic, a wetting agent, an antistatic agent. Further, a stabilizer such as an organic acid such as tartaric acid, citric acid, succinic acid, fumaric acid, etc. may also be added.

The above-mentioned binder includes preferably hydroxypropyl cellulose, polyethylene glycol and polyvinylpyrrolidone, etc.

The rapid release preparation can be prepared by mixing the above-mentioned components, and if necessary, further kneading the mixture, and molding it based on a usual technology of producing preparations. The above-mentioned mixing is conducted by generally used methods, for example, mixing, kneading. Specifically, when a rapid release preparation is formed, for example, into a particle, it can be prepared, according to the same means as in the above-mentioned method for preparing a core of a sustained release preparation, by mixing the components using a vertical granulator, universal kneader (manufactured by Hata Iron Works Co., Ltd.), fluidized bed granulator FD-5S (manufactured by Powrex Corporation), etc., then, subjecting the mixture to a wet extrusion granulation method, fluidized bed granulation method, etc.

Thus obtained rapid release preparation and sustained release preparation may be themselves made into products or made into products appropriately together with preparation excipients etc., separately, by an ordinary method, then, may be administered simultaneously or may be administered in combination at any administration interval, or they may be themselves made into one oral administration preparation (e.g., granule, fine particle, tablet, capsule) or made into one oral administration preparation together with preparation excipients etc. It may also be permissible that they are manufactured into granules or fine particles, and filled in the same capsule to be used as a preparation for oral administration.

[3] Sublingual, buccal or intraoral quick disintegrating agent and preparation thereof.

Sublingual, buccal or intraoral quick disintegrating agents may be a solid preparation such as tablet etc., or may be an oral mucosa membrane patch (film).

The sublingual, buccal or intraoral quick disintegrating agent is preferably a preparation containing the compound of the present invention or the concomitant drug and an excipient. It may contain also auxiliary agents such as a lubricant, isotonizing agent, hydrophilic carrier, water-dispersible polymer, stabilizer etc. Further, for easy absorption and increased bioavailability, β-cyclodextrin or β-cyclodextrin derivatives (e.g., hydroxypropyl-β-cyclodextrin), etc. may also be contained.

The above-mentioned excipient includes lactose, sucrose, D-mannitol, starch, crystalline cellulose, light anhydrous silicic acid, etc. The lubricant includes magnesium stearate, calcium stearate, talc, colloidal silica, etc., and particularly preferably magnesium stearate and colloidal silica. The isotonizing agent includes sodium chloride, glucose, fructose, mannitol, sorbitol, lactose, saccharose, glycerin, urea, etc., and particularly preferably mannitol. The hydrophilic carrier includes swellable hydrophilic carriers such as crystalline cellulose, ethyl cellulose, crosslinkable polyvinylpyrrolidone, light anhydrous silicic acid, silicic acid, dicalcium phosphate, calcium carbonate etc., and particularly preferably crystalline cellulose (e.g., crystalline cellulose, etc.). The water-dispersible polymer includes gums (e.g., gum tragacanth, acacia gum, guar gum), alginates (e.g., sodium alginate), cellulose derivatives (e.g., methyl cellulose, carboxymethyl cellulose, hydroxymethyl cellulose, hydroxypropyl cellulose, hydroxypropylmethyl cellulose), gelatin, aqueous starch, polyacrylic acids (e.g., Carbomer), polymethacrylic acid, polyvinyl alcohol, polyethylene glycol, polyvinylpyrrolidone, polycarbophil, ascorbate, palmitates, etc., and preferably hydroxypropylmethyl cellulose, polyacrylic acid, alginate, gelatin, carboxymethyl cellulose, polyvinylpyrrolidone, polyethylene glycol, etc., particularly preferably hydroxypropylmethyl cellulose. The stabilizer includes cysteine, thiosorbitol, tartaric acid, citric acid, sodium carbonate, ascorbic acid, glycine, sodium sulfite, etc., and particularly preferably citric acid and ascorbic acid.

The sublingual, buccal or intraoral quick disintegrating agent can be manufactured by mixing the compound of the present invention or the concomitant drug and an excipient by a per se known method. Further, if desired, auxiliary agents such as a lubricant, isotonizing agent, hydrophilic carrier, water-dispersible polymer, stabilizer, colorant, sweetening agent, antiseptic etc. may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol etc. if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably hydroxypropyl cellulose, hydroxypropylmethyl cellulose), excipient etc. are dissolved in a solvent such as water etc., and the resulted solution is cast to give a film. Further, additives such as a plasticizer, a stabilizer, an antioxidant, an antiseptic, a colorant, a buffer, a sweetening agent etc. may also be added. For imparting suitable elasticity to the film, glycols such as polyethylene glycol, propylene glycol, etc. may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably about 10 micron to about 1,000 micron) by an application tool such as a doctor blade etc., then, the solution is dried to form a film. It may be advantageous that thus formed film is dried at room temperature or under heat, and cut into given area.

The intraoral quick disintegrating preparation is preferably solid quick diffuse preparation composed of a network body comprising the compound of the present invention or the concomitant drug, and a water-soluble or water-diffusible carrier which is inert to the compound of the present invention or the concomitant drug. This network body is obtained by sublimating a solvent from the composition constituted of a solution prepared by dissolving compound of the present invention or the concomitant drug in a suitable solvent.

The composition of an intraoral quick disintegrating agent preferably contains a matrix forming agent and a secondary component in addition to the compound of the present invention or the concomitant drug.

The matrix forming agent includes animal proteins or vegetable proteins such as gelatins, dextrins, soybean, wheat and psyllium seed protein etc.; rubber substances such as arabic gum, guar gum, agar, xanthane, etc.; polysaccharides; alginic acids; carboxymethyl celluloses; carrageenans; dextrans; pectins; synthetic polymers such as polyvinylpyrrolidone, etc.; substances derived from a gelatin-arabic gum complex, etc. Further, it includes saccharides such as mannitol, dextrose, lactose, galactose, trehalose, etc.; cyclic saccharides such as cyclodextrin etc.; inorganic salts such as sodium phosphate, sodium chloride and aluminum silicate, etc.; amino acids having 2 to 12 carbon atoms such as glycine, L-alanine, L-aspartic acid, L-glutamic acid, L-hydroxyproline, L-isoleucine, L-leucine, L-phenylalanine, etc.

One or more of the matrix forming agent(s) can be introduced in a solution or suspension before solidification. Such matrix forming agent may be present in addition to a surfactant, or may be present with the surfactant excluded. The matrix forming agents may help to keep the compound of the present invention or the concomitant drug diffused in the solution or suspension, in addition to formation of the matrix.

The composition may contain secondary components such as a preservative, an antioxidant, a surfactant, a thickening agent, a colorant, a pH controlling agent, a flavoring agent, a sweetening agent, a food taste masking agent, etc. The suitable colorant includes red, black and yellow iron oxides, and FD & C dyes such as FD & C Blue 2, FD & C Red 40, etc. manufactured by Elis and Eberald. Examples of the suitable flavoring agent include mint, raspberry, licorice, orange, lemon, grape fruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatine, etc. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1% by weight to about 50% by weight, preferably from about 0.1% by weight to about 30% by weight, and is preferably a preparation (such as the above-mentioned sublingual agent, buccal etc.) which can dissolve 90% or more the compound of the present invention or the concomitant drug (into water) within the time range of about 1 minute to about 60 minutes, preferably of about 1 minute to 15 minutes, more preferably of about 2 minutes to about 5 minutes, and intraoral quick disintegrating preparations which are disintegrated within the range of 1 second to 60 seconds, preferably of 1 to 30 seconds, further preferably of 1 to 10 seconds after being placed in the oral cavity.

The content of the above-mentioned excipient in the whole preparation is from about 10% by weight to about 99% by weight, preferably from about 30% by weight to about 90% by weight. The content of β-cyclodextrin or β-cyclodextrin derivative in the whole preparation is from 0 to about 30% by weight. The content of the lubricant in the whole preparation is from about 0.01% by weight to about 10% by weight, preferably from about 1% by weight to about 5% by weight. The content of the isotonizing agent in the whole preparation is from about 0.1% by weight to about 90% by weight, preferably from about 10% by weight to about 70% by weight. The content of the hydrophilic carrier in the whole preparation is from about 0.1% by weight to about 50% by weight, preferably from about 10% by weight to about 30% by weight. The content of the water-dispersible polymer in the whole preparation is from about 0.1 to about 30% by weight, preferably from about 10% by weight to about 25% by weight. The content of the stabilizer in the whole preparation is from about 0.1% by weight to about 10% by weight, preferably from about 1% by weight to about 5% by weight. The above-mentioned preparation may further contain additives such as a colorant, a sweetening agent, an antiseptic, etc., if necessary.

The dose of the combination drug of the present invention differs depending on the kind of the compound of the present invention; age, body weight, condition; drug form, administration method, administration period etc., and for example, for a cancer patient (adult, body weight: about 60 kg), the combination drug is administered intravenously, at a dose of about 0.01 to about 1,000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times a day in divided portions. Of course, since the dose as described above varies depending on various conditions, it may be sometimes sufficient to administer smaller amounts than the above-mentioned dosage, and further, it may be sometimes necessary to administer greater amounts than that.

The amount of the concomitant n drug can be set at any value unless side effects are problematical. The daily dosage in terms of the combination drug differs depending on the severity of symptoms, age, sex, body weight, sensitivity difference of the subject, administration time and interval, property, prescription, and kind of the pharmaceutical preparation, kind of effective ingredient, etc., and not particularly limited; for example, in the case of oral administration, the dose of the drug is usually from about 0.001 mg to 2,000 mg, preferably from about 0.01 mg to 500 mg, further preferably from about 0.1 mg to 100 mg, per 1 kg body weight of a mammal, which is usually administered once to four times a day in divided portions.

In administration of the combination drug of the present invention, the compound of the present invention may be administered after administration of the combination drug or the combination drug may be administered after administration of the compound of the present invention, though the compound of the present invention and the combination drug may be administered simultaneously. When administered at a time interval, the interval differs depending on the effective ingredient to be administered, drug form and administration method. For example, when the combination drug is administered first, the compound of the present invention is administered within time range of from 1 minute to 3 days, preferably from 10 minutes to 1 day, more preferably from 15 minutes to 1 hour after administration of the combined drug. When the compound of the present invention is administered first, the combined drug is administered within time range of from 1 minute to 1 day, preferably from 10 minutes to 6 hours, more preferably from 15 minutes to 1 hour after administration of the compound of the present invention.

In a preferable administration method, for example, the combination drug formulated into an oral administration preparation is administered orally at a daily dose of about 0.001 mg/kg to 200 mg/kg, and 15 minutes later, the compound of the present invention formulated into an oral administration preparation is administered orally at a daily dose of about 0.005 mg/kg to 100 mg/kg.

Furthermore, the compound of the present invention or the combination agent of the present invention can be used concurrently with a non-drug therapy. To be precise, the compound of the present invention or the combination agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization and (7) radiotherapy.

For example, by using the compound of the present invention or the combination agent of the present invention before and after an operation and the like, or by using before and after a treatment combining two or three kinds thereof, effects of prevention of resistance expression, elongation of Disease-Free Survival, suppression of cancer metastasis or recurrence, apothanasia and the like can be obtained.

In addition, a treatment with the compound of the present invention or the combination agent of the present invention can be combined with a supporting therapy [(i) administration of antibiotic (e.g., β-lactam such as pansporin and the like, macrolides such as clarithromycin and the like etc.) for complication with various infectious diseases, (ii) administration of high-calorie infusion, amino acid preparation or general vitamin preparation for malnutrition improvement, (iii) administration of morphine for pain mitigation, (iv) administration of medicament for ameliorating side effects such as nausea, vomiting, anorexia, diarrhea, leucopenia, thrombocytopenia, hemoglobin concentration decrease, hair loss, hepatopathy, renopathy, DIC, fever and the like, and (v) administration of medicament for suppressing multiple drug resistance of cancer etc.].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administration of the compound of the present invention or the combination agent of the present invention before the surgery, etc., for example, it can be administrated once about 30 min to 24 hr before the surgery, etc., or in 1 to 3 cycles about 3 to 6 months before the surgery, etc. In this way, the surgery, etc. can be conducted easily because, for example, a cancer tissue can be reduced by administering the compound of the present invention or the combination agent of the present invention before the surgery, and the like.

As a period for administration of the compound of the present invention or the combination agent of the present invention after the surgery and the like, for example, it can be administrated repeatedly about 30 min to 24 hr after the surgery, and the like in a unit of several weeks to 3 months. In this way, the effect of the surgery and the like can be enhanced by administering the compound of the present invention or the combination agent of the present invention after the surgery and the like.

EXAMPLES

The present invention is explained in detail by way of the following Examples, Formulation Examples and Experimental Examples but these do not limit the present invention.

The elution in column chromatography in Examples was performed under observation by TLC (thin-layer chromatography). In the TLC observation, Kieselgel 60F$_{254}$ plate (Merck) or NH TLC plate manufactured by Fuji Silysia Chemical Ltd. was used as a TLC plate, the solvent used as an elution solvent in the column chromatography was used as a developing solvent, and the means of detection used was an UV detector. As silica gel for column, Kieselgel 60F$_{254}$ (70-230 mesh) manufactured by Merck or Chromatorex NH DM1020 (basic silica gel, 100-200 mesh) manufactured by Fuji Silysia Chemical Ltd. or Combiflash system and RediSep R$_f$ silica cartridges manufactured by Teledyne ISCO was used. The ratio of solvents in silica gel chromatography is a volume ratio of the solvents mixed. In addition, % means percentage by weight unless otherwise specified.

Proton nuclear magnetic resonance spectra were obtained on a varian Gemini-200 MHz, a varian Gemini-300 MHz, a Varian mercury plus 300 MHz, a Bruker Avance III plus 400 MHz, a Bruker AV 300 MHz or a Bruker AV 500 MHz, respectively. Spectra are given in ppm (δ) and coupling constants, J, are reported in Hertz. Tetramethylsilane was used as an internal standard for proton spectra.

The abbreviations used in Examples mean the following:

s: singlet,
br: broad,
d: doublet,
t: triplet,
q: quartet,
dd: double doublet,
m: multiplet,
J: coupling constant,
Hz: hertz,
DMSO: dimethyl sulfoxide,
CDCl$_3$: deuterated chloroform,
CD$_3$OD: deuterated methanol,
CSA: [(1S,4R)-7,7-dimethyl-2-oxobicyclo[2.2.1]hept-1-yl]methanesulfonic acid,
DMA: N,N-dimethylacetamide,
DMF: N,N-dimethylformamide,
$^1$H-NMR: proton nuclear magnetic resonance,
MeCN: acetonitrile,
MeOH: methanol,
NH (at column chromatography): Chromatorex™ NH (Fuji Silysia),
PTSA: p-toluenesulfonic acid monohydrate,
THF: tetrahydrofuran,
TFA: trifluoroacetic acid.

Preparative HPLC was performed at conditions: Column: Fuji C18 (300×25) or YMC CombiPrep. Hydrosphere C18 (50×20 mm); Wavelength 220 nm; Mobile phase: A MeCN (0.1% TFA); B water (0.1% TFA).

The sequence numbers in the sequence listing in the present specification show the following respective sequences.

[SEQ ID NO: 1]—Shows the base sequence of the primer used in Experimental Example 1A.

[SEQ ID NO: 2]—Shows the base sequence of the primer used in Experimental Example 1A.

[SEQ ID NO: 3]—Shows the base sequence of the primer used in Experimental Example 1A.

[SEQ ID NO: 4]—Shows the base sequence of the primer used in Experimental Example 1A.

Example 1

Preparation of 2,2-dimethyl-6-(pyridin-4-yl)-2,3-dihydrothieno[3,2-d]pyrimidin-4(1H)-one

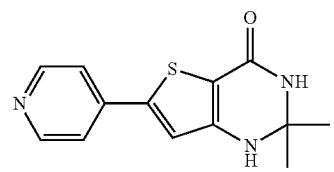 [SMILES: CC1(C)NC(=O)c2sc(-c3ccncc3)cc2N1]

Step 1

Preparation of 3-chloro-3-(pyridin-4-yl)acrylonitrile

To ice-cooled DMF (32.1 mL, 0.400 mol) was added POCl$_3$ (18.6 mL, 0.200 mol) dropwise with stirring over 1 h. After 30 min, the mixture was allowed to warm to room temperature. Then, 4-acetylpyridine (11.1 mL, 0.100 mol) was added dropwise over 2 h. DMF (50 mL) was added additionally and the mixture was maintained at room temperature with a water bath. Hydroxylamine hydrochloride (13.9 g, 200 mmol) was added portion wise over 2 h being careful to keep the reaction temperature under 80° C. DMF (50 mL) was added again and hydroxylamine hydrochloride (13.9 g, 200 mmol) was added portion wise over 30 min. Then, the mixture was heated at 80° C. After 1.5 h, the mixture was allowed to cool to room temperature and stirring was continued overnight. The mixture was cooled to 0° C., water (500 mL) was added, and the mixture was neutralized with sodium hydrogen carbonate. Water (500 mL) was added again to dissolve all, and the mixture was extracted with ethyl acetate (500 mL, 3×200 mL). The combined organic layers were washed with saturated aqueous sodium hydrogen carbonate and brine, dried over magnesium sulfate, filtered and concentrated at reduced pressure. The black residue obtained was dissolved with ethyl acetate (300 mL) and the solution was filtered through a pad of silica gel (100 g). The silica gel was washed with ethyl acetate (1 L). The filtrate was concentrated at reduced pressure to give a gray solid. $^1$H NMR analysis indicated the purity was about 60%. This solid was triturated with dichloromethane (100 mL) and filtered. The filtrate was purified by column chromatography (120 g×2, silica, Combiflash, dichloromethane to 50:50 dichloromethane/ethyl acetate) to afford the title compound (5.97 g, 36%) as a white solid:

$^1$H NMR (300 MHz, DMSO-d$_6$) δ 7.25 (1H, s), 7.77 (2H, dd, J=4.5, 1.5 Hz), 8.77 (2H, dd, J=4.5, 2.0 Hz).

Step 2

Preparation of methyl 3-amino-5-(pyridin-4-yl)thiophene-2-carboxylate

To a stirred solution of sodium methoxide (2.12 g, 39.3 mmol) in methanol (59 mL) was added methyl thioglycolate (3.51 mL, 39.3 mmol). After 10 min, 3-chloro-3-(pyridin-4-yl)acrylonitrile (6.47 g, 39.3 mmol) was added, and the mixture was heated at 50° C. After 1 h, the mixture was concentrated to about a half volume at reduced pressure and poured into water (500 mL). Extraction with ethyl acetate/tetrahydrofuran (4:1, 500 mL), washing with brine, drying over magnesium sulfate, filtration and concentration at reduced pressure gave the title compound (8.81 g, 96%) as a yellow solid:

$^1$H NMR (300 MHz, DMSO-d$_6$) δ 3.79 (3H, s), 6.62 (2H, br s), 7.21 (1H, s), 7.61 (2H, dd, J=4.5, 1.5 Hz), 8.63 (2H, dd, J=4.5, 1.5 Hz).

Step 3

Preparation of 3-amino-5-(pyridin-4-yl)thiophene-2-carboxylic acid

A mixture of methyl 3-amino-5-(pyridin-4-yl)thiophene-2-carboxylate (2.34 g, 10 mmol), sodium methoxide (1.62 g, 30 mmol), methanol (40 mL) and water (10 mL) was refluxed for 4 h. The mixture was allowed to cool to room temperature and stirring was continued overnight. The mixture was cooled under ice-bath, then conc. HCl (2.48 mL, 30 mmol) was added (pH was approx. 4). The resultant yellow precipitate was collected by filtration and washed with water and methanol to afford the title compound (2.02 g, 92%) as a yellow solid:

$^1$H NMR (300 MHz, DMSO-d$_6$) δ 7.20 (1H, s), 7.62 (2H, dd, J=4.8, 1.5 Hz), 8.62 (2H, d, J=6.3 Hz), 2H of amino portion and 1H of carboxylic acid were not observed independently.

Step 4

Preparation of 3-amino-5-(pyridin-4-yl)thiophene-2-carboxamide

A mixture of 3-amino-5-(pyridin-4-yl)thiophene-2-carboxylic acid (0.220 g, 1.00 mmol), ammonium chloride (0.267 g, 5.00 mmol), triethylamine (0.70 mL, 5.0 mmol) and DMF (3.0 mL) was stirred for 5 min. 1-Hydroxybenzotriazole (0.204 g, 1.50 mmol) and 1-ethyl-3-(3-dimethylaminopropyl)carbodiimide hydrochloride (0.286 g, 1.50 mmol) were added and stirring was continued overnight. Then, DMF (2 mL), ammonium chloride (0.267 g, 5.00 mmol), triethylamine (0.70 mL, 5.0 mmol), 1-hydroxybenzotriazole (0.204 g, 1.50 mmol) and 1-ethyl-3-(3-dimethylaminopropyl)carbodiimide hydrochloride (0.286 g, 1.50 mmol) were added again. After 6 h, the mixture was poured into aqueous sodium hydrogen carbonate (50 mL). Extraction with ethyl acetate-tetrahydrofuran (2:1, 2×30 mL), drying over magnesium sulfate, filtration and concentration at reduced pressure gave the title compound (0.185 g, 84%) as a yellow solid:

$^1$H NMR (300 MHz, DMSO-d$_6$) δ 6.54 (2H, br s), 7.06 (2H, br s), 7.18 (1H, s), 7.54-7.58 (2H, m), 8.61 (2H, d, J=6.3 Hz).

Step 5

Preparation of 2,2-dimethyl-6-(pyridin-4-yl)-2,3-dihydrothieno[3,2-d]pyrimidin-4(1H)-one A mixture of 3-amino-5-(pyridin-4-yl)thiophene-2-carboxamide (150 mg, 0.68 mmol), p-toluenesulfonic acid monohydrate (50 mg) and acetone (10 mL) in toluene (20 mL) was heated to reflux overnight. After removal of the solvent, the residue was purified by column chromatography on silica gel (MeOH: dichloromethane=1:9) to afford the title compound (130 mg, yield 74%) as an orange solid:

$^1$H NMR (300 MHz, DMSO-d$_6$) δ 1.42 (6H, s), 7.62-7.65 (3H, m), 8.59-8.61 (2H, m).

Example 2

Preparation of 6'-(pyridin-4-yl)-1'H-spiro[cyclopentane-1,2'-thieno[3,2-d]pyrimidin]-4'(3'H)-one

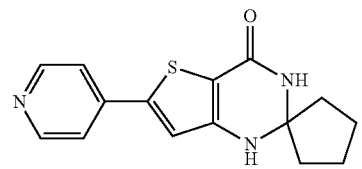 [SMILES: O=C1NC2(CCCC2)Nc2cc(-c3ccncc3)sc21]

A mixture of 3-amino-5-(pyridin-4-yl)thiophene-2-carboxamide (150 mg, 0.68 mmol), p-toluenesulfonic acid monohydrate (50 mg) and cyclopentan-1-one (10 ml) in toluene (20 ml) was heated to reflux overnight. After removal of the solvent, the residue was purified by column chromatography on silica gel (MeOH: dichloromethane=1:9) to afford the title compound (140 mg, yield 72%) as an orange solid:

$^1$H NMR (300 MHz, DMSO-d$_6$) δ 1.66-1.69 (4H, m), 1.83-1.89 (4H, m), 7.16 (1H, s), 7.24 (1H, s), 7.62 (2H, dd, J=6.0 Hz), 7.80 (1H, s), 8.60-8.61 (2H, m).

Example 3

Preparation of 2-phenyl-6-(pyridin-4-yl)-2,3-dihydrothieno[3,2-d]pyrimidin-4(1H)-one

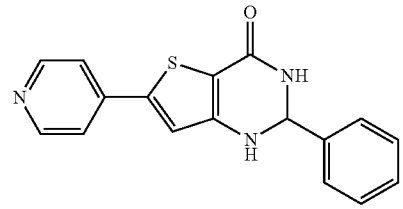 [SMILES: O=C1NC(c2ccccc2)Nc2cc(-c3ccncc3)sc21]

A mixture of 3-amino-5-(pyridin-4-yl)thiophene-2-carboxamide (99.9 mg, 0.456 mmol), p-toluenesulfonic acid monohydrate (8.67 mg, 0.046 mmol), benzaldehyde (0.056 mL, 0.547 mmol) and toluene (5 mL) was refluxed for 2 h. The reaction didn't occur. After cooling, AcOH (3 mL) was added, and the mixture was refluxed for 3 h. The reaction mixture was concentrated in vacuo. The residue was suspended in DMSO (3 mL) and the insoluble materials were filtered off. The filtrate was purified by preparative HPLC (ODS column, 0.1% TFA, water-MeCN=95:5-0:100). The fractions containing the object were basified by sat. aqueous sodium hydrogen carbonate, and the organic materials were extracted with EtOAc. The organic layer was dried over magnesium sulfate and concentrated in vacuo to afford the title compound (4.0 mg, yield 2.86%) as a yellow solid:

$^1$H NMR (DMSO-d$_6$) δ 5.82 (1H, m), 7.22 (1H, s), 7.35-7.44 (3H, m), 7.51-7.55 (2H, m), 7.62-7.65 (5H, m), 8.06 (1H, br s), 8.60-8.62 (3H, m).

Example 4

Preparation of 1'-methyl-6'-(pyridin-4-yl)-1'H-spiro[cyclopentane-1,2'-thieno[3,2-d]pyrimidin]-4'(3'H)-one

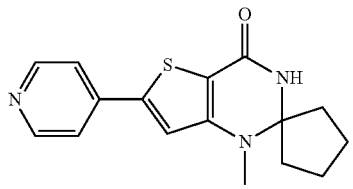 [SMILES: CN1c2cc(-c3ccncc3)sc2C(=O)NC12CCCC2]

Step 1

Preparation of methyl 3-(methylamino)-5-(pyridin-4-yl)thiophene-2-carboxylate

To a stirred solution of methyl 3-amino-5-(pyridin-4-yl) thiophene-2-carboxylate (1.21 g, 5.00 mmol) in DMF (25 mL) was added sodium hydride (60%, 0.220 g, 5.50 mmol). After 10 min, iodomethane (0.34 mL, 5.5 mmol) was added and stirring was continued for 2.5 h. The mixture was poured into a mixture of water (60 mL) and sat. aqueous sodium hydrogen carbonate (60 mL). Ethyl acetate (100 mL) and THF (25 mL) were added to the mixture for extraction, and the insoluble precipitate was removed by filtration. The organic layer was washed with brine, dried over magnesium sulfate, filtrated and concentrated at reduced pressure. The obtained residue was purified by column chromatography (Combiflash, 40 g silica gel, hexanes to ethyl acetate) to afford the title compound (0.533 g, 43%) as an orange solid.
$^1$H NMR (300 MHz, DMSO-d$_6$) δ 3.00 (3H, s), 3.75 (3H, s), 6.80 (1H, m), 7.53 (1H, s), 7.72 (2H, dd, J=1.5, 4.5 Hz), 8.64 (2H, dd, J=1.8, 4.5 Hz). This product contained about 16% N—N'-dimethylated derivative as a minor byproduct.

Step 2

Preparation of 3-(methylamino)-5-(pyridin-4-yl)thiophene-2-carboxylic acid

A mixture of methyl 3-(methylamino)-5-(pyridin-4-yl)thiophene-2-carboxylate (0.533 g, 2.15 mmol), sodium methoxide (0.348 g, 6.45 mmol), methanol (8.0 mL) and water (2.0 mL) was heated at reflux for 4 h. The mixture was cooled in an ice-bath and conc. HCl (0.533 mL, 6.45 mmol) was added to adjust the pH to 4. The resultant yellow precipitate was collected by filtration and washed with water and methanol to afford the title compound (0.342 g, 68%) as a yellow solid:
$^1$H NMR (300 MHz, DMSO-d$_6$) δ 2.98 (3H, s), 7.50 (1H, s), 7.72 (2H, dd, J=1.5, 4.5 Hz), 8.61-8.63 (2H, m); 1H of amino portion and 1H of carboxylic acid were not observed.

Step 3

Preparation of 3-(methylamino)-5-(pyridin-4-yl)thiophene-2-carboxamide

A mixture of 3-(methylamino)-5-(pyridin-4-yl)thiophene-2-carboxylic acid (0.342 g, 1.46 mmol), ammonium chloride (0.781 g, 14.6 mmol), triethylamine (2.05 mL, 14.6 mmol) and DMF (8.7 mL) was stirred for 5 min. Then, 1-hydroxybenzotriazole (0.592 g, 4.38 mmol) and 1-ethyl-3-(3-dimethylaminopropyl) carbodiimide hydrochloride (0.840 g, 4.38 mmol) were added and stirring was continued for 3 days. The mixture was poured into a mixture of sat. aqueous sodium hydrogen carbonate (100 mL) and water (60 mL). Extraction with ethyl acetate-tetrahydrofuran (3:1, 2×100 mL), washing with sat. aqueous sodium hydrogen carbonate and brine, drying over magnesium sulfate, filtration and concentration at reduced pressure gave a yellow solid. This solid was triturated with dichloromethane, and the precipitate was collected by filtration to afford the title compound (0.219 g, 64%) as a yellow solid:
$^1$H NMR (300 MHz, DMSO-d$_6$) δ 2.94 (3H, d, J=5.1 Hz), 7.06 (2H, br s), 7.25 (1H, d, J=5.4 Hz), 7.49 (1H, s), 7.65 (2H, dd, J=1.5, 4.5 Hz), 8.62 (2H, dd, J=1.8, 4.5 Hz).

The filtrate was purified by column chromatography (Combiflash, 12 g silica gel, dichloromethane to ethyl acetate) to afford the additional portion of the additional title compound (0.034 g, 10%) as an orange solid.

Step 4

Preparation of 1'-methyl-6'-(pyridin-4-yl)-1'H-spiro[cyclopentane-1,2'-thieno[3,2-d]pyrimidin]-4'(3'H)-one A mixture of 3-(methylamino)-5-(pyridin-4-yl)thiophene-2-carboxamide (300 mg, 1.29 mmol), p-toluenesulfonic acid monohydrate (120 mg) and cyclopentan-1-one (10 mL) in toluene (30 mL) was heated to reflux overnight. After removal of the solvent, the residue was purified by column chromatography on silica gel (MeOH: DCM=1:9) to afford the title compound (200 mg, yield 52%) as an orange solid:
$^1$H NMR (300 MHz, CDCl$_3$) δ 1.77-1.82 (4H, m), 1.92-2.12 (4H, m), 2.97 (3H, s), 5.65 (1H, br s), 7.00 (1H, s), 7.48 (2H, dd, J=4.5, 1.5 Hz), 8.63 (2H, dd, J=4.5, 1.5 Hz).

Example 5

Preparation of 6'-(pyridin-4-yl)-2,3,5,6-tetrahydro-1'H-spiro [pyran-4,2'-thieno[3,2-d]pyrimidin]-4'(3'H)-one

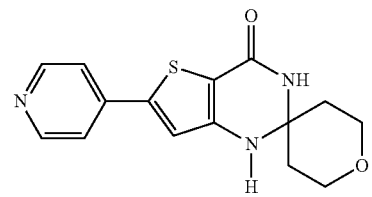 [SMILES: O=C1NC2(CCOCC2)Nc2cc(-c3ccncc3)sc21]

A mixture of 3-amino-5-(pyridin-4-yl)thiophene-2-carboxamide (0.078 g, 0.36 mmol), tetrahydro-4H-pyran-4-one (0.200 g, 2.00 mmol), p-toluenesulfonic acid monohydrate (0.076 g, 0.40 mmol) and toluene (3.0 mL) was stirred for 2 h at 90° C. The mixture was poured into aqueous sodium hydrogen carbonate (50 mL). Extraction with ethyl acetate/tetrahydrofuran (2:1, 2×30 mL), drying over magnesium sulfate, filtration and concentration at reduced pressure gave an oil. The oil was purified by column chromatography (12 g, silica, Combiflash, dichloromethane to 80:20 dichloromethane/methanol) to afford the title compound (0.050 g, 46%) as a yellow solid:

$^1$H NMR (300 MHz, DMSO-d$_6$) δ 1.86 (4H, m), 3.63-3.73 (4H, m), 7.22 (1H, s), 7.35 (1H, br s), 7.63 (2H, d, J=5.4 Hz), 7.85 (1H, br s), 8.61 (2H, d, J=4.8 Hz).

Example 6

Preparation of 6'-(pyridin-4-yl)-1'H-spiro[cyclohexane-1,2'-thieno[3,2-d]pyrimidin]-4'(3'H)-one

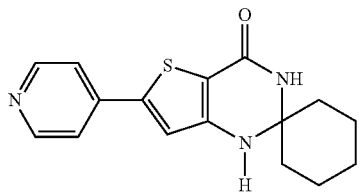 [SMILES: O=C1NC2(CCCCC2)Nc2cc(-c3ccncc3)sc21]

A mixture of 3-amino-5-(pyridin-4-yl)thiophene-2-carboxamide (0.110 g, 0.500 mmol), cyclohexanone (0.245 g, 2.50 mmol), p-toluenesulfonic acid monohydrate (0.105 g, 0.550 mmol) and toluene (5.0 mL) was stirred for 1 h at 90° C. The mixture was poured into aqueous sodium hydrogen carbonate (30 mL). Extraction with ethyl acetate/tetrahydrofuran (2:1, 2×30 mL), drying over magnesium sulfate, filtration and concentration at reduced pressure gave an oil. The oil was purified by column chromatography (12 g, silica, Combiflash, dichloromethane to 80:20 dichloromethane/methanol) to afford the title compound (0.053 g, 36%) as a yellow solid:

$^1$H NMR (300 MHz, DMSO-d$_6$) δ 1.15-1.30 (1H, m), 1.40-1.66 (7H, m), 1.81-1.93 (2H, m), 7.15 (1H, br s), 7.18 (1H, s), 7.61 (2H, dd, J=4.5, 1.5 Hz), 7.63 (1H, br s), 8.61 (2H, dd, J=4.8, 1.8 Hz).

Example 7

Preparation of 1,2,2-trimethyl-6-(pyridin-4-yl)-2,3-dihydrothieno[3,2-d]pyrimidin-4(1H)-one

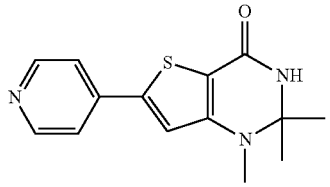 [SMILES: CN1c2cc(-c3ccncc3)sc2C(=O)NC1(C)C]

A mixture of 3-(methylamino)-5-(pyridin-4-yl)thiophene-2-carboxamide (400 mg, 1.72 mmol), p-toluenesulfonic acid monohydrate (150 mg) and acetone (40 mL) in toluene (40 mL) was heated to reflux overnight. After removal of the solvent, the residue was purified by column chromatography on silica gel (MeOH: dichloromethane=1:9) to afford the title compound (30 mg, yield 6%) as an orange solid:

$^1$H NMR (300 MHz, DMSO-d$_6$): δ 1.42 (6H, s), 2.93 (3H, s), 7.56 (1H, s), 7.68 (2H, dd, J=4.2, 1.8 Hz), 8.61 (2H, dd, J=4.8, 1.8 Hz).

Example 8

Preparation of 2-ethyl-2-methyl-6-(pyridin-4-yl)-2,3-dihydrothieno[3,2-d]pyrimidin-4(1H)-one

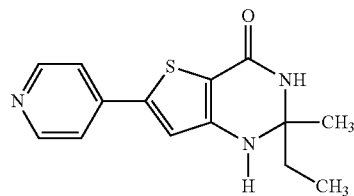 [SMILES: CCC1(C)NC(=O)c2sc(-c3ccncc3)cc2N1]

A mixture of 3-amino-5-(pyridin-4-yl)thiophene-2-carboxamide (0.108 g, 0.500 mmol), 2-butanone (1.0 mL), p-toluenesulfonic acid monohydrate (0.0096 g, 0.050 mmol) and acetic acid (3.0 mL) was stirred for 1 h at 70° C. The reaction mixture was poured into aqueous sodium hydrogen carbonate (200 mL). Extraction with ethyl acetate (200 mL, 100 mL), washing with aqueous sodium hydrogen carbonate, drying over magnesium sulfate, filtration and concentration at reduced pressure gave a residue, which was triturated with dichloromethane/ethyl acetate (1:1, 6 mL), and the precipitate was collected by filtration to afford the title compound (0.095 g, 69%) as a yellow solid:

$^1$H NMR (300 MHz, DMSO-d$_6$) δ 0.89 (3H, t, J=7.5 Hz), 1.36 (3H, s), 1.63-1.77 (2H, m), 7.09 (1H, br s), 7.14 (1H, s), 7.59 (1H, br s), 7.62 (2H, dd, J=4.5, 1.5 Hz), 8.60 (2H, dd, J=4.5, 1.5 Hz).

Example 9

Preparation of benzyl 4'-oxo-6'-(pyridin-4-yl)-3',4'-dihydro-1'H-spiro[piperidine-4,2'-thieno[3,2-d]pyrimidine]-1-carboxylate

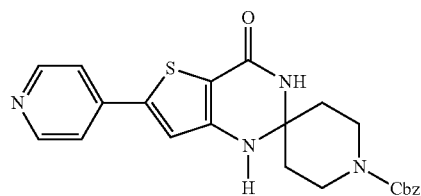 [SMILES: O=C1NC2(CCN(C(=O)OCc3ccccc3)CC2)Nc2cc(-c3ccncc3)sc21]

A mixture of 3-amino-5-(pyridin-4-yl)thiophene-2-carboxamide (0.219 g, 1.00 mmol), benzyl 4-oxo-1-piperidinecarboxylate (0.700 g, 3.00 mmol), p-toluenesulfonic acid monohydrate (0.211 g, 1.10 mmol) and toluene (10.0 mL) was stirred for 2 h at 90° C. Then, acetic acid (10.0 mL) was added, and the mixture was stirred for 1 h at 80° C. After removal of the solvent at reduced pressure, the obtained residue was poured into aqueous sodium hydrogen carbonate (200 mL). Extraction with ethyl acetate (200 mL, 100 mL), drying over magnesium sulfate, filtration and concentration at reduced pressure gave a solid. The solid was triturated with ethyl acetate/dichloromethane (1:1, 10 mL), and the precipitate was collected by filtration to afford the title compound (0.276 g, 64%) as a yellow solid:
¹H NMR (300 MHz, DMSO-d₆) δ 1.74-1.92 (4H, m), 3.33-3.37 (2H, m), 3.67-3.72 (2H, m), 5.09 (2H, s), 7.20 (1H, s), 7.30-7.39 (6H, m), 7.63 (2H, dd, J=4.8, 1.8 Hz), 7.84 (1H, br s), 8.62 (2H, dd, J=4.5, 1.5 Hz).

Example 10

Preparation of 2,2-diethyl-6-(pyridin-4-yl)-2,3-dihydrothieno[3,2-d]pyrimidin-4(1H)-one

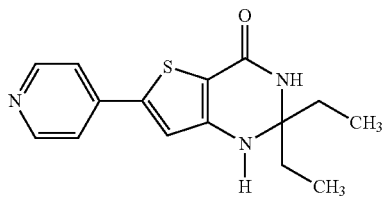 [SMILES: CCC1(CC)NC(=O)c2sc(-c3ccncc3)cc2N1]

A mixture of 3-amino-5-(pyridin-4-yl)thiophene-2-carboxamide (0.108 g, 0.500 mmol), 3-pentanone (1.0 mL), p-toluenesulfonic acid monohydrate (0.0096 g, 0.050 mmol) and acetic acid (3.0 mL) was stirred for 3 h at 70° C. The reaction mixture was poured into aqueous sodium hydrogen carbonate (200 mL). Extraction with ethyl acetate (100 mL, 50 mL), washing with aqueous sodium hydrogen carbonate, drying over magnesium sulfate, filtration and concentration at reduced pressure gave a residue, which was purified by column chromatography (40 g, silica, Combiflash, dichloromethane to 90:10 dichloromethane/methanol), then triturated with ethyl acetate. The precipitate was collected by filtration to afford the title compound (0.040 g, 28%) as a yellow solid:
¹H NMR (300 MHz, DMSO-d₆) δ 0.88 (6H, t, J=7.2 Hz), 1.61-1.69 (4H, m), 7.03 (1H, br s), 7.12 (1H, s), 7.50 (1H, br s), 7.61 (2H, dd, J=4.5, 1.5 Hz), 8.60 (2H, dd, J=4.5, 1.5 Hz).

Example 11

Preparation of 6'-(pyridin-4-yl)-1'H-spiro[cyclopentane-1,2'-thieno[2,3-d]pyrimidin]-4'(3'H)-one

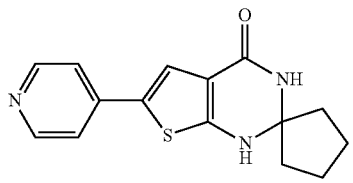 [SMILES: O=C1NC2(CCCC2)Nc2sc(-c3ccncc3)cc21]

Step 1

Preparation of ethyl 2-amino-5-(pyridin-4-yl)thiophene-3-carboxylate

A solution of 4-methylpyridine (3.7 g, 40 mmol) and bis(dimethylamino)-tert-butoxymethane (8.44 g, 48 mmol) in DMF (10 mL) was heated at reflux for 12 hours under a nitrogen atmosphere and then concentrated under vacuum to give a tan solid. The product was re-crystallized from cyclohexane to give compound 4-(2-dimethylaminovinyl)pyridine (5.0 g, yield 85%) as light yellow crystals. A solution of 4-(2-dimethylaminovinyl)pyridine (5.0 g, 33.8 mmol), ethyl cyanoacetate (3.8 g, 33.8 mmol), sulfur (8.6 g, 270.2 mmol) and morpholine (1 mL) in EtOH (50 mL) was heated at 80° C. under a nitrogen atmosphere for 3 hours and chilled in ice. The resulting crystals were collected by filtration, washed with hexane, and dried to give the title compound (5.5 g, 66% yield) as an orange solid:
¹H NMR (300 MHz, CDCl₃): δ 1.38 (3H, t, J=7.2 Hz), 4.31 (2H, q, J=7.2 Hz), 6.24 (2H, br s), 7.27 (2H, dd, J=4.5, 1.5 Hz), 7.49 (1H, s), 8.50 (2H, dd, J=4.8, 1.8 Hz).

Step 2

Preparation of 2-amino-5-(pyridin-4-yl)thiophene-3-carboxylic acid

To a solution of ethyl 2-amino-5-(pyridin-4-yl)thiophene-3-carboxylate (400 mg, 1.53 mmol) in EtOH (50 mL) was added a solution of lithium hydroxide monohydrate (256 mg, 6.1 mmol) in water (5 mL). The reaction mixture was heated to 80° C. for 2 hour. After removal of the solvent, the residue was dissolved in water and the organic materials were extracted with AcOEt (50 mL). The organic layer was discarded, and the aqueous layer was neutralized with 2N HCl aqueous solution to pH=5 or 6, upon with a precipitate formed. The solid was collected by filtration and dried to give the title compound (277 mg, 77%) as an orange solid:
¹H NMR (300 MHz, DMSO-d₆): δ 7.40 (2H, dd, J=1.5, 4.5 Hz), 7.59 (1H, s), 7.65-7.72 (2H, m), 8.39-8.43 (2H, m), 12.19-12.27 (1H, m).

Step 3

Preparation of 2-amino-5-(pyridin-4-yl)thiophene-3-carboxamide

To a solution of 2-amino-5-(pyridin-4-yl)thiophene-3-carboxylic acid (2.20 g, 10 mmol), ammonium chloride (1.09 g, 20 mmol), 1-ethyl-3-(3-dimethylaminopropyl)carbodiimide hydrochloride (2.30 g, 30 mmol) and 1-hydroxybenzotriazole (1800 mg, 12 mmol) in DMF (100 mL) was added triethylamine (3.0 g, 30 mmol) at room temperature. The reaction mixture was stirred overnight at room temperature. After removal of the solvent, the residue was purified by column chromatography on silica gel (MeOH: DCM=1:19) to give the title compound (1100 mg, 50%) as a brown solid:
¹H NMR (400 MHz, CD₃OD): δ 7.44 (2H, d, J=6.0 Hz), 7.79 (1H, s), 8.40 (2H, d, J=6.4 Hz).

Step 4

Preparation of 6'-(pyridin-4-yl)-1'H-spiro[cyclopentane-1,2'-thieno[2,3-d]pyrimidin]-4'(3'H)-one A mixture of 2-amino-5-(pyridin-4-yl)thiophene-3-carboxamide (300 mg, 1.29 mmol), p-toluenesulfonic acid (150 mg) and cyclopentan-1-one (10 mL) in toluene (30 mL) was heated to reflux for overnight. After removal of the solvent, the residue was purified by column chromatography on silica gel (MeOH: dichloromethane=1:9) to afford the crude title compound (90 mg), which was further purified by preparative TLC to give the title compound (55 mg, yield 15%) as a brown solid.

¹H NMR (400 MHz, DMSO-d₆): δ 1.68-1.70 (4H, m), 1.85-1.88 (4H, m), 7.45 (2H, d, J=6.0 Hz), 7.64 (1H, s), 7.74 (1H, s), 8.31 (1H, s), 8.44 (2H, d, J=6.0 Hz).

Example 12

Preparation of 2,2-dimethyl-6-(pyridin-4-yl)-2,3-dihydrothieno[2,3-d]pyrimidin-4(1H)-one

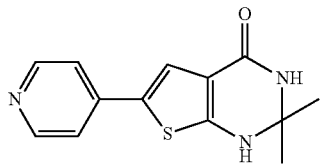 [SMILES: CC1(C)NC(=O)c2cc(-c3ccncc3)sc2N1]

A mixture of 2-amino-5-(pyridin-4-yl)thiophene-3-carboxamide (300 mg, 1.37 mmol), p-toluenesulfonic acid monohydrate (150 mg) and acetone (30 mL) in toluene (30 mL) was heated to reflux overnight. After removal of the solvent, the residue was purified by column chromatography on silica gel (MeOH: dichloromethane=1:9) to afford the crude title compound (70 mg), which was further purified by preparative TLC to give the title compound (37 mg, yield 10%) as an orange solid:

¹H NMR (400 MHz, CD₃OD): δ 1.58 (6H, s), 7.49 (2H, dd, J=4.8, 1.6 Hz), 7.64 (1H, s), 8.43 (2H, d, J=6.0 Hz).

Example 13

Preparation of 2-methyl-2-propyl-6-(pyridin-4-yl)-2,3-dihydrothieno[3,2-d]pyrimidin-4(1H)-one

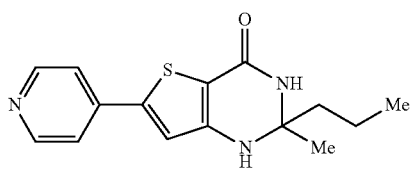 [SMILES: CCCC1(C)NC(=O)c2sc(-c3ccncc3)cc2N1]

A mixture of 3-amino-5-(pyridin-4-yl)thiophene-2-carboxamide (0.108 g, 0.500 mmol), 2-pentanone (3.0 mL), p-toluenesulfonic acid monohydrate (0.0095 g, 0.050 mmol) and acetic acid (3.0 mL) was stirred for 2 h at 70° C. then for 3 h at 80° C. in a sealed tube. The mixture was poured into sat. aqueous sodium hydrogen carbonate (150 mL). Extraction with ethyl acetate-tetrahydrofuran (2:1, 150 mL), drying over magnesium sulfate, filtration and concentration at reduced pressure gave an oil. The oil was triturated with dichloromethane, and the precipitate was collected by filtration to afford the title compound (0.0632 g, 44%) as a yellow solid:

¹H NMR (300 MHz, DMSO-d₆) δ 0.87 (3H, t, J=7.2 Hz), 1.37-1.42 (5H, m), 1.63-1.67 (2H, m), 7.10 (1H, br s), 7.13 (1H, s), 7.60-7.63 (3H, m), 8.60 (2H, dd, J=4.5, 1.5 Hz).

Example 14

Preparation of tert-butyl 4'-oxo-6'-(pyridin-4-yl)-3',4'-dihydro-1'H-spiro[piperidine-4,2'-thieno[3,2-d]pyrimidine]-1-carboxylate

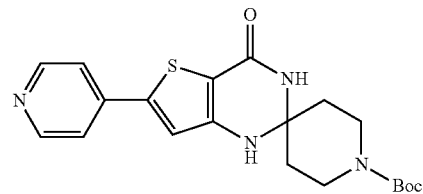 [SMILES: CC(C)(C)OC(=O)N1CCC2(CC1)NC(=O)c1sc(-c3ccncc3)cc1N2]

A mixture of 3-amino-5-(pyridin-4-yl)thiophene-2-carboxamide (0.108 g, 0.500 mmol), N-Boc-piperidin-4-one (0.600 mg, 3.00 mmol), p-toluenesulfonic acid monohydrate (0.0095 g, 0.050 mmol) and acetic acid (3.0 mL) was stirred for 1 h at 70° C. The mixture was poured into sat. aqueous sodium hydrogen carbonate (100 mL). Extraction with ethyl acetate-tetrahydrofuran (3:1, 100 mL), drying over magnesium sulfate, filtration and concentration at reduced pressure gave a solid. The solid was triturated with ethyl acetate-dichloromethane, and the precipitate was collected by filtration to afford the title compound (0.184 g, 92%) as a yellow solid:

¹H NMR (300 MHz, DMSO-d₆) δ 1.40 (9H, s), 1.67-1.88 (4H, m), 3.23-3.33 (2H, m), 3.58-3.64 (2H, m), 7.19 (1H, s), 7.31 (1H, br s), 7.63 (2H, d, J=6.3 Hz), 7.81 (1H, br s), 8.61 (2H, d, J=6.0 Hz).

Example 15

Preparation of 1-ethyl-2,2-dimethyl-6-(pyridin-4-yl)-2,3-dihydrothieno[3,2-d]pyrimidin-4(1H)-one

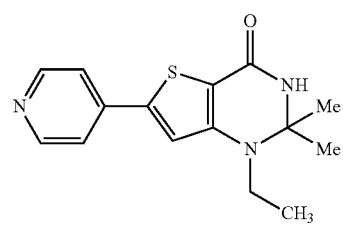 [SMILES: CCN1c2cc(-c3ccncc3)sc2C(=O)NC1(C)C]

Step 1

Preparation of methyl 3-(ethylamino)-5-(pyridin-4-yl)thiophene-2-carboxylate

To a stirred solution of methyl 3-amino-5-(pyridin-4-yl)thiophene-2-carboxylate (1.21 g, 5.00 mmol) in DMF (25 mL) was added sodium hydride (60%, 0.220 g, 5.50 mmol). After 10 min, iodoethane (0.44 mL, 5.5 mmol) was added and stirring was continued for 4 h. The mixture was poured into water (60 mL) and sat. aqueous sodium hydrogen carbonate (60 mL). Ethyl acetate (120 mL) and THF (60 mL) were added to the mixture for extraction and the insoluble precipitate was removed by filtration. The organic layer was washed with brine, dried over magnesium sulfate, filtrated and concentrated at reduced pressure. The obtained residue was purified by column chromatography (Combiflash, 40 g silica gel, hexanes to 30:70 hexanes/ethyl acetate) to afford the title compound (0.636 g, 48%) as an orange solid:

$^1$H NMR (300 MHz, DMSO-$d_6$) δ 1.19 (3H, t, J=7.2 Hz), 3.35-3.44 (2H, m), 3.76 (3H, s), 6.79-6.83 (1H, m), 7.57 (1H, s), 7.73 (2H, dd, J=4.8 Hz, 1.8 Hz), 8.64 (2H, dd, J=4.8, 1.8 Hz).

Step 2

Preparation of 3-(ethylamino)-5-(pyridin-4-yl)thiophene-2-carboxylic acid

A mixture of methyl 3-(ethylamino)-5-(pyridin-4-yl)thiophene-2-carboxylate (0.636 g, 2.42 mmol), sodium methoxide (0.393 g, 7.27 mmol), methanol (10 mL) and water (2.5 mL) was refluxed overnight. The mixture was cooled in an ice-bath and conc. HCl (0.600 mL, 7.27 mmol) was added to adjust the pH to 4. The resultant yellow precipitate was collected by filtration and washed with water and methanol to afford the title compound (0.415 g, 69%) as an orange solid:

$^1$H NMR (300 MHz, DMSO-$d_6$) δ 1.18 (3H, t, J=6.9 Hz), 3.33-3.41 (2H, m), 7.54 (1H, s), 7.70 (2H, dd, J=4.5, 1.5 Hz), 8.62 (2H, dd, J=4.5, 1.5 Hz); 1H of amino portion and 1H of carboxylic acid were not observed.

Step 3

Preparation of 3-(ethylamino)-5-(pyridin-4-yl)thiophene-2-carboxamide

A mixture of 3-(ethylamino)-5-(pyridin-4-yl)thiophene-2-carboxylic acid (0.415 g, 1.67 mmol), ammonium chloride (0.893 g, 16.7 mmol), triethylamine (2.35 mL, 16.7 mmol) and DMF (10 mL) was stirred for 5 min. Then, 1-hydroxybenzotriazole (0.676 g, 5.00 mmol) and 1-ethyl-3-(3-dimethylaminopropyl) carbodiimide hydrochloride (0.956 g, 5.00 mmol) were added and stirring was continued for 3 days. The mixture was then poured into sat. aqueous sodium hydrogen carbonate (100 mL) and water (60 mL). Extraction with ethyl acetate-tetrahydrofuran (3:1, 2×100 mL), washing with sat. aqueous sodium hydrogen carbonate and brine, drying over magnesium sulfate, filtration and concentration at reduced pressure gave a yellow solid. This solid was triturated with dichloromethane, and the precipitate was collected by filtration to afford the title compound (0.258 g, 62%) as a yellow solid:

$^1$H NMR (300 MHz, DMSO-$d_6$) δ 1.17 (3H, t, J=6.9 Hz), 3.30-3.34 (2H, m), 7.07 (2H, br s), 7.31-7.35 (1H, m), 7.52 (1H, s), 7.65 (2H, dd, J=4.8, 1.5 Hz), 8.62 (2H, dd, J=4.8, 1.8 Hz).

Step 4

Preparation of 1-ethyl-2,2-dimethyl-6-(pyridin-4-yl)-2,3-dihydrothieno[3,2-d]pyrimidin-4(1H)-one A mixture of 3-(ethylamino)-5-(pyridin-4-yl)thiophene-2-carboxamide (0.100 g, 0.400 mmol), acetone (3.0 mL), p-toluenesulfonic acid monohydrate (0.0095 g, 0.050 mmol) and acetic acid (2.0 mL) was stirred overnight at 70° C. in a sealed tube. The mixture was poured into sat. aqueous sodium hydrogen carbonate (100 mL). Extraction with ethyl acetate-tetrahydrofuran (2:1, 100 mL), drying over magnesium sulfate, filtration and concentration at reduced pressure gave an oil. The oil was purified by column chromatography (Combiflash, 12 g silica gel, hexane to ethyl acetate) to afford the title compound (0.0898 g, 63%) as a yellow solid:

$^1$H NMR (300 MHz, DMSO-$d_6$) δ 1.18 (3H, t, J=6.9 Hz), 1.46 (6H, s), 3.36-3.44 (2H, m), 7.51 (1H, s), 7.65-7.73 (3H, m), 8.62 (2H, d, J=5.7 Hz).

Example 16

Preparation of 2-iso-propyl-2-methyl-6-(pyridin-4-yl)-2,3-dihydrothieno[3,2-d]pyrimidin-4(1H)-one

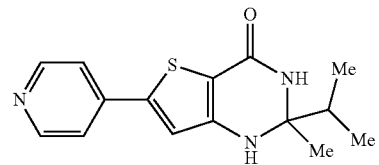 [SMILES: CC(C)C1(C)NC(=O)c2sc(-c3ccncc3)cc2N1]

A mixture of 3-amino-5-(pyridin-4-yl)thiophene-2-carboxamide (0.108 g, 0.500 mmol), 3-methyl-2-butanone (3.0 mL), p-toluenesulfonic acid monohydrate (0.0095 g, 0.050 mmol) and acetic acid (3.0 mL) was stirred overnight at 70° C. in a sealed tube. The mixture was poured into sat. aqueous sodium hydrogen carbonate (150 mL). Extraction with ethyl acetate-tetrahydrofuran (3:1, 2×100 mL), drying over magnesium sulfate, filtration and concentration at reduced pressure gave a solid. This solid was dissolved with DMF-dichloromethane (2:5, 7 mL) and purified by column chromatography (Combiflash, 12 g silica gel, ethyl acetate to 90:10 ethyl acetate/methanol), then recrystallized from methanol-ethyl acetate to afford the title compound (0.0125 g, 8.7%) as a yellow solid:

$^1$H NMR (300 MHz, DMSO-$d_6$) δ 0.90-0.94 (6H, m), 1.32 (3H, s), 2.01-2.08 (1H, m), 7.11 (1H, br s), 7.13 (1H, s), 7.60-7.62 (3H, m), 8.60 (2H, d, J=6.3 Hz).

Example 17

Preparation of 6'-(pyridin-4-yl)-1'H-spiro[piperidine-4,2'-thieno[3,2-d]pyrimidin]-4'(3'H)-one

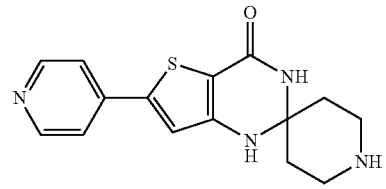 [SMILES: O=C1NC2(CCNCC2)Nc2cc(-c3ccncc3)sc21]

A mixture of tert-butyl 4'-oxo-6'-(pyridin-4-yl)-3',4'-dihydro-1'H-spiro[piperidine-4,2'-thieno[3,2-d]pyrimidine]-1-carboxylate (0.154 g, 0.385 mmol) and trifluoroacetic acid (3.0 mL) was stirred for 1 h at room temperature. The mixture was poured into sat. aqueous sodium hydrogen carbonate (100 mL), ethyl acetate (70 mL) and tetrahydrofuran (30 mL). After shaking well, the yellow precipitate was collected by filtration. This solid was suspended in ethyl acetate-dichloromethane (1:2, 10 mL) and the mixture was heated to 60° C.

After 10 min, the precipitate was collected by filtration to afford the title compound (0.107 mg, 93%) as a yellow solid:

$^1$H NMR (300 MHz, DMSO-d$_6$) δ 1.63-1.71 (3H, m), 1.77-1.85 (2H, m), 2.71-2.77 (4H, m), 7.20 (1H, s), 7.21 (1H, br s), 7.61 (2H, d, J=6.0 Hz), 7.70 (1H, br s), 8.61 (2H, dd, J=4.5, 1.5 Hz).

Example 18

Preparation of 2,2-dimethyl-1-propyl-6-(pyridin-4-yl)-2,3-dihydrothieno[3,2-d]pyrimidin-4(1H)-one

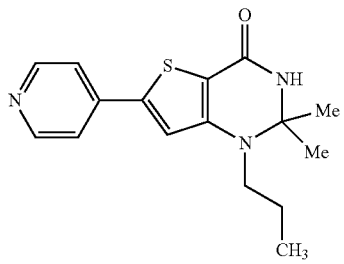 [SMILES: CCCN1c2cc(-c3ccncc3)sc2C(=O)NC1(C)C]

Step 1

Preparation of methyl 3-(propylamino)-5-(pyridin-4-yl) thiophene-2-carboxylate

To a stirred solution of methyl 3-amino-5-(pyridin-4-yl)thiophene-2-carboxylate (1.21 g, 5.00 mmol) in DMF (25 mL) was added sodium hydride (60%, 0.220 g, 5.50 mmol). After 10 min, 1-iodopropane (0.537 mL, 5.50 mmol) was added and stirring was continued overnight. The mixture was poured into water (60 mL) and sat. aqueous sodium hydrogen carbonate (60 mL). Ethyl acetate (100 mL) and THF (33 mL) were added to the mixture for extraction. The organic layer was washed with brine, dried over magnesium sulfate, filtrated and concentrated at reduced pressure. The obtained residue was purified by column chromatography (Combiflash, 40 g silica gel, hexanes to 30:70 hexanes/ethyl acetate) to afford the title compound (0.573 g, 41%) as a yellow solid:

$^1$H NMR (300 MHz, DMSO-d$_6$) δ 0.93 (3H, t, J=7.5 Hz), 1.52-1.62 (2H, m), 3.30-3.37 (2H, m), 3.75 (3H, s), 6.88 (1H, t, J=6.3 Hz), 7.56 (1H, s), 7.73 (2H, dd, J=4.8, 1.8 Hz), 8.64 (2H, dd, J=4.8, 1.8 Hz).

Step 2

Preparation of 3-(propylamino)-5-(pyridin-4-yl) thiophene-2-carboxylic acid

A mixture of methyl 3-(propylamino)-5-(pyridin-4-yl) thiophene-2-carboxylate (0.573 g, 2.07 mmol), sodium methoxide (0.335 g, 6.21 mmol), methanol (8.0 mL) and water (2.0 mL) was refluxed overnight. The mixture was cooled in an ice-bath and conc. HCl (0.510 mL, 6.21 mmol) was added. The resultant yellow precipitate was collected by filtration and washed with water and methanol to afford the title compound (0.477 g, 88%) as a yellow solid:

$^1$H NMR (300 MHz, DMSO-d$_6$) δ 0.93 (3H, t, J=7.5 Hz), 1.53-1.62 (2H, m), 3.29-3.33 (2H, m), 7.55 (1H, s), 7.72 (2H, dd, J=4.5, 1.5 Hz), 8.62 (2H, dd, J=4.5, 1.5 Hz); 1H of amino portion and 1H of carboxylic acid were not observed.

Step 3

Preparation of 3-(propylamino)-5-(pyridin-4-yl) thiophene-2-carboxamide

A mixture of 3-(propylamino)-5-(pyridin-4-yl)thiophene-2-carboxylic acid (0.477 g, 1.82 mmol), ammonium chloride (0.974 g, 18.2 mmol), triethylamine (2.56 mL, 18.2 mmol) and DMF (11 mL) was stirred for 5 min. Then, 1-hydroxybenzotriazole (0.743 g, 5.50 mmol) and 1-ethyl-3-(3-dimethylaminopropyl)carbodiimide hydrochloride (1.05 g, 5.50 mmol) were added and stirring was continued for 3 days. The mixture was then poured into sat. aqueous sodium hydrogen carbonate (100 mL) and water (60 mL). Extraction with ethyl acetate-tetrahydrofuran (3:1, 2×100 mL), washing with sat. aqueous sodium hydrogen carbonate and brine, drying over magnesium sulfate, filtration and concentration at reduced pressure gave a yellow solid. This solid was triturated with dichloromethane, and the precipitate was collected by filtration to afford the title compound (0.374 g, 79%) as a yellow solid:

$^1$H NMR (300 MHz, DMSO-d$_6$) δ 0.92 (3H, t, J=7.5 Hz), 1.52-1.59 (2H, m), 3.22-3.29 (2H, m), 7.06 (2H, br s), 7.44-7.48 (1H, m), 7.53 (1H, s), 7.65 (2H, dd, J=4.5, 1.5 Hz), 8.61 (2H, dd, J=4.5, 1.5 Hz).

Step 4

Preparation of 2,2-dimethyl-1-propyl-6-(pyridin-4-yl)-2,3-dihydrothieno[3,2-d]pyrimidin-4(1H)-one A mixture of 3-(propylamino)-5-(pyridin-4-yl)thiophene-2-carboxamide (0.130 g, 0.500 mmol), acetone (3.0 mL), p-toluenesulfonic acid monohydrate (0.0095 g, 0.050 mmol) and acetic acid (2.0 mL) was stirred for 2 days at 70° C. in a sealed tube. The mixture was poured into sat. aqueous sodium hydrogen carbonate (100 mL). Extraction with ethyl acetate-tetrahydrofuran (2:1, 100 mL), drying over magnesium sulfate, filtration and concentration at reduced pressure gave an oil. The oil was purified by column chromatography (Combiflash, 12 g silica gel, hexane to ethyl acetate), then washed with ethyl acetate to afford the title compound (0.094 g, 62%) as a yellow solid:

$^1$H NMR (300 MHz, DMSO-d$_6$) δ 0.94 (3H, t, J=7.5 Hz), 1.45 (6H, s), 1.54-1.62 (2H, m), 3.24-3.29 (2H, m), 7.47 (1H, s), 7.70 (1H, br s), 7.73 (2H, dd, J=4.8, 1.8 Hz), 8.62 (2H, dd, J=4.8, 1.5 Hz).

Example 19

Preparation of 1-butyl-2,2-dimethyl-6-(pyridin-4-yl)-2,3-dihydrothieno[3,2-d]pyrimidin-4(1H)-one

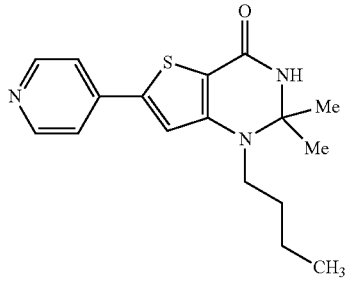 [SMILES: CCCCN1c2cc(-c3ccncc3)sc2C(=O)NC1(C)C]

Step 1

Preparation of methyl 3-(butylamino)-5-(pyridin-4-yl)thiophene-2-carboxylate

To a stirred solution of methyl 3-amino-5-(pyridin-4-yl)thiophene-2-carboxylate (1.21 g, 5.00 mmol) in DMF (25 mL) was added sodium hydride (60%, 0.220 g, 5.50 mmol). After 10 min, 1-iodobutane (0.626 mL, 5.50 mmol) was added and stirring was continued for 5 h. The mixture was poured into water (60 mL) and sat. aqueous sodium hydrogen carbonate (60 mL). Ethyl acetate (100 mL) and THF (33 mL) were added to the mixture for extraction, and the insoluble precipitate was filtered off. The organic layer was washed with brine, dried over magnesium sulfate, filtrated and concentrated at reduced pressure. The obtained residue was purified by column chromatography (Combiflash, 40 g silica gel, hexanes to 30:70 hexanes/ethyl acetate) to afford the title compound (0.460 g, 32%) as a yellow oil:

$^1$H NMR (300 MHz, DMSO-$d_6$) δ 0.93 (3H, t, J=7.5 Hz), 1.31-1.43 (2H, m), 1.51-1.61 (2H, m), 3.33-3.40 (2H, m), 3.76 (3H, s), 6.84 (1H, m), 7.58 (1H, s), 7.72 (2H, dd, J=4.8, 1.8 Hz), 8.64 (2H, dd, J=4.8, 1.8 Hz). This solid contained some impurity but was used in the next reaction without further purification.

Step 2

Preparation of 3-(butylamino)-5-(pyridin-4-yl)thiophene-2-carboxylic acid

A mixture of methyl 3-(butylamino)-5-(pyridin-4-yl)thiophene-2-carboxylate (0.460 g, 1.58 mmol), sodium methoxide (0.257 g, 4.75 mmol), methanol (6.4 mL) and water (1.6 mL) was refluxed overnight. The mixture was cooled in an ice-bath and conc. HCl (0.390 mL, 4.75 mmol) was added. The resultant yellow precipitate was collected by filtration and washed with water and methanol to afford the title compound (0.370 g, 85%) as a yellow solid:

$^1$H NMR (300 MHz, DMSO-$d_6$) δ 0.92 (3H, t, J=7.5 Hz), 1.33-1.41 (2H, m), 1.51-1.58 (2H, m), 3.32-3.36 (2H, m), 7.55 (1H, s), 7.70-7.72 (2H, d, J=6.3 Hz), 8.62 (2H, d, J=6.3 Hz); 1H of amino portion and 1H of carboxylic acid were not observed.

Step 3

Preparation of 3-(butylamino)-5-(pyridin-4-yl)thiophene-2-carboxamide

A mixture of 3-(butylamino)-5-(pyridin-4-yl)thiophene-2-carboxylic acid (0.370 g, 1.34 mmol), ammonium chloride (0.717 g, 13.4 mmol), triethylamine (1.88 mL, 13.4 mmol) and DMF (8.0 mL) was stirred for 5 min. Then, 1-hydroxybenzotriazole (0.541 g, 4.00 mmol) and 1-ethyl-3-(3-dimethylaminopropyl)carbodiimide hydrochloride (0.767 g, 4.00 mmol) were added and stirring was continued for 3 days. The mixture was then poured into sat. aqueous sodium hydrogen carbonate (100 mL) and water (60 mL). Extraction with ethyl acetate-tetrahydrofuran (3:1, 2×100 mL), washing with sat. aqueous sodium hydrogen carbonate and brine, drying over magnesium sulfate, filtration and concentration at reduced pressure gave a yellow solid. This solid was triturated with dichloromethane, and the precipitate was collected by filtration to afford the title compound (0.202 g, 55%) as a yellow solid. The filtrate was purified by column chromatography (Combiflash, 12 g silica gel, dichloromethane to ethyl acetate) to afford the additional title compound (0.067 g, 18%):

$^1$H NMR (300 MHz, DMSO-$d_6$) δ 0.92 (3H, t, J=7.5 Hz), 1.31-1.57 (4H, m), 3.25-3.33 (2H, m), 7.06 (2H, br s), 7.42 (1H, m), 7.53 (1H, s), 7.65 (2H, dd, J=4.8, 1.8 Hz), 8.62 (2H, dd, J=4.5, 1.5 Hz).

Step 4

Preparation of 1-butyl-2,2-dimethyl-6-(pyridin-4-yl)-2,3-dihydrothieno[3,2-d]pyrimidin-4(1H)-one A mixture of 3-(butylamino)-5-(pyridin-4-yl)thiophene-2-carboxamide (0.100 g, 0.400 mmol), acetone (3.0 mL), p-toluenesulfonic acid monohydrate (0.0095 g, 0.050 mmol) and acetic acid (2.0 mL) was stirred for 3 days at 70° C. in a sealed tube. The mixture was poured into sat. aqueous sodium hydrogen carbonate (100 mL). Extraction with ethyl acetate-tetrahydrofuran (2:1, 100 mL), drying over magnesium sulfate, filtration and concentration at reduced pressure gave an oil. The oil was purified by column chromatography (Combiflash, 12 g silica gel, hexane to ethyl acetate) to afford the title compound (0.0879 g, 70%) as a yellow solid:

$^1$H NMR (300 MHz, DMSO-$d_6$) δ 0.94 (3H, t, J=7.2 Hz), 1.34-1.56 (10H, m), 3.27-3.33 (2H, m), 7.44 (1H, s), 7.70-7.72 (3H, m), 8.62 (2H, d, J=6.0 Hz).

Example 20

Preparation of 2-ethyl-1,2-dimethyl-6-(pyridin-4-yl)-2,3-dihydrothieno[3,2-d]pyrimidin-4(1H)-one

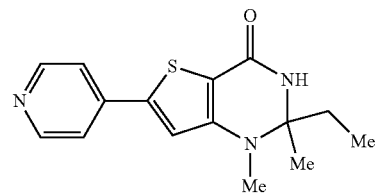 [SMILES: CCC1(C)NC(=O)c2sc(-c3ccncc3)cc2N1C]

A mixture of 3-(methylamino)-5-(pyridin-4-yl)thiophene-2-carboxamide (0.094 g, 0.40 mmol), 2-butanone (3.0 mL), p-toluenesulfonic acid monohydrate (0.0095 g, 0.050 mmol) and acetic acid (2.0 mL) was stirred for 3 days at 70° C. in a sealed tube. The mixture was poured into sat. aqueous sodium hydrogen carbonate (150 mL). Extraction with ethyl acetate-tetrahydrofuran (2:1, 100 mL, 50 mL), drying over magnesium sulfate, filtration and concentration at reduced pressure gave an oil. The oil was purified by column chromatography (Combiflash, 12 g silica gel, hexanes to ethyl acetate), then triturated with ethyl acetate-hexanes (1:1), and the precipitate was collected by filtration to afford the title compound (0.0578 g, 63%) as a yellow solid:

$^1$H NMR (300 MHz, DMSO-d$_6$) δ 0.88 (3H, t, J=7.5 Hz), 1.36 (3H, s), 1.57-1.67 (1H, m), 1.86-1.99 (1H, m), 2.90 (3H, s), 7.56 (1H, s), 7.65 (1H, br s), 7.68 (2H, dd, J=1.5, 4.5 Hz), 8.61-8.63 (2H, m).

Example 21

Preparation of 6'-(pyridin-4-yl)-4,5-dihydro-1'H-spiro[furan-3,2'-thieno[3,2-d]pyrimidin]-4'(3'H)-one

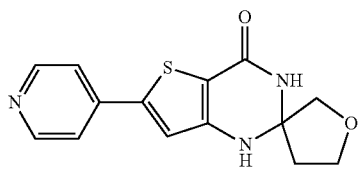 [SMILES: O=C1NC2(CCOC2)Nc2cc(-c3ccncc3)sc21]

A mixture of 3-amino-5-(pyridin-4-yl)thiophene-2-carboxamide (0.108 g, 0.500 mmol), dihydro-3(2H)-furanone (0.215 g, 2.50 mmol), p-toluenesulfonic acid monohydrate (0.0095 g, 0.050 mmol) and acetic acid (3.0 mL) was stirred for 5 h at 80° C. in a sealed tube. The mixture was poured into sat. aqueous sodium hydrogen carbonate (100 mL). Extraction with ethyl acetate-tetrahydrofuran (2:1, 100 mL, 50 mL), drying over magnesium sulfate, filtration and concentration at reduced pressure gave an oil. This oil was purified by column chromatography (Combiflash, 12 g silica gel, dichloromethane to 90:10 dichloromethane/methanol) to afford the title compound (0.0165 g, 11%) as a yellow solid:

$^1$H NMR (300 MHz, DMSO-d$_6$) δ 2.13-2.23 (2H, m), 3.61 (1H, d, J=8.7 Hz), 3.77 (1H, d, J=9.0 Hz), 3.85-3.91 (2H, m), 7.21 (1H, s), 7.63-7.66 (3H, m), 8.07 (1H, br s), 8.62 (2H, dd, J=1.8, 4.8 Hz).

Example 22

Preparation of 2-methyl-6-(pyridin-4-yl)-2-(2,2,2-trifluoroethyl)-2,3-dihydrothieno[3,2-d]pyrimidin-4(1H)-one

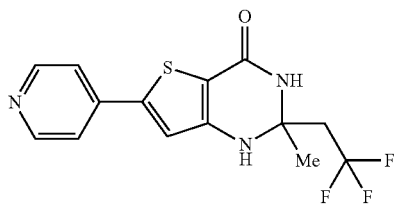 [SMILES: CC1(CC(F)(F)F)NC(=O)c2sc(-c3ccncc3)cc2N1]

A mixture of 3-amino-5-(pyridin-4-yl)thiophene-2-carboxamide (0.108 g, 0.500 mmol), 4,4,4-trifluoro-2-butanone (2.0 mL), p-toluenesulfonic acid monohydrate (0.0095 g, 0.050 mmol) and acetic acid (3.0 mL) was stirred for 2 h at 70° C. in a sealed tube. The mixture was heated to 80° C. After 3 days, the mixture was poured into sat. aqueous sodium hydrogen carbonate (150 mL). Extraction with ethyl acetate-tetrahydrofuran (2:1, 100 mL, 50 mL), drying over magnesium sulfate, filtration and concentration at reduced pressure gave an oil. This oil was purified by column chromatography (Combiflash, 12 g silica gel, dichloromethane to ethyl acetate), then triturated with ethyl acetate-hexanes (1:1), and the precipitate was collected by filtration to afford the title compound (0.0249 g, 15%) as a yellow solid:

$^1$H NMR (300 MHz, DMSO-d$_6$) δ 1.56 (3H, s), 2.69-2.76 (2H, m), 7.20 (1H, s), 7.42 (1H, br s), 7.65 (2H, d, J=5.1 Hz), 7.89 (1H, br s), 8.62 (2H, d, J=4.8 Hz).

Example 23

Preparation of 1,2-diethyl-2-methyl-6-(pyridin-4-yl)-2,3-dihydrothieno[3,2-d]pyrimidin-4(1H)-one

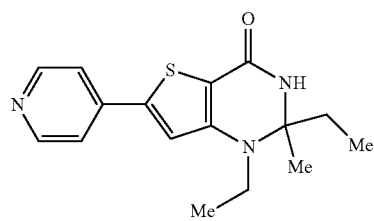 [SMILES: CCN1c2cc(-c3ccncc3)sc2C(=O)NC1(C)CC]

A mixture of 3-(ethylamino)-5-(pyridin-4-yl)thiophene-2-carboxamide (0.100 g, 0.400 mmol), 2-butanone (2.5 mL), p-toluenesulfonic acid monohydrate (0.0095 g, 0.050 mmol) and acetic acid (2.0 mL) was stirred for 1 h at 120° C. in a sealed tube. Then, this mixture was stirred for 3 h at 150° C. in a sealed tube. The mixture was poured into sat. aqueous sodium hydrogen carbonate (150 mL). Extraction with ethyl acetate (100 mL), drying over magnesium sulfate, filtration and concentration at reduced pressure gave an oil. The oil was purified by column chromatography (Combiflash, 40 g silica gel, dichloromethane to ethyl acetate) to afford the title compound (0.0547 g, 45%) as a yellow solid:

$^1$H NMR (300 MHz, DMSO-d$_6$) δ 0.87 (3H, t, J=6.9 Hz), 1.18 (3H, t, J=6.6 Hz), 1.44 (3H, s), 1.55-1.66 (1H, m), 1.87-2.01 (1H, m), 3.33-3.42 (2H, m), 7.48 (1H, s), 7.66 (1H, br s), 7.71 (2H, d, J=4.8 Hz), 8.62 (2H, d, J=4.8 Hz).

Example 24

Preparation of 2,2-diethyl-1-methyl-6-(pyridin-4-yl)-2,3-dihydrothieno[3,2-d]pyrimidin-4(1H)-one

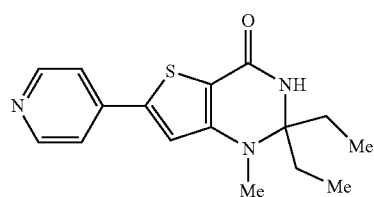 [SMILES: CCC1(CC)NC(=O)c2sc(-c3ccncc3)cc2N1C]

A mixture of 3-(methylamino)-5-(pyridin-4-yl)thiophene-2-carboxamide (0.094 g, 0.40 mmol), 3-pentanone (2.5 mL), p-toluenesulfonic acid monohydrate (0.0095 g, 0.050 mmol) and acetic acid (2.0 mL) was stirred for 1 h at 120° C. in a sealed tube. Then, this mixture was stirred for 1.5 h at 150° C. in a sealed tube. The mixture was poured into sat. aqueous sodium hydrogen carbonate (150 mL). Extraction with ethyl acetate (100 mL), drying over magnesium sulfate, filtration and concentration at reduced pressure gave an oil. This oil was purified by column chromatography (Combiflash, 40 g silica gel, dichloromethane to 95:5 dichloromethane/methanol), then triturated with ethyl acetate/hexanes (1:1), and the precipitate was collected by filtration to afford the title compound (0.0281 g, 23%) as a yellow solid:

$^1$H NMR (300 MHz, DMSO-$d_6$) δ 0.86 (6H, t, J=7.2 Hz), 1.50-1.62 (2H, m), 1.81-1.93 (2H, m), 2.88 (3H, s), 7.51 (1H s), 7.55 (1H, br s), 7.68 (2H, d, J=6.0 Hz), 8.61 (2H, d, J=6.0 Hz).

Example 25

Preparation of 2-butyl-2-methyl-6-(pyridin-4-yl)-2,3-dihydrothieno[3,2-d]pyrimidin-4(1H)-one

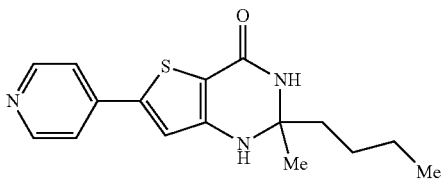 [SMILES: CCCCC1(C)NC(=O)c2sc(-c3ccncc3)cc2N1]

A mixture of 3-amino-5-(pyridin-4-yl)thiophene-2-carboxamide (0.108 g, 0.500 mmol), 2-hexanone (2.0 mL), p-toluenesulfonic acid monohydrate (0.0095 g, 0.050 mmol) and acetic acid (2.0 mL) was stirred for 3 h at 80° C. in a sealed tube. The mixture was poured into sat. aqueous sodium hydrogen carbonate (150 mL). Extraction with ethyl acetate (100 mL), drying over magnesium sulfate, filtration and concentration at reduced pressure gave an oil. This oil was purified by column chromatography (Combiflash, 12 g silica gel, dichloromethane to 90:10 dichloromethane/methanol), then triturated with ethyl acetate, and the precipitate was collected by filtration to afford the title compound (0.0747 g, 50%) as a yellow solid:

$^1$H NMR (300 MHz, DMSO-$d_6$) δ 0.87 (3H, t, J=6.6 Hz), 1.17-1.37 (7H, m), 1.65-1.68 (2H, m), 7.10 (1H, br s), 7.13 (1H, s), 7.61-7.63 (3H, m), 8.60 (2H, dd, J=1.5, 4.5 Hz).

Example 26

Preparation of 1,2,2-triethyl-6-(pyridin-4-yl)-2,3-dihydrothieno[3,2-d]pyrimidin-4(1H)-one

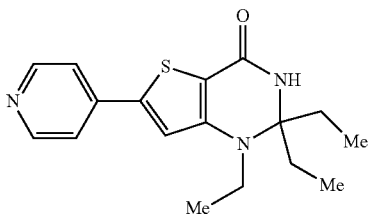 [SMILES: CCN1c2cc(-c3ccncc3)sc2C(=O)NC1(CC)CC]

A mixture of 3-(ethylamino)-5-(pyridin-4-yl)thiophene-2-carboxamide (0.100 g, 0.400 mmol), 3-pentanone (3.0 mL), p-toluenesulfonic acid monohydrate (0.0095 g, 0.050 mmol) and acetic acid (3.0 mL) was stirred for 1 h at 120° C. in a sealed tube. Then, this mixture was stirred for 2 h at 150° C. and stirring was continued for 2 days at 110° C. in a sealed tube. The mixture was poured into sat. aqueous sodium hydrogen carbonate (150 mL). Extraction with ethyl acetate (100 mL), drying over magnesium sulfate, filtration and concentration at reduced pressure gave an oil. This oil was purified by column chromatography (Combiflash, 40 g silica gel, dichloromethane to ethyl acetate), then recrystallized from ethyl acetate, and the precipitate was collected by filtration to afford the title compound (0.0194 g, 12%) as a yellow solid:

$^1$H NMR (300 MHz, DMSO-$d_6$) δ 0.88 (6H, t, J=7.2 Hz), 1.21 (3H, t, J=6.9 Hz), 1.49-1.60 (2H, m), 1.83-1.95 (2H, m), 3.33-3.37 (2H, m), 7.42 (1H, s), 7.49 (1H, br s), 7.70 (2H, dd, J=1.5, 4.5 Hz), 8.61 (2H, dd, J=1.5, 4.5 Hz).

Example 27

Preparation of 1'-ethyl-6'-(pyridin-4-yl)-1'H-spiro[cyclopentane-1,2'-thieno[3,2-d]pyrimidin]-4'(3'H)-one

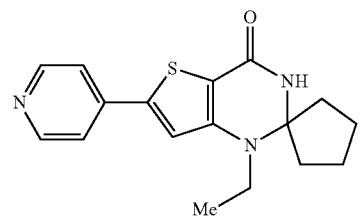 [SMILES: CCN1c2cc(-c3ccncc3)sc2C(=O)NC12CCCC2]

A mixture of 3-(ethylamino)-5-(pyridin-4-yl)thiophene-2-carboxamide (0.100 g, 0.400 mmol), cyclopentanone (2.0 mL), p-toluenesulfonic acid monohydrate (0.0095 g, 0.050 mmol) and acetic acid (2.0 mL) was stirred for 2 h at 100° C. in a sealed tube. The mixture was poured into sat. aqueous sodium hydrogen carbonate (150 mL). Extraction with ethyl acetate (100 mL, 50 mL), drying over magnesium sulfate, filtration and concentration at reduced pressure gave an oil. This oil was purified by column chromatography (Combiflash, 40 g silica gel, dichloromethane to ethyl acetate), then triturated with ethyl acetate, and the precipitate was collected by filtration to afford the title compound (0.0434 g, 28%) as a yellow solid:

$^1$H NMR (300 MHz, DMSO-$d_6$) δ 1.15 (3H, t, J=6.9 Hz), 1.63-1.99 (8H, m), 3.33-3.40 (2H, m), 7.57 (1H, s), 7.72 (2H, dd, J=1.5, 4.5 Hz), 7.91 (1H, br s), 8.61-8.63 (2H, m).

Example 28

Preparation of 2-ethyl-2-propyl-6-(pyridin-4-yl)-2,3-dihydrothieno[3,2-d]pyrimidin-4(1H)-one

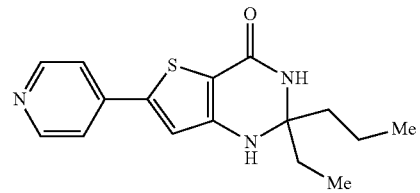 [SMILES: CCCC1(CC)NC(=O)c2sc(-c3ccncc3)cc2N1]

A mixture of 3-amino-5-(pyridin-4-yl)thiophene-2-carboxamide (0.108 g, 0.500 mmol), 3-hexanone (2.0 mL), p-toluenesulfonic acid monohydrate (0.0095 g, 0.050 mmol) and acetic acid (2.0 mL) was stirred overnight at 80° C. in a sealed tube. The mixture was poured into sat. aqueous sodium hydrogen carbonate (150 mL). Extraction with ethyl acetate (100 mL), drying over magnesium sulfate, filtration and concentration at reduced pressure gave an oil. This oil was purified by column chromatography (Combiflash, 12 g silica gel, dichloromethane to 90:10 dichloromethane/methanol), then recrystallized from methanol, and the precipitate was collected by filtration. This yellow solid contained methanol, so it was stirred in ethyl acetate (5.0 mL) for 30 min at 70° C. After cooling, the precipitate was collected by filtration to afford the title compound (0.0334 g, 22%) as a yellow solid:

$^1$H NMR (300 MHz, DMSO-$d_6$) δ 0.84-0.90 (6H, m), 1.33-1.42 (2H, m), 1.57-1.69 (4H, m), 7.04 (1H, br s), 7.11 (1H, s), 7.50 (1H, br s), 7.61 (2H, dd, J=1.5, 4.5 Hz), 8.60 (2H, dd, J=1.8, 4.5 Hz).

Example 29

Preparation of 1'-ethyl-6'-(pyridin-4-yl)-2,3,5,6-tetrahydro-1'H-spiro[pyran-4,2'-thieno[3,2-d]pyrimidin]-4'(3'H)-one

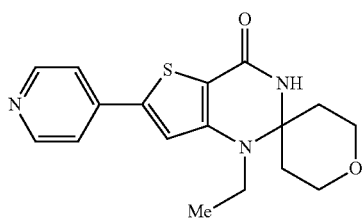 [SMILES: CCN1c2cc(-c3ccncc3)sc2C(=O)NC12CCOCC2]

A mixture of 3-(ethylamino)-5-(pyridin-4-yl)thiophene-2-carboxamide (0.100 g, 0.400 mmol), tetrahydro-4H-pyran-4-one (1.0 mL), p-toluenesulfonic acid monohydrate (0.0095 g, 0.050 mmol) and acetic acid (2.0 mL) was stirred for 3 h at 100° C. in a sealed tube. The mixture was poured into sat. aqueous sodium hydrogen carbonate (150 mL). Extraction with ethyl acetate/THF (4:1, 100 mL, 50 mL), drying over magnesium sulfate, filtration and concentration at reduced pressure gave an oil. This oil was purified by column chromatography (Combiflash, 12 g silica gel, dichloromethane to 90:10 dichloromethane/methanol), then triturated with ethyl acetate, and the precipitate was collected by filtration to afford the title compound (0.0715 g, 54%) as a yellow solid:

$^1$H NMR (300 MHz, DMSO-$d_6$) δ 1.12 (3H, t, J=6.9 Hz), 1.88-1.99 (4H, m), 3.48 (2H, dd, J=7.2, 14.1 Hz), 3.72 (4H, m), 7.62 (1H, s), 7.72 (2H, dd, J=1.5, 4.5 Hz), 7.96 (1H, br s), 8.63 (2H, dd, J=1.5, 4.5 Hz).

Example 30

Preparation of 1-benzyl-2,2-dimethyl-6-(pyridin-4-yl)-2,3-dihydrothieno[3,2-d]pyrimidin-4(1H)-one

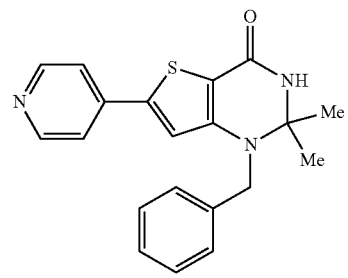 [SMILES: CC1(C)NC(=O)c2sc(-c3ccncc3)cc2N1Cc1ccccc1]

Step 1

Preparation of methyl 3-(benzylamino)-5-(pyridin-4-yl) thiophene-2-carboxylate

A mixture of methyl 3-amino-5-(pyridin-4-yl)thiophene-2-carboxylate (1.17 g, 5.00 mmol), benzaldehyde (1.0 mL, 1.0 g, 10 mmol), sodium triacetoxyborohydride (4.24 g, 20.0 mmol), acetic acid (0.60 g, 10 mmol) and THF (30 mL) was stirred for 3 days. The mixture was poured into sat. aqueous sodium hydrogen carbonate (150 mL). The organic materials were extracted with ethyl acetate (100 mL, 50 mL). The combined organic layer was washed with brine, dried over magnesium sulfate, filtrated and concentrated at reduced pressure. The obtained residue was purified by column chromatography (Combiflash, 40 g silica gel, hexanes to ethyl acetate) to afford the title compound (1.22 g, 75%) as a yellow solid:

$^1$H NMR (300 MHz, DMSO-$d_6$) δ 3.77 (3H, s), 4.61 (2H, d, J=6.6 Hz), 7.22-7.40 (6H, m), 7.56 (1H, s), 7.66 (2H, dd, J=1.8, 4.8 Hz), 8.62 (2H, dd, J=1.5, 4.5 Hz).

Step 2

Preparation of 3-(benzylamino)-5-(pyridin-4-yl) thiophene-2-carboxylic acid

A mixture of methyl 3-(benzylamino)-5-(pyridin-4-yl) thiophene-2-carboxylate (1.22 g, 3.76 mmol), sodium methoxide (0.61 g, 11 mmol), methanol (15 mL) and water (3.75 mL) was heated at reflux for 1 h. THF (10 mL) was added to the reaction mixture. After heating overnight, the mixture was cooled in an ice-bath, and conc. HCl (0.931 mL, 11.3 mmol) was added to the mixture. After 10 min, the resulting yellow precipitate was collected by filtration and washed with water and methanol to afford the title compound (1.16 g, 99%) as a yellow solid:

$^1$H NMR (300 MHz, DMSO-$d_6$) δ 4.59 (2H, s), 7.22-7.43 (6H, m), 7.54 (1H, s), 7.65 (2H, dd, J=1.5, 4.5 Hz), 8.61 (2H, dd, J=1.5, 4.5 Hz), 12.52 (1H, br s).

Step 3

Preparation of 3-(benzylamino)-5-(pyridin-4-yl) thiophene-2-carboxamide

A mixture of 3-(benzylamino)-5-(pyridin-4-yl)thiophene-2-carboxylic acid (1.16 g, 3.73 mmol), ammonium chloride (2.00 g, 37.3 mmol), triethylamine (5.23 mL, 3.80 g, 37.3 mmol) and DMF (19 mL) was stirred for 10 min. Then, 1-hydroxybenzotri-azole (1.51 g, 11.2 mmol) and 1-ethyl-3-(3-dimethylaminopropyl) carbodiimide hydrochloride (2.15 g, 11.2 mmol) were added and stirring was continued for 3 days. The mixture was then poured into sat. aqueous sodium hydrogen carbonate (100 mL) and water (100 mL). The mixture was extracted with ethyl acetate (2×100 mL), and the organic layer was washed with sat. aqueous sodium hydrogen carbonate and brine, dried over magnesium sulfate and filtrated. The filtrate was concentrated at reduced pressure to give a yellow solid. This solid was triturated with dichloromethane (20 mL), and the precipitate was collected by filtration to afford the title compound (0.689 g, 59%) as a yellow solid. The filtrate was purified by column chromatography (Combiflash, 12 g silica gel, dichloromethane to ethyl acetate) to afford the additional title compound (0.103 g, 8.9%) as an yellow solid:

$^1$H NMR (300 MHz, DMSO-$d_6$) δ 4.54 (2H, d, J=6.3 Hz), 7.14 (2H, br s), 7.23-7.38 (5H, m), 7.55 (1H, s), 7.59 (2H, dd, J=1.5, 4.5 Hz), 7.87 (1H, t, J=6.6 Hz), 8.60 (2H, dd, J=1.8, 4.5 Hz).

Step 4

Preparation of 1-benzyl-2,2-dimethyl-6-(pyridin-4-yl)-2,3-dihydrothieno[3,2-d]pyrimidin-4(1H)-one A mixture of 3-(benzylamino)-5-(pyridin-4-yl)thiophene-2-carboxamide (0.124 g, 0.400 mmol), acetone (3.0 mL), p-toluenesulfonic acid monohydrate (0.0095 g, 0.050 mmol) and acetic acid (2.0 mL) was stirred for 3 days at 70° C. in a sealed tube. The mixture was poured into sat. aqueous sodium hydrogen carbonate (150 mL). Extraction with ethyl acetate (100 mL, 50 mL), drying over magnesium sulfate, filtration and concentration at reduced pressure gave an oil. This oil was purified by column chromatography (Combiflash, 40 g silica gel, dichloromethane to ethyl acetate), then triturated with ethyl acetate/hexanes (1:1), and the precipitate was collected by filtration to afford the title compound (0.0841 g, 60%) as a yellow solid:

$^1$H NMR (300 MHz, DMSO-$d_6$) δ 1.46 (6H, s), 4.66 (2H, s), 7.22-7.36 (5H, m), 7.42 (1H, s), 7.61 (2H, dd, J=1.5, 4.5 Hz), 7.84 (1H, br s), 8.58 (2H, dd, J=1.8, 4.5 Hz).

Example 31

Preparation of 1'-ethyl-6'-(pyridin-4-yl)-1'H-spiro[cyclohexane-1,2'-thieno[3,2-d]pyrimidin]-4'(3'H)-one

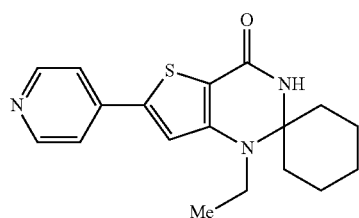 [SMILES: CCN1c2cc(-c3ccncc3)sc2C(=O)NC12CCCCC2]

A mixture of 3-(ethylamino)-5-(pyridin-4-yl)thiophene-2-carboxamide (0.100 g, 0.400 mmol), cyclohexanone (2.0 mL, 1.9 g, 19 mmol), p-toluenesulfonic acid monohydrate (0.0095 g, 0.050 mmol) and acetic acid (2.0 mL) was stirred overnight at 100° C. in a sealed tube. The mixture was poured into sat. aqueous sodium hydrogen carbonate (150 mL). Extraction with ethyl acetate (100 mL, 30 mL), drying over magnesium sulfate, filtration and concentration at reduced pressure gave a solid. The solid was triturated with DMF/dichloromethane, then the precipitate was collected by filtration to afford the title compound (0.0738 g, 56%) as a yellow solid:

$^1$H NMR (300 MHz, DMSO-$d_6$) δ 1.11-1.22 (4H, m), 1.54-1.66 (7H, m), 1.99-2.01 (2H, m), 3.43-3.50 (2H, m), 7.54 (1H, br s), 7.56 (1H, s), 7.70-7.72 (2H, m), 8.61-8.63 (2H, m).

Example 32

Preparation of 2,2-dipropyl-6-(pyridin-4-yl)-2,3-dihydrothieno[3,2-d]pyrimidin-4(1H)-one

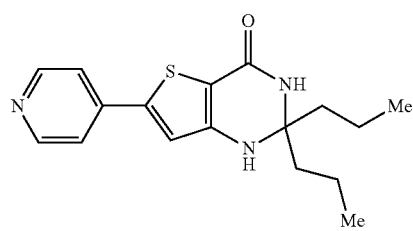 [SMILES: CCCC1(CCC)NC(=O)c2sc(-c3ccncc3)cc2N1]

A mixture of 3-amino-5-(pyridin-4-yl)thiophene-2-carboxamide (0.120 g, 0.550 mmol), 4-heptanone (1.0 mL), p-toluenesulfonic acid monohydrate (0.0095 g, 0.050 mmol) and acetic acid (1.5 mL) was stirred for 1 h at 100° C. in a sealed tube. Then, this mixture was stirred for 2 h at 120° C. and stirring was continued for 2 h at 110° C. The mixture was poured into sat. aqueous sodium hydrogen carbonate (150 mL). Extraction with ethyl acetate, drying over magnesium sulfate, filtration and concentration at reduced pressure gave a solid. This solid was triturated with dichloromethane (10 mL), and the precipitate was collected by filtration. Then, the obtained solid was stirred at 60° C. in ethyl acetate (5 mL). After 10 min, the mixture was cooled, and the precipitate was collected by filtration to afford the title compound (0.0406 g, 23%) as a yellow solid:

$^1$H NMR (300 MHz, DMSO-$d_6$) δ 0.86 (6H, t, J=7.2 Hz), 1.34-1.63 (8H, m), 7.05 (1H, br s), 7.10 (1H, s), 7.51 (1H, br s), 7.61 (2H, dd, J=1.2, 4.5 Hz), 8.60 (2H, dd, J=1.5, 4.5 Hz).

Example 33

Preparation of 6'-(pyridin-4-yl)-1'H-spiro[cycloheptane-1,2'-thieno[3,2-d]pyrimidin]-4'(3'H)-one

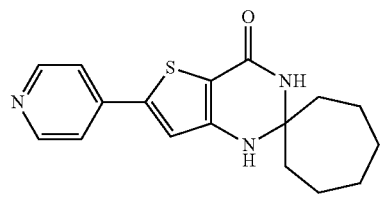 [SMILES: O=C1NC2(CCCCCC2)Nc2cc(-c3ccncc3)sc21]

A mixture of 3-amino-5-(pyridin-4-yl)thiophene-2-carboxamide (0.108 g, 0.500 mmol), cycloheptanone (1.0 mL), p-toluenesulfonic acid monohydrate (0.0095 g, 0.050 mmol)

and acetic acid (2.0 mL) was stirred for 2 h at 110° C. in a sealed tube. Then, this mixture was poured into sat. aqueous sodium hydrogen carbonate. Extraction with ethyl acetate, washing with brine, drying over magnesium sulfate, filtration and concentration at reduced pressure were carried out. This residue was purified by column chromatography (Combiflash, 12 g silica gel, dichloromethane to 90:10 dichloromethane/methanol), then recrystallized from methanol-ethyl acetate and the crystals were collected by filtration to afford the title compound (0.0226 g, 14%) as a yellow solid:

$^1$H NMR (300 MHz, DMSO-d$_6$) δ 1.52 (8H, m), 1.86-2.02 (4H, m), 7.13 (1H, s), 7.26 (1H, brs), 7.62 (2H, dd, J=4.8, 1.8 Hz), 7.74 (1H, br s), 8.61 (2H, dd, J=4.8, 1.5 Hz).

Example 34

Preparation of 2,2-dimethyl-6-(1H-pyrazol-4-yl)-2,3-dihydrothieno[3,2-d]pyrimidin-4(1H)-one

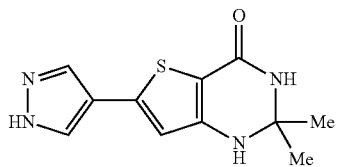 [SMILES: CC1(C)NC(=O)c2sc(-c3cn[nH]c3)cc2N1]

Step 1

Preparation of methyl 3-(2,2,2-trifluoroacetamido)thiophene-2-carboxylate

To a stirred solution of methyl 3-amino-thiophene-2-carboxylate (25.0 g, 159 mmol) in acetonitrile (325 mL) at 0° C. were added pyridine (15.5 mL) and trifluoroacetic anhydride (29.3 mL). After 5 min, the mixture was allowed to warm to room temperature and the mixture was stirred for an additional 20 min. The mixture was poured into ice-water (3.0 L) and the mixture was stirred for 15 min. The precipitate was collected by filtration, washed with water and dried under vacuum to afford the title compound (37.3 g, 93%) as a pink solid:

$^1$H NMR (300 MHz, DMSO-d$_6$) δ 3.86 (3H, s), 7.72 (1H, d, J=5.4 Hz), 8.03 (1H, d, J=5.4 Hz), 11.17 (1H, br s).

Step 2

Preparation of methyl 5-bromo-3-(2,2,2-trifluoroacetamido)thiophene-2-carboxylate To stirred tetrahydrofuran (100 mL) at −78° C. were added dropwise diisopropylamine (9.00 mL, 63.9 mmol) and n-butyl lithium (37.1 mL, 59.4 mmol, 1.6 M solution in n-hexane) successively. The reaction mixture was allowed to warm to 0° C. and stirred for additional 10 min. The mixture was cooled to −78° C. again and methyl 3-(2,2,2-trifluoroacetamido)thiophene-2-carboxylate (4.56 g, 18.0 mmol) was added to the mixture. After 1 h, bromine (2.78 mL, 54.0 mmol) was added to the mixture, and stirring was continued at −78° C. for 2 h and at room temperature for 30 min. The mixture was then poured into sat. aqueous sodium hydrogen carbonate (180 mL). Extraction with ethyl acetate (150 mL), washing with brine, drying over magnesium sulfate, filtration and concentration at reduced pressure gave an oil. The oil was purified by column chromatography (Combiflash, 12 g silica gel, hexanes to 90:10 hexanes/ethyl acetate) to afford a mixture of the title compound and methyl 3-aminothiophene-2-carboxylate (1.86 g) as a white solid. The ratio was about 2:1 estimated by $^1$H NMR analysis:

$^1$H NMR (300 MHz, DMSO-d$_6$) δ 3.84 (3H, s), 7.79 (1H, s), 11.22 (1H, br s).

Step 3

Preparation of methyl 3-amino-5-bromothiophene-2-carboxylate

A mixture of methyl 5-bromo-3-(2,2,2-trifluoroacetamido) thiophene-2-carboxylate (1.86 g), potassium carbonate (3.72 g, 26.9 mmol), methanol (40 mL) and water (10 mL) was stirred at room temperature for 1.5 h. The mixture was concentrated in vacuo and then ethyl acetate and water were added to the residue for extraction. The organic layer was dried over magnesium sulfate, filtered and concentrated in vacuo. The residue was purified by column chromatography (Combiflash, silica gel, hexanes to 90:10 hexanes/ethyl acetate) to afford the title compound (0.781 g, 18% from methyl 3-(2,2,2-trifluoroacetamido)thiophene-2-carboxylate) as a white solid:

$^1$H NMR (300 MHz, DMSO-d$_6$) δ 3.70 (3H, s), 6.69 (2H, br s), 6.75 (1H, s).

Step 4

Preparation of 3-amino-5-bromothiophene-2-carboxylic acid

A mixture of methyl 3-amino-5-bromothiophene-2-carboxylate (0.236 g, 1.00 mmol), sodium methoxide (0.162 g, 3.00 mmol), methanol (4.0 mL) and water (1.0 mL) was stirred at 75° C. for 5 h. The mixture was cooled in an ice-bath and conc. HCl (0.250 mL, 3.00 mmol) was added. The mixture was concentrated in vacuo to remove methanol. The residue was triturated with water, and the precipitate was collected by filtration and washed with water to afford the title compound (0.154 g, 69%) as a pale orange solid:

$^1$H NMR (300 MHz, DMSO-d$_6$) δ 6.72 (1H, s). The 2H of the amino group and 1H of carboxylate were not observed respectively.

Step 5

Preparation of 3-amino-5-bromothiophene-2-carboxamide

A mixture of 3-amino-5-bromothiophene-2-carboxylic acid (0.154 g, 0.690 mmol), ammonium chloride (0.369 g, 6.90 mmol), triethylamine (0.964 mL, 6.90 mmol) and DMF (4.0 mL) was stirred for 10 min. Then, 1-hydroxybenzotriazole (0.284 g, 2.10 mmol) and 1-ethyl-3-(3-dimethylaminopropyl)carbodiimide hydrochloride (0.403 g, 2.10 mmol) were added and stirring was continued for 4 days. The mixture was then poured into sat. aqueous sodium hydrogen carbonate (100 mL). Extraction with ethyl acetate (60 mL, 20 mL), washing with brine, drying over magnesium sulfate, filtration and concentration at reduced pressure gave an oil. This oil was purified by column chromatography (Combiflash, silica gel, hexanes to 90:10 hexanes/ethyl acetate) to afford the title compound (0.118 g, 78%) as a brown oil:

¹H NMR (300 MHz, DMSO-d₆) δ 6.56 (2H, br s), 6.70 (1H, s), 6.92 (2H, br s).

Step 6

Preparation of 6-bromo-2,2-dimethyl-2,3-dihydrothieno[3,2-d]pyrimidin-4(1H)-one

A mixture of 3-amino-5-bromothiophene-2-carboxamide (0.118 g, 0.530 mmol), acetone (2.0 mL), p-toluenesulfonic acid monohydrate (0.0095 g, 0.050 mmol) and acetic acid (1.0 mL) was stirred for 1 h at 70° C. The mixture was poured into sat. aqueous sodium hydrogen carbonate (100 mL). Extraction with ethyl acetate (70 mL), washing with brine, drying over magnesium sulfate, filtration and concentration at reduced pressure gave the title compound (0.125 g, 90%) as a brown solid:

¹H NMR (300 MHz, DMSO-d₆) δ 1.38 (6H, s), 6.69 (1H, s), 7.18 (1H, br s), 7.56 (1H, br s).

Step 7

Preparation of 2,2-dimethyl-6-(1H-pyrazol-4-yl)-2,3-dihydrothieno[3,2-d]pyrimidin-4(1H)-one A mixture of 6-bromo-2,2-dimethyl-2,3-dihydrothieno[3,2-d]pyrimidin-4(1H)-one (0.125 g, 0.480 mmol), 4-pyrazoleboronic acid pinacol ester (0.279 g, 1.44 mmol), sodium carbonate (0.254 g, 2.40 mmol), 1,2-dimethoxyethane (2.4 mL) and water (1.2 mL) was purged with argon. Then, 1,1'-bis (diphenylphosphino)ferrocenepalladium (II) dichloride dichloromethane adduct (0.041 g, 0.050 mmol) was added to the mixture and the mixture was purged with argon again. The mixture was stirred at 120° C. for 4 h in a sealed tube. The mixture was poured into sat. aqueous sodium hydrogen carbonate (50 mL). Extraction with ethyl acetate/THF (3:1, 2×50 mL), drying over magnesium sulfate, filtration and concentration at reduced pressure were carried out. The residue was purified by column chromatography (Combiflash, 12 g silica gel, dichloromethane to 90:10 dichloromethane/methanol). The fractions containing the desired product were collected. Some amount of starting material was recovered, reacted and purified with the above conditions again. The fractions containing the desired product were combined and concentrated in vacuo. This residue was further purified by column chromatography (Combiflash, 12 g silica gel, ethyl acetate to 90:10 ethyl acetate/methanol), then triturated with dichloromethane. The precipitate was collected by filtration to afford the title compound (0.0308 g, 26%) as a yellow solid:

¹H NMR (300 MHz, DMSO-d₆) δ 1.40 (6H, s), 6.61 (1H, s), 6.98 (1H, s), 7.36 (1H, s), 7.80 (1H, s), 8.16 (1H, s), 13.12 (1H, br s).

Example 35

Preparation of 6-(pyridin-4-yl)-2',3',5',6'-tetrahydro-1H-spiro [thieno[3,2-d]pyrimidine-2,4'-thiopyran]-4 (3H)-one

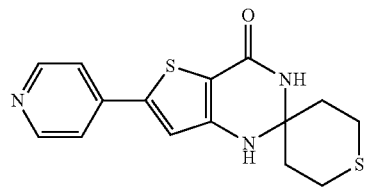 [SMILES: O=C1NC2(CCSCC2)Nc2cc(-c3ccncc3)sc21]

To a solution of 3-amino-5-(pyridin-4-yl)thiophene-2-carboxamide (0.200 g, 0.910 mmol) and tetrahydrothiopyran-4-one (0.528 g, 4.55 mmol) in glacial acetic acid (6 mL) was added p-toluenesulfonic acid monohydrate (0.017 g, 0.091 mmol). The mixture was heated at 80° C. overnight. Then, the mixture was concentrated, and then the residue was dissolved in methanol (20 mL). Solid NaHCO₃ (1.00 g, 11.9 mmol) was added, and the mixture was stirred briefly. The solvent was then removed, and the obtained residue was chromatographed (Combiflash, silica gel, dichloromethane to 93:7 dichloromethane/methanol) to give the title compound (0.263 g, 91%) as a yellow solid:

¹H NMR (500 MHz, DMSO-d₆) δ 1.90-1.96 (2H, m), 2.17-2.20 (2H, m), 2.63-2.65 (2H, m), 2.78-2.83 (2H, m), 7.18 (1H, s), 7.27 (1H, s), 7.61-7.62 (2H, m), 7.79 (1H, s), 8.61-8.62 (2H, m).

Example 36

Preparation of 6-(pyridin-4-yl)-2',3',5',6'-tetrahydro-1H-spiro [thieno[3,2-d]pyrimidine-2,4'-thiopyran]-4 (3H)-one 1',1'-dioxide

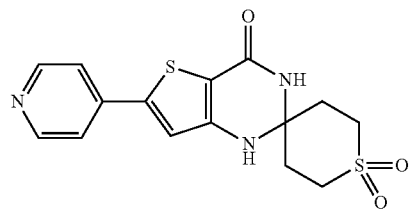 [SMILES: O=C1NC2(CCS(=O)(=O)CC2)Nc2cc(-c3ccncc3)sc21]

Step 1

Preparation of tetrahydro-4H-thiopyran-4-one 1,1-dioxide

To a stirred solution of tetrahydrothiopyran-4-one (0.400 g, 3.40 mmol) in acetonitrile (4.5 mL) was added Na₂EDTA (3 mL, 0.0004 M in water). Solid NaHCO₃ (2.70 g, 32.0 mmol) and OXONE (trade name, 6.30 g, 10.3 mmol) were combined separately and this dry mixture was added to the reaction mixture over 30 min. Then, the reaction was allowed to stir for 50 min. The mixture was diluted with dichloromethane (80 mL) and the white inorganic material was removed by filtration. The filtrate was dried over magnesium sulfate and concentrated to give the title compound (0.326 g, 64%) as a white solid:

$^1$H NMR (300 MHz, CDCl$_3$) δ 2.97-3.01 (4H, m), 3.36-3.41 (4H, m).

Step 2

Preparation of 6-(pyridin-4-yl)-2',3',5',6'-tetrahydro-1H-spiro [thieno[3,2-d]pyrimidine-2,4'-thiopyran]-4(3H)-one 1',1'-dioxide To a stirred solution of 3-amino-5-(pyridin-4-yl)thiophene-2-carboxamide (0.050 g, 0.23 mmol) in acetic acid (3 mL) were added tetrahydro-4H-thiopyran-4-one 1,1-dioxide (0.068 g, 0.46 mmol) and p-toluenesulfonic acid (0.0040 g, 0.023 mmol). The mixture was heated at 80° C. overnight. Then, the solvent was removed and the obtained residue was taken up in methanol (20 mL). Solid NaHCO$_3$ (1.5 g) was added, and the mixture was stirred for 10 min. The cloudy suspension was filtered and the collected solids were washed with methanol (20 mL) followed by water (30 mL) to give the title compound (0.0195 g, 24%) as a yellow solid:

$^1$H NMR (500 MHz, DMSO-d$_6$) δ 2.29-2.38 (4H, m), 3.16-3.27 (4H, m), 7.21 (1H, s), 7.56 (1H, s), 7.65 (2H, d, J=5.5 Hz), 8.06 (1H, s), 8.62 (2H, d, J=6.0 Hz).

Example 37

Preparation of N-methyl-4'-oxo-6'-(pyridin-4-yl)-3',4'-dihydro-1H,1'H-spiro[piperidine-4,2'-thieno[3,2-d]pyrimidine]-1-carboxamide

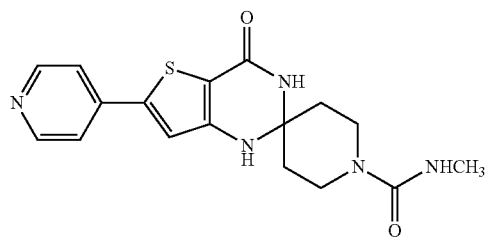 [SMILES: CNC(=O)N1CCC2(CC1)NC(=O)c1sc(-c3ccncc3)cc1N2]

A stirred solution of 6'-(pyridin-4-yl)-1'H-spiro [piperidine-4,2'-thieno[3,2-d]pyrimidin]-4'(3'H)-one (0.065 g, 0.22 mmol) and triethylamine (0.090 mL, 0.66 mmol) in tetrahydrofuran (5 mL) was cooled to 0° C. in an ice bath. Methylisocyanate (0.014 g, 0.24 mmol) was added, and the reaction was allowed to warm to room temperature overnight. Then, the solvent was removed and the obtained residue was diluted with methanol (25 mL) and the mixture was stirred with solid NaHCO$_3$ (1.5 g) for 20 min. Then, the solids were removed by filtration. The filtrate was concentrated to give a yellow solid, which was triturated with water (20 mL) and collected by filtration. This solid product was triturated with ethyl acetate to give the title compound (0.0439 g, 61%) as a yellow solid:

$^1$H NMR (500 MHz, DMSO-d$_6$) δ 1.68-1.73 (2H, m), 1.81-1.84 (2H, m), 2.56 (3H, d, J=4.0 Hz), 3.20-3.24 (2H, m), 3.56-3.59 (2H, m), 6.44-6.45 (1H, m), 7.19 (1H, s), 7.28 (1H, s), 7.62-7.63 (2H, m), 7.77 (1H, s), 8.61-8.62 (2H, m).

Example 38

Preparation of 1-(phenylcarbonyl)-6'-(pyridin-4-yl)-1'H-spiro [piperidine-4,2'-thieno[3,2-d]pyrimidin]-4'(3'H)-one

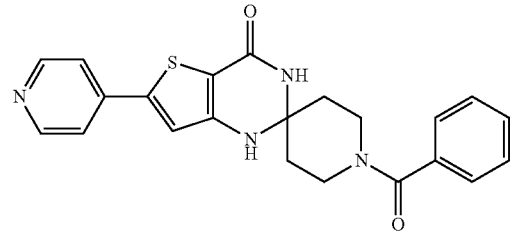 [SMILES: O=C1NC2(CCN(C(=O)c3ccccc3)CC2)Nc2cc(-c3ccncc3)sc21]

A stirred solution of 6'-(pyridin-4-yl)-1'H-spiro [piperidine-4,2'-thieno[3,2-d]pyrimidin]-4'(3'H)-one (0.0500 g, 0.170 mmol) and triethylamine (0.070 mL, 0.51 mmol) in tetrahydrofuran (4 mL) was cooled to 0° C. in an ice bath. A solution of benzoyl chloride (0.0260 g, 0.190 mmol) in tetrahydrofuran (0.1 mL) was added, and the reaction was allowed to warm to room temperature overnight. Then, the solvent was removed and the obtained residue was diluted with methanol (25 mL) and the mixture was stirred with solid NaHCO$_3$ (1.5 g) for 20 min. Then, the solids were removed by filtration. The filtrate was concentrated to give a yellow solid, which was triturated with water and collected by filtration. This solid product was recrystallized from hot methanol/hexanes to give the title compound (0.0315 g, 45%) as a yellow solid:

$^1$H NMR (500 MHz, DMSO-d$_6$) δ 1.82-1.97 (4H, m), 3.41-3.97 (4H, m), 7.21 (1H, s), 7.36-7.38 (3H, m), 7.46-7.47 (3H, m), 7.63-7.64 (2H, m), 7.84 (1H, s), 8.61-8.62 (2H, m).

Example 39

Preparation of 1-(phenylacetyl)-6'-(pyridin-4-yl)-1'H-spiro [piperidine-4,2'-thieno[3,2-d]pyrimidin]-4'(3'H)-one

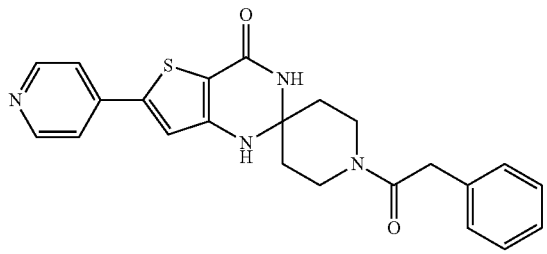 [SMILES: O=C1NC2(CCN(C(=O)Cc3ccccc3)CC2)Nc2cc(-c3ccncc3)sc21]

To a stirred solution of 6'-(pyridin-4-yl)-1'H-spiro [piperidine-4,2'-thieno[3,2-d]pyrimidin]-4'(3'H)-one (0.050 g, 0.17 mmol) in DMF (5 mL) were added phenylacetic acid (0.030 g, 0.22 mmol), N,N-diisopropylethylamine (0.12 mL, 0.68 mmol), 1-ethyl-3-(3-dimethylaminopropyl)carbodiimide hydrochloride (0.050 g, 0.26 mmol) and hydroxybenzotriazole (0.035 g, 0.26 mmol). The mixture was allowed to stir overnight. Then, the reaction was poured into saturated NaHCO$_3$ (75 mL) and the mixture was extracted with 3:1 tetrahydrofuran/ethyl acetate (3×75 mL). The combined organic layers were concentrated and the residue was diluted with water (5 mL) and sonicated for 1 min. Then, the solids were collected by filtration to give the title compound (0.0151 g, 21%) as a yellow solid:

$^1$H NMR (500 MHz, DMSO-$d_6$) δ 1.68-1.76 (2H, m), 1.77-1.84 (2H, m), 3.30-3.35 (1H, m), 3.43-3.47 (1H, m), 3.69-3.78 (3H, m), 3.85-3.88 (1H, m), 7.18 (1H, s), 7.22-7.24 (3H, m), 7.30-7.33 (3H, m), 7.62-7.63 (2H, m), 7.83 (1H, s), 8.60-8.62 (2H, m).

Example 40

Preparation of 6-(pyridin-4-yl)-2',3',5',6'-tetrahydro-1H-spiro [thieno[3,2-d]pyrimidine-2,4'-thiopyran]-4(3H)-one 1'-oxide

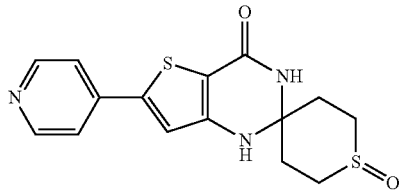 [SMILES: O=C1NC2(CCS(=O)CC2)Nc2cc(-c3ccncc3)sc21]

Step 1

Preparation of tetrahydro-4H-thiopyran-4-one 1-oxide

To a stirred solution of tetrahydrothiopyran-4-one (0.500 g, 4.30 mmol) in 15:1 methanol/water (10 mL) was added sodium periodate (0.962 g, 4.50 mmol). The mixture was allowed to stir overnight. Then, the reaction was diluted with ethyl acetate (50 mL) and the white solid was filtered off. The filtrate was concentrated several times with ethyl acetate to give the title compound (0.241 g, 42%) as a white solid:

$^1$H NMR (300 MHz, DMSO-$d_6$) δ 1.75-1.80 (2H, m), 2.01-2.11 (2H, m), 2.68-2.82 (4H, m).

Step 2

Preparation of 6-(pyridin-4-yl)-2',3',5',6'-tetrahydro-1H-spiro [thieno[3,2-d]pyrimidine-2,4'-thiopyran]-4(3H)-one 1'-oxide To a stirred solution of 3-amino-5-(pyridin-4-yl)thiophene-2-carboxamide (0.050 g, 0.23 mmol) in acetic acid (3 mL) were added tetrahydro-4H-thiopyran-4-one 1-oxide (0.061 g, 0.46 mmol) and p-toluenesulfonic acid (0.0040 g, 0.023 mmol). The mixture was heated at 80° C. overnight. Then, the solvent was removed and the obtained residue was taken up in methanol (20 mL). Solid NaHCO$_3$ (1.5 g) was added, and the mixture was stirred for 10 min. The mixture was filtered, and the filtrate was chromatographed (Combiflash, silica gel, dichloromethane to 80:20 dichloromethane/methanol) to give the title compound (0.0127 g, 16%) as a yellow solid:

$^1$H NMR (300 MHz, DMSO-$d_6$) δ 2.07-2.12 (2H, m), 2.27-2.34 (2H, m), 2.87-2.91 (2H, m), 3.00-3.09 (2H, m), 7.18 (1H, s), 7.54 (1H, s), 7.64-7.66 (2H, m), 7.96 (1H, s), 8.61-8.63 (2H, m).

Example 41

Preparation of 6-(2-aminopyrimidin-4-yl)-2,2-dimethyl-2,3-dihydrothieno[3,2-d]pyrimidin-4(1H)-one

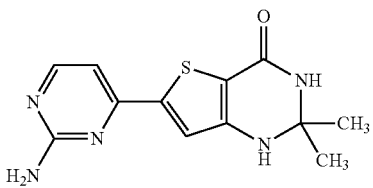

Step 1

Preparation of 2-(methylsulfonyl)-4-(tributylstannanyl)pyrimidine

To a mixture of 2-(methylthio)-4-(tri-n-butylstannyl)pyrimidine (0.800 g, 1.92 mmol) in dichloromethane (110 mL) at 0° C. was added 3-chloroperbenzoic acid (~77%, 0.946 g, 4.22 mmol), and the reaction was stirred at 0° C. for 7 h. Then, the reaction mixture was washed with sat. sodium bisulfite (30 mL), sat. NaHCO$_3$ (2×50 mL) and brine (50 mL), dried over magnesium sulfate, filtered and concentrated, and the residue was purified by flash chromatography (Combiflash, neutral alumina, hexanes to 80:20 hexanes/ethyl acetate) to give the title compound (0.397 g, 46%) as a colorless oil:

$^1$H NMR (300 MHz, CDCl$_3$) δ 0.80-1.80 (27H, m), 3.37 (3H, s), 7.60-7.66 (1H, m), 8.63-8.69 (1H, m).

Step 2

Preparation of 2,2-dimethyl-6-[2-(methylsulfonyl)pyrimidin-4-yl]-2,3-dihydrothieno[3,2-d]pyrimidin-4(1H)-one A mixture of 6-bromo-2,2-dimethyl-2,3-dihydrothieno[3,2-d]pyrimidin-4(1H)-one (0.110 g, 0.420 mmol), 2-(methylsulfonyl)-4-(tributylstannyl)pyrimidine (0.225 g, 0.504 mmol) and tetrakis(triphenylphosphine)palladium (0) (0.097 g, 0.084 mmol) in 1,4-dioxane (10 mL) was purged with nitrogen and microwave-irradiated at 150° C. for 1 h. Then, the reaction mixture was cooled, and concentrated with silica gel, and the residue was purified by flash chromatography (Combiflash, silica gel, ethyl acetate) to give the title compound (0.080 g, 56%) as a yellow solid:

$^1$H NMR (300 MHz, DMSO-$d_6$) δ 1.43 (6H, s), 3.44 (3H, s), 7.21 (1H, s), 7.55 (1H, s), 7.84 (1H, s), 8.27 (1H, d, J=5.4 Hz), 9.06 (1H, d, J=5.4 Hz).

Step 3

Preparation of 6-(2-aminopyrimidin-4-yl)-2,2-dimethyl-2,3-dihydrothieno[3,2-d]pyrimidin-4(1H)-one A mixture of 2,2-dimethyl-6-[2-(methylsulfonyl)pyrimidin-4-yl]-2,3-dihydrothieno[3,2-d]pyrimidin-4(1H)-one (0.044 g, 0.13 mmol) and 7 M ammonia in methanol (2.0 mL, 14 mmol) in 1,4-dioxane (8 mL) was microwave-irradiated at 120° C. for 75 min. Then, the reaction mixture was cooled, and concentrated with silica gel, and the residue was purified twice by flash chromatography (Combiflash, silica gel, ethyl acetate to 90:10 ethyl acetate/methanol) to give the title compound (0.019 g, 53%) as a yellow solid:
$^1$H NMR (500 MHz, DMSO-d$_6$) δ 1.41 (6H, s), 6.73 (2H, s), 7.00 (1H, s), 7.02 (1H, d, J=5.0 Hz), 7.21 (1H, s), 7.63 (1H, s), 8.28 (1H, d, J=5.0 Hz).

Example 42

Preparation of methyl (2-methyl-4-oxo-6-(pyridin-4-yl)-1,2,3,4-tetrahydrothieno[3,2-d]pyrimidin-2-yl)acetate

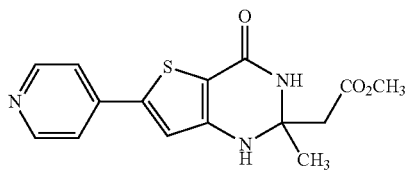 [SMILES: COC(=O)CC1(C)NC(=O)c2sc(-c3ccncc3)cc2N1]

To a mixture of 3-amino-5-(pyridin-4-yl)thiophene-2-carboxamide (0.11 g, 0.50 mmol) and methyl acetoacetate (0.54 mL, 5.0 mmol) in methanol (15 mL) was added 1 drop of concentrated hydrochloric acid, and the reaction was heated at 55° C. for 15 h and with reflux for 24 h. Then, the reaction mixture was cooled, and concentrated with NaHCO$_3$ (0.5 g) and silica gel (5 mL), and the residue was purified by flash chromatography (Combiflash, silica gel, dichloromethane to 90:10 dichloromethane/methanol) to give the title compound (0.075 g, 47%) as a yellow solid:
$^1$H NMR (300 MHz, DMSO-d$_6$) δ 1.54 (3H, s), 2.67-2.80 (2H, m), 3.55 (3H, s), 7.19 (1H, s), 7.32 (1H, s), 7.64 (2H, dd, J=4.5, 1.8 Hz), 7.75 (1H, s), 8.61 (2H, dd, J=4.5, 1.5 Hz).

Example 43

Preparation of 1-acetyl-6'-(pyridin-4-yl)-1'H-spiro[piperidine-4,2'-thieno[3,2-d]pyrimidin]-4'(3'H)-one

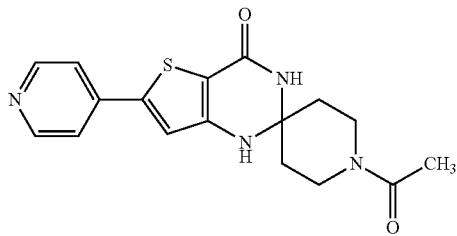 [SMILES: CC(=O)N1CCC2(CC1)NC(=O)c1sc(-c3ccncc3)cc1N2]

To a stirred solution of 1-acetyl-4-piperidone (0.130 g, 0.920 mmol) and p-toluenesulfonic acid monohydrate (0.004 g, 0.02 mmol) in acetic acid (4 mL) was added 3-amino-5-(pyridin-4-yl)thiophene-2-carboxamide (0.050 g, 0.23 mmol). The mixture was heated at 80° C. for 5 h. Then, the reaction was allowed to cool to room temperature and concentrated. The obtained residue was dissolved in methanol (25 mL) and the solution was stirred with solid NaHCO$_3$ (1.5 g) for 20 min. Then, the solution was filtered, and the filtrate was concentrated. The obtained residue was triturated with H$_2$O. The obtained yellow solid was triturated with hot ethyl acetate to give the title compound (0.0407 g, 52%) as a yellow solid:
$^1$H NMR (500 MHz, DMSO-d$_6$) δ 1.70-1.93 (4H, m), 2.01 (3H, s), 3.27-3.32 (1H, m), 3.41-3.45 (1H, m), 3.60-3.63 (1H, m), 3.81-3.84 (1H, m), 7.20 (1H, s), 7.33 (1H, s), 7.63 (2H, d, J=6.0 Hz), 7.84 (1H, s), 8.61 (2H, d, J=6.0 Hz).

Example 44

Preparation of methyl 4'-oxo-6'-(pyridin-4-yl)-3',4'-dihydro-1H,1'H-spiro[piperidine-4,2'-thieno[3,2-d]pyrimidine]-1-carboxylate

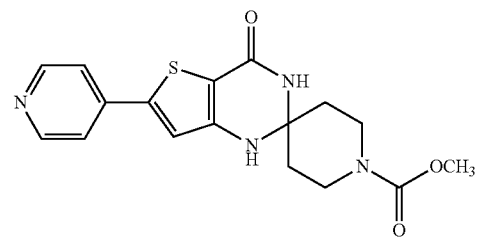 [SMILES: COC(=O)N1CCC2(CC1)NC(=O)c1sc(-c3ccncc3)cc1N2]

Step 1

Preparation of methyl 4-oxopiperidine-1-carboxylate

To a solution of 4-piperidone monohydrate hydrochloride (3.07 g, 20.0 mmol) in water (12 mL) cooled to 0° C. was added a cooled solution (also at 0° C.) of potassium carbonate (6.97 g, 50.4 mmol) in water (40 mL). Methyl chloroformate (2.80 g, 29.6 mmol) was added, and the mixture was allowed to stir for 2 h, still at 0° C. Then, the mixture was extracted with dichloromethane (3×40 mL), and the extract was dried over MgSO$_4$, and concentrated. The obtained residue was chromatographed (silica gel, dichloromethane to 95:5 dichloromethane/methanol) to give the title compound (2.96 g, 94%) as a viscous clear liquid:
$^1$H NMR (300 MHz, DMSO-d$_6$) δ 2.37 (4H, t, J=6.3 Hz), 3.64 (3H, s), 3.66 (4H, t, J=6.3 Hz).

Step 2

Preparation of methyl 4'-oxo-6'-(pyridin-4-yl)-3',4'-dihydro-1H,1'H-spiro[piperidine-4,2'-thieno[3,2-d]pyrimidine]-1-carboxylate To a stirred solution of methyl 4-oxopiperidine-1-carboxylate (0.145 g, 0.920 mmol) and p-toluenesulfonic acid monohydrate (0.004 g, 0.02 mmol) in acetic acid (4 mL) was added 3-amino-5-(pyridin-4-yl)thiophene-2-carboxamide (0.050 g, 0.23 mmol). The mixture was heated at 80° C. for 5 h. Then, the reaction was allowed to cool to room temperature and concentrated. The obtained residue was dissolved in methanol (25 mL) and the solution was stirred with solid NaHCO$_3$ (1.5 g) for 20 min. Then, the solution was filtered, and the filtrate was concentrated. The obtained residue was triturated with H$_2$O. The obtained yellow solid was triturated with hot ethyl acetate. The obtained solid was recrystallized from ethyl acetate/methanol to give the title compound (0.0327 g, 40%) as a yellow solid:
$^1$H NMR (300 MHz, DMSO-d$_6$) δ 1.72-1.79 (2H, m), 1.86-1.91 (2H, m), 3.29-3.37 (2H, m), 3.60 (3H, s), 3.60-3.68 (2H, m), 7.20 (1H, s), 7.33 (1H, s), 7.62-7.64 (2H, m), 7.83 (1H, s), 8.60-8.63 (2H, m).

Example 45

Preparation of N-methyl-2-(2-methyl-4-oxo-6-(pyridin-4-yl)-1,2,3,4-tetrahydrothieno[3,2-d]pyrimidin-2-yl)acetamide

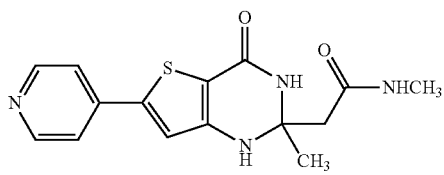 [SMILES: CNC(=O)CC1(C)NC(=O)c2sc(-c3ccncc3)cc2N1]

A mixture of 3-amino-5-(pyridin-4-yl)thiophene-2-carboxamide (0.132 g, 0.600 mmol) and p-toluenesulfonic acid monohydrate (0.023 g, 0.12 mmol) in N-methyl-3-oxobutanamide (2 mL) and acetic acid (6 mL) was stirred at 50° C. for 15 h and at 75° C. for 5 h. Then, the reaction mixture was cooled and concentrated. The residue was dissolved in methanol (15 mL), and the solution was concentrated with NaHCO$_3$ (1 g) and silica gel, and the residue was purified by flash chromatography (Combiflash, silica gel, ethyl acetate to 90:10 ethyl acetate /methanol) to give a crude product as a yellow solid.

Trituration with methanol gave the title compound (0.023 g, 12%) as a yellow solid:
$^1$H NMR (500 MHz, DMSO-d$_6$) δ 1.48 (3H, s), 2.45-2.55 (1H, m), 2.58 (3H, d, J=4.5 Hz), 2.65 (1H, d, J=14.5 Hz), 7.13 (1H, s), 7.25 (1H, s), 7.57-7.65 (3H, m), 7.97 (1H, d, J=4.5 Hz), 8.61 (2H, d, J=6.0 Hz).

Example 46

Preparation of 6'-(1H-pyrazol-4-yl)-1'H-spiro[cyclopentane-1,2'-thieno[3,2-d]pyrimidin]-4'(3'H)-one

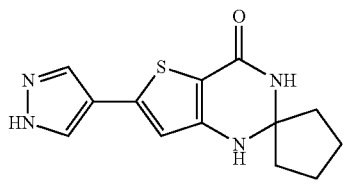 [SMILES: O=C1NC2(CCCC2)Nc2cc(-c3cn[nH]c3)sc21]

A mixture of 3-amino-5-bromothiophene-2-carboxamide (0.072 g, 0.33 mmol) and p-toluenesulfonic acid monohydrate (0.013 g, 0.066 mmol) in cyclopentanone (2 mL) and acetic acid (1 mL) was stirred at 70° C. for 2 h. Then, the reaction mixture was cooled, carefully poured into sat. NaHCO$_3$ (50 mL), and extracted with 2:1 ethyl acetate/tetrahydrofuran (2×50 mL). The combined organic layers were washed with brine (50 mL), dried over magnesium sulfate, filtered, and concentrated to give crude 6'-bromo-1'H-spiro[cyclopentane-1,2'-thieno[3,2-d]pyrimidin]-4'(3'H)-one as a brown gum (0.174 g), which was used without further purification. A mixture of the crude 6'-bromo-1'H-spiro[cyclopentane-1,2'-thieno[3,2-d]pyrimidin]-4'(3'H)-one (0.172 g), 4-(4,4,5,5-tetramethyl-1,3,2-dioxaborolan-2-yl)-1H-pyrazole (0.349 g, 1.80 mmol), 2 M sodium carbonate (1.2 mL, 2.4 mmol) and 1,1'-bis(diphenylphosphino)ferrocenepalladium (II) dichloride dichloromethane adduct (0.073 g, 0.090 mmol) in 1,4-dioxane (3 mL) was microwave-irradiated at 140° C. for 1 h. Then, the reaction mixture was cooled, and concentrated with silica gel, and the residue was purified by flash chromatography (Combiflash, silica gel, ethyl acetate to 90:10 ethyl acetate/methanol), and purified again by flash chromatography (Combiflash, silica gel, dichloromethane to 90:10 dichloromethane/methanol) to give the title compound (0.045 g, 2 step yield 50%) as a yellow solid:
$^1$H NMR (300 MHz, DMSO-d$_6$) δ 1.58-1.73 (4H, m), 1.75-1.90 (4H, m), 6.63 (1H, s), 7.09 (1H, s), 7.52 (1H, s), 7.80 (1H, s), 8.16 (1H, s), 13.12 (1H, br s).

Example 47

Preparation of 6'-(1H-pyrazol-4-yl)-1'H-spiro[cyclohexane-1,2'-thieno[3,2-d]pyrimidin]-4'(3'H)-one

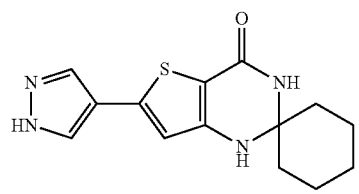 [SMILES: O=C1NC2(CCCCC2)Nc2cc(-c3cn[nH]c3)sc21]

A mixture of 3-amino-5-bromothiophene-2-carboxamide (221 mg, 1 mmol), PTSA (9.5 mg, 0.050 mmol), cyclohexanone (2.94 g, 30.0 mmol) and acetic acid (2 mL) was stirred at 90° C. for 2 h. Then, the mixture was poured into saturated aqueous NaHCO$_3$ (100 mL). Extraction with EtOAc (100 mL), washing with brine, drying over MgSO$_4$, filtration and concentration under reduced pressure gave a yellow solid. This residue was mixed with 4-(4,4,5,5-tetramethyl-1,3,2-dioxaborolan-2-yl)-1H-pyrazole (582 mg, 3.00 mmol), sodium carbonate (530 mg, 5.00 mmol), 1,2-dimethoxyethane (2 mL) and water (2 mL). The mixture was purged with argon. Then, 1,1'-bis(diphenylphosphino) ferrocenepalladium (II) dichloride dichloromethane adduct (82 mg, 0.100 mmol) was added, and the mixture was purged with argon again. This mixture was refluxed overnight. Then, the mixture was poured into saturated aqueous NaHCO$_3$ (200 mL) and EtOAc (200 mL). After shaking, the insoluble materials were filtered off. From the filtrate, the organic layer was collected, washed with brine, dried over MgSO$_4$, filtered and concentrated in vacuo. This residue was purified by column chromatography (Purif, silica gel, EtOAc to 90:10 EtOAc/MeOH) to afford a yellow solid (86 mg). This solid was triturated with EtOAc/hexane and collected by filtration to afford the title compound (78.7 mg, 27%) as a yellow solid:
$^1$H NMR (300 MHz, DMSO-d$_6$) δ 1.25-1.78 (8H, m), 1.82-1.88 (2H, m), 6.66 (1H, s), 6.98 (1H, s), 7.32 (1H, s), 7.79 (1H, br s), 8.15 (1H, br s), 13.12 (1H, br s).

Example 48

Preparation of 2-methyl-6-(1H-pyrazol-4-yl)-2-(2,2,2-trifluoroethyl)-2,3-dihydrothieno[3,2-d]pyrimidin-4(1H)-one

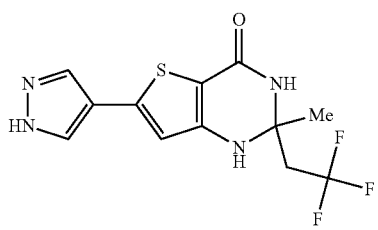 [SMILES: CC1(CC(F)(F)F)NC(=O)c2sc(-c3cn[nH]c3)cc2N1]

A mixture of 3-amino-5-bromothiophene-2-carboxamide (221 mg, 1.0 mmol), 4,4,4-trifluorobutan-2-one (1.26 g, 10 mmol), PTSA (19.0 mg, 0.1 mmol) and acetic acid (2 mL) was microwave-irradiated at 120° C. for 1 h. Then, the mixture was poured into saturated aqueous NaHCO$_3$ (100 mL). Extraction with EtOAc (100 mL), washing with brine, drying over MgSO$_4$, filtration and concentration under reduced pressure gave a yellow solid. This residue was mixed with 4-(4,4,5,5-tetramethyl-1,3,2-dioxaborolan-2-yl)-1H-pyrazole (582 mg, 3.0 mmol), sodium carbonate (530 mg, 5.0 mmol), 1,2-dimethoxyethane (5 mL) and water (2.5 mL). The mixture was purged with argon. Then, 1,1'-bis(diphenylphosphino)ferrocenepalladium (II) dichloride dichloromethane adduct (82 mg, 0.10 mmol) was added, and the mixture was purged with argon again. This mixture was refluxed for 6 h. Then, the mixture was poured into saturated aqueous NaHCO$_3$ (200 mL) and EtOAc (200 mL), and the mixture was shaken well. The insoluble materials were filtered off. From the filtrate, the organic layer was collected, washed with brine, dried over MgSO$_4$, filtered and concentrated under reduced pressure. This residue was purified by column chromatography (Purif, silica gel, 95:5 hexane/EtOAc to EtOAc) to afford a yellow solid (105 mg). This solid was triturated with EtOAc/hexane and collected by filtration to afford the title compound (89.3 mg, 28%) as a yellow solid:

$^1$H NMR (300 MHz, DMSO-d$_6$) δ 1.54 (3H, s), 2.61-2.79 (2H, m), 6.86 (1H, s), 7.27 (1H, s), 7.60 (1H, s), 7.83 (1H, br s), 8.19 (1H, br s), 13.13 (1H, br s).

Example 49

Preparation of 6'-(pyridin-4-yl)-1'H-spiro[cyclobutane-1,2'-thieno[3,2-d]pyrimidin]-4'(3'H)-one

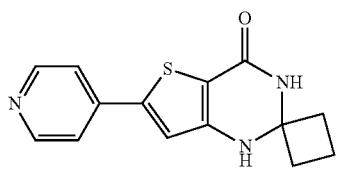 [SMILES: O=C1NC2(CCC2)Nc2cc(-c3ccncc3)sc21]

A mixture of 3-amino-5-(pyridin-4-yl)thiophene-2-carboxamide (110 mg, 0.502 mmol), PTSA (9.5 mg, 0.050 mmol), cyclobutanone (1.0 mL, 13.3 mmol) and acetic acid (1 mL) was stirred at 80° C. for 16 h. Then, the mixture was poured into saturated aqueous NaHCO$_3$ (100 mL). Extraction with EtOAc (100 mL), washing with brine, drying over MgSO$_4$, filtration and concentration under reduced pressure gave a yellow solid. This residue was purified by column chromatography (Purif, silica gel, EtOAc to 95:5 EtOAc/MeOH) to afford yellow solid (30 mg). This solid was triturated with EtOAc/hexane and collected by filtration to afford the title compound (25.6 mg, 19%) as a yellow solid:

$^1$H NMR (300 MHz, DMSO-d$_6$) δ 1.72-1.79 (2H, m), 2.22-2.37 (4H, m), 7.20 (1H, s), 7.64 (2H, dd, J=1.5 Hz, 4.5 Hz), 7.69 (1H, br s), 8.21 (1H, br s), 8.61 (2H, dd, J=4.8, 1.8 Hz).

Example 50

Preparation of 2-methyl-6-(pyridin-4-yl)-2-(trifluoromethyl)-2,3-dihydrothieno[3,2-d]pyrimidin-4(1H)-one

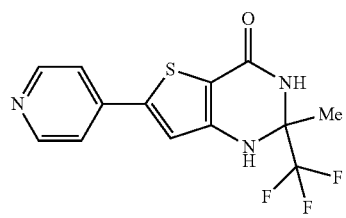 [SMILES: CC1(C(F)(F)F)NC(=O)c2sc(-c3ccncc3)cc2N1]

A mixture of 3-amino-5-(pyridin-4-yl)thiophene-2-carboxamide (110 mg, 0.502 mmol), 1,1,1-trifluoroacetone (1 mL, 11.2 mmol), PTSA (9.5 mg, 0.050 mmol), MgSO$_4$ (60.4 mg, 0.50 mmol) and DMF (1 mL) was microwave-irradiated at 100° C. for 1 h then at 130° C. for 3 h. Then, the mixture was poured into saturated aqueous NaHCO$_3$ (100 mL). Extraction with EtOAc (100 mL), washing with brine, drying over MgSO$_4$, filtration and concentration under reduced pressure gave a yellow solid. This residue was purified by column chromatography (Purif, NH, hexane to EtOAc) to afford a yellow solid. This solid was triturated with EtOAc/hexane and collected by filtration to afford the title compound (94.3 mg, 60%) as a yellow solid:

$^1$H NMR (300 MHz, DMSO-d$_6$) δ 1.61 (3H, s), 7.20 (1H, s), 7.65 (2H, dd, J=4.5 Hz, 1.8 Hz), 7.99 (1H, br s), 8.54 (1H, br s), 8.63 (2H, dd, J=4.5 Hz, 1.8 Hz).

Example 51

Preparation of 1,2,2-trimethyl-6-(1H-pyrazol-4-yl)-2,3-dihydrothieno[3,2-d]pyrimidin-4(1H)-one

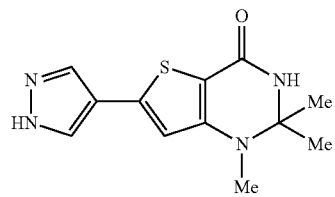 [SMILES: CN1c2cc(-c3cn[nH]c3)sc2C(=O)NC1(C)C]

Step 1

Preparation of methyl 5-bromo-3-(methylamino)thiophene-2-carboxylate

A mixture of methyl 5-bromo-3-[(trifluoroacetyl)amino]thiophene-2-carboxylate(same as methyl 5-bromo-3-(2,2,2-trifluoroacetamido)thiophene-2-carboxylate described in Step 2 of Example 34) (996 mg, 3.00 mmol), potassium carbonate (829 mg, 6.00 mmol), DMF (6 mL) and methyl iodide (0.225 mL, 3.60 mmol) was stirred at 60° C. for 4 h. Then, the mixture was poured into saturated aqueous NaHCO$_3$ (100 mL). Extraction with EtOAc (100 mL), washing with saturated aqueous NaHCO$_3$ and brine, drying over MgSO$_4$, filtration and concentration under reduced pressure gave brown oil. This residue was mixed with potassium carbonate (415 mg, 3.00 mmol), MeOH (20 mL) and water (10 mL). The mixture was stirred overnight at room temperature. Then, the mixture was poured into saturated aqueous NaHCO$_3$ (100 mL). Extraction with EtOAc (100 mL), washing with brine, drying over MgSO$_4$, filtration and concentration under reduced pressure gave brown oil. This residue was purified by column chromatography (Purif, silica gel, hexane to 70:30 hexane/EtOAc) to afford the title compound (674 mg, 90%) as a white solid:
$^1$H NMR (300 MHz, DMSO-d$_6$) δ 2.89 (3H, d, J=5.1 Hz), 3.70 (3H, s), 6.82-6.88 (1H, m), 7.05 (1H, s).

Step 2

Preparation of 5-bromo-3-(methylamino)thiophene-2-carboxamide

A mixture of 3 M sodium hydroxide (2.5 mL, 7.50 mmol), MeOH (10 mL) and methyl 5-bromo-3-(methylamino)thiophene-2-carboxylate (674 mg, 2.69 mmol) was stirred at 70° C. overnight. Then, the mixture was cooled in ice-water bath, and 6 M HCl (0.9 mL, 5.40 mmol) was added. The mixture was concentrated under reduced pressure to give a yellow solid. This residue was mixed with ammonium chloride (2.88 g, 53.9 mmol), triethylamine (7.51 mL, 53.9 mmol) and DMF (27 mL). The mixture was stirred for 5 min, then 1-hydroxybenzotriazole (2.19 g, 16.2 mmol) and 1-ethyl-3-(3-dimethylaminopropyl) carbodiimide hydrochloride (3.10 g, 16.2 mmol) were added. The stirring was continued for 3 days. The reaction mixture was poured into saturated aqueous NaHCO$_3$ (200 mL). Extraction with EtOAc (200 mL), washing with saturated NaHCO$_3$, drying over MgSO$_4$, filtration and concentration under reduced pressure gave brown oil. This oil was purified by column chromatography (Purif, silica gel, hexane to EtOAc) to afford the title compound (536 mg, 85%) as a pale brown solid:
$^1$H NMR (300 MHz, DMSO-d$_6$) δ 2.83 (3H, d, J=5.1 Hz), 6.92 (2H, br s), 6.98 (1H, s), 7.30-7.33 (1H, m).

Step 3

Preparation of 6-bromo-1,2,2-trimethyl-2,3-dihydrothieno[3,2-d]pyrimidin-4(1H)-one A mixture of 5-bromo-3-(methylamino)thiophene-2-carboxamide (536 mg, 2.28 mmol), acetone (4.00 mL, 54.5 mmol), PTSA (21.7 mg, 0.114 mmol) and acetic acid (2 mL) was stirred for 2 h at 70° C. Then, the mixture was poured into saturated aqueous NaHCO$_3$ (100 mL). Extraction with EtOAc (100 mL), washing with brine, drying over MgSO$_4$, filtration and concentration under reduced pressure gave a brown solid. This solid was triturated with EtOAc/hexane and collected by filtration to afford the title compound (381 mg, 61%) as yellow solid:
$^1$H NMR (300 MHz, DMSO-d$_6$) δ 1.39 (6H, s), 2.84 (3H, s), 7.07 (1H, s), 7.64 (1H, br s).

Step 4

Preparation of 1,2,2-trimethyl-6-(1H-pyrazol-4-yl)-2,3-dihydrothieno[3,2-d]pyrimidin-4(1H)-one A mixture of 6-bromo-1,2,2-trimethyl-2,3-dihydrothieno[3,2-d]pyrimidin-4(1H)-one (138 mg, 0.50 mmol), 4-(4,4,5,5-tetramethyl-1,3,2-dioxaborolan-2-yl)-1H-pyrazole (291 mg, 1.50 mmol), sodium carbonate (265 mg, 2.50 mmol), 1,2-dimethoxyethane (5 mL) and water (2.5 mL) was purged with argon. Then, 1,1'-bis(diphenylphosphino)ferrocenepalladium (II) dichloride dichloromethane adduct (40.8 mg, 0.050 mmol) was added, and the mixture was purged with argon again. This mixture was refluxed for 18 h. Then, the mixture was poured into saturated aqueous NaHCO$_3$ (100 mL) and EtOAc (100 mL), and the mixture was shaken well. The insoluble materials were filtered off. From the filtrate, the organic layer was collected, washed with brine, dried over MgSO$_4$, filtered and concentrated under reduced pressure. This residue was purified by column chromatography (Purif, silica gel, 95:5 hexane/EtOAc to EtOAc, then EtOAc to 90:10 EtOAc/MeOH) to afford a white solid (60 mg). This solid was triturated with EtOAc/hexane and collected by filtration to afford the title compound (50.3 mg, 38%) as a white solid:
$^1$H NMR (300 MHz, DMSO-d$_6$) δ 1.40 (6H, s), 2.87 (3H, s), 6.97 (1H, s), 7.44 (1H, br s), 7.84 (1H, br s), 8.16 (1H, br s), 13.12 (1H, br s).

Example 52

Preparation of 2,2-dimethyl-1-(1-methylethyl)-6-(pyridin-4-yl)-2,3-dihydrothieno[3,2-d]pyrimidin-4(1H)-one

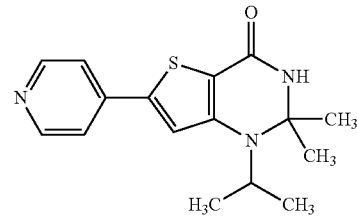 [SMILES: CC(C)N1c2cc(-c3ccncc3)sc2C(=O)NC1(C)C]

Step 1

Preparation of methyl 3-[(1-methylethyl)amino]-5-(pyridin-4-yl)thiophene-2-carboxylate To a mixture of methyl 3-amino-5-(pyridin-4-yl)thiophene-2-carboxylate (0.469 g, 2.00 mmol), 2-methoxypropene (0.29 mL, 3.0 mmol) and acetic acid (0.114 mL, 2.00 mmol) in dichloromethane (6 mL) was added sodium triacetoxyborohydride (0.636 g, 3.00 mmol), and the reaction was stirred at room temperature overnight. Then, the reaction mixture was poured into sat. NaHCO$_3$ (70 mL) and extracted with ethyl acetate (2×50 mL). The combined organic layers were washed with brine (50 mL), dried over magnesium sulfate, filtered, and concentrated, and the residue was purified by flash chromatography (Combiflash, silica gel, hexanes to ethyl acetate) to give the title compound (0.256 g, 46%) as a yellow solid:

¹H NMR (300 MHz, DMSO-d₆) δ 1.22 (6H, d, J=6.6 Hz), 3.76 (3H, s), 3.84-3.95 (1H, m), 6.62 (1H, d, J=8.7 Hz), 7.60 (1H, s), 7.73 (2H, dd, J=4.5, 1.5 Hz), 8.64 (2H, dd, J=4.5, 1.8 Hz).

Step 2

Preparation of 3-[(1-methylethyl)amino]-5-(pyridin-4-yl) thiophene-2-carboxylic acid A mixture of methyl 3-[(1-methylethyl)amino]-5-(pyridin-4-yl)thiophene-2-carboxylate (0.250 g, 0.905 mmol) and 2 M sodium hydroxide (1.36 mL, 2.72 mmol) in methanol (5 mL) was heated at 70° C. for 3 h. Then, the reaction was cooled to room temperature and concentrated. The obtained residue was dissolved in water (5 mL) and acidified with 1 M HCl (2.7 mL) and 4 drops of acetic acid. The resulting yellow precipitate was collected by filtration, washed with water and dried to give the title compound (0.229 g, 96%) as a yellow solid:

¹H NMR (500 MHz, DMSO-d₆) δ 1.21 (6H, d, J=6.5 Hz), 3.80-3.95 (1H, m), 6.60 (1H, br s), 7.56 (1H, s), 7.71 (2H, dd, J=4.5, 1.5 Hz), 8.62 (2H, dd, J=4.5, 1.5 Hz), 12.45 (1H, br s).

Step 3

Preparation of 2,2-dimethyl-1-(1-methylethyl)-6-(pyridin-4-yl)-2,3-dihydrothieno[3,2-d]pyrimidin-4(1H)-one A mixture of 3-[(1-methylethyl)amino]-5-(pyridin-4-yl) thiophene-2-carboxylic acid (0.225 g, 0.858 mmol), ammonium chloride (0.459 g, 8.58 mmol) and triethylamine (1.21 mL, 8.58 mmol) in DMF (5 mL) was stirred at room temperature for 15 min. To the resulting mixture was added 1-(3-(dimethylamino)propyl)-3-ethyl carbodiimide hydrochloride (0.493 g, 2.57 mmol), and 1-hydroxybenzotriazole (0.347 g, 2.57 mmol) and the reaction was stirred at room temperature for 65 h. Then, the reaction mixture was diluted with sat. NaHCO₃ (120 mL) and extracted with ethyl acetate (3×100 mL). The combined organic layers were washed with water (2×50 mL) and brine (100 mL), dried over magnesium sulfate, filtered and concentrated to give crude 3-[(1-methylethyl)amino]-5-(pyridin-4-yl)thiophene-2-carboxamide (0.225 g) as an orange solid. A mixture of 3-[(1-methylethyl) amino]-5-(pyridin-4-yl)thiophene-2-carboxamide (0.105 g) and 2-methoxypropene (1.53 mL, 16.0 mmol) in acetic acid (1.5 mL) was heated at 35° C. overnight. Then, the reaction mixture was cooled to room temperature and concentrated. The obtained residue was dissolved in methanol (10 mL), and the solution was concentrated with NaHCO₃ (1 g) and silica gel (5 mL), and the residue was purified by flash chromatography (Combiflash, silica gel, ethyl acetate to 95:5 ethyl acetate /methanol) to give the title compound (0.063 g, 2 step yield 52%) as an orange solid:

¹H NMR (500 MHz, DMSO-d₆) δ 1.36 (6H, d, J=7.0 Hz), 1.50 (6H, s), 3.92-3.98 (1H, m), 7.52 (1H, s), 7.69 (1H, s), 7.75 (2H, dd, J=4.5, 1.5 Hz), 8.61 (2H, dd, J=4.5, 1.5 Hz).

Example 53

Preparation of phenyl 4'-oxo-6'-(pyridin-4-yl)-3',4'-dihydro-1H,1'H-spiro[piperidine-4,2'-thieno[3,2-d]pyrimidine]-1-carboxylate

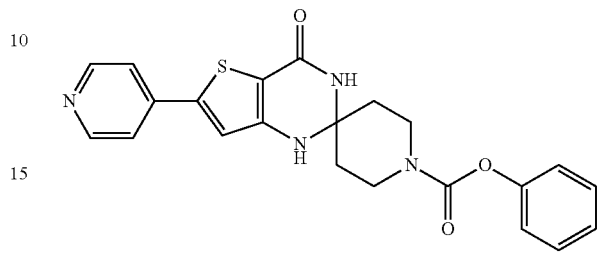

Step 1

Preparation of phenyl 1,4-dioxa-8-azaspiro[4.5]decane-8-carboxylate

To a stirred solution of 1,4-dioxa-8-azaspiro[4.5]decane (2.00 g, 13.9 mmol) and triethylamine (2.90 mL, 20.9 mmol) in ethyl acetate (50 mL) at 0° C. was added phenyl chloroformate (2.10 mL, 13.9 mmol). The mixture was allowed to warm to room temperature overnight. Then, the mixture was filtered to remove triethylamine hydrochloride salts. The filtrate was concentrated, and the obtained residue was chromatographed (silica gel, hexanes to 50:50 hexanes/ethyl acetate) to give the title compound (3.48 g, 95%) as a white solid:

¹H NMR (500 MHz, DMSO-d₆) δ 1.69 (4H, br s), 3.50-3.64 (4H, m), 3.93 (4H, s), 7.12-7.14 (2H, m), 7.20-7.23 (1H, m), 7.36-7.39 (2H, m).

Step 2

Preparation of phenyl 4-oxopiperidine-1-carboxylate

To a stirred solution of phenyl 1,4-dioxa-8-azaspiro[4.5] decane-8-carboxylate (0.500 g, 2.50 mmol) in acetone (20 mL) was added indium(III) trifluoromethanesulfonate (0.014 g, 0.025 mmol). The reaction was heated at 100° C. for 20 min. Then, the reaction was allowed to cool to room temperature overnight. The mixture was then concentrated, and the obtained residue was chromatographed (silica gel, hexanes to 40:60 hexanes/ethyl acetate) to give the title compound (0.322 g, 58%) as a white solid:

¹H NMR (500 MHz, DMSO-d₆) δ 2.36-2.37 (4H, m), 3.74 (2H, br s), 3.88 (2H, br s), 7.16-7.18 (2H, m), 7.22-7.25 (1H, m), 7.38-7.42 (2H, m).

Step 3

Preparation of phenyl 4'-oxo-6'-(pyridin-4-yl)-3',4'-dihydro-1H,1'H-spiro[piperidine-4,2'-thieno[3,2-d]pyrimidine]-1-carboxylate To a stirred solution of phenyl 4-oxopiperidine-1-carboxylate (0.322 g, 1.46 mmol) and p-toluenesulfonic acid monohydrate (0.0040 g, 0.023 mmol) in acetic acid (4 mL) was added 3-amino-5-(pyridin-4-yl)thiophene-2-carboxamide (0.050 g, 0.23 mmol). The mixture was heated at 80° C. for 5 h. Then, the mixture was cooled to room temperature and concentrated. The obtained residue was dissolved in methanol (25 mL), and the solution was stirred with solid NaHCO₃ (1.5 g) for 20 min. Then, the solution was filtered, and the filtrate concentrated. The obtained residue was triturated with H₂O. The obtained yellow solid was triturated with hot ethyl acetate to give the title compound (0.0745 g, 77%) as a yellow solid:

¹H NMR (500 MHz, DMSO-d₆) δ 1.81-2.05 (4H, m), 3.43-3.57 (2H, m), 3.72-3.85 (2H, m), 7.12 (2H, d, J=8.0 Hz), 7.21-7.24 (2H, m), 7.38-7.41 (3H, m), 7.64 (2H, d, J=6.0 Hz), 7.88 (1H, s), 8.62 (2H, d, J=6.0 Hz).

Example 54

Preparation of methyl 2-methyl-4-oxo-6-(pyridin-4-yl)-1,2,3,4-tetrahydrothieno[3,2-d]pyrimidine-2-carboxylate

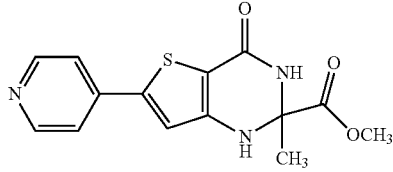 [SMILES: COC(=O)C1(C)NC(=O)c2sc(-c3ccncc3)cc2N1]

A mixture of 3-amino-5-(pyridin-4-yl)thiophene-2-carboxamide (0.044 g, 0.20 mmol) in methyl 2,2-dimethoxypropanoate (0.3 mL) and trifluoroacetic acid (0.5 mL) was stirred at room temperature for 1 h. Then, the reaction mixture was concentrated, and the obtained residue was dissolved in methanol (10 mL), and the solution was concentrated with NaHCO₃ (0.5 g) and silica gel (2 mL), and the residue was purified by flash chromatography (Combiflash, silica gel, dichloromethane to 90:10 dichloromethane/methanol) to give a crude product. Trituration with hexanes/ethyl acetate gave the title compound (0.026 g, 42%) as a yellow solid:

¹H NMR (500 MHz, DMSO-d₆) δ 1.59 (3H, s), 3.65 (3H, s), 7.22 (1H, s), 7.64 (2H, dd, J=4.5, 2.0 Hz), 8.09 (1H, s), 8.32 (1H, s), 8.61 (2H, dd, J=4.5, 1.5 Hz).

Example 55

Preparation of N,N-dimethyl-2-(2-methyl-4-oxo-6-(pyridin-4-yl)-1,2,3,4-tetrahydrothieno[3,2-d]pyrimidin-2-yl)acetamide

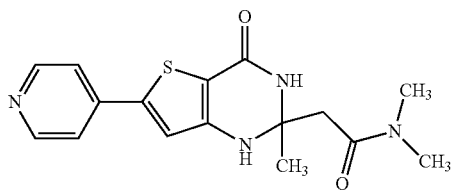 [SMILES: CN(C)C(=O)CC1(C)NC(=O)c2sc(-c3ccncc3)cc2N1]

A mixture of 3-amino-5-(pyridin-4-yl)thiophene-2-carboxamide (0.044 g, 0.20 mmol) in N,N-dimethyl-3-oxobutanamide (0.3 mL) and acetic acid (1 mL) was stirred at 60° C. for 20 h. Then, the reaction mixture was cooled to room temperature and concentrated. The residue was dissolved in methanol (10 mL), and the solution was concentrated with NaHCO₃ (0.5 g) and silica gel (2 mL), and the residue was purified by flash chromatography (Combiflash, silica gel, ethyl acetate to 90:10 ethyl acetate/methanol) to give a crude product.

Trituration with methanol gave the title compound (0.027 g, 41%) as a yellow solid:

¹H NMR (300 MHz, DMSO-d₆) δ 1.53 (3H, s), 2.77 (1H, d, J=15.5 Hz), 2.82 (3H, s), 2.89 (1H, d, J=15.5 Hz), 2.94 (3H, s), 7.13 (1H, s), 7.28 (1H, s), 7.53 (1H, s), 7.61 (2H, dd, J=4.5, 1.5 Hz), 8.61 (2H, dd, J=4.5, 1.5 Hz).

Example 56

Preparation of 2-methyl-4-oxo-6-(pyridin-4-yl)-1,2,3,4-tetrahydrothieno[3,2-d]pyrimidine-2-carboxylic acid

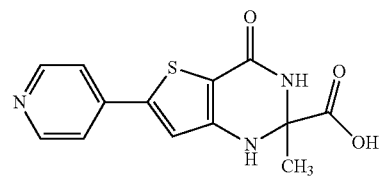 [SMILES: CC1(C(=O)O)NC(=O)c2sc(-c3ccncc3)cc2N1]

A mixture of methyl 2-methyl-4-oxo-6-(pyridin-4-yl)-1,2,3,4-tetrahydrothieno[3,2-d]pyrimidine-2-carboxylate (0.152 g, 0.500 mmol) and 2 M sodium hydroxide (0.75 mL, 1.5 mmol) in methanol (10 mL) was stirred at room temperature for 3 h, and the resulting suspension was stored at −20° C. for 65 h. Then, the reaction mixture was warmed to room temperature, and the precipitate was collected by filtration and washed with methanol (1 mL) to give a yellow solid. This yellow solid was partitioned between ethyl acetate (25 mL) and water (10 mL), and the ethyl acetate layer was extracted with water (2×5 mL). The combined aqueous layers were acidified with acetic acid to a pH of 5 to 6, and the resulting orange precipitate was collected by filtration and washed with water to give an orange solid. Trituration with acetonitrile/methanol gave the title compound (0.031 g, 21%) as an orange solid:

¹H NMR (300 MHz, DMSO-d₆) δ 1.57 (3H, s), 7.21 (1H, s), 7.64 (2H, dd, J=4.5, 1.5 Hz), 7.94 (1H, s), 8.17 (1H, s), 8.61 (2H, dd, J=4.5, 1.5 Hz), 13.03 (1H, br s).

Example 57

Preparation of 2,2-dimethyl-6-(pyrimidin-4-yl)-2,3-dihydrothieno[3,2-d]pyrimidin-4(1H)-one

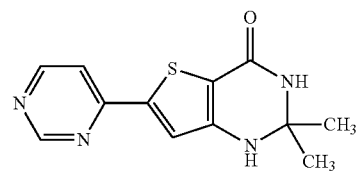

To a solution of 2,2-dimethyl-6-[2-(methylsulfonyl)pyrimidin-4-yl]-2,3-dihydrothieno[3,2-d]pyrimidin-4(1H)-one (0.034 g, 0.10 mmol) in ethanol (2 mL) and methanol (15 mL) was added sodium borohydride (0.092 g, 2.4 mmol) in four portions over 20 min, and the reaction was stirred at room temperature for 15 h. Then, the reaction mixture was concentrated, the residue was dissolved in water (15 mL), and the solution was extracted with 75:25 ethyl acetate/tetrahydrofuran (2×40 mL). The combined organic layers were washed with brine (30 mL), dried over magnesium sulfate, filtered, and concentrated, and the residue was purified by flash chromatography (silica gel, ethyl acetate to 90:10 ethyl acetate/methanol) to give the title compound (0.012 g, 46%) as a yellow solid:

$^1$H NMR (300 MHz, DMSO-d$_6$) δ 1.42 (6H, s), 7.13 (1H, s), 7.42 (1H, s), 7.74 (1H, s), 8.00 (1H, d, J=5.1 Hz), 8.84 (1H, d, J=5.4 Hz), 9.14 (1H, s).

Example 58

Preparation of 1,2-dimethyl-6-(1H-pyrazol-4-yl)-2-(2,2,2-trifluoroethyl)-2,3-dihydrothieno[3,2-d]pyrimidin-4(1H)-one A mixture of 5-bromo-3-(methylamino)thiophene-2-carboxamide (236 mg, 1.0 mmol), 4,4,4-trifluorobutan-2-one (1.26 g, 10 mmol), PTSA (17.2 mg, 0.10 mmol), MgSO$_4$ (120 mg) and DMA (2 mL) was microwave-irradiated at 150° C. for 1.5 h. The mixture was poured into saturated aqueous NaHCO$_3$, extracted with EtOAc, washed with water and brine, and dried over Na$_2$SO$_4$. After removal of the solvent at reduced pressure, a brown crystalline solid was obtained. A flask was charged with this solid, 1,2-dimethoxyethane (5 mL), 4-(4,4,5,5-tetramethyl-1,3,2-dioxaborolan-2-yl)-1H-pyrazole (582 mg, 3.0 mmol), sodium carbonate (300 mg, 5.0 mmol) and water (2.5 mL). The flask was purged with argon. Then, bis(diphenylphosphino) ferrocenepalladium (II) dichloride dichloromethane adduct (82 mg, 0.10 mmol) was added to the mixture. The flask was purged with argon again. After stirring at 120° C. for 8 h, water and EtOAc were added to quench the reaction. The organic layer was collected, washed with water and brine, dried over Na$_2$SO$_4$ and filtered. After removal of the solvent at reduced pressure, the residue was purified by column chromatography (Purif, silica gel, hexane to EtOAc) to give a yellow solid. This solid was crystallized from EtOAc/heptane and collected by filtration to afford the title compound (81 mg, 25%) as a pale yellow solid:

$^1$H NMR (300 MHz, DMSO-d$_6$) δ 1.59 (3H, s), 2.55-2.75 (1H, m), 2.84-3.03 (1H, m), 2.92 (3H, s), 7.00 (1H, s), 7.73 (1H, s), 7.85 (1H, br s), 8.19 (1H, br s), 13.15 (1H, br s).

Example 59

Preparation of 1,2,2-trimethyl-6-(1,3-oxazol-5-yl)-2,3-dihydrothieno[3,2-d]pyrimidin-4(1H)-one

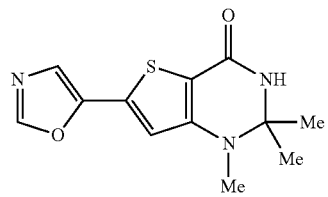 [SMILES: CN1c2cc(-c3cnco3)sc2C(=O)NC1(C)C]

Step 1

Preparation of 1,2,2-trimethyl-4-oxo-1,2,3,4-tetrahydrothieno[3,2-d]pyrimidine-6-carbaldehyde To a stirred suspension of 6-bromo-1,2,2-trimethyl-2,3-dihydrothieno[3,2-d]pyrimidin-4(1H)-one (259 mg, 0.941 mmol) in THF (10 mL) at −78° C. was added dropwise 1.6 M n-butyllithium in hexane (1.29 mL, 2.07 mmol). After 20 min, DMF (0.146 mL, 1.88 mmol) was added, and the mixture was allowed to −30° C. for 30 min. The mixture was poured into water (50 mL) and brine (50 mL). Extraction with EtOAc (100 mL), washing with brine, drying over MgSO$_4$, filtration and concentration under reduced pressure gave the title compound (205 mg, 97%) as yellow solid:

$^1$H NMR (300 MHz, DMSO-d$_6$) δ 1.42 (6H, s), 2.90 (3H, s), 7.71 (1H, s), 8.06 (1H, br s), 9.90 (1H, s).

Step 2

Preparation of 1,2,2-trimethyl-6-(1,3-oxazol-5-yl)-2,3-dihydrothieno[3,2-d]pyrimidin-4(1H)-one A mixture of 1,2,2-trimethyl-4-oxo-1,2,3,4-tetrahydrothieno[3,2-d]pyrimidine-6-carbaldehyde (100 mg, 0.446 mmol), MS4A powder (100 mg) and 2 M ethylamine in THF (2.00 mL, 4.00 mmol) was stirred for 1 h at room temperature. Then, the mixture was concentrated under reduced pressure to give a yellow solid. Then, the residue was suspended with 2 M ethylamine in THF (2.00 mL, 4.00 mmol) and MgSO$_4$ (100 mg). The mixture was stirred overnight and concentrated under reduced pressure to give yellow solid. Then, the residue was suspended with 2 M ethylamine in THF (2.00 mL, 4.00 mmol). The mixture was stirred for 4 h and concentrated under reduced pressure to give yellow solid. Then, 1-[(isocyanomethyl)sulfonyl]-4-methylbenzene (131 mg, 0.669 mmol), potassium carbonate (123 mg, 0.892 mmol) and MeOH (3 mL) were added to the residue, and the mixture was stirred at 60° C. for 1 h. 1-[(Isocyanomethyl) sulfonyl]-4-methylbenzene (131 mg, 0.669 mmol) and potassium carbonate (123 mg, 0.892 mmol) were added again, and the mixture was stirred at 60° C. overnight. 1-[(Isocyanomethyl) sulfonyl]-4-methylbenzene (131 mg, 0.669 mmol) and potassium carbonate (123 mg, 0.892 mmol) were added again, and the mixture was stirred at 60° C. for 2 h. The mixture was poured into saturated aqueous NaHCO₃ (80 mL) and extracted with EtOAc (80 mL), and the extract was washed with brine, dried over MgSO₄, filtered and concentrated under reduced pressure to afford orange gum. This residue was purified by column chromatography (Purif, NH, 95:5 hexane/EtOAc to EtOAc) and preparative HPLC (YMC CombiPrep. Hydrosphere C18). The fractions containing the title compound were collected and basified by addition of saturated aqueous NaHCO₃. Extraction with EtOAc, drying over MgSO₄, filtration and concentration under reduced pressure gave the title compound (11.5 mg, 9.8%) as pale yellow solid:

¹H NMR (300 MHz, DMSO-d₆) δ 1.41 (6H, s), 2.90 (3H, s), 7.23 (1H, s), 7.66 (1h, s), 7.71 (1H, br s), 8.48 (1H, s).

Example 60

Preparation of 1,2-dimethyl-6-(1H-pyrazol-4-yl)-2-(trifluoromethyl)-2,3-dihydrothieno[3,2-d]pyrimidin-4(1H)-one

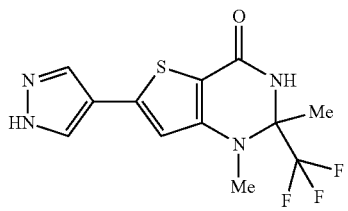 [SMILES: CN1c2cc(-c3cn[nH]c3)sc2C(=O)NC1(C)C(F)(F)F]

A mixture of 5-bromo-3-(methylamino)thiophene-2-carboxamide (235 mg, 1.00 mmol), 1,1,1-trifluoroacetone (2.00 mL, 22.3 mmol), PTSA (19.0 mg, 0.100 mmol), MgSO₄ (120 mg, 1.00 mmol) and DMF (2 mL) was microwave-irradiated at 130° C. for 2 h then at 140° C. for 4 h. Then, the mixture was poured into saturated aqueous NaHCO₃ (100 mL). Extraction with EtOAc (100 mL×2), washing with brine, drying over MgSO₄, filtration and concentration under reduced pressure gave a dark solid. This residue was mixed with sodium carbonate (530 mg, 5.00 mmol), 4-(4,4,5,5-tetramethyl-1,3,2-dioxaborolan-2-yl)-1H-pyrazole (582 mg, 3.00 mmol), 1,2-dimethoxyethane (2.5 mL) and water (5 mL). The mixture was purged with argon. Then, 1,1'-bis (diphenylphosphino) ferrocenepalladium (II) dichloride dichloromethane adduct (82 mg, 0.10 mmol) was added, and the mixture was purged with argon again. This mixture was refluxed overnight. Then, the mixture was poured into saturated aqueous NaHCO₃ and extracted with EtOAc, and the extract was dried over MgSO₄, filtered and concentrated at reduced pressure to give a dark oil. This residue was purified by column chromatography (Purif, silica gel, hexane to EtOAc) to give a dark solid (29 mg). This solid was triturated with EtOAc/hexane and collected by filtration to afford the title compound (13.6 mg, 4.3%) as a beige solid:

¹H NMR (300 MHz, DMSO-d₆) δ 1.74 (3H, s), 3.08 (3H, s), 7.06 (1H, s), 7.87 (1H, br s), 8.20 (1H, br s), 8.33 (1H, s), 13.16 (1H, br s).

Example 61

Preparation of 6-(1H-imidazol-1-yl)-1,2,2-trimethyl-2,3-dihydrothieno[3,2-d]pyrimidin-4(1H)-one

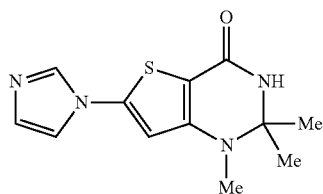 [SMILES: CN1c2cc(-n3ccnc3)sc2C(=O)NC1(C)C]

A mixture of 6-bromo-1,2,2-trimethyl-2,3-dihydrothieno[3,2-d]pyrimidin-4(1H)-one (138 mg, 0.50 mmol), imidazole (68.1 mg, 1.00 mmol), copper (powder) (6.35 mg, 0.10 mmol) and water (2 mL) was refluxed for 1 h. The mixture was concentrated under reduced pressure. DMF (2 mL), cesium carbonate (326 mg, 1.00 mmol), imidazole (408 mg, 6.00 mmol) and copper(I) iodide (19.1 mg, 0.10 mmol) were added to the residue, and the mixture was purged with argon. Then, the mixture was stirred at 140° C. for 4 h. Then, the mixture was poured into saturated aqueous NaHCO₃ (100 mL) and extracted with EtOAc/THF (2:1, 100 mL×2), and the extract was dried over MgSO₄, filtered and concentrated under reduced pressure. The residual oil was purified by column chromatography (silica gel, EtOAc to 80:20 EtOAc/MeOH) to give a solid (56 mg). The solid was triturated with EtOAc/hexane, collected by filtration and washed with water to afford the title compound (10.4 mg, 7.9%) as a pale yellow solid:

¹H NMR (300 MHz, DMSO-d₆) δ 1.43 (6H, s), 2.90 (3H, s), 7.12 (1H, br s), 7.18 (1H, s), 7.63 (1H, br s), 7.68 (1H, br s), 8.22 (1H, br s).

Example 62

Preparation of tert-butyl [2-oxo-2-(4'-oxo-6'-(pyridin-4-yl)-3',4'-dihydro-1H,1'H-spiro[piperidine-4,2'-thieno[3,2-d]pyrimidin]-1-yl)ethyl]carbamate

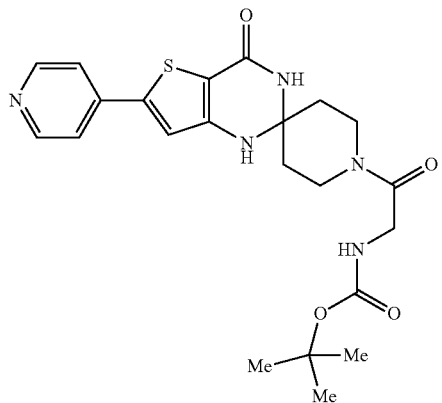 [SMILES: CC(C)(C)OC(=O)NCC(=O)N1CCC2(CC1)NC(=O)c1sc(-c3ccncc3)cc1N2]

The title compound (2.2 mg, 6.0%) was synthesized in a manner similar to Example 64 except that N-(tert-butoxycarbonyl)-L-phenylalanine was replaced with N-(tert-butoxycarbonyl)glycine.

MS (ESI⁺) 458 (MH⁺).

Example 63

Preparation of 1-glycyl-6'-(pyridin-4-yl)-1'H-spiro[piperidine-4,2'-thieno[3,2-d]pyrimidin]-4'(3'H)-one

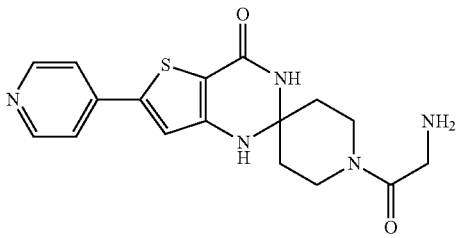 [SMILES: NCC(=O)N1CCC2(CC1)NC(=O)c1sc(-c3ccncc3)cc1N2]

A mixture of 6'-(pyridin-4-yl)-1'H-spiro[piperidine-4,2'-thieno[3,2-d]pyrimidin]-4'(3'H)-one in DMF (0.16 M, 0.50 mL, 0.080 mmol), N-(tert-butoxycarbonyl)glycine in DMF (0.192 M, 0.50 mL, 0.096 mmol) and a solution of 1-hydroxybenzotriazole and 1-ethyl-3-(3-dimethylaminopropyl)carbodiimide hydrochloride in DMF (0.192 M, 0.50 mL, 0.096 mmol for each) was stirred for 16 h at room temperature. The reaction mixture was extracted with EtOAc (3.5 mL) and 2% aqueous sodium hydrogen carbonate (1 mL). After evaporating the organic solvent, 1 M methanesulfonic acid in MeCN (0.5 mL) was added to the residue. The mixture was stirred for 16 h at room temperature. After neutralizing the reaction mixture with 1 M N-ethyl-N-(1-methylethyl)propan-2-amine (0.5 mL), the crude product was chromatographed on preparative HPLC (YMC CombiPrep. Hydrosphere C18, 10 mM $NH_4HCO_3$ in water/MeCN) to afford the title compound (0.8 mg, 2.8%):
MS (ESI$^+$) 358 (MH$^+$).

Example 64

Preparation of tert-butyl [(1S)-1-benzyl-2-oxo-2-(4'-oxo-6'-(pyridin-4-yl)-3',4'-dihydro-1H,1'H-spiro[piperidine-4,2'-thieno[3,2-d]pyrimidin]-1-yl)ethyl]carbamate

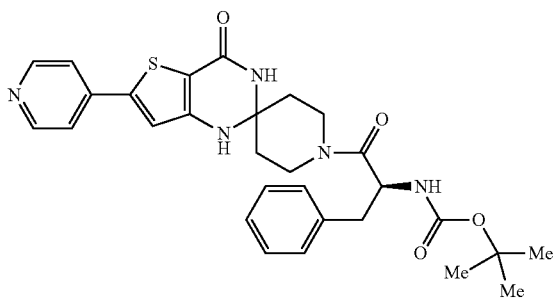 [SMILES: CC(C)(C)OC(=O)N[C@@H](Cc1ccccc1)C(=O)N1CCC2(CC1)NC(=O)c1sc(-c3ccncc3)cc1N2]

A mixture of 6'-(pyridin-4-yl)-1'H-spiro[piperidine-4,2'-thieno[3,2-d]pyrimidin]-4'(3'H)-one in DMF (0.16 M, 0.50 mL, 0.08 mmol), N-(tert-butoxycarbonyl)-L-phenylalanine in DMF (0.192 M, 0.50 mL, 0.096 mmol) and a solution of 1-hydroxybenzotriazole and 1-ethyl-3-(3-dimethylaminopropyl) carbodiimide hydrochloride in DMF (0.192 M, 0.50 mL, 0.096 mmol each) was stirred for 16 h at room temperature. The reaction mixture was extracted with EtOAc (3.5 mL) and 2% aqueous sodium hydrogen carbonate (1 mL). After evaporating the organic solvent, the crude product was chromatographed on preparative HPLC (YMC CombiPrep. Hydrosphere C18, 10 mM $NH_4HCO_3$ in water/MeCN) to afford the title compound (16.5 mg, 37%):

$^1$H NMR (400 MHz, DMSO-d$_6$) δ 1.28 (9H, s), 1.68-1.92 (4H, m), 2.71-2.93 (4H, m), 3.62-3.91 (2H, m), 4.63 (1H, m), 7.15 (1H, br s), 7.21-7.33 (5H, m), 7.65 (2H, d, J=4.8 Hz), 8.61 (2H, d, J=4.8 Hz). MS (ESI$^+$) 548 (MH$^+$).

Example 65

Preparation of tert-butyl [3-oxo-3-(4'-oxo-6'-(pyridin-4-yl)-3',4'-dihydro-1H,1'H-spiro[piperidine-4,2'-thieno[3,2-d]pyrimidin]-1-yl)propyl]carbamate

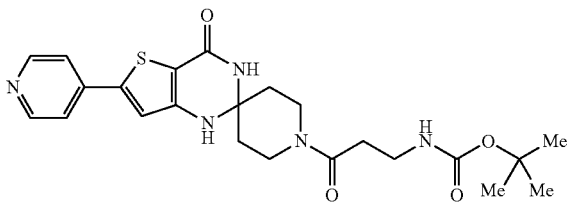 [SMILES: CC(C)(C)OC(=O)NCCC(=O)N1CCC2(CC1)NC(=O)c1sc(-c3ccncc3)cc1N2]

The title compound (11.0 mg, 29%) was synthesized in a manner similar to Example 64 except that N-(tert-butoxycarbonyl)-L-phenylalanine was replaced with N-(tert-butoxycarbonyl)-β-alanine.

MS (ESI$^+$) 472 (MH$^+$).

Example 66

Preparation of 1-(methoxyacetyl)-6'-(pyridin-4-yl)-1'H-spiro [piperidine-4,2'-thieno[3,2-d]pyrimidin]-4'(3'H)-one

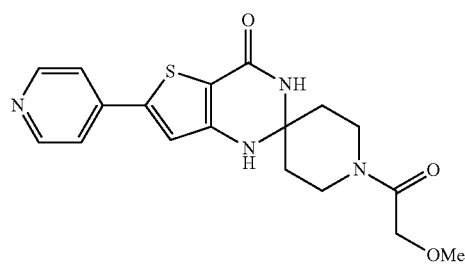 [SMILES: COCC(=O)N1CCC2(CC1)NC(=O)c1sc(-c3ccncc3)cc1N2]

The title compound (7.0 mg, 23.5%) was synthesized in a manner similar to Example 64 except that N-(tert-butoxycarbonyl)-L-phenylalanine was replaced with methoxyacetic acid.

MS (ESI$^+$) 373 (MH$^+$).

Example 67

Preparation of 1-(3-methoxypropanoyl)-6'-(pyridin-4-yl)-1'H-spiro[piperidine-4,2'-thieno[3,2-d]pyrimidin]-4'(3'H)-one

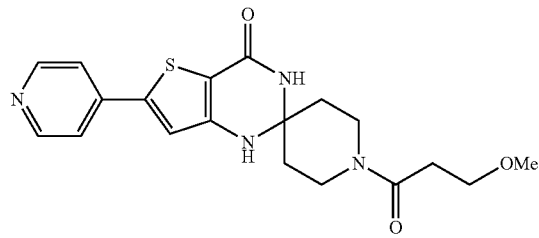 [SMILES: COCCC(=O)N1CCC2(CC1)NC(=O)c1sc(-c3ccncc3)cc1N2]

The title compound (6.7 mg, 22%) was synthesized in a manner similar to Example 64 except that N-(tert-butoxycarbonyl)-L-phenylalanine was replaced with 3-methoxypropanoic acid.
MS (ESI$^+$) 387 (MH$^+$).

Example 68

Preparation of methyl 4-oxo-4-(4'-oxo-6'-(pyridin-4-yl)-3',4'-dihydro-1H,1'H-spiro[piperidine-4,2'-thieno[3,2-d]pyrimidin]-1-yl)butanoate

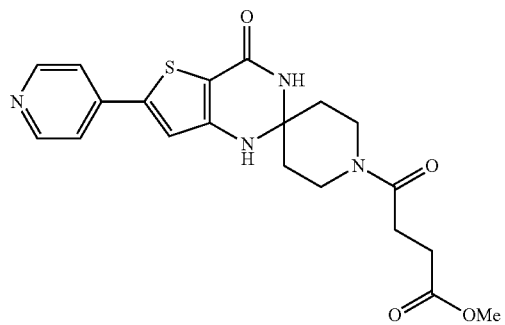 [SMILES: COC(=O)CCC(=O)N1CCC2(CC1)NC(=O)c1sc(-c3ccncc3)cc1N2]

The title compound (7.5 mg, 23%) was synthesized in a manner similar to Example 64 except that N-(tert-butoxycarbonyl)-L-phenylalanine was replaced with 4-methoxy-4-oxobutanoic acid.
MS (ESI$^+$) 415 (MH$^+$).

Example 69

Preparation of 6'-(pyridin-4-yl)-1-(pyridin-2-ylcarbonyl)-1'H-spiro[piperidine-4,2'-thieno[3,2-d]pyrimidin]-4'(3'H)-one

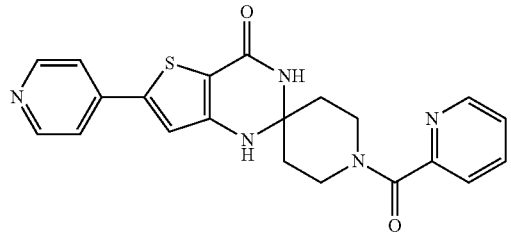 [SMILES: O=C1NC2(CCN(C(=O)c3ccccn3)CC2)Nc2cc(-c3ccncc3)sc21]

The title compound (11.0 mg, 34%) was synthesized in a manner similar to Example 64 except that N-(tert-butoxycarbonyl)-L-phenylalanine was replaced with pyridine-2-carboxylic acid.
MS (ESI$^+$) 406 (MH$^+$).

Example 70

Preparation of 6'-(pyridin-4-yl)-1-(pyridin-3-ylcarbonyl)-1'H-spiro[piperidine-4,2'-thieno[3,2-d]pyrimidin]-4'(3'H)-one

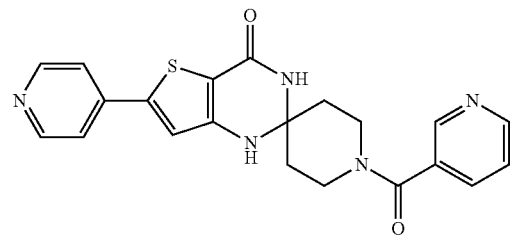 [SMILES: O=C1NC2(CCN(C(=O)c3cccnc3)CC2)Nc2cc(-c3ccncc3)sc21]

The title compound (9.1 mg, 28%) was synthesized in a manner similar to Example 64 except that N-(tert-butoxycarbonyl)-L-phenylalanine was replaced with pyridine-3-carboxylic acid.
MS (ESI$^+$) 406 (MH$^+$).

Example 71

Preparation of 6'-(pyridin-4-yl)-1-(pyridin-4-ylcarbonyl)-1'H-spiro[piperidine-4,2'-thieno[3,2-d]pyrimidin]-4'(3'H)-one

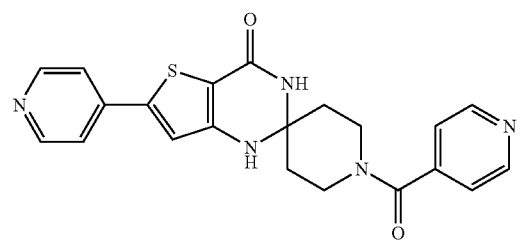 [SMILES: O=C1NC2(CCN(C(=O)c3ccncc3)CC2)Nc2cc(-c3ccncc3)sc21]

The title compound (5.9 mg, 18%) was synthesized in a manner similar to Example 64 except that N-(tert-butoxycarbonyl)-L-phenylalanine was replaced with pyridine-4-carboxylic acid.
MS (ESI$^+$) 406 (MH$^+$).

Example 72

Preparation of 6'-(pyridin-4-yl)-1-(tetrahydrofuran-2-ylcarbonyl)-1'H-spiro[piperidine-4,2'-thieno[3,2-d]pyrimidin]-4'(3'H)-one

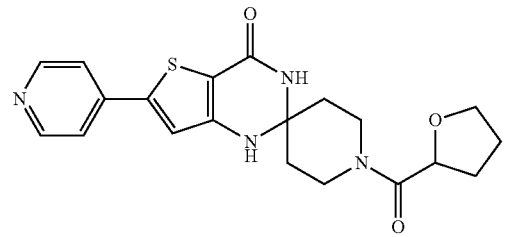 [SMILES: O=C1NC2(CCN(C(=O)C3CCCO3)CC2)Nc2cc(-c3ccncc3)sc21]

The title compound (3.4 mg, 11%) was synthesized in a manner similar to Example 64 except that N-(tert-butoxycarbonyl)-L-phenylalanine was replaced with tetrahydrofuran-2-carboxylic acid.
MS (ESI$^+$) 399 (MH$^+$).

Example 73

Preparation of N-[2-oxo-2-(4'-oxo-6'-(pyridin-4-yl)-3',4'-dihydro-1H,1'H-spiro[piperidine-4,2'-thieno[3,2-d]pyrimidin]-1-yl)ethyl]acetamide

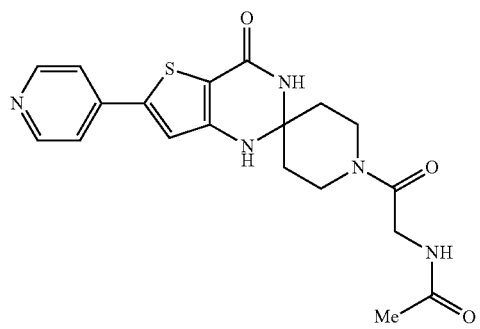 [SMILES: CC(=O)NCC(=O)N1CCC2(CC1)NC(=O)c1sc(-c3ccncc3)cc1N2]

The title compound (6.4 mg, 20%) was synthesized in a manner similar to Example 64 except that N-(tert-butoxycarbonyl)-L-phenylalanine was replaced with N-acetylglycine.

MS (ESI$^+$) 400 (MH$^+$).

Example 74

Preparation of 6'-(pyridin-4-yl)-1-(3,3,3-trifluoropropanoyl)-1'H-spiro[piperidine-4,2'-thieno[3,2-d]pyrimidin]-4'(3'H)-one

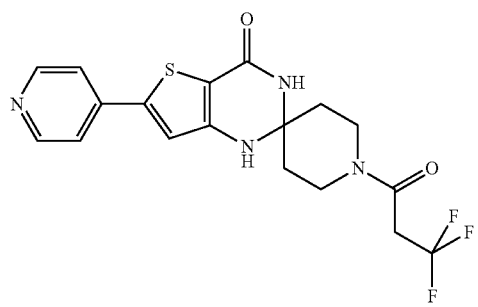 [SMILES: O=C1NC2(CCN(C(=O)CC(F)(F)F)CC2)Nc2cc(-c3ccncc3)sc21]

The title compound (10.9 mg, 33%) was synthesized in a manner similar to Example 64 except that N-(tert-butoxycarbonyl)-L-phenylalanine was replaced with 3,3,3-trifluoropropanoic acid.

MS (ESI$^+$) 411 (MH$^+$).

Example 75

Preparation of 1-(3-phenylpropanoyl)-6'-(pyridin-4-yl)-1'H-spiro[piperidine-4,2'-thieno[3,2-d]pyrimidin]-4'(3'H)-one

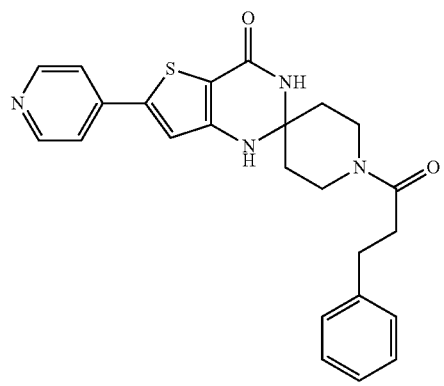 [SMILES: O=C1NC2(CCN(C(=O)CCc3ccccc3)CC2)Nc2cc(-c3ccncc3)sc21]

The title compound (5.4 mg, 16%) was synthesized in a manner similar to Example 64 except that N-(tert-butoxycarbonyl)-L-phenylalanine was replaced with 3-phenylpropanoic acid.

MS (ESI$^+$) 433 (MH$^+$).

Example 76

Preparation of 1-[(1-phenylcyclopropyl)carbonyl]-6'-(pyridin-4-yl)-1'H-spiro[piperidine-4,2'-thieno[3,2-d]pyrimidin]-4'(3'H)-one

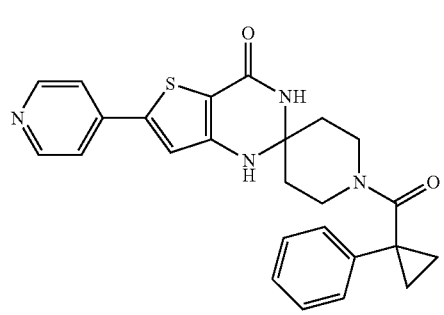 [SMILES: O=C1NC2(CCN(C(=O)C3(c4ccccc4)CC3)CC2)Nc2cc(-c3ccncc3)sc21]

The title compound (7.0 mg, 20%) was synthesized in a manner similar to Example 64 except that N-(tert-butoxycarbonyl)-L-phenylalanine was replaced with 1-phenylcyclopropanecarboxylic acid.

MS (ESI$^+$) 445 (MH$^+$).

Example 77

Preparation of 1-(1H-indol-3-ylacetyl)-6'-(pyridin-4-yl)-1'H-spiro[piperidine-4,2'-thieno[3,2-d]pyrimidin]-4'(3'H)-one

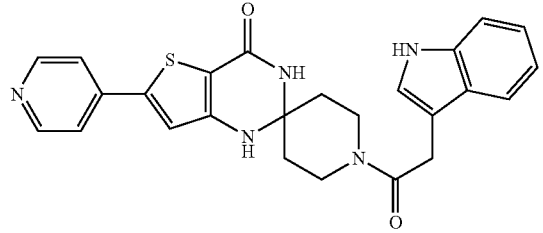 [SMILES: O=C1NC2(CCN(C(=O)Cc3c[nH]c4ccccc34)CC2)Nc2cc(-c3ccncc3)sc21]

The title compound (8.0 mg, 22%) was synthesized in a manner similar to Example 64 except that N-(tert-butoxycarbonyl)-L-phenylalanine was replaced with 1H-indol-3-ylacetic acid.
MS (ESI+) 458 (MH+).

Example 78

Preparation of ethyl (4'-oxo-6'-(pyridin-4-yl)-3',4'-dihydro-1H,1'H-spiro[piperidine-4,2'-thieno[3,2-d]pyrimidin]-1-yl)acetate

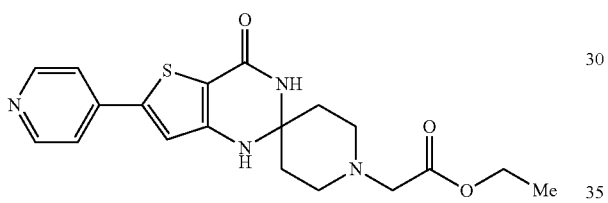

A mixture of 6'-(pyridin-4-yl)-1'H-spiro[piperidine-4,2'-thieno[3,2-d]pyrimidin]-4'(3'H)-one in DMF (0.16 M, 0.50 mL, 0.080 mmol), ethyl bromoacetate in DMF (0.20 M, 1.0 mL, 0.20 mmol) and potassium carbonate (40 mg, 0.29 mmol) was stirred at 40° C. for 16 h. The reaction mixture was extracted with EtOAc (3.5 mL) and 2% aqueous sodium hydrogen carbonate (1 mL). After evaporating the organic solvent, the crude product was chromatographed on preparative HPLC (YMC CombiPrep. Hydrosphere C18, 10 mM $NH_4HCO_3$ in water/MeCN) to afford the title compound (6.5 mg, 21%):
MS (ESI+) 387 (MH+).

Example 79

Preparation of 1-(2-cyclohexyl-2-oxoethyl)-6'-(pyridin-4-yl)-1'H-spiro[piperidine-4,2'-thieno[3,2-d]pyrimidin]-4'(3'H)-one

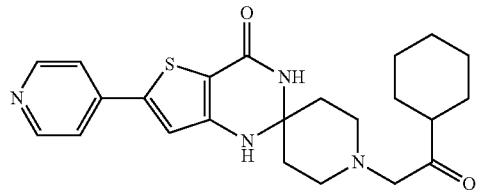 [SMILES: O=C1NC2(CCN(CC(=O)C3CCCCC3)CC2)Nc2cc(-c3ccncc3)sc21]

The title compound (9.1 mg, 27%) was synthesized in a manner similar to Example 78 except that ethyl bromoacetate was replaced with 2-bromo-1-cyclohexylethanone.
MS (ESI+) 425 (MH+).

Example 80

Preparation of 1-ethyl-6'-(pyridin-4-yl)-1'H-spiro[piperidine-4,2'-thieno[3,2-d]-pyrimidin]-4'(3'H)-one

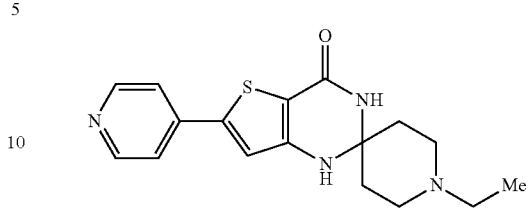

A mixture of 6'-(pyridin-4-yl)-1'H-spiro[piperidine-4,2'-thieno[3,2-d]pyrimidin]-4'(3'H)-one in DMF (0.16 M, 0.50 mL, 0.080 mmol), acetaldehyde in DMF (0.20 M, 1 mL, 0.20 mmol) and sodium triacetoxyborohydride (40 mg, 0.19 mmol) was stirred for 16 h at room temperature. The reaction mixture was extracted with EtOAc (3.5 mL) and 2% aqueous sodium hydrogen carbonate (1 mL). After evaporating the organic solvent, the crude product was chromatographed on preparative HPLC (YMC CombiPrep. Hydrosphere C18, 10 mM $NH_4HCO_3$ in water/MeCN) to afford the title compound (2.4 mg, 9.1%):
MS (ESI+): 329 (MH+).

Example 81

Preparation of 1-benzyl-6'-(pyridin-4-yl)-1'H-spiro[piperidine-4,2'-thieno[3,2-d]pyrimidin]-4'(3'H)-one

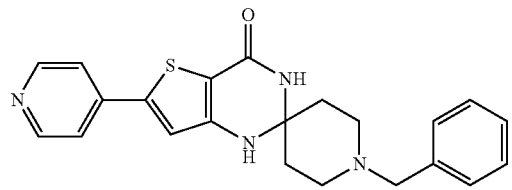 [SMILES: O=C1NC2(CCN(Cc3ccccc3)CC2)Nc2cc(-c3ccncc3)sc21]

The title compound (9.3 mg, 30%) was synthesized in a manner similar to Example 80 except that acetaldehyde was replaced with benzaldehyde.
MS (ESI+) 391 (MH+).

Example 82

Preparation of 6'-(pyridin-4-yl)-1-(pyridin-4-ylmethyl)-1'H-spiro[piperidine-4,2'-thieno[3,2-d]pyrimidin]-4'(3'H)-one

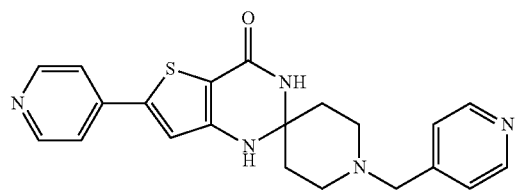 [SMILES: O=C1NC2(CCN(Cc3ccncc3)CC2)Nc2cc(-c3ccncc3)sc21]

The title compound (6.8 mg, 22%) was synthesized in a manner similar to Example 80 except that acetaldehyde was replaced with pyridine-4-carbaldehyde.
MS (ESI+) 392 (MH+).

Example 83

Preparation of 1-[(1-methyl-1H-pyrrol-2-yl)methyl]-6'-(pyridin-4-yl)-1'H-spiro[piperidine-4,2'-thieno[3,2-d]pyrimidin]-4'(3'H)-one

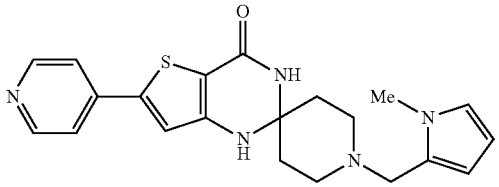 [SMILES: Cn1cccc1CN1CCC2(CC1)NC(=O)c1sc(-c3ccncc3)cc1N2]

The title compound (3.3 mg, 11%) was synthesized in a manner similar to Example 80 except that acetaldehyde was replaced with 1-methyl-1H-pyrrole-2-carbaldehyde.

MS (ESI+) 394 (MH+).

Example 84

Preparation of 6-(2-fluoropyridin-4-yl)-2,2-dimethyl-2,3-dihydrothieno[3,2-d]pyrimidin-4(1H)-one

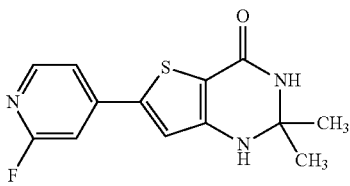 [SMILES: CC1(C)NC(=O)c2sc(-c3ccnc(F)c3)cc2N1]

A mixture of 6-bromo-2,2-dimethyl-2,3-dihydrothieno[3,2-d]pyrimidin-4(1H)-one (0.052 g, 0.20 mmol), 2-fluoro-4-(4,4,5,5-tetramethyl-1,3,2-dioxaborolan-2-yl)pyridine (0.085 g, 0.60 mmol), 2 M sodium carbonate (0.30 mL, 0.60 mmol) and 1,1'-bis(diphenylphosphino)ferrocenepalladium (II) dichloride dichloromethane adduct (0.033 g, 0.040 mmol) in 1,4-dioxane (2 mL) was degassed with nitrogen and heated at 70° C. for 15 h. Then, the reaction was cooled to room temperature, and concentrated with silica gel (2 mL), and the residue was purified by flash chromatography (silica gel, ethyl acetate to 80:20 ethyl acetate/methanol) to give the title compound (0.038 g, 69%) as a yellow solid:

$^1$H NMR (300 MHz, DMSO-$d_6$) δ 1.42 (6H, s), 7.19 (1H, s), 7.24 (1H, s), 7.51 (1H, s), 7.60 (1H, d, J=4.8 Hz), 7.71 (1H, s), 8.27 (1H, d, J=5.4 Hz).

Example 85

Preparation of 6-(2-aminopyridin-4-yl)-2,2-dimethyl-2,3-dihydrothieno[3,2-d]pyrimidin-4(1H)-one

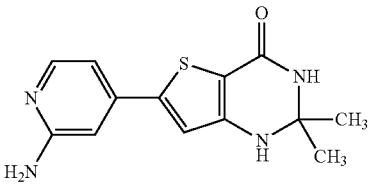 [SMILES: CC1(C)NC(=O)c2sc(-c3ccnc(N)c3)cc2N1]

A mixture of 6-bromo-2,2-dimethyl-2,3-dihydrothieno[3,2-d]pyrimidin-4(1H)-one (0.039 g, 0.15 mmol), 4-(4,4,5,5-tetramethyl-1,3,2-dioxaborolan-2-yl)pyridin-2-amine (0.022 g, 0.10 mmol), 2 M sodium carbonate (0.075 mL, 0.15 mmol) and 1,1'-bis(diphenylphosphino)ferrocenepalladium (II) dichloride dichloromethane adduct (0.024 g, 0.030 mmol) in 1,4-dioxane (0.5 mL) was microwave-irradiated at 140° C. for 1 h. Reactions were repeated on 0.10 mmol and 0.20 mmol scales (based on the boronic ester). The reaction mixtures were combined, and concentrated with silica gel (10 mL), and the residue was purified by flash chromatography (silica gel, ethyl acetate to 90:10 ethyl acetate/methanol) to give a crude product as a yellow solid, which was further purified by preparative HPLC. Preparative HPLC was carried out on a Varian Prostar 210 HPLC system using a Phenomenex Luna C18(2) column with UV detection at 254 nm and a solvent gradient of 95:5 solvent A/solvent B to 5:95 solvent A/solvent B (solvent A=water with 0.1% v/v trifluoroacetic acid; solvent B=acetonitrile with 0.1% v/v trifluoroacetic acid). Upon concentration, a TFA salt was obtained, which was dissolved in methanol (10 mL), and the solution was concentrated with NaHCO$_3$ (0.2 g) and silica gel (1 mL). Flash chromatography (silica gel, dichloromethane to 85:15 dichloromethane/methanol) gave the title compound (0.012 g, 11%) as a yellow solid:

$^1$H NMR (500 MHz, DMSO-$d_6$) δ 1.41 (6H, s), 6.07 (2H, s), 6.62 (1H, d, J=1.0 Hz), 6.72 (1H, dd, J=5.0, 1.5 Hz), 6.92 (1H, s), 7.07 (1H, s), 7.58 (1H, s), 7.93 (1H, d, J=5.5 Hz).

Example 86

Preparation of 7-bromo-1,2,2-trimethyl-6-(1H-pyrazol-4-yl)-2,3-dihydrothieno[3,2-d]pyrimidin-4(1H)-one To a stirred solution of 1,2,2-trimethyl-6-(1H-pyrazol-4-yl)-2,3-dihydrothieno[3,2-d]pyrimidin-4(1H)-one (0.111 g, 0.423 mmol) in acetic acid (5 mL) was added bromine (0.030 mL, 0.582 mmol) at room temperature. After 1 h, the precipitate was collected by filtration and washed with EtOAc to give a yellow solid (111 mg). The obtained solid was mixed with acetone (4 mL), acetic acid (1 mL) and PTSA (4.0 mg, 0.021 mmol), and this mixture was stirred at 60° C. for 2 h. The mixture was poured into saturated aqueous NaHCO₃ and extracted with EtOAc, and the extract was dried over MgSO₄ and concentrated under reduced pressure to give a yellow solid. This residue was mixed with acetone (4 mL), acetic acid (1 mL) and PTSA (4.0 mg, 0.021 mmol). The mixture was stirred at 60° C. overnight. Then, the mixture was poured into saturated aqueous NaHCO₃ and extracted with EtOAc, and the extract was dried over MgSO₄ and concentrated under reduced pressure. The residue was purified by column chromatography (Purif, silica gel, 95:5 hexane/EtOAc to EtOAc) to give a white solid. This solid was triturated with EtOAc/hexane and collected by filtration to afford the title compound (36.2 mg, 25%) as a white solid:

$^1$H NMR (300 MHz, DMSO-d₆) δ 1.41 (6H, s), 2.68 (3H, s), 7.97-8.33 (3H, m), 13.36 (1H, br s).

Example 87

Preparation of 6-(3,5-dimethyl-1H-pyrazol-4-yl)-1,2,2-trimethyl-2,3-dihydrothieno[3,2-d]pyrimidin-4(1H)-one

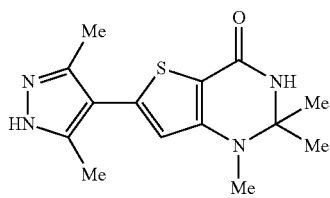 [SMILES: Cc1n[nH]c(C)c1-c1cc2c(s1)C(=O)NC(C)(C)N2C]

A mixture of 6-bromo-1,2,2-trimethyl-2,3-dihydrothieno[3,2-d]pyrimidin-4(1H)-one (138 mg, 0.50 mmol), 3,5-dimethyl-4-(4,4,5,5-tetramethyl-1,3,2-dioxaborolan-2-yl)-1H-pyrazole (333 mg, 1.50 mmol), sodium carbonate (265 mg, 2.50 mmol), 1,2-dimethoxyethane (5 mL) and water (2 mL) was purged with argon. Then, 1,1'-bis(diphenylphosphino)ferrocenepalladium (II) dichloride dichloromethane adduct (40.8 mg, 0.050 mmol) was added, and the mixture was purged with argon again. This mixture was refluxed for 18 h. Then, the mixture was poured into saturated aqueous NaHCO₃ (100 mL) and EtOAc (100 mL), and the mixture was shaken well. The insoluble materials were filtered off. From the filtrate, the organic layer was collected, washed with brine, dried over MgSO₄, filtered and concentrated under reduced pressure. This residue was purified by column chromatography (Purif, silica gel, 95:5 hexane/EtOAc to EtOAc, then EtOAc to 90:10 EtOAc/MeOH). The obtained yellow solid was triturated with EtOAc/hexane and collected by filtration to afford the title compound (52.2 mg, 36%) as a pale yellow solid:

$^1$H NMR (300 MHz, DMSO-d₆) δ 1.41 (6H, s), 2.29-2.33 (6H, m), 2.88 (3H, s), 6.65 (1H, s), 7.44 (1H, br s), 12.53 (1H, br s).

Example 88

Preparation of ethyl [2,2-dimethyl-4-oxo-6-(1H-pyrazol-4-yl)-3,4-dihydrothieno[3,2-d]pyrimidin-1(2H)-yl]acetate

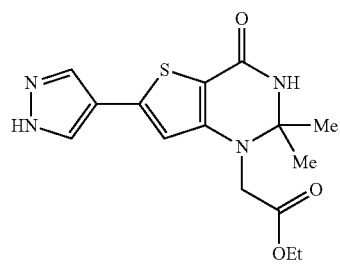 [SMILES: CCOC(=O)CN1c2cc(-c3cn[nH]c3)sc2C(=O)NC1(C)C]

Step 1

Preparation of methyl 3-[(trifluoroacetyl)amino]thiophene-2-carboxylate

To a solution of methyl 3-aminothiophene-2-carboxylate (50 g, 0.31 mmol) in MeCN (650 mL) were added pyridine (31 mL) and trifluoroacetic anhydride (58.6 mL) at 0° C. After stirring at that temperature for 5 min, the mixture was allowed to room temperature and the stirring was continued for 10 min. Then, ice-water (6.0 L) was added to quench the reaction. After stirring for 20 min, the precipitate was collected by filtration and washed with water. The title compound (80 g, quant.) was obtained as a pale brown solid:

$^1$H NMR (300 MHz, DMSO-d₆) δ 3.86 (3H, s), 7.72 (1H, d, J=5.4 Hz), 8.03 (1H, d, J=5.4 Hz), 11.17 (1H, br s).

Step 2

Preparation of methyl 5-bromo-3-[(trifluoroacetyl)amino]thiophene-2-carboxylate

To a solution of N-(1-methylethyl)propan-2-amine (20 mL, 142 mmol) in THF (200 mL) was added 1.6 M n-butyllithium in hexane (84.2 mL, 132 mmol) at 0° C. After stirring at this temperature for 15 min, the mixture was cooled to –78° C. Then, a solution of methyl 3-[(trifluoroacetyl)amino]thiophene-2-carboxylate (10.1 g, 40.0 mmol) in THF (50 mL) was added slowly. After additional stirring at –78° C. for 1 h, 1,2-dibromoethane (20.6 mL, 238 mmol) was added at once. The mixture was stirred at –78° C. for 30 min and at room temperature for 30 min. The mixture was poured into saturated aqueous NaHCO₃ (600 mL) and extracted with EtOAc. The combined extracts were washed with brine, and then dried over Na₂SO₄. After removal of the solvent at reduced pressure, the residue was purified by column chromatography (Purif, silica gel, hexane to 10:90 hexane/EtOAc) to give the title compound (5.30 g, 41%) as a yellow solid:

$^1$H NMR (300 MHz, CDCl₃) δ 3.94 (3H, s), 8.11 (1H, s), 11.15 (1H, br s).

Step 3

Preparation of methyl 3-amino-5-bromothiophene-2-carboxylate

A mixture of methyl 5-bromo-3-[(trifluoroacetyl)amino]thiophene-2-carboxylate (5.30 g, 16.0 mmol), potassium carbonate (10.2 g, 70.4 mmol), MeOH (100 mL) and water (25 mL) was stirred at room temperature for 2 h. After removal of the solvent at reduced pressure, the residue was extracted with EtOAc, and the extract was washed with water and brine, dried over $Na_2SO_4$ and filtered. After removal of the solvent at reduced pressure, the residue was purified by column chromatography (Purif, silica gel, hexane to 10:90 hexane/EtOAc) to give the title compound (3.32 g, 88%) as a yellow solid:

$^1$H NMR (300 MHz, DMSO-$d_6$) δ 3.70 (3H, s), 6.68 (2H, br s), 6.75 (1H, s).

Step 4

Preparation of 3-amino-5-bromo-N-(4-methoxybenzyl)thiophene-2-carboxamide

To a solution of methyl 3-amino-5-bromothiophene-2-carboxylate (1.2 g, 5.08 mmol) in MeOH (15 mL) was added sodium hydroxide (0.61 g, 15.2 mmol) and water (5 mL). After stirring at 60° C. for 5 h, 6 M HCl (1.58 mL) was added to the mixture to adjust the pH to 10. After removal of the solvent at reduced pressure, the residue was dissolved in DMF (35 mL). Then, 1-hydroxybenzotriazole (4.1 g, 30.5 mmol), 1-ethyl-3-(3-dimethylaminopropyl)carbodiimide hydrochloride (4.7 g, 30.5 mmol) and 4-methoxybenzyl amine (3.76 mL, 25.4 mmol) were added. After stirring at room temperature for 17 h, water was added to quench the reaction. The organic materials were extracted with EtOAc. The combined extracts were washed with water and brine, dried over $Na_2SO_4$ and filtered. After removal of the solvent at reduced pressure, the residue was purified by column chromatography (Purif, silica gel, 90:10 hexane/EtOAc to 50:50 hexane/EtOAc) to give the title compound (1.46 g, 84%) as a yellow gum:

$^1$H NMR (300 MHz, CDCl$_3$) δ 3.80 (3H, s), 4.47 (2H, d, J=5.5 Hz), 5.43 (1H, br s), 5.64 (2H, br s), 6.58 (1H, s), 6.82-6.93 (2H, m), 7.21-7.32 (2H, m).

Step 5

Preparation of ethyl (6-bromo-2,2-dimethyl-4-oxo-3,4-dihydrothieno[3,2-d]pyrimidin-1(2H)-yl)acetate A mixture of 3-amino-5-bromo-N-(4-methoxybenzyl)thiophene-2-carboxamide (0.80 g, 2.34 mmol), MgSO$_4$ (320 mg), acetone (2.5 mL), PTSA (20 mg) and DMA (0.5 mL) was microwave-irradiated at 120° C. for 1 h then at 130° C. for 0.5 h. Then, the mixture was poured into saturated aqueous NaHCO$_3$ and extracted with EtOAc, and the extract was washed with water and brine, dried over Na$_2$SO$_4$ and filtered. After removal of the solvent at reduced pressure, the residue was purified by column chromatography (Purif, silica gel, 90:10 hexane/EtOAc to 60:40 hexane/EtOAc) to give a pale brown crystalline solid (685 mg). This solid was dissolved in DMF (20 mL) and sodium hydride (50%, 128 mg, 2.67 mmol) was added at 0° C. After stirring at room temperature for 20 min, ethyl bromoacetate (0.30 mL, 2.67 mmol) was added. After stirring at room temperature for 1 h, water and EtOAc were added to quench the reaction. The organic layer was collected, washed with water and brine, dried over Na$_2$SO$_4$ and filtered. After removal of the solvent at reduced pressure, the residue was purified by column chromatography (Purif, NH, 90:10 hexane/EtOAc to 60:40 hexane/EtOAc) to give brown oil. This brown oil was dissolved in TFA (5.0 mL), and the mixture was stirred at 70° C. for 30 min. After removal of the solvent at reduced pressure, the residue was treated with saturated aqueous NaHCO$_3$. The organic materials were extracted with EtOAc, and the extract was washed with brine, dried over Na$_2$SO$_4$ and filtered. After removal of the solvent at reduced pressure, a yellow crystalline solid (628 mg) was obtained. This solid (370 mg) was dissolved in acetone (2 mL) and DMA (1 mL). To the solution were added PTSA (17 mg) and MgSO$_4$ (150 mg). The mixture was microwave-irradiated at 120° C. for 1 h. Then, water and EtOAc were added to quench the reaction. The organic materials were extracted with EtOAc, and the extract was washed with water and brine, dried over Na$_2$SO$_4$ and filtered. After removal of the solvent at reduced pressure, the residue was purified by column chromatography (Purif, silica gel, 90:10 hexane/EtOAc to 25:75 hexane/EtOAc) to give the title compound (135 mg, 28%) as a pale yellow solid:

$^1$H NMR (300 MHz, DMSO-$d_6$) δ 1.21 (3H, t, J=7.0 Hz), 1.39 (6H, s), 4.14 (2H, q, J=7.0 Hz), 4.20 (2H, s), 6.98 (1H, s), 7.71 (1H, br s).

Step 6

Preparation of ethyl [2,2-dimethyl-4-oxo-6-(1H-pyrazol-4-yl)-3,4-dihydrothieno[3,2-d]pyrimidin-1(2H)-yl]acetate A flask was charged with ethyl (6-bromo-2,2-dimethyl-4-oxo-3,4-dihydrothieno[3,2-d]pyrimidin-1(2H)-yl)acetate (120 mg, 0.346 mmol), tert-butyl 4-(4,4,5,5-tetramethyl-1,3,2-dioxaborolan-2-yl)-1H-pyrazole-1-carboxylate (288 mg, 0.978 mmol), K$_3$PO$_4$ (277 mg, 1.3 mmol) and DMF (1 mL). The flask was purged with argon. Then, 1,1'-bis(diphenylphosphino) ferrocenepalladium (II) dichloride dichloromethane adduct (8.0 mg, 0.0098 mmol) was added to the mixture. The flask was purged with argon again. After stirring at 50° C. for 18 h and at 80° C. for 18 h, water and EtOAc were added to quench the reaction. The organic materials were extracted with EtOAc. The combined extracts were washed with water and brine, dried over Na$_2$SO$_4$ and filtered. After removal of the solvent at reduced pressure, the residue was purified by column chromatography (Purif, silica gel, EtOAc to 90:10 EtOAc/MeOH), then crystallized from MeOH/EtOAc/heptane to give the title compound (5.6 mg, 5%) as a brown solid:

$^1$H NMR (300 MHz, DMSO-$d_6$) δ 1.22 (3H, t, J=7.1 Hz), 1.40 (6H, s), 4.10-4.25 (4H, m), 6.86 (1H, s), 7.52 (1H, s), 7.80 (1H, br s), 8.14 (1H, br s), 13.13 (1H, br s).

Example 89

Preparation of 2,2-dimethyl-1-(2-(morpholin-4-yl)-2-oxoethyl)-6-(1H-pyrazol-4-yl)-2,3-dihydrothieno[3,2-d]pyrimidin-4(1H)-one

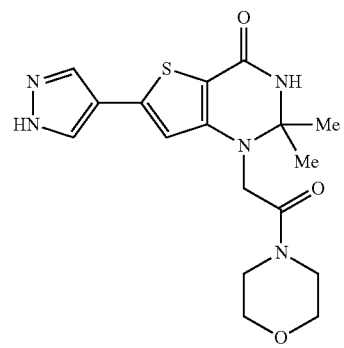 [SMILES: CC1(C)NC(=O)c2sc(-c3cn[nH]c3)cc2N1CC(=O)N1CCOCC1]

Step 1

Preparation of 6-bromo-3-(4-methoxybenzyl)-2,2-dimethyl-2,3-dihydrothieno[3,2-d]pyrimidin-4(1H)-one A mixture of 3-amino-5-bromo-N-(4-methoxybenzyl)thiophene-2-carboxamide (160 mg, 0.47 mmol), MgSO$_4$ (60 mg), 2,2-dimethoxypropane (0.5 mL), PTSA (8.6 mg, 0.050 mmol) and DMA (0.5 mL) was stirred at 120° C. for 1 h by using microwave reactor. Then, the mixture was poured into saturated aqueous NaHCO$_3$. The organic materials were extracted with AcOEt. The combined extracts were washed with water and brine, and then dried over Na$_2$SO$_4$. After removal of the solvent at reduced pressure, the residue was purified by column chromatography (silica gel, 90:10 hexane/EtOAc to 40:60 hexane/EtOAc) to give the title compound (112 mg, 62%) as a pale brown solid:

$^1$H NMR (300 MHz, DMSO-d$_6$) δ 1.37 (6H, s), 3.71 (3H, s), 4.54 (2H, s), 6.72 (1H, s), 6.86 (2H, d, J=8.7 Hz), 7.18 (2H, d, J=8.7 Hz), 7.26 (1H, br s).

Step 2

Preparation of 5-bromo-3-[(2-(morpholin-4-yl)-2-oxoethyl)amino]thiophene-2-carboxamide To a solution of 6-bromo-3-(4-methoxybenzyl)-2,2-dimethyl-2,3-dihydrothieno[3,2-d]pyrimidin-4(1H)-one (500 mg, 1.31 mmol) in DMF (13 mL) was added NaH (50%, 94 mg, 1.97 mmol) at 0° C. After stirring at room temperature for 15 min, ethyl bromoacetate (0.16 mL, 1.44 mmol) was added at once. After stirring at room temperature for 0.5 h, the mixture was poured into saturated aqueous NaHCO$_3$. The organic materials were extracted with EtOAc. To the aqueous layer was added 1 M HCl until pH 5. The organic materials were extracted with EtOAc. The combined extracts were washed with water and brine, and then dried over Na$_2$SO$_4$. After removal of the solvent at reduced pressure, the residual brown oil was mixed with N-ethyl-N-(1-methylethyl)propan-2-amine (0.24 mL, 1.37 mmol) and morpholine (0.072 mL, 0.82 mmol) in DMF (5 mL), and HATU (312 mg, 0.82 mmol) was added. After stirring at room temperature for 1 h, water and EtOAc were added to quench the reaction. The organic materials were extracted with EtOAc. The combined extracts were washed with water and brine, dried over Na$_2$SO$_4$ and filtered. After removal of the solvent at reduced pressure, the residue was purified by column chromatography (Purif, silica gel, 95:5 hexane-EtOAc to EtOAc) to give a brown oil. After the oil was dissolved in TFA (2 mL), the mixture was stirred at 70° C. for 2 h. After removal of the solvent at reduced pressure, saturated aqueous NaHCO$_3$ was added. The organic materials were extracted with EtOAc. The combined extracts were washed with brine, dried over Na$_2$SO$_4$ and filtered. After removal of the solvent at reduced pressure, the residue was triturated with EtOAc and collected by filtration to afford the title compound (97 mg) as a brown solid. After concentration of the filtrate, the residue was purified by column chromatography (Purif, silica gel, 95:5 hexane/EtOAc to EtOAc then to 90:10 EtOAc/MeOH) to give the title compound (27 mg) as a brown solid. Total yield of the title compound (97+27 mg) was 27%:

$^1$H NMR (300 MHz, DMSO-d$_6$) δ 3.39-3.51 (4H, m), 3.53-3.65 (4H, m), 4.09 (2H, d, J=4.9 Hz), 6.93 (2H, br s), 7.03 (1H, s), 7.84 (1H, t, J=4.9 Hz).

Step 3

Preparation of 6-bromo-2,2-dimethyl-1-(2-(morpholin-4-yl)-2-oxoethyl)-2,3-dihydrothieno[3,2-d]pyrimidin-4(1H)-one A mixture of 5-bromo-3-[(2-(morpholin-4-yl)-2-oxoethyl)amino]thiophene-2-carboxamide (120 mg, 0.345 mmol), CSA (10 mg), 2,2-dimethoxypropane (1.0 mL) and DMA (1 mL) was stirred at 80° C. for 0.5 h. Then, water and saturated aqueous NaHCO$_3$ were added to quench the reaction. The precipitate was collected by filtration to afford the title compound (66 mg) as a pale brown solid. From the filtrate, the organic layer was collected, washed with water and brine, dried over Na$_2$SO$_4$ and filtered. The filtrate was concentrated under reduced pressure to afford the title compound (50 mg) as a pale brown solid. Total yield of the title compound (66+50 mg) was 87%:

$^1$H NMR (300 MHz, DMSO-d$_6$) δ 1.38 (6H, s), 3.39-3.52 (4H, m), 3.53-3.69 (4H, m), 4.26 (2H, s), 6.85 (1H, s), 7.61 (1H, br s).

Step 4

Preparation of 2,2-dimethyl-1-(2-(morpholin-4-yl)-2-oxoethyl)-6-(1H-pyrazol-4-yl)-2,3-dihydrothieno[3,2-d]pyrimidin-4(1H)-one A flask was charged with 6-bromo-2,2-dimethyl-1-(2-(morpholin-4-yl)-2-oxoethyl)-2,3-dihydrothieno[3,2-d]pyrimidin-4(1H)-one (115 mg, 0.296 mmol), Na$_2$CO$_3$ (89 mg, 1.48 mmol), 1,2-dimethoxyethane (2 mL), water (1 mL) and tert-butyl 4-(4,4,5,5-tetramethyl-1,3,2-dioxaborolan-2-yl)-1H-pyrazole-1-carboxylate (261 mg, 0.888 mmol). The flask was purged with argon. Then, 1,1'-bis(diphenylphosphino)ferrocenepalladium (II) dichloride dichloromethane adduct (24 mg, 0.0296 mmol) was added to the mixture. The flask was purged with argon again. After stirring at 100° C. for 3 h, water and EtOAc were added to quench the reaction. The insoluble materials were filtered off, and NaCl was added to the filtrate. The organic materials were extracted with EtOAc/THF, and the extract was concentrated under reduced pressure. The residue was purified by column chromatography (Purif, silica gel, EtOAc to 80:20 EtOAc/MeOH), then crystallized from MeOH/EtOAc/hexane to give the title compound (31 mg, 27%) as a pale brown solid:

$^1$H NMR (300 MHz, DMSO-d$_6$) δ 1.40 (6H, s), 3.39-3.71 (8H, m), 4.26 (2H, s), 6.69 (1H, s), 7.43 (1H, s), 7.79 (1H, br s), 8.12 (1H, br s), 13.12 (1H, br s).

Example 90

Preparation of 4,4-difluoro-1'-methyl-6'-(1H-pyrazol-4-yl)-1'H-spiro[cyclohexane-1,2'-thieno[3,2-d]pyrimidin]-4'(3'H)-one

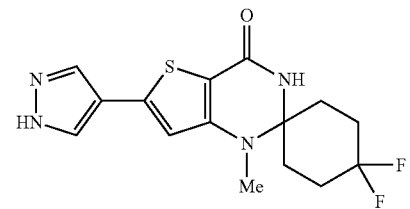 [SMILES: CN1c2cc(-c3cn[nH]c3)sc2C(=O)NC12CCC(F)(F)CC2]

A mixture of 1,2,2-trimethyl-6-(1H-pyrazol-4-yl)-2,3-dihydrothieno[3,2-d]pyrimidin-4(1H)-one (131 mg, 0.50 mmol), 1 M aqueous HCl (2.5 mL, 2.5 mmol) and MeOH (2.5 mL) was stirred at 50° C. for 1 h. After addition of saturated aqueous NaHCO₃, the organic materials were extracted with EtOAc. After removal of the solvent at reduced pressure, the residue was mixed with 4,4-difluorocyclohexanone (335 mg, 2.5 mmol), CSA (12 mg, 0.050 mmol), MgSO₄ (96 mg, 1.0 mmol) and DMA (1 mL). After stirred at 80° C. for 1.5 h, saturated aqueous NaHCO₃ and EtOAc were added to quench the reaction. The organic materials were extracted with EtOAc. The combined extracts were washed with water and brine, dried over Na₂SO₄ and filtered. After removal of the solvent at reduced pressure, the residue was purified by column chromatography (Purif, silica gel, 90:10 hexane/EtOAc to EtOAc), then crystallized from MeOH/EtOAc/hexane to give the title compound (121 mg, 72%) as a yellow solid:

¹H NMR (300 MHz, DMSO-d₆) δ 1.83-2.40 (8H, m), 2.91 (3H, s), 7.05 (1H, s), 7.76 (1H, s), 7.86 (1H, br s), 8.18 (1H, br s), 13.13 (1H, br s).

Example 91

Preparation of 1,2,2-trimethyl-6-(1H-pyrrolo[2,3-b]pyridin-4-yl)-2,3-dihydrothieno[3,2-d]pyrimidin-4(1H)-one

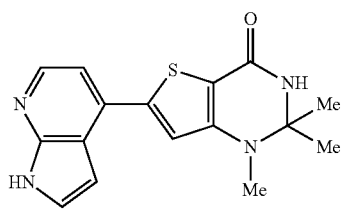 [SMILES: CN1c2cc(-c3ccnc4[nH]ccc34)sc2C(=O)NC1(C)C]

Step 1

Preparation of 4-(4,4,5,5-tetramethyl-1,3,2-dioxaborolan-2-yl)-1H-pyrrolo[2,3-b]pyridine To a suspension of 4-chloro-1H-pyrrolo[2,3-b]pyridine (1.00 g, 6.55 mmol), 4,4,4',4',5,5,5',5'-octamethyl-2,2'-bi-1,3,2-dioxaborolane (2.16 g, 8.52 mmol), biphenyl-2-yl(dicyclohexyl) phosphane (575 mg, 1.64 mmol) and potassium acetate (2.25 g, 22.9 mmol) in 1,2-dimethoxyethane (20 mL) was added tris(dibenzylideneacetone)dipalladium(0) (600 mg, 0.655 mmol). The mixture was degassed and stirred at 90° C. for 5 h under argon atmosphere. To the resulting mixture were added EtOAc (100 mL) and water (50 mL). An insoluble material was removed by filtration and the layers of the filtrate were separated. The aqueous layer was extracted with EtOAc (10 mL). The combined organic layers were washed with brine (10 mL), dried over Na₂SO₄ and concentrated under reduced pressure. The residue was triturated with EtOAc/hexane (1:1, 10 mL) to give pale yellow solid (442 mg, 28%). The filtrate was concentrated under reduced pressure, and the residue was purified by column chromatography (Purif, silica gel, 90:10 hexane/EtOAc to 60:40 hexane/EtOAc) to give the title compound (320 mg, 20%, total yield=762 mg, 48%) as a colorless solid:

¹H NMR (300 MHz, DMSO-d₆) 1.35 (12H, s), 6.66 (1H, dd, J=3.2, 1.9 Hz), 7.28 (1H, d, J=4.5 Hz), 7.51 (1H, t, J=3.2 Hz), 8.21 (1H, d, J=4.5 Hz), 11.63 (1H, br s).

Step 2

Preparation of 1,2,2-trimethyl-6-(1H-pyrrolo[2,3-b]pyridin-4-yl)-2,3-dihydrothieno[3,2-d]pyrimidin-4(1H)-one A mixture of 6-bromo-1,2,2-trimethyl-2,3-dihydrothieno[3,2-d]pyrimidin-4(1H)-one (138 mg, 0.50 mmol), 4-(4,4,5,5-tetramethyl-1,3,2-dioxaborolan-2-yl)-1H-pyrrolo[2,3-b]pyridine (183 mg, 0.75 mmol), cesium carbonate (489 mg, 1.50 mmol), 1,2-dimethoxyethane (5 mL) and water (1 mL) was purged with argon. Then, 1,1'-bis(diphenylphosphino)ferrocenepalladium (II) dichloride dichloromethane adduct (40.8 mg, 0.050 mmol) was added, and the mixture was purged with argon again. This mixture was refluxed for 18 h. Then, the mixture was poured into saturated aqueous NaHCO₃ (100 mL) and extracted with 2:1 EtOAc/THF (100 mL×3), and the extract was dried over MgSO₄, filtered and concentrated under reduced pressure. This residue was purified by column chromatography (Purif, silica gel, 95:5 hexane/EtOAc to EtOAc then to 90:10 EtOAc/MeOH). The obtained yellow solid was triturated with EtOAc/hexane, and the precipitate was collected by filtration to afford the title compound (46.9 mg, 30%) as a pale yellow solid:

¹H NMR (300 MHz, DMSO-d₆) δ 1.45 (6H, s), 2.97 (3H, s), 6.86-6.87 (1H, m), 7.41-7.45 (2H, m), 7.63-7.64 (1H, m), 7.71 (1H, br s), 8.26 (1H, d, J=5.1 Hz), 11.94 (1H, br s).

Example 92

Preparation of 1,2,2-trimethyl-6-quinolin-4-yl-2,3-dihydrothieno[3,2-d]pyrimidin-4(1H)-one

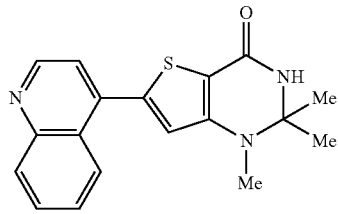 [SMILES: CN1c2cc(-c3ccnc4ccccc34)sc2C(=O)NC1(C)C]

A mixture of 6-bromo-1,2,2-trimethyl-2,3-dihydrothieno[3,2-d]pyrimidin-4(1H)-one (138 mg, 0.50 mmol), quinolin-4-ylboronic acid (173 mg, 1.00 mmol), cesium carbonate (489 mg, 1.50 mmol), 1,2-dimethoxyethane (5 mL) and water (1 mL) was purged with argon. Then, 1,1'-bis(diphenylphosphino) ferrocenepalladium (II) dichloride dichloromethane adduct (40.8 mg, 0.050 mmol) was added, and the mixture was purged with argon again. This mixture was refluxed for 18 h. Then, the mixture was poured into saturated aqueous NaHCO₃ (100 mL) and extracted with EtOAc (100 mL), and the extract was washed with brine, dried over MgSO₄, filtered and concentrated under reduced pressure. This residue was purified by column chromatography (Purif, silica gel, 95:5 hexane/EtOAc to EtOAc then to 90:10 EtOAc/MeOH). The obtained yellow solid (62 mg) was triturated with EtOAc/hexane, and the precipitate was collected by filtration to afford the title compound (47.2 mg, 29%) as a pale yellow solid:

¹H NMR (300 MHz, DMSO-d₆) δ 1.47 (6H, s), 2.49 (3H, s), 7.27 (1H, s), 7.63 (1H, d, J=4.5 Hz), 7.69-7.76 (2H, m), 7.86 (1H, t, J=7.8 Hz), 8.13 (1H, d, J=8.4 Hz), 8.32 (1H, d, J=8.7 Hz), 8.95 (1H, d, J=4.8 Hz).

Example 93

Preparation of 1'-methyl-6'-(1H-pyrazol-4-yl)-1'H-spiro[cyclopentane-1,2'-thieno[3,2-d]pyrimidin]-4'(3'H)-one

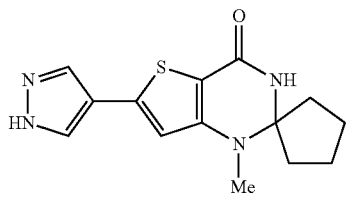 [SMILES: CN1c2cc(-c3cn[nH]c3)sc2C(=O)NC12CCCC2]

Step 1

Preparation of 3-(methylamino)-5-(1H-pyrazol-4-yl)thiophene-2-carboxamide dihydrochloride A mixture of 1,2,2-trimethyl-6-(1H-pyrazol-4-yl)-2,3-dihydrothieno[3,2-d]pyrimidin-4(1H)-one (262 mg, 1.00 mmol), 1 M HCl (5 mL) and MeOH (5 mL) was stirred at 50° C. for 1 h. The mixture was concentrated under reduced pressure to afford the title compound (292 mg, 99%) as a pale yellow solid. This material was used for the next reaction without further purification.

Step 2

Preparation of 1'-methyl-6'-(1H-pyrazol-4-yl)-1'H-spiro[cyclopentane-1,2'-thieno[3,2-d]pyrimidin]-4'(3'H)-one A mixture of 3-(methylamino)-5-(1H-pyrazol-4-yl)thiophene-2-carboxamide dihydrochloride (145 mg, 0.491 mmol), saturated aqueous NaHCO$_3$ (50 mL) and EtOAc (50 mL) was shaken well. The organic layer was collected, dried over MgSO$_4$, filtered and concentrated under reduced pressure. This residue was mixed with cyclopentanone (2.00 mL, 22.6 mmol), PTSA (9.34 mg, 0.049 mmol), MgSO$_4$ (118 mg, 0.982 mmol) and DMF (2 mL). This mixture was stirred at 80° C. overnight. The mixture was poured into saturated aqueous NaHCO$_3$ and extracted with 3:1 EtOAc/THF (100 mL), and the extract was dried over MgSO$_4$, filtered and concentrated under reduced pressure. The residue was purified by column chromatography (Purif, silica gel, 95:5 hexane/EtOAc to EtOAc then to 90:10 EtOAc/MeOH) to afford a yellow solid. This solid was triturated with EtOAc, and the precipitate was collected by filtration to afford the title compound (75.4 mg, 53%) as a yellow solid:

$^1$H NMR (300 MHz, DMSO-d$_6$) δ 1.56-1.73 (4H, m), 1.81-2.03 (4H, m), 2.87 (3H, s), 6.99 (1H, s), 7.67 (1H, br s), 7.84 (1H, br s), 8.17 (1H, br s), 13.12 (1H, br s).

Example 94

Preparation of 1'-methyl-6'-(1H-pyrazol-4-yl)-1'H-spiro[cyclohexane-1,2'-thieno[3,2-d]pyrimidin]-4'(3'H)-one

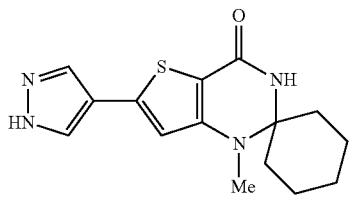 [SMILES: CN1c2cc(-c3cn[nH]c3)sc2C(=O)NC12CCCCC2]

A mixture of 3-(methylamino)-5-(1H-pyrazol-4-yl)thiophene-2-carboxamide dihydrochloride (145 mg, 0.491 mmol), saturated aqueous NaHCO$_3$ (50 mL) and EtOAc (50 mL) was shaken well. The organic layer was collected, dried over MgSO$_4$, filtered and concentrated under reduced pressure. This residue was mixed with cyclohexanone (2 mL, 19.3 mmol), PTSA (93 mg, 0.491 mmol), MgSO$_4$ (118 mg, 0.982 mmol) and DMF (2 mL). This mixture was stirred at 80° C. overnight. The mixture was poured into saturated aqueous NaHCO$_3$ and extracted with 3:1 EtOAc/THF (100 mL), and the extract was dried over MgSO$_4$, filtered and concentrated under reduced pressure. The residue was purified by column chromatography (Purif, silica gel, 95:5 hexane/EtOAc to EtOAc then to 90:10 EtOAc/MeOH) to afford a yellow solid. This solid was triturated with EtOAc/hexane, and the precipitate was collected by filtration to afford the title compound (24.5 mg, 16%) as a yellow solid:

$^1$H NMR (300 MHz, DMSO-d$_6$) δ 1.16-1.90 (10H, m), 2.90 (3H, s), 7.00 (1H, s), 7.27 (1H, br s), 7.84 (1H, br s), 8.17 (1H, br s), 13.12 (1H, br s).

Example 95

Preparation of 7'-bromo-1'-methyl-6'-(1H-pyrazol-4-yl)-1'H-spiro[cyclopentane-1,2'-thieno[3,2-d]pyrimidin]-4'(3'H)-one

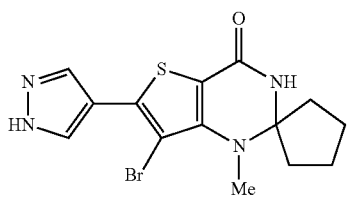 [SMILES: CN1c2c(sc(-c3cn[nH]c3)c2Br)C(=O)NC12CCCC2]

Step 1

Preparation of 4-bromo-3-(methylamino)-5-(1H-pyrazol-4-yl)thiophene-2-carboxamide dihydrochloride A mixture of 7-bromo-1,2,2-trimethyl-6-(1H-pyrazol-4-yl)-2,3-dihydrothieno[3,2-d]pyrimidin-4(1H)-one (171 mg, 0.50 mmol), 1 M HCl (2.5 mL, 2.50 mmol) and MeOH (5 mL) was stirred at 50° C. for 1 h. The mixture was concentrated under reduced pressure to afford the title compound (182 mg, 97%) as a pale yellow solid. This material was used for the next reaction without further purification.

Step 2

Preparation of 7'-bromo-1'-methyl-6'-(1H-pyrazol-4-yl)-1'H-spiro[cyclopentane-1,2'-thieno[3,2-d]pyrimidin]-4'(3'H)-one A mixture of 4-bromo-3-(methylamino)-5-(1H-pyrazol-4-yl)thiophene-2-carboxamide dihydrochloride (90 mg, 0.267 mmol), saturated aqueous NaHCO₃ (50 mL) and EtOAc (50 mL) was shaken well. The organic layer was collected, dried over MgSO₄, filtered and concentrated under reduced pressure. This residue was mixed with cyclopentanone (2.00 mL, 22.6 mmol), PTSA (5.1 mg, 0.027 mmol), MgSO₄ (64.2 mg, 0.533 mmol) and DMF (2 mL). This mixture was stirred at 80° C. for 4 h. The mixture was poured into saturated aqueous NaHCO₃ and extracted with 3:1 EtOAc/THF (100 mL), and the extract was dried over MgSO₄, filtered and concentrated under reduced pressure. The residue was purified by column chromatography (Purif, silica gel, 95:5 hexane/EtOAc to EtOAc) to afford a white solid. This solid was triturated with EtOAc, and the precipitate was collected by filtration to afford the title compound (41.7 mg, 43%) as a white solid:
$^1$H NMR (300 MHz, DMSO-d₆) δ 1.67-1.92 (8H, m), 2.64 (3H, s), 7.98 (1H, br s), 8.13 (1H, br s), 8.35 (1H, br s), 13.35 (1H, br s).

Example 96

Preparation of 7'-bromo-1'-methyl-6'-(1H-pyrazol-4-yl)-1'H-spiro[cyclohexane-1,2'-thieno[3,2-d]pyrimidin]-4'(3'H)-one

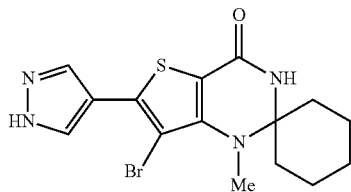 [SMILES: CN1c2c(sc(-c3cn[nH]c3)c2Br)C(=O)NC12CCCCC2]

A mixture of 4-bromo-3-(methylamino)-5-(1H-pyrazol-4-yl)thiophene-2-carboxamide dihydrochloride (90 mg, 0.267 mmol), saturated aqueous NaHCO₃ (50 mL) and EtOAc (50 mL) was shaken well. The organic layer was collected, dried over MgSO₄, filtered and concentrated under reduced pressure. This residue was mixed with cyclohexanone (2.00 mL, 19.3 mmol), PTSA (93 mg, 0.491 mmol), MgSO₄ (64.2 mg, 0.533 mmol) and DMF (2 mL). This mixture was stirred at 80° C. for 4 h. The mixture was poured into saturated aqueous NaHCO₃ and extracted with 3:1 EtOAc/THF (100 mL), and the extract was dried over MgSO₄, filtered and concentrated under reduced pressure. The residue was purified by column chromatography (Purif, silica gel, 95:5 hexane/EtOAc to EtOAc) to afford a white solid. This solid was triturated with EtOAc, and the precipitate was collected by filtration to afford the title compound (46.2 mg, 46%) as a white solid:
$^1$H NMR (300 MHz, DMSO-d₆) δ 1.25-1.55 (8H, m), 1.91-1.97 (2H, m), 2.60 (3H, s), 7.90 (1H, br s), 8.01 (1H, br s), 8.32 (1H, br s), 13.36 (1H, br s).

Example 97

Preparation of 1,2,2-trimethyl-6-(5-methyl-1H-pyrazol-4-yl)-2,3-dihydrothieno[3,2-d]pyrimidin-4(1H)-one

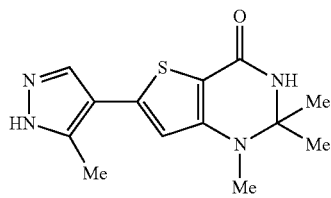 [SMILES: Cc1[nH]ncc1-c1cc2c(s1)C(=O)NC(C)(C)N2C]

A mixture of 6-bromo-1,2,2-trimethyl-2,3-dihydrothieno[3,2-d]pyrimidin-4(1H)-one (138 mg, 0.50 mmol), 3-methyl-4-(4,4,5,5-tetramethyl-[1,3,2]dioxaborolan-2-yl)-1H-pyrazole (208 mg, 1.00 mmol), cesium carbonate (489 mg, 1.50 mmol), 1,2-dimethoxyethane (5 mL) and water (1 mL) was purged with argon. Then, 1,1'-bis(diphenylphosphino)ferrocenepalladium (II) dichloride dichloromethane adduct (40.8 mg, 0.050 mmol) was added, and the mixture was purged with argon again. This mixture was refluxed for 18 h. After cooling to room temperature, 3-methyl-4-(4,4,5,5-tetramethyl-[1,3,2]dioxaborolan-2-yl)-1H-pyrazole (0.208 g, 1.00 mmol), Cs₂CO₃ (0.489 g, 1.50 mmol), 1,2-dimethoxyethane (5 mL) and water (1 mL) were added. The mixture was purged with argon. Then, 1,1'-bis(diphenylphosphino)ferrocenepalladium (II) dichloride dichloromethane adduct (0.041 g, 0.050 mmol) was added, and the mixture was purged with argon again. The mixture was refluxed for 6 h. Then, the mixture was poured into saturated aqueous NaHCO₃ (100 mL) and extracted with EtOAc (100 mL), and the extract was washed with brine, dried over MgSO₄, filtered and concentrated under reduced pressure. This residue was purified by column chromatography (Purif, silica gel, 95:5 hexane/EtOAc to EtOAc). The obtained yellow solid was triturated with EtOAc and collected by filtration to afford the title compound (52.7 mg, 38%) as a pale yellow solid:
$^1$H NMR (300 MHz, DMSO-d₆) δ 1.40 (6H, s), 2.40 (3H, br s), 2.88 (3H, s), 6.86 (1H, s), 7.44 (1H, br s), 7.77 (0.6H, br s), 8.10 (0.4H, br s), 12.86 (1H, m).

Example 98

Preparation of tert-butyl 4'-oxo-6'-(pyridin-4-yl)-3',4'-dihydro-1H,1'H-spiro[piperidine-3,2'-thieno[3,2-d]pyrimidine]-1-carboxylate

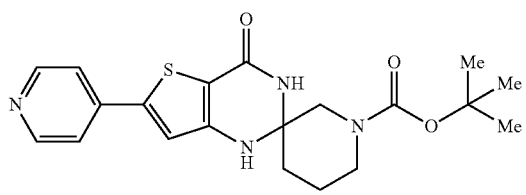 [SMILES: CC(C)(C)OC(=O)N1CCCC2(C1)NC(=O)c1sc(-c3ccncc3)cc1N2]

A mixture of 3-amino-5-(pyridin-4-yl)thiophene-2-carboxamide (110 mg, 0.50 mmol), CSA (12 mg, 0.050 mmol), tert-butyl 3-oxopiperidine-1-carboxylate (199 mg, 1.0 mmol), MgSO₄ (96 mg, 1.0 mmol) and DMA (1.0 mL) was stirred at 80° C. for 1 h. Then, water, saturated aqueous NaHCO₃ and EtOAc were added to quench the reaction. The organic materials were extracted with EtOAc. The combined extracts were washed with water and brine, dried over Na₂SO₄ and filtered. After removal of the solvent at reduced pressure, the residue was purified by column chromatography (Purif, silica gel, EtOAc to 90:10 EtOAc/MeOH) to give a yellow crystalline solid (72 mg). This material included some impurities. To remove the impurities, crystallization from EtOAc/hexane and following filtration were carried out. The filtrate was concentrated under reduced pressure, and the residue was purified by crystallization (MeOH/EtOAc/hexane) to give the title compound (15 mg, 7%) as a yellow solid:
¹H NMR (300 MHz, DMSO-d₆) δ 1.19 (9H, br s), 1.64-1.96 (4H, m), 2.87-3.05 (2H, m), 3.58-3.70 (1H, m), 3.84-4.01 (1H, m), 7.20 (1H, br s), 7.28 (1H, br s), 7.56-7.66 (2H, m), 7.77 (1H, br s), 8.55-8.76 (2H, m).

Example 99

Preparation of tert-butyl 1'-methyl-4'-oxo-6'-(1H-pyrazol-4-yl)-3',4'-dihydro-1H,1'H-spiro[piperidine-4,2'-thieno[3,2-d]pyrimidine]-1-carboxylate

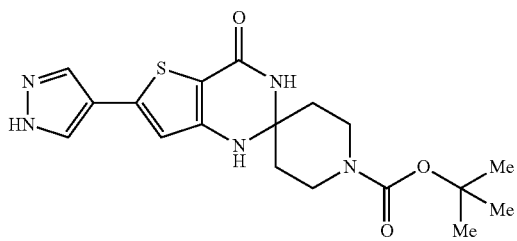 [SMILES: CC(C)(C)OC(=O)N1CCC2(CC1)NC(=O)c1sc(-c3cn[nH]c3)cc1N2]

A mixture of 1,2,2-trimethyl-6-(1H-pyrazol-4-yl)-2,3-dihydrothieno[3,2-d]pyrimidin-4(1H)-one (131 mg, 0.50 mmol), 1 M aqueous HCl (2.5 mL, 2.5 mmol) and MeOH (2.5 mL) was stirred at 50° C. for 1 h. After addition of saturated aqueous NaHCO₃, and the organic materials were extracted with EtOAc. The combined extracts were washed with brine, dried over Na₂SO₄ and filtered. After removal of the solvent at reduced pressure, the residue was mixed with tert-butyl 4-oxopiperidine-1-carboxylate (498 mg, 2.5 mmol), CSA (12 mg, 0.050 mmol), MgSO₄ (96 mg, 1.0 mmol) and DMA (2 mL). After stirred at 80° C. for 1 h, saturated aqueous NaHCO₃ and EtOAc were added to quench the reaction. The organic materials were extracted with EtOAc. The combined extracts were washed with water and brine, dried over Na₂SO₄ and filtered. After removal of the solvent at reduced pressure, the residue was purified by crystallization (EtOAc/hexane) to give the title compound (163 mg, 81%) as a pale yellow solid:
¹H NMR (300 MHz, DMSO-d₆) δ 1.43 (9H, s), 1.70-1.97 (4H, m), 2.89 (3H, s), 3.04-3.27 (2H, m), 3.68-3.92 (2H, m), 7.03 (1H, s), 7.64 (1H, s), 7.85 (1H, br s), 8.17 (1H, br s), 13.14 (1H, br s).

Example 100

Preparation of tert-butyl 4'-oxo-6'-(pyridin-4-yl)-3',4'-dihydro-1'H,8H-spiro[8-azabicyclo[3.2.1]octane-3,2'-thieno[3,2-d]pyrimidine]-8-carboxylate

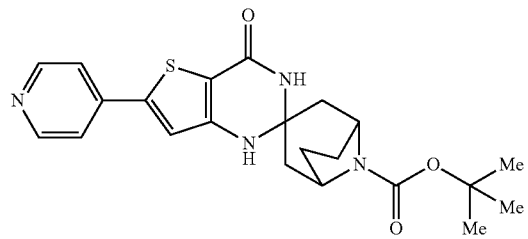 [SMILES: CC(C)(C)OC(=O)N1C2CCC1CC1(C2)NC(=O)c2sc(-c3ccncc3)cc2N1]

A mixture of 3-amino-5-(pyridin-4-yl)thiophene-2-carboxamide (110 mg, 0.50 mmol), CSA (12 mg, 0.050 mmol), tert-butyl 3-oxo-8-azabicyclo[3.2.1]octane-8-carboxylate (225 mg, 1.0 mmol), MgSO₄ (96 mg, 1.00 mmol) and DMA (1 mL) was stirred at 80° C. for 1.5 h. Then, saturated aqueous sodium hydrogen carbonate and EtOAc were added to quench the reaction. The organic materials were extracted with EtOAc. The combined extracts were washed with water and brine, dried over Na₂SO₄ and filtered. After removal of the solvent at reduced pressure, the residue was purified by column chromatography (Purif, silica gel, EtOAc to 93:7 EtOAc/MeOH) to give a yellow solid. Crystallization from MeOH/EtOAc/hexane and following filtration were carried out to remove impurity as a yellow solid. The filtrate was concentrated under reduced pressure, and the residue was purified by crystallization (MeOH/EtOAc/hexane) to give the title compound (5.8 mg, 3%) as a yellow solid:
¹H NMR (300 MHz, DMSO-d₆) δ 1.42 (9H, s), 1.74-1.95 (4H, m), 2.05-2.25 (4H, m), 4.03-4.13 (2H, m), 6.67 (1H, br s), 7.40 (1H, s), 7.62-7.70 (2H, m), 7.80 (1H, br s), 8.54-8.67 (2H, m).

Example 101

Preparation of 7-bromo-2,2-dimethyl-6-(1H-pyrazol-4-yl)-2,3-dihydrothieno[3,2-d]pyrimidin-4(1H)-one

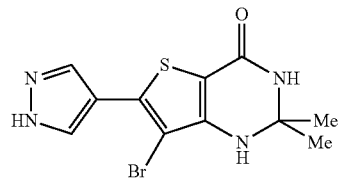 [SMILES: CC1(C)NC(=O)c2sc(-c3cn[nH]c3)c(Br)c2N1]

To a solution of 2,2-dimethyl-6-(1H-pyrazol-4-yl)-2,3-dihydrothieno[3,2-d]pyrimidin-4(1H)-one (248 mg, 1.00 mmol) in acetic acid (5 mL) was added slowly bromine (0.077 mL, 1.50 mmol) with vigorous stirring. After 3 min, the mixture was poured into saturated aqueous NaHCO₃ and extracted with EtOAc, and the extract was dried over MgSO₄, filtered and concentrated under reduced pressure to give a yellow solid. This residue was mixed with acetone (5.0 mL, 68.1 mmol), PTSA (9.5 mg, 0.050 mmol), MgSO₄ (120 mg, 1.00 mmol) and DMF (1 mL). This mixture was stirred at 60° C. for 1 h. Then, the mixture was poured into saturated aqueous NaHCO₃ and extracted with EtOAc, and the extract was dried over MgSO₄, filtered and concentrated under reduced pressure. The residue was purified by column chromatography (silica gel, hexane to EtOAc) to give a pale yellow solid (100 mg). This solid was triturated with EtOAc and collected by filtration to afford the title compound (69.9 mg, 21%) as a pale yellow solid:

¹H NMR (300 MHz, DMSO-d₆) δ 1.45 (6H, s), 6.69 (1H, br s), 7.65 (1H, br s), 7.95 (1H, br s), 8.30 (1H, br s), 13.33 (1H, br s).

Example 102

Preparation of 7'-bromo-6'-(1H-pyrazol-4-yl)-1'H-spiro [cyclohexane-1,2'-thieno[3,2-d]pyrimidin]-4'(3'H)-one

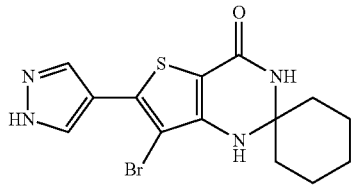 [SMILES: O=C1NC2(CCCCC2)Nc2c1sc(-c1cn[nH]c1)c2Br]

A mixture of 7-bromo-2,2-dimethyl-6-(1H-pyrazol-4-yl)-2,3-dihydrothieno[3,2-d]pyrimidin-4(1H)-one (50 mg, 0.153 mmol), 1 M HCl (0.5 mL, 0.50 mmol) and MeOH (2.5 mL) was stirred at 50° C. After 1 h, the mixture was poured into saturated aqueous NaHCO₃ and extracted with EtOAc, and the extract was dried over MgSO₄, filtered and concentrated under reduced pressure. The residue was mixed with MgSO₄ (18.4 mg, 0.153 mmol), cyclohexanone (1 mL, 9.65 mmol), PTSA (2.9 mg, 0.015 mmol) and DMF (1 mL). The mixture was stirred at 80° C. for 1 h. The mixture was poured into saturated aqueous NaHCO₃ and extracted with EtOAc, and the extract was dried over MgSO₄, filtered and concentrated under reduced pressure. The residue was purified by column chromatography (Purif, silica gel, hexane to EtOAc). Then, the obtained oil was triturated with EtOAc, and the precipitate was collected by filtration to afford the title compound (16.9 mg, 30%) as a pale yellow solid:

¹H NMR (300 MHz, DMSO-d₆) δ 1.34-1.86 (10H, m), 6.24 (1H, br s), 7.67 (1H, br s), 7.95 (1H, br s), 8.31 (1H, br s), 13.33 (1H, br s).

Example 103

Preparation of tert-butyl 4'-oxo-6'-(pyridin-4-yl)-3',4'-dihydro-1H,1'H-spiro[pyrrolidine-3,2'-thieno[3,2-d]pyrimidine]-1-carboxylate

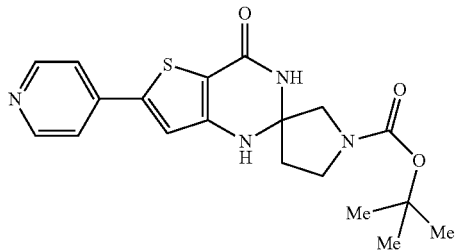 [SMILES: CC(C)(C)OC(=O)N1CCC2(C1)NC(=O)c1sc(-c3ccncc3)cc1N2]

A mixture of 3-amino-5-(pyridin-4-yl)thiophene-2-carboxamide (150 mg, 0.68 mmol), CSA (16 mg, 0.068 mmol), tert-butyl 3-oxopyrrolidine-1-carboxylate (380 mg, 2.05 mmol), MgSO₄ (131 mg, 1.37 mmol) and DMA (1.0 mL) was stirred at 80° C. for 5 h. Then, saturated aqueous NaHCO₃ and EtOAc were added to quench the reaction. The organic materials were extracted with EtOAc. The combined extracts were washed with water and brine, dried over Na₂SO₄ and filtered. After removal of the solvent at reduced pressure, the residue was purified by column chromatography (Purif, silica gel, 80:20 hexane/EtOAc to EtOAc), then crystallized from MeOH/EtOAc to give the title compound (20 mg, 8%) as a yellow solid:

¹H NMR (300 MHz, DMSO-d₆) δ 1.32-1.48 (9H, m), 2.03-2.24 (2H, m), 3.33-3.53 (4H, m), 7.21 (1H, s), 7.58-7.63 (1H, m), 7.65 (2H, d, J=5.3 Hz), 8.11 (1H, br s), 8.62 (2H, d, J=5.3 Hz).

Example 104

Preparation of 1,2-dimethyl-6-(5-methyl-1H-pyrazol-4-yl)-2-(2,2,2-trifluoroethyl)-2,3-dihydrothieno[3,2-d]pyrimidin-4(1H)-one

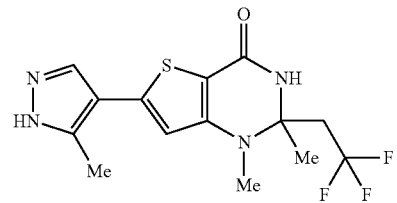 [SMILES: Cc1[nH]ncc1-c1cc2c(s1)C(=O)NC(C)(CC(F)(F)F)N2C]

Step 1

Preparation of 6-bromo-1,2-dimethyl-2-(2,2,2-trifluoroethyl)-2,3-dihydrothieno[3,2-d]pyrimidin-4(1H)-one A mixture of 5-bromo-3-(methylamino)thiophene-2-carboxamide (940 mg, 4.0 mmol), 4,4,4-trifluorobutan-2-one (5.04 g, 40 mmol), CSA (93 mg, 0.40 mmol), MgSO₄ (576 mg, 6.0 mmol) and DMA (4 mL) was microwave-irradiated at 150° C. for 1 h. The mixture was poured into saturated aqueous NaHCO₃. The organic materials were extracted with EtOAc. The combined extracts were washed with water and brine, dried over Na₂SO₄ and filtered. After removal of the solvent at reduced pressure, the residue was purified by column chromatography (Purif, NH, 90:10 hexane/EtOAc to 50:50 hexane/EtOAc) to give a yellow solid. The solid was purified by crystallization from EtOAc/heptane to give the title compound (431 mg, 31%) as a yellow solid:

¹H NMR (300 MHz, DMSO-d₆) δ 1.58 (3H, s), 2.53-2.73 (1H, m), 2.84-3.05 (1H, m), 2.88 (3H, s), 7.10 (1H, s), 7.91 (1H, br s).

Step 2

Preparation of 1,2-dimethyl-6-(5-methyl-1H-pyrazol-4-yl)-2-(2,2,2-trifluoroethyl)-2,3-dihydrothieno[3,2-d]pyrimidin-4(1H)-one A flask was charged with 6-bromo-1,2-dimethyl-2-(2,2,2-trifluoroethyl)-2,3-dihydrothieno[3,2-d]pyrimidin-4(1H)- one (420 mg, 1.22 mmol), tert-butyl 3-methyl-4-(4,4,5,5-tetramethyl-1,3,2-dioxaborolan-2-yl)-1H-pyrazole-1-carboxylate (1.13 g, 3.7 mmol), sodium carbonate (366 mg, 6.1 mmol), 1,2-dimethoxyethane (6 mL) and water (3 mL). The flask was purged with argon. Then, 1,1'-bis(diphenylphosphino) ferrocenepalladium (II) dichloride dichloromethane adduct (98 mg, 0.12 mmol) was added to the mixture. The flask was purged with argon again. After stirring at 100° C. for 2 h, 8 M aqueous NaOH (1 mL) was added. After stirring at 100° C. for 1 h, the organic materials were extracted with EtOAc. The combined extracts were washed with brine, dried over $Na_2SO_4$ and filtered. After removal of the solvent at reduced pressure, the residue was purified by column chromatography (Purif, silica gel, 80:20 hexane/EtOAc to EtOAc), then crystallized from MeOH/EtOAc/heptane) to give the title compound (212 mg, 50%) as a pale yellow solid:

$^1$H NMR (300 MHz, DMSO-$d_6$) δ 1.59 (3H, s), 2.40 (3H, br s), 2.55-2.79 (1H, m), 2.84-3.06 (1H, m), 2.93 (3H, s), 6.88 (1H, s), 7.71 (1H, s), 7.79 (0.6H, br s), 8.12 (0.4H, br s), 12.87 (1H, br s).

Example 105

Preparation of 6'-(5-methyl-1H-pyrazol-4-yl)-1'H-spiro [cyclohexane-1,2'-thieno[3,2-d]pyrimidin]-4'(3'H)-one

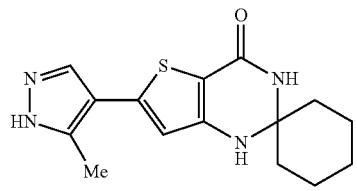

A mixture of 2,2-dimethyl-6-(5-methyl-1H-pyrazol-4-yl)-2,3-dihydrothieno[3,2-d]pyrimidin-4(1H)-one (0.090 g, 0.343 mmol), 1 M HCl (1.2 mL, 1.2 mmol) and MeOH (4 mL) was stirred at 50° C. for 2 h. Then, the reaction mixture was poured into excess saturated aqueous $NaHCO_3$ and extracted with EtOAc, and the extract was dried over $MgSO_4$, filtered and concentrated under reduced pressure. The residue was mixed with cyclohexanone (2 mL, 19.3 mmol), $MgSO_4$ (0.041 g, 0.343 mmol), PTSA (3.3 mg, 0.017 mmol) and DMF (2 mL). The mixture was stirred at 80° C. for 3 h. The mixture was poured into saturated aqueous $NaHCO_3$ and extracted with EtOAc, and the extract was dried over $MgSO_4$, filtered and concentrated under reduced pressure. The residue was purified by column chromatography (Purif, silica gel, 95:5 hexane/EtOAc to EtOAc then to 90:10 EtOAc/MeOH). The obtained oil was purified again by column chromatography (Purif, silica gel, 95:5 hexane/EtOAc to EtOAc) to give a yellow solid. This solid was triturated with EtOAc/hexane and collected by filtration to afford the title compound (42.8 mg, 41%) as a yellow solid:

$^1$H NMR (300 MHz, DMSO-$d_6$) δ 1.17-1.26 (1H, m), 1.43-1.62 (7H, m), 1.85-1.88 (2H, m), 2.38 (3H, m), 6.60 (1H, s), 6.98 (1H, br s), 7.30 (1H, br s), 7.68 (0.6H, br s), 8.03 (0.4H, br s), 12.77 (0.4H, br s), 12.87 (0.6H, br s).

Example 106

Preparation of 2-methyl-6-(5-methyl-1H-pyrazol-4-yl)-2-(2,2,2-trifluoroethyl)-2,3-dihydrothieno[3,2-d]pyrimidin-4(1H)-one

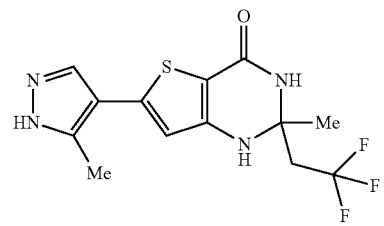 [SMILES: Cc1[nH]ncc1-c1cc2c(s1)C(=O)NC(C)(CC(F)(F)F)N2]

A mixture of 2,2-dimethyl-6-(5-methyl-1H-pyrazol-4-yl)-2,3-dihydrothieno[3,2-d]pyrimidin-4(1H)-one, 1 M HCl (1.2 mL, 1.2 mmol) and MeOH (4 mL) was stirred at 50° C. for 2 h. Then, the reaction mixture was poured into excess saturated aqueous $NaHCO_3$ and extracted with EtOAc, and the extract was dried over $MgSO_4$, filtered and concentrated under reduced pressure. The residue was mixed with 4,4,4-trifluorobutan-2-one (0.433 g, 3.43 mmol), CSA (7.97 mg, 0.034 mmol), $MgSO_4$ (0.041 g, 0.343 mmol) and DMA (1 mL). The mixture was microwave-irradiated at 140° C. for 1 h. The mixture was poured into saturated aqueous $NaHCO_3$ and extracted with EtOAc, and the extract was dried over $MgSO_4$, filtered and concentrated under reduced pressure. The residue was purified by column chromatography (Purif, silica gel, 95:5 hexane/EtOAc to EtOAc then to 90:10 EtOAc/MeOH). The obtained oil was purified again by column chromatography (Purif, silica gel, 95:5 hexane/EtOAc to EtOAc) to give yellow oil. This oil was dissolved with small amount of EtOAc and poured into heptane (100 mL) with stirring. After 5 min, the precipitate was collected by filtration to afford the title compound (33.5 mg, 30%) as a yellow solid:

$^1$H NMR (300 MHz, DMSO-$d_6$) δ 1.54 (3H, s), 2.33 (1H, br s), 2.39 (2H, br s), 2.63-2.78 (2H, m), 6.58 (1H, s), 7.24 (1H, br s), 7.58 (1H, br s), 7.73 (0.6H, br s), 8.10 (0.4H, br s), 12.80 (0.4H, br s), 12.88 (0.6H, br s).

Example 107

Preparation of 7-bromo-2,2-dimethyl-6-(5-methyl-1H-pyrazol-4-yl)-2,3-dihydrothieno[3,2-d]pyrimidin-4(1H)-one

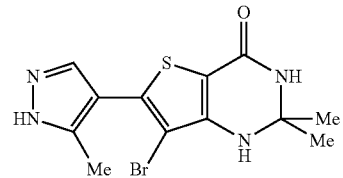 [SMILES: Cc1[nH]ncc1-c1sc2c(c1Br)NC(C)(C)NC2=O]

To a vigorously stirred solution of 2,2-dimethyl-6-(5-methyl-1H-pyrazol-4-yl)-2,3-dihydrothieno[3,2-d]pyrimidin-4(1H)-one (0.080 g, 0.305 mmol) in acetic acid (2 mL) was added slowly bromine (0.019 mL, 0.366 mmol). After 5 min, the mixture was poured into excess saturated aqueous $NaHCO_3$ and extracted with EtOAc, and the extract was dried over $MgSO_4$, filtered and concentrated under reduced pressure. The residue was mixed with acetone (5 mL), PTSA (3 mg) and DMF (1 mL). The mixture was stirred for 30 min at 70° C. and poured into saturated aqueous NaHCO$_3$ and extracted with EtOAc, and the extract was dried over MgSO$_4$, filtered and concentrated under reduced pressure. The residue was purified by column chromatography (Purif, silica gel, 95:5 hexane/EtOAc to EtOAc) to give a yellow solid. This solid was triturated with EtOAc/hexane, and the precipitate was collected by filtration to afford the title compound (65.4 mg, 63%) as a yellow solid:

$^1$H NMR (300 MHz, DMSO-d$_6$) δ 1.46 (6H, s), 2.27 (1H, br s), 2.34 (2H, br s), 6.67 (1H, br s), 7.65 (1H, br s), 7.78 (0.6H, br s), 8.11 (0.4H, br s), 12.94 (0.4H, br s), 12.99 (0.6H, br s).

Example 108

Preparation of 2,2-dimethyl-6-(5-methyl-1H-pyrazol-4-yl)-2,3-dihydrothieno[3,2-d]pyrimidin-4(1H)-one

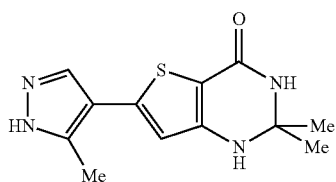 [SMILES: Cc1[nH]ncc1-c1cc2c(s1)C(=O)NC(C)(C)N2]

Step 1

Preparation of 4-bromo-3-methyl-1H-pyrazole hydrobromide

To a stirred solution of 3-methylpyrazole (23.2 mL, 289 mmol) in acetic acid (100 mL) was added dropwise bromine (15.6 mL, 303 mmol) over 10 min. After 10 min, the mixture was diluted with EtOAc (200 mL), and the precipitate was collected by filtration to afford the title compound (53.4 g, 76%) as a white solid:

$^1$H NMR (300 MHz, DMSO-d$_6$) δ 2.16 (3H, s), 7.64 (1H, s), 7.96 (2H, br s).

Step 2

Preparation of tert-butyl 4-bromo-3-methyl-1H-pyrazole-1-carboxylate

To a stirred mixture of 4-bromo-3-methyl-1H-pyrazole hydrobromide (53.4 g, 221 mmol) and sodium carbonate (70.2 g, 662 mmol) were added THF (420 mL) and water (210 mL), and then di-tert-butyl dicarbonate (61.5 mL, 265 mmol) and N,N-dimethylpyridin-4-amine (1.348 g, 11.0 mmol) were added. After overnight, di-tert-butyl dicarbonate (10.3 mL, 44.2 mmol) was added. After 30 min, the mixture was poured into water and extracted with EtOAc (500 mL), and the extract was dried over MgSO$_4$, filtered and concentrated under reduced pressure. The residual oil was purified by column chromatography (Purif, silica gel, hexane to 50:50 hexane/EtOAc) to afford the crude title compound (57.4 g, quant.) as a colorless oil. This material included regioisomer and was used in next reaction without further purification.

Step 3

Preparation of tert-butyl 3-methyl-4-(4,4,5,5-tetramethyl-1,3,2-dioxaborolan-2-yl)-1H-pyrazole-1-carboxylate A mixture of tert-butyl 4-bromo-3-methyl-1H-pyrazole-1-carboxylate (9.2 g, 35.2 mmol), 4,4,4',4',5,5,5',5'-octamethyl-2,2'-bi-1,3,2-dioxaborolane (9.39 g, 37.0 mmol), potassium acetate (10.4 g, 106 mmol) and 1,2-dimethoxyethane (100 mL) was purged with argon. Then, 1,1'-bis(diphenylphosphino) ferrocenepalladium (II) dichloride dichloromethane adduct (2.88 g, 3.52 mmol) was added, and the mixture was purged with argon again. The mixture was stirred at 90° C. overnight. After cooled to room temperature, the mixture was filtered, and the filtrate was concentrated under reduced pressure. The residue was suspended in 1:1 EtOAc/hexane and filtered. The filtrate was concentrated under reduced pressure. The residue was purified by column chromatography (Purif, silica gel, hexane to 70:30 hexane/EtOAc) to afford the crude title compound (7.0 g, 65%) as a colorless oil:

$^1$H NMR (300 MHz, CDCl$_3$) δ 1.32 (12H, s), 1.62 (9H, s), 2.42 (3H, s), 8.26 (1H, s). This material included some impurities and was used in next reaction without further purification.

Step 4

Preparation of 2,2-dimethyl-6-(5-methyl-1H-pyrazol-4-yl)-2,3-dihydrothieno[3,2-d]pyrimidin-4(1H)-one A mixture of 6-bromo-2,2-dimethyl-2,3-dihydrothieno[3,2-d]pyrimidin-4(1H)-one (522 mg, 2 mmol), tert-butyl 3-methyl-4-(4,4,5,5-tetramethyl-1,3,2-dioxaborolan-2-yl)-1H-pyrazole-1-carboxylate (1.85 g, 6.00 mmol), cesium carbonate (3.26 g, 10.0 mmol), 1,2-dimethoxyethane (20 mL) and water (5 mL) was purged with argon. Then, 1,1'-bis(diphenylphosphino) ferrocenepalladium (II) dichloride dichloromethane adduct (163 mg, 0.20 mmol) was added, and the mixture was purged with argon again. The mixture was refluxed for 2 h. Then, sodium carbonate (636 mg, 6.00 mmol) was added. After 30 min, 8 M NaOH (1.5 mL, 12 mmol) was added. After 3 h, the mixture was cooled to room temperature, and poured into water (100 mL) and EtOAc (200 mL). The insoluble materials were filtered off, and the organic layer was collected from the filtrate. This organic layer was washed with brine, dried over MgSO$_4$, filtered and concentrated under reduced pressure. The residual oil was purified by column chromatography (Purif, silica gel, 95:5 hexane/EtOAc to EtOAc), then triturated with EtOAc, and the precipitate was collected by filtration to afford the title compound (312 mg, 60%) as a pale yellow solid:

$^1$H NMR (300 MHz, DMSO-d$_6$) δ 1.40 (6H, s), 2.37 (3H, br s), 6.53 (1H, s), 6.96 (1H, br s), 7.34 (1H, br s), 7.70 (0.6H, br s), 8.06 (0.4H, br s), 12.85 (1H, m).

Example 109

Preparation of 1'-ethyl-6'-(5-methyl-1H-pyrazol-4-yl)-1'H-spiro [cyclopentane-1,2'-thieno[3,2-d]pyrimidin]-4'(3'H)-one

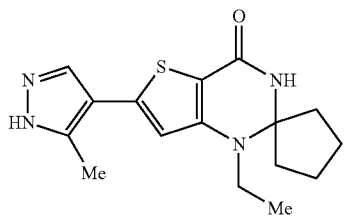 [SMILES: CCN1c2cc(-c3cn[nH]c3C)sc2C(=O)NC12CCCC2]

Step 1

Preparation of methyl 5-bromo-3-(ethylamino)thiophene-2-carboxylate

A mixture of methyl 5-bromo-3-[(trifluoroacetyl)amino]thiophene-2-carboxylate (3.18 g, 9.58 mmol), iodoethane (3.8 mL, 47.9 mmol), cesium carbonate (7.80 g, 24.0 mmol) and DMF (10 mL) was stirred at 70° C. for 3 h. Then, water and EtOAc were added to quench the reaction. The organic materials were extracted with EtOAc. The combined extracts were washed with water and brine, dried over $Na_2SO_4$ and filtered. After removal of the solvent at reduced pressure, the residue was dissolved in MeOH (15 mL). To the solution were added potassium carbonate (3.97 g, 28.7 mmol) and water (10 mL). The mixture was stirred at room temperature for 2 h. After removal of the solvent at reduced pressure, the organic materials were extracted with EtOAc. The combined extracts were washed with brine, dried over $Na_2SO_4$ and filtered. After removal of the solvent at reduced pressure, the residue was purified by column chromatography (Purif, silica gel, hexane to 90:10 hexane/EtOAc) to give the title compound (2.46 g, 97%) as a light green oil:
$^1$H NMR (300 MHz, DMSO-$d_6$) δ 1.12 (3H, t, J=7.4 Hz), 3.27 (2H, q, J=7.4 Hz), 3.71 (3H, s), 6.79-6.95 (1H, m), 7.09 (1H, s).

Step 2

Preparation of 5-bromo-3-(ethylamino)thiophene-2-carboxamide

To a solution of methyl 5-bromo-3-(ethylamino)thiophene-2-carboxylate (2.46 g, 9.31 mmol) in MeOH (30 mL) was added a solution of sodium hydroxide (1.12 g, 27.9 mmol) in water (15 mL). After stirring at 60° C. for 4 h, 6 M aqueous HCl (2.9 mL) was added to the mixture to adjust the pH to 10. After removal of the solvent at reduced pressure, the residue was diluted with DMF (70 mL). Then, triethylamine (25.8 mL, 186 mmol) and ammonium chloride (10.0 g, 186 mmol) were added. After stirring at room temperature for 10 min, 1-ethyl-3-(3-dimethylaminopropyl)carbodiimide hydrochloride (10.7 g, 55.9 mmol) and 1-hydroxybenzotriazole (7.55 g, 55.9 mmol) were added to the mixture and the stirring was continued for 17 h. Then, water and EtOAc were added to quench the reaction. The organic materials were extracted with EtOAc. The combined extracts were washed with water and brine, dried over $Na_2SO_4$ and filtered. After removal of the solvent at reduced pressure, the residue was purified by column chromatography (Purif, silica gel, hexane to 70:30 hexane/EtOAc) to give the title compound (0.97 g, 42%) as a pale green solid:
$^1$H NMR (300 MHz, DMSO-$d_6$) δ 1.11 (3H, t, J=7.1 Hz), 3.13-3.26 (2H, m), 6.93 (2H, br s), 7.00 (1H, s), 7.41 (1H, t, J=5.9 Hz).

Step 3

Preparation of 6'-bromo-1'-ethyl-1'H-spiro[cyclopentane-1,2'-thieno[3,2-d]pyrimidin]-4'(3'H)-one A mixture of 5-bromo-3-(ethylamino)thiophene-2-carboxamide (500 mg, 2.0 mmol), cyclopentanone (0.53 mL, 6.0 mmol), CSA (46 mg, 0.20 mmol), $MgSO_4$ (384 mg, 4.0 mmol) and DMA (1.5 mL) was stirred at 90° C. for 1 day. The mixture was poured into saturated aqueous $NaHCO_3$. The organic materials were extracted with EtOAc. The combined extracts were washed with water and brine, dried over $Na_2SO_4$ and filtered. After removal of the solvent at reduced pressure, the residue was purified by column chromatography (Purif, silica gel, 95:5 hexane/EtOAc to 50:50 hexane/EtOAc) to give a brown solid. The solid was washed with EtOAc to give the title compound (352 mg, 56%) as a pale brown solid:
$^1$H NMR (300 MHz, DMSO-$d_6$) δ 1.07 (3H, t, J=7.1 Hz), 1.52-1.79 (4H, m), 1.79-2.01 (4H, m), 3.27 (2H, q, J=7.1 Hz), 7.09 (1H, s), 7.80 (1H, br s).

Step 4

Preparation of 1'-ethyl-6'-(5-methyl-1H-pyrazol-4-yl)-1'H-spiro [cyclopentane-1,2'-thieno[3,2-d]pyrimidin]-4'(3'H)-one A flask was charged with 6'-bromo-1'-ethyl-1'H-spiro [cyclopentane-1,2'-thieno[3,2-d]pyrimidin]-4'(3'H)-one (158 mg, 0.50 mmol), tert-butyl 3-methyl-4-(4,4,5,5-tetramethyl-1,3,2-dioxaborolan-2-yl)-1H-pyrazole-1-carboxylate (463 mg, 1.5 mmol), sodium carbonate (150 mg, 2.5 mmol), 1,2-dimethoxyethane (3.0 mL) and water (1.5 mL). The flask was purged with argon. Then, 1,1'-bis(diphenylphosphino)ferrocenepalladium (II) dichloride dichloromethane adduct (41 mg, 0.050 mmol) was added to the mixture. The flask was purged with argon again. After stirring at 100° C. for 1 h, 8 M aqueous NaOH (0.5 mL) was added. After stirring at 100° C. for 1 h, organic materials were extracted with EtOAc. The combined extracts were washed with brine, dried over $Na_2SO_4$ and filtered. After removal of the solvent at reduced pressure, the residue was purified by column chromatography (Purif, silica gel, 50:50 hexane/EtOAc to EtOAc), then crystallized from MeOH/EtOAc/hexane to give the title compound (86 mg, 54%) as a yellow solid:
$^1$H NMR (300 MHz, DMSO-$d_6$) δ 1.13 (3H, t, J=7.0 Hz), 1.54-1.79 (4H, m), 1.79-2.03 (4H, m), 2.40 (3H, br s), 3.30 (2H, q, J=7.0 Hz), 6.85 (1H, s), 7.60 (1H, s), 7.79 (0.6H, br s), 8.13 (0.4H, br s), 12.85 (1H, br s).

Example 110

Preparation of 1-ethyl-2-methyl-6-(5-methyl-1H-pyrazol-4-yl)-2-(2,2,2-trifluoroethyl)-2,3-dihydrothieno[3,2-d]pyrimidin-4(1H)-one

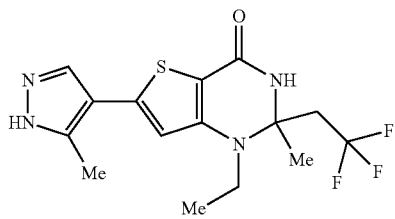 [SMILES: CCN1c2cc(-c3cn[nH]c3C)sc2C(=O)NC1(C)CC(F)(F)F]

A mixture of 5-bromo-3-(ethylamino)thiophene-2-carboxamide (250 mg, 1.0 mmol), 4,4,4-trifluorobutan-2-one (1.0 mL), CSA (23 mg, 0.10 mmol), MgSO$_4$ (192 mg, 2.0 mmol) and DMA (0.5 mL) was microwave-irradiated at 150° C. for 1 h. The mixture was poured into saturated aqueous NaHCO$_3$. The organic materials were extracted with EtOAc. The combined extracts were washed with water and brine, dried over Na$_2$SO$_4$ and filtered. After removal of the solvent at reduced pressure, the residue was purified by column chromatography (Purif, silica gel, 90:10 hexane/EtOAc to 50:50 hexane/EtOAc) to give a brown crystalline solid. A flask was charged with this solid, 1,2-dimethoxyethane (3 mL), tert-butyl 3-methyl-4-(4,4,5,5-tetramethyl-1,3,2-dioxaborolan-2-yl)-1H-pyrazole-1-carboxylate (555 mg, 1.8 mmol), sodium carbonate (180 mg, 3.0 mmol) and water (1.5 mL). The flask was purged with argon. Then, 1,1'-bis(diphenylphosphino)ferrocenepalladium (II) dichloride dichloromethane adduct (49 mg, 0.060 mmol) was added to the mixture. The flask was purged with argon again. After stirring at 100° C. for 6 h, organic materials were extracted with EtOAc. The combined extracts were washed with brine, dried over Na$_2$SO$_4$ and filtered. After removal of the solvent at reduced pressure, the residue was purified by column chromatography (Purif, silica gel, 50:50 hexane/EtOAc to EtOAc), then crystallized from MeOH/EtOAc/heptane) to give the title compound (37 mg, 10%) as a pale brown solid:

$^1$H NMR (300 MHz, DMSO-d$_6$) δ 1.16 (3H, t, J=7.0 Hz), 1.69 (3H, s), 2.40 (3H, br s), 2.53-2.71 (1H, m), 2.74-3.00 (1H, m), 3.32-3.50 (2H, m), 6.83 (1H, s), 7.66 (1H, s), 7.80 (0.6H, br s), 8.14 (0.4H, br s), 12.85 (1H, br s).

Example 111

Preparation of 5-ethyl-N,N-dimethyl-4-(1,2,2-trimethyl-4-oxo-1,2,3,4-tetrahydrothieno[3,2-d]pyrimidin-6-yl)-1H-pyrazole-1-sulfonamide

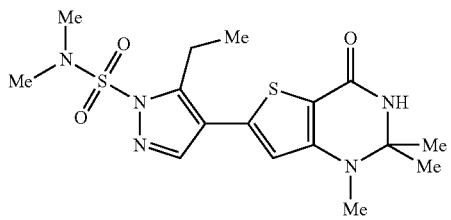 [SMILES: CCc1c(-c2cc3c(s2)C(=O)NC(C)(C)N3C)cnn1S(=O)(=O)N(C)C]

Step 1

Preparation of N,N-dimethyl-1H-pyrazole-1-sulfonamide

To a stirred solution of pyrazole (12 g, 176 mmol) in THF (200 mL) was added portionwise sodium hydride (50%, 8.46 g, 212 mmol) at 0° C. After 20 min, dimethylsulfamoyl chloride (17 mL, 157 mmol) was added dropwise, and the stirring was continued for 1 h at the same temperature. Then, the mixture was allowed to room temperature for 1 h. The mixture was poured into saturated aqueous NaHCO$_3$ (400 mL) and extracted with EtOAc (400 mL), and the extract was dried over MgSO$_4$, filtered and concentrated under reduced pressure. The residue was purified by column chromatography (Purif, silica gel, hexane to 50:50 hexane/EtOAc) to afford the title compound (25.3 g, 82%) as a colorless oil:

$^1$H NMR (300 MHz, CDCl$_3$) δ 2.95 (6H, s), 6.40 (1H, m), 7.75 (1H, m), 7.99 (1H, d, J=2.7 Hz).

Step 2

Preparation of 5-ethyl-N,N-dimethyl-1H-pyrazole-1-sulfonamide

To a stirred solution of N,N-dimethyl-1H-pyrazole-1-sulfonamide (25.3 g, 144 mmol) in THF (200 mL) at −78° C. was added dropwise 1.6 M n-butyllithium in hexane (99 ml, 159 mmol). After 30 min, iodoethane (12.8 mL, 159 mmol) was added dropwise. The reaction mixture was stirred at −78° C. for 30 min and allowed to room temperature slowly. After 1 h, the stirring became difficult by formation of white precipitate. THF (200 mL) was added dropwise to give yellow solution. The stirring was continued for 2 h. Then, the mixture was poured into saturated aqueous NaHCO$_3$ (600 mL) and extracted with EtOAc (400 mL×2), and the extract was dried over MgSO$_4$, filtered and concentrated under reduced pressure. The residue was purified by column chromatography (Purif, silica gel, hexane to 30:70 hexane/EtOAc) to afford the title compound (19.8 g, 68%) as colorless liquid:

$^1$H NMR (300 MHz, CDCl$_3$) δ 1.30 (3H, t, J=7.8 Hz), 2.94 (2H, dd, J=15.0, 7.5 Hz), 3.03 (6H, s), 6.13 (1H, br s), 7.55 (1H, br s).

Step 3

Preparation of 4-bromo-5-ethyl-N,N-dimethyl-1H-pyrazole-1-sulfonamide

To a stirred solution of 5-ethyl-N,N-dimethyl-1H-pyrazole-1-sulfonamide (19.8 g, 97 mmol) in THF (300 mL) was added 1-bromopyrrolidine-2,5-dione (20.8 g, 117 mmol). The mixture was stirred for 2 h at 50° C. The mixture was concentrated under reduced pressure, and the residue was poured into saturated aqueous NaHCO$_3$. Extraction with EtOAc, washing with brine, drying over MgSO$_4$, filtration and concentration under reduced pressure gave a yellow oil. This residue was purified by column chromatography (Purif, silica gel, hexane to 50:50 hexane/EtOAc) to afford the title compound (26.2 g, 95%) as a yellow oil:

$^1$H NMR (300 MHz, CDCl$_3$) δ 1.24 (3H, t, J=7.5 Hz), 2.97 (2H, dd, J=15.0 Hz, 7.8 Hz), 3.06 (6H, s), 7.54 (1H, s).

Step 4

Preparation of 5-ethyl-N,N-dimethyl-4-(4,4,5,5-tetramethyl-1,3,2-dioxaborolan-2-yl)-1H-pyrazole-1-sulfonamide A mixture of 4-bromo-5-ethyl-N,N-dimethyl-1H-pyrazole-1-sulfonamide (13.0 g, 46.1 mmol), 4,4,4',4',5,5,5',5'-octamethyl-2,2'-bi-1,3,2-dioxaborolane (12.3 g, 48.4 mmol), potassium acetate (13.6 g, 138 mmol) and 1,2-dimethoxyethane (300 mL) was purged with argon. Then, 1,1'-bis(diphenylphosphino)ferrocenepalladium (II) dichloride dichloromethane adduct (3.76 g, 4.61 mmol) was added, and the mixture was purged with argon again. The mixture was stirred at 90° C. overnight. After cooled to room temperature, the mixture was filtered, and the filtrate was concentrated under reduced pressure. The residue was suspended in 1:1 EtOAc/hexane and filtered. The filtrate was concentrated under reduced pressure. The residue was purified by column chromatography (Purif, silica gel, hexane to 70:30 hexane/EtOAc). The obtained oil was settled at room temperature overnight to give precipitate. This precipitate was collected by filtration and washed with hexane to afford the title compound (6.32 g, 42%) as a white solid:

$^1$H NMR (300 MHz, CDCl$_3$) δ 1.25 (3H, t, J=7.5 Hz), 1.31 (12H, s), 3.03 (6H, s), 3.17 (2H, dd, J=15.0, 7.5 Hz), 7.75 (1H, s).

Step 5

Preparation of 5-ethyl-N,N-dimethyl-4-(1,2,2-trimethyl-4-oxo-1,2,3,4-tetrahydrothieno[3,2-d]pyrimidin-6-yl)-1H-pyrazole-1-sulfonamide A mixture of 6-bromo-1,2,2-trimethyl-2,3-dihydrothieno[3,2-d]pyrimidin-4(1H)-one (138 mg, 0.50 mmol), 5-ethyl-N,N-dimethyl-4-(4,4,5,5-tetramethyl-1,3,2-dioxaborolan-2-yl)-1H-pyrazole-1-sulfonamide (329 mg, 1.00 mmol), cesium carbonate (815 mg, 2.50 mmol), 1,2-dimethoxyethane (5 mL) and water (1.25 mL) was purged with argon. Then, 1,1'-bis(diphenylphosphino) ferrocenepalladium (II) dichloride dichloromethane adduct (40.8 mg, 0.050 mmol) was added, and the mixture was purged with argon again. The mixture was stirred at 90° C. for 1 h. The mixture was poured into water (100 mL) and EtOAc (200 mL). The insoluble materials were filtered off, and the organic layer was collected from the filtrate. This organic layer was washed with brine, dried over MgSO$_4$, filtered and concentrated under reduced pressure. The residual oil was purified by column chromatography (Purif, silica gel, 95:5 hexane/EtOAc to EtOAc) to afford the title compound (139 mg, 70%) as a yellow solid:

$^1$H NMR (300 MHz, DMSO-d$_6$) δ 1.24 (3H, t, J=7.5 Hz), 1.42 (6H, s), 2.90 (3H, s), 3.01 (6H, s), 3.09 (2H, dd, J=14.1, 6.9 Hz), 7.04 (1H, s), 7.59 (1H, br s), 8.16 (1H, s).

Example 112

Preparation of 7-bromo-2-methyl-6-(1H-pyrazol-4-yl)-2-(2,2,2-trifluoroethyl)-2,3-dihydrothieno[3,2-d]pyrimidin-4(1H)-one

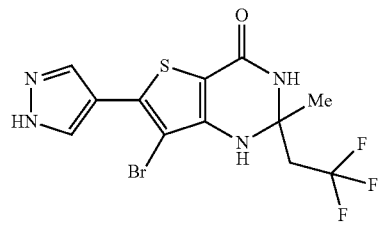 [SMILES: CC1(CC(F)(F)F)NC(=O)c2sc(-c3cn[nH]c3)c(Br)c2N1]

Step 1

Preparation of 3-amino-4-bromo-5-(1H-pyrazol-4-yl)thiophene-2-carboxamide

A mixture of 7-bromo-2,2-dimethyl-6-(1H-pyrazol-4-yl)-2,3-dihydrothieno[3,2-d]pyrimidin-4(1H)-one (243 mg, 0.743 mmol), 1 M HCl (2.60 mL, 2.60 mmol) and MeOH (7 mL) was stirred at 50° C. for 2 h. The mixture was poured into saturated aqueous NaHCO$_3$ and extracted with 3:1 EtOAc/THF, and the extract was dried over MgSO$_4$, filtered and concentrated under reduced pressure to afford the title compound (147 mg, 69%) as a pale yellow solid.

Step 2

Preparation of 7-bromo-2-methyl-6-(1H-pyrazol-4-yl)-2-(2,2,2-trifluoroethyl)-2,3-dihydrothieno[3,2-d]pyrimidin-4(1H)-one A mixture of 3-amino-4-bromo-5-(1H-pyrazol-4-yl)thiophene-2-carboxamide (90 mg, 0.313 mmol), 4,4,4-trifluorobutan-2-one (395 mg, 3.13 mmol), CSA (7.28 mg, 0.031 mmol), MgSO$_4$ (37.7 mg, 0.313 mmol) and DMA (2 mL) was microwave-irradiated at 150° C. for 3 h. The mixture was poured into saturated aqueous NaHCO$_3$ and extracted with EtOAc, and the extract was dried over MgSO$_4$, filtered and concentrated under reduced pressure. The residue was purified by column chromatography (Purif, silica gel, 95:5 hexane/EtOAc to EtOAc). The obtained solid was triturated with EtOAc, and the precipitate was collected by filtration to afford the title compound (29.2 mg, 24%) as a white solid:

$^1$H NMR (300 MHz, DMSO-d$_6$) δ 1.59 (3H, s), 2.64-2.84 (2H, m), 6.91 (1H, s), 7.87 (1H, s), 7.97 (1H, br s), 8.30 (1H, br s), 13.35 (1H, br s).

Example 113

Preparation of 6-(5-ethyl-1H-pyrazol-4-yl)-1,2,2-trimethyl-2,3-dihydrothieno[3,2-d]pyrimidin-4(1H)-one

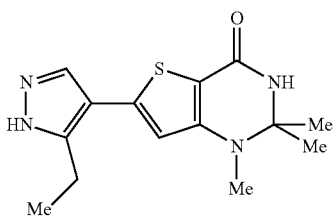 [SMILES: CCc1[nH]ncc1-c1cc2c(s1)C(=O)NC(C)(C)N2C]

A mixture of 5-ethyl-N,N-dimethyl-4-(1,2,2-trimethyl-4-oxo-1,2,3,4-tetrahydrothieno[3,2-d]pyrimidin-6-yl)-1H-pyrazole-1-sulfonamide (129 mg, 0.325 mmol) and TFA (2.00 mL, 26.0 mmol) was stirred for 1 h at room temperature. The mixture was poured into saturated aqueous $NaHCO_3$ and extracted with EtOAc, and the extract was dried over $MgSO_4$, filtered and concentrated under reduced pressure. The residue was mixed with acetone (5 mL, 68.1 mmol), $MgSO_4$ (78 mg, 0.649 mmol), PTSA (6.2 mg, 0.032 mmol) and DMF (1 mL). This mixture was stirred at 60° C. for 1 h. The mixture was poured into saturated aqueous $NaHCO_3$ and extracted with 3:1 EtOAc/THF, and the extract was dried over $MgSO_4$, filtered and concentrated under reduced pressure. The residue was purified by column chromatography (Purif, silica gel, hexane to EtOAc then to 80:20 EtOAc/MeOH). The obtained solid was triturated with EtOAc and collected by filtration to afford the title compound (41.2 mg, 44%) as a pale yellow solid:
$^1$H NMR (300 MHz, DMSO-$d_6$) δ 1.23 (3H, t, J=7.8 Hz), 1.40 (6H, s), 2.72-2.88 (5H, m), 6.84 (1H, s), 7.44 (1H, s), 7.76 (0.67H, br s), 8.08 (0.33H, br s), 12.79 (0.33H, br s), 12.88 (0.67H, br s).

Example 114

Preparation of 1-ethyl-2,2-dimethyl-6-(5-methyl-1H-pyrazol-4-yl)-2,3-dihydrothieno[3,2-d]pyrimidin-4(1H)-one

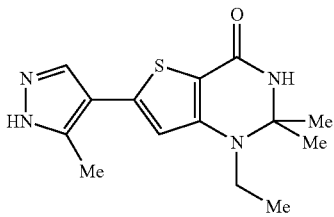 [SMILES: CCN1c2cc(-c3cn[nH]c3C)sc2C(=O)NC1(C)C]

A mixture of 1-ethyl-2-methyl-6-(5-methyl-1H-pyrazol-4-yl)-2-(2,2,2-trifluoroethyl)-2,3-dihydrothieno[3,2-d]pyrimidin-4(1H)-one (120 mg, 0.335 mmol) and TFA (1.0 mL) was stirred at room temperature for 1 day. After removal of the solvent at reduced pressure, the residue was treated with saturated aqueous $NaHCO_3$. The organic materials were extracted with EtOAc. The combined extracts were washed with brine, dried over $Na_2SO_4$ and filtered. After removal of the solvent at reduced pressure, the residue was purified by column chromatography (Purif, silica gel, EtOAc) to give a yellow crystalline solid. The solid was dissolved in DMA (1.5 mL). To the mixture, 2,2-dimethoxypropane (1.5 mL), CSA (15 mg) and $MgSO_4$ (100 mg) were added. The mixture was stirred at 80° C. for 2 h. The mixture was poured into saturated aqueous $NaHCO_3$. The organic materials were extracted with EtOAc. The combined extracts were washed with water and brine, dried over $Na_2SO_4$ and filtered. After removal of the solvent at reduced pressure, the residue was purified by column chromatography (Purif, silica gel, EtOAc) to give a yellow crystalline solid. The solid was mixed with MeOH (1.0 mL) and 1 M aqueous HCl (1.0 mL). After stirring at 50° C. for 1 h, saturated aqueous $NaHCO_3$ was added to the mixture. The organic materials were extracted with EtOAc. The combined extracts were washed with brine, dried over $Na_2SO_4$ and filtered. After removal of the solvent at reduced pressure, the residue was dissolved in acetic acid (0.50 mL). To the solution were added acetone (1.0 mL) and PTSA (10 mg). After stirring at 60° C. for 1 h, saturated aqueous $NaHCO_3$ and EtOAc were added to the mixture. The organic materials were extracted with EtOAc. The combined extracts were washed with brine, and then dried over $Na_2SO_4$. After removal of the solvent at reduced pressure, the residue was purified by column chromatography (Purif, silica gel, 90:10 hexane/EtOAc to EtOAc), then crystallized from EtOAc/heptane to give the title compound (24 mg, 24%) as a colorless solid:
$^1$H NMR (300 MHz, DMSO-$d_6$) δ 1.16 (3H, t, J=7.0 Hz), 1.44 (6H, s), 2.39 (3H, br s), 3.35 (2H, q, J=7.0 Hz), 6.78 (1H, s), 7.37 (1H, s), 7.79 (0.6H, br s), 8.12 (0.4H, br s), 12.84 (1H, br s).

Example 115

Preparation of 1-(2,2-difluoroethyl)-2,2-dimethyl-6-(5-methyl-1H-pyrazol-4-yl)-2,3-dihydrothieno[3,2-d]pyrimidin-4(1H)-one

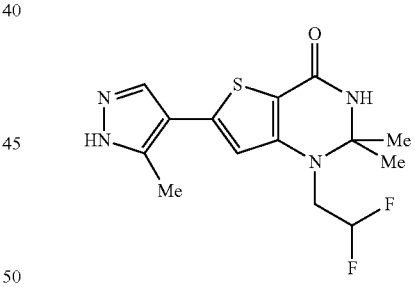

Step 1

Preparation of methyl 5-bromo-3-[(2,2-difluoroethyl)amino]thiophene-2-carboxylate A mixture of methyl 5-bromo-3-[(trifluoroacetyl)amino]thiophene-2-carboxylate (500 mg, 1.51 mmol), 2,2-difluoroethyl trifluoromethanesulfonate (441 mg, 2.06 mmol), cesium carbonate (1.23 g, 3.78 mmol) and DMF (10 mL) was microwave-irradiated at 90° C. for 1 h. Then, water was added to quench the reaction. The organic materials were extracted with EtOAc. The combined extracts were washed with water and brine, dried over $Na_2SO_4$ and filtered. After removal of the solvent at reduced pressure, the residue was dissolved in MeOH (3 mL). To the solution were added potassium carbonate (100 mg) and water (1.5 mL). The mixture was stirred at room temperature for 0.5 h. After removal of the solvent at reduced pressure, the organic materials were extracted with EtOAc. The combined extracts were washed with brine, dried over Na$_2$SO$_4$ and filtered. After removal of the solvent at reduced pressure, the residue was purified by column chromatography (Purif, silica gel, hexane to 85:15 hexane/EtOAc) to give the title compound (290 mg, 64%) as a yellow solid:

$^1$H NMR (300 MHz, CDCl$_3$) δ 3.51-3.67 (2H, m), 3.80 (3H, s), 5.60-6.09 (1H, m), 6.69 (1H, s), 7.05 (1H, br s).

Step 2

Preparation of 5-bromo-3-[(2,2-difluoroethyl)amino]thiophene-2-carboxamide

To a solution of methyl 5-bromo-3-[(2,2-difluoroethyl)amino]thiophene-2-carboxylate (285 mg, 0.95 mmol) in MeOH (3.0 mL) was added a solution of sodium hydroxide (114 mg, 2.85 mmol) in water (1.5 mL). After stirring at 60° C. for 4 h, 6 M aqueous HCl (0.3 mL) was added to the mixture to adjust the pH to 10. After removal of the solvent at reduced pressure, the residue was diluted with DMF (5 mL). Then, triethylamine (2.6 mL, 19 mmol) and ammonium chloride (1.02 g, 19 mmol) were added. After stirring at room temperature for 5 min, 1-ethyl-3-(3-dimethylaminopropyl)carbodiimide hydrochloride (1.09 g, 5.70 mmol) and 1-hydroxybenzotriazole (0.77 g, 5.70 mmol) were added to the mixture and the stirring was continued for 17 h. Then, water and EtOAc were added to quench the reaction. The organic materials were extracted with EtOAc. The combined extracts were washed with water and brine, dried over Na$_2$SO$_4$ and filtered. After removal of the solvent at reduced pressure, the residue was purified by column chromatography (Purif, silica gel, hexane to 70:30 hexane/EtOAc) to give the title compound (130 mg, 48%) as a yellow solid:

$^1$H NMR (300 MHz, CDCl$_3$) δ 3.41-3.83 (2H, m), 5.12 (2H, br s), 5.57-6.15 (1H, m), 6.75 (1H, s), 7.73 (1H, br s).

Step 3

Preparation of 1-(2,2-difluoroethyl)-2,2-dimethyl-6-(5-methyl-1H-pyrazol-4-yl)-2,3-dihydrothieno[3,2-d]pyrimidin-4(1H)-one A mixture of 5-bromo-3-[(2,2-difluoroethyl)amino]thiophene-2-carboxamide (130 mg, 0.456 mmol), 2,2-dimethoxypropane (1 mL), CSA (11 mg, 0.046 mmol), MgSO$_4$ (110 mg, 0.912 mmol) and DMA (1 mL) was stirred at 90° C. for 2 h. Then, saturated aqueous NaHCO$_3$ and EtOAc were added to quench the reaction. The organic materials were extracted with EtOAc. The combined extracts were washed with water and brine, dried over Na$_2$SO$_4$ and filtered. After removal of the solvent at reduced pressure, a colorless crystalline solid was obtained. A flask was charged with the solid, 1,2-dimethoxyethane (3.0 mL), tert-butyl 3-methyl-4-(4,4,5,5-tetramethyl-1,3,2-dioxaborolan-2-yl)-1H-pyrazole-1-carboxylate (422 mg, 1.37 mmol), sodium carbonate (137 mg, 2.28 mmol) and water (1.5 mL). The flask was purged with argon. Then, 1,1'-bis(diphenylphosphino)ferrocenepalladium (II) dichloride dichloromethane adduct (37 mg, 0.046 mmol) was added to the mixture. The flask was purged with argon. After stirring at 100° C. for 2 h, 8 M aqueous NaOH (0.5 mL) was added. After stirring at 100° C. for 1 h, the organic materials were extracted with EtOAc. The combined extracts were washed with brine, dried over Na$_2$SO$_4$ and filtered. After removal of the solvent at reduced pressure, the residue was purified by column chromatography (Purif, silica gel, 80:20 hexane/EtOAc to EtOAc), then crystallized from EtOAc/hexane to give the title compound (78 mg, 52%) as a yellow solid:

$^1$H NMR (300 MHz, DMSO-d$_6$) δ 1.44 (6H, s), 2.39 (3H, br s), 3.78 (2H, td, J=15.1, 3.8 Hz), 5.95-6.44 (1H, m), 6.88 (1H, s), 7.58 (1H, s), 7.78 (0.6H, br s), 8.11 (0.4H, br s), 12.88 (1H, br s).

Example 116

Preparation of 2,2-dimethyl-6-(5-{[(2-phenylethyl)amino]methyl}-1H-pyrazol-4-yl)-2,3-dihydrothieno[3,2-d]pyrimidin-4(1H)-one

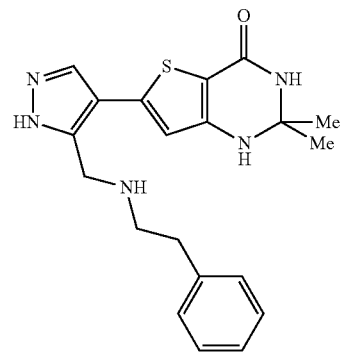 [SMILES: CC1(C)NC(=O)c2sc(-c3cn[nH]c3CNCCc3ccccc3)cc2N1]

Step 1

Preparation of 4-bromo-1-{[2-(trimethylsilyl)ethoxy]methyl}-1H-pyrazole-5-carbaldehyde To a stirred suspension of 4-bromo-1H-pyrazole-5-carbaldehyde (1.93 g, 11 mmol) in THF (50 mL) was added sodium hydride (0.484 g, 12.1 mmol) at 0° C. After 10 min, [2-(chloromethoxy)ethyl](trimethyl)silane (2.34 mL, 13.2 mmol) was added. After 2 h, the mixture was poured into saturated aqueous NaHCO$_3$ and extracted with EtOAc (100 mL), and the extract was dried over MgSO$_4$, filtered and concentrated under reduced pressure. The residue was purified by column chromatography (Purif, silica gel, hexane to 80:20 hexane/EtOAc) to afford the title compound (2.30 g, 69%) as a colorless oil:

$^1$H NMR (300 MHz, CDCl$_3$) δ 0.00 (9H, s), 0.94 (2H, t, J=8.1 Hz), 3.60 (2H, t, J=8.1 Hz), 5.48 (2H, s), 7.70 (1H, s), 10.00 (1H, s).

Step 2

Preparation of (5-formyl-1-{[2-(trimethylsilyl)ethoxy]methyl}-1H-pyrazol-4-yl)boronic acid A mixture of 4-bromo-1-[[2-(trimethylsilyl)ethoxy]methyl]-1H-pyrazole-5-carbaldehyde (2.00 g, 6.55 mmol), 4,4,4',4',5,5,5',5'-octamethyl-2,2'-bi-1,3,2-dioxaborolane (1.75 g, 6.88 mmol), potassium acetate (1.93 g, 19.7 mmol) and 1,2-dimethoxyethane (40 mL) was purged with argon. Then, 1,1'-bis(diphenylphosphino)ferrocenepalladium (II) dichloride dichloromethane adduct (0.535 g, 0.655 mmol) was added, and the mixture was purged with argon again. The mixture was stirred at 90° C. overnight. After cooled to room temperature, the mixture was filtered, and the filtrate was concentrated under reduced pressure. The residue was purified by column chromatography (Purif, silica gel, hexane to 70:30 hexane/EtOAc) to afford the title compound (571 mg, 25%) as a colorless oil:

¹H NMR (300 MHz, CDCl₃) δ 0.00 (9H, s), 0.98 (2H, t, J=6.0 Hz), 1.23 (12H, s), 3.68 (2H, t, J=8.1 Hz), 5.56 (2H, s), 8.81 (1H, s), 10.11 (1H, s).

Step 3

Preparation of 4-(2,2-dimethyl-4-oxo-1,2,3,4-tetrahydrothieno[3,2-d]pyrimidin-6-yl)-1-{[2-(trimethylsilyl)ethoxy]methyl}-1H-pyrazole-5-carbaldehyde A mixture of 6-bromo-2,2-dimethyl-2,3-dihydrothieno[3,2-d]pyrimidin-4(1H)-one (0.444 g, 1.70 mmol), (5-formyl-1-{[2-(trimethylsilyl)ethoxy]methyl}-1H-pyrazol-4-yl)boronic acid (0.554 g, 2.05 mmol), cesium carbonate (2.77 g, 8.50 mmol), 1,2-dimethoxyethane (15 mL) and water (4 mL) was purged with argon. Then, 1,1'-bis(diphenylphosphino)ferrocenepalladium (II) dichloride dichloromethane adduct (0.139 g, 0.17 mmol) was added, and the mixture was purged with argon again. The mixture was refluxed for 2 h. Then, the mixture was poured into water (100 mL) and EtOAc (100 mL). The insoluble materials were filtered off, and the organic layer was collected from the filtrate. This organic layer was washed with brine, dried over MgSO₄ and concentrated under reduced pressure. The residual oil was purified by column chromatography (Purif, silica gel, 95:5 hexane/EtOAc to EtOAc) to afford the title compound (374 mg, 54%) as a yellow solid:

¹H NMR (300 MHz, DMSO-d₆) δ 0.03 (9H, s), 0.90 (2H, t, J=7.8 Hz), 1.44 (6H, s), 3.65 (2H, t, J=7.8 Hz), 5.58 (2H, s), 7.15 (1H, br s), 7.26 (1H, s), 7.51 (1H, br s), 8.58 (1H, s), 10.03 (1H, s).

Step 4

Preparation of 2,2-dimethyl-6-(5-{[(2-phenylethyl)amino]methyl}-1H-pyrazol-4-yl)-2,3-dihydrothieno[3,2-d]pyrimidin-4(1H)-one A mixture of 4-(2,2-dimethyl-4-oxo-1,2,3,4-tetrahydrothieno[3,2-d]pyrimidin-6-yl)-1-{[2-(trimethylsilyl)ethoxy]methyl}-1H-pyrazole-5-carbaldehyde (122 mg, 0.30 mmol), 2-phenylethanamine (0.151 mL, 1.20 mmol) and THF (5 mL) was stirred at room temperature overnight. Then, sodium borohydride (0.023 g, 0.60 mmol) and MeOH (2 mL) were added. After 30 min, the mixture was poured into saturated aqueous NaHCO₃ and extracted with EtOAc, and the extract was dried over MgSO₄, filtered and concentrated under reduced pressure. The residue was purified by column chromatography (Purif, NH, 95:5 hexane/EtOAc to EtOAc then to 80:20 EtOAc/MeOH) to afford 2,2-dimethyl-6-(5-{[(2-phenylethyl)amino]methyl}-1-{[2-(trimethylsilyl)ethoxy]methyl}-1H-pyrazol-4-yl)-2,3-dihydrothieno[3,2-d]pyrimidin-4(1H)-one (140 mg). 2,2-Dimethyl -6-(5-{[(2-phenylethyl)amino]methyl}-1-{[2-(trimethylsilyl)ethoxy]methyl}-1H-pyrazol-4-yl)-2,3-dihydrothieno[3,2-d]pyrimidin-4(1H)-one (140 mg) was dissolved with N,N,N,N-tetrabutylammonium fluoride (1.0 M in THF, 3.0 mL, 3.00 mmol) and the mixture was stirred at 60° C. overnight. The mixture was filtered, and the filtrate was poured into saturated aqueous NaHCO₃ and extracted with EtOAc, and the extract was dried over MgSO₄, filtered and concentrated under reduced pressure. The residue was purified by column chromatography (Purif, NH, 95:5 hexane/EtOAc to EtOAc then to 80:20 EtOAc/MeOH) to afford the title compound (27.5 mg, 24%) as a colorless oil:

¹H NMR (300 MHz, DMSO-d₆) δ 1.40 (6H, s), 2.74 (4H, m), 3.88 (2H, m), 6.63 (1H, br s), 6.93 (1H, s), 7.16-7.28 (5H, m), 7.33 (1H, s), 7.70 (0.67H, br s), 8.05 (0.33H, br s), 12.92 (1H, br s).

Example 117

Preparation of 1,2,2,7-tetramethyl-6-(1H-pyrazol-4-yl)-2,3-dihydrothieno[3,2-d]pyrimidin-4(1H)-one

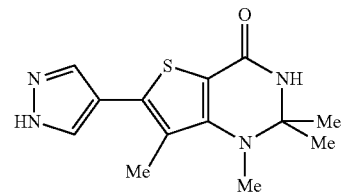 [SMILES: Cc1c(-c2cn[nH]c2)sc2c1N(C)C(C)(C)NC2=O]

Step 1

Preparation of methyl 4-methyl-3-[(trifluoroacetyl)amino]thiophene-2-carboxylate To a stirred solution of methyl 3-amino-4-methylthiophene-2-carboxylate (50 g, 292 mmol) in MeCN (600 mL) were added pyridine (28.6 mL, 350 mmol) and trifluoroacetic anhydride (58.6 mL, 421 mmol) at 0° C. After 5 min, the mixture was allowed to room temperature and the stirring was continued for 2 h. The mixture was poured into ice-water (2.5 L) and the mixture was stirred for 20 min. Then, extraction with EtOAc (1 L), washing with brine, drying over MgSO₄, filtration and concentration under reduced pressure gave brown oil. This residue was purified by column chromatography (Purif, silica gel, hexane to 50:50 hexane/EtOAc) to afford the title compound (74.8 g, 96%) as an orange oil:

¹H NMR (300 MHz, CDCl₃) δ 2.24 (3H, s), 3.90 (3H, s), 7.72 (1H, s), 9.68 (1H, br s).

Step 2

Preparation of methyl 5-bromo-4-methyl-3-[(trifluoroacetyl)amino]thiophene-2-carboxylate To a stirred mixture of methyl 4-methyl-3-[(trifluoroacetyl)amino]thiophene-2-carboxylate (11.7 g, 43.8 mmol) and acetic acid (150 mL) was added 1-bromopyrrolidine-2,5-dione (15.6 g, 88.0 mmol) at room temperature. Then, this mixture was stirred at 80° C. for 6 h. After cooling to room temperature, the mixture was poured into water (600 mL) and brine (300 mL). The precipitate was collected by filtration, washed with water, dried under vacuum to afford the title compound (9.40 g, 62%) as a white solid:

¹H NMR (300 MHz, CDCl₃) δ 2.15 (3H, s), 3.89 (3H, s), 9.62 (1H, br s).

Step 3

Preparation of methyl 5-bromo-4-methyl-3-(methylamino)thiophene-2-carboxylate

A mixture of methyl 5-bromo-4-methyl-3-[(trifluoroacetyl)amino]thiophene-2-carboxylate (9.40 g, 27.2 mmol), K$_2$CO$_3$ (7.51 g, 54.3 mmol), iodomethane (2.04 mL, 32.6 mmol) and DMF (60 mL) was stirred at 60° C. for 6 h. The mixture was poured into water (200 mL) and extracted with EtOAc (200 mL), and the extract was washed with brine, dried over MgSO$_4$, filtered and concentrated under reduced pressure. The residue was mixed with K$_2$CO$_3$ (4.13 g, 29.9 mmol), MeOH (200 mL) and water (100 mL). The mixture was stirred at room temperature overnight. Then, the mixture was concentrated under reduced pressure to about a half volume, and poured into saturated aqueous NaHCO$_3$ (300 mL). Extraction with EtOAc (400 mL), washing with brine, drying over MgSO$_4$, filtration and concentration under reduced pressure gave an orange solid. This residue was purified by column chromatography (Purif, silica gel, hexane to 50:50 hexane/EtOAc) to afford the title compound (4.46 g, 62%) as a pale yellow solid:
$^1$H NMR (300 MHz, CDCl$_3$) δ 2.08 (3H, s), 3.24 (3H, s), 3.86 (3H, s).

Step 4

Preparation of 5-bromo-4-methyl-3-(methylamino)thiophene-2-carboxamide

Sodium hydroxide (4.27 g, 107 mmol) was dissolved with water (35 mL) and MeOH (140 mL). Then, methyl 5-bromo-4-methyl-3-(methylamino)thiophene-2-carboxylate (4.46 g, 16.7 mmol) was added to the mixture. The mixture was stirred at 70° C. overnight. After cooling in ice-water bath, 6 M HCl (11.9 mL, 71.4 mmol) was added, and the mixture was concentrated under reduced pressure. The residue was co-evaporated with toluene twice to give a yellow solid. This residue was mixed with ammonium chloride (38.1 g, 712 mmol), triethylamine (99 mL, 712 mmol) and DMF (300 mL), and the mixture was stirred for 5 min. Then, 1-hydroxybenzotriazole (32.7 g, 214 mmol) and 1-ethyl-3-(3-dimethylaminopropyl)carbodiimide hydrochloride (40.9 g, 214 mmol) were added to the mixture, and stirring was continued for 3 days. The reaction mixture was poured into saturated aqueous NaHCO$_3$ (1 L). Extraction with EtOAc (1 L), washing with saturated NaHCO$_3$, drying over MgSO$_4$, filtration and concentration under reduced pressure gave a brown oil. This oil was purified by column chromatography (Purif, silica gel, hexane to EtOAc) to afford the title compound (2.34 g, 56%) as a brown oil:
$^1$H NMR (300 MHz, DMSO-d$_6$) δ 2.26 (3H, s), 2.98 (3H, d, J=5.4 Hz), 5.35 (2H, br s), 6.82 (1H, br s).

Step 5

Preparation of 6-bromo-1,2,2,7-tetramethyl-2,3-dihydrothieno[3,2-d]pyrimidin-4(1H)-one A mixture of 5-bromo-4-methyl-3-(methylamino)thiophene-2-carboxamide (2.34 g, 9.39 mmol), acetone (10 mL, 136 mmol), MgSO$_4$ (1.13 g, 9.39 mmol), PTSA (0.089 g, 0.47 mmol) and DMF (10 mL) was stirred at 60° C. overnight. The mixture was poured into saturated aqueous NaHCO$_3$ and extracted with EtOAc, and the extract was dried over MgSO$_4$ and concentrated under reduced pressure. The residue was purified by column chromatography (Purif, NH, 98:2 hexane/EtOAc to 50:50 hexane/EtOAc) to afford the title compound (1.17 g, 43%) as a pale orange solid:
$^1$H NMR (300 MHz, DMSO-d$_6$) δ 1.39 (6H, s), 2.08 (3H, s), 2.56 (3H, s), 7.87 (1H, br s).

Step 6

Preparation of 1,2,2,7-tetramethyl-6-(1H-pyrazol-4-yl)-2,3-dihydrothieno[3,2-d]pyrimidin-4(1H)-one A mixture of 6-bromo-1,2,2,7-tetramethyl-2,3-dihydrothieno[3,2-d]pyrimidin-4(1H)-one (145 mg, 0.50 mmol), tert-butyl 4-(4,4,5,5-tetramethyl-1,3,2-dioxaborolan-2-yl)pyrazole-1-carboxylate (441 mg, 1.50 mmol), cesium carbonate (815 mg, 2.50 mmol), 1,2-dimethoxyethane (5 mL) and water (1.25 mL) was purged with argon. Then, 1,1'-bis(diphenylphosphino)ferrocenepalladium (II) dichloride dichloromethane adduct (40.8 mg, 0.050 mmol) was added, and the mixture was purged with argon again. The mixture was stirred at 90° C. overnight. The mixture was poured into water (100 mL) and EtOAc (100 mL). The insoluble materials were filtered off, and the organic layer was collected from the filtrate. This organic layer was washed with brine, dried over MgSO$_4$ and concentrated under reduced pressure. The residual oil was purified by column chromatography (Purif, silica gel, 95:5 hexane/EtOAc to EtOAc then to 80:20 EtOAc/MeOH), then triturated with EtOAc/hexane. The solid was collected by filtration to afford the title compound (65.2 mg, 47%) as a white solid:
$^1$H NMR (300 MHz, DMSO-d$_6$) δ 1.39 (6H, s), 2.15 (3H, s), 2.57 (3H, s), 7.70 (1H, s), 7.76 (1H, br s), 8.09 (1H, br s), 13.21 (1H, br s).

Example 118

Preparation of 2-fluoro-1'-methyl-6'-(5-methyl-1H-pyrazol-4-yl)-1'H-spiro[cyclohexane-1,2'-thieno[3,2-d]pyrimidin]-4'(3'H)-one

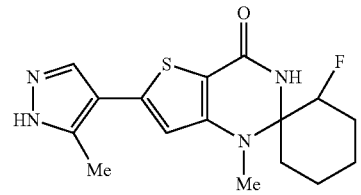 [SMILES: Cc1[nH]ncc1-c1cc2c(s1)C(=O)NC1(CCCCC1F)N2C]

Step 1

Preparation of 3-(methylamino)-5-(5-methyl-1H-pyrazol-4-yl)thiophene-2-carboxamide A mixture of 1,2,2-trimethyl-6-(5-methyl-1H-pyrazol-4-yl)-2,3-dihydrothieno[3,2-d]pyrimidin-4(1H)-one (378 mg, 1.37 mmol), 1 M HCl (4.79 mL) and MeOH (12 mL) was stirred for 2 h at 50° C. The mixture was poured into excess saturated aqueous NaHCO$_3$ and extracted with 3:1 EtOAc/THF, and the extract was dried over MgSO$_4$, filtered and concentrated under reduced pressure. The residue was triturated with ethanol (6 mL) and collected by filtration to afford the title compound (183 mg, 57%) as a pale yellow solid:

¹H NMR (300 MHz, DMSO-d₆) δ 2.40 (3H, m), 2.90 (3H, d, J=5.1 Hz), 6.73 (2H, br s), 6.80 (1H, s), 7.23-7.28 (1H, m), 7.73 (0.67H, br s), 8.06 (0.33H, br s), 12.75 (0.33H, br s), 12.83 (0.67H, br s).

Step 2

Preparation of 2-fluoro-1'-methyl-6'-(5-methyl-1H-pyrazol-4-yl)-1'H-spiro[cyclohexane-1,2'-thieno[3,2-d]pyrimidin]-4'(3'H)-one A mixture of 3-(methylamino)-5-(5-methyl-1H-pyrazol-4-yl)thiophene-2-carboxamide (70 mg, 0.30 mmol), 2-fluorocyclohexanone (105 mg, 0.90 mmol), CSA (7.0 mg, 0.030 mmol), MgSO₄ (72 mg, 0.60 mmol) and DMA (1 mL) was stirred at 70° C. for 5.5 h. Then, saturated aqueous NaHCO₃ and EtOAc were added to quench the reaction. The organic materials were extracted with EtOAc. The combined extracts were washed with water and brine, dried over Na₂SO₄ and filtered. After removal of the solvent at reduced pressure, the residue was purified by column chromatography (Purif, silica gel, 80:20 hexane/EtOAc to EtOAc), then crystallized from MeOH/EtOAc/hexane to give the title compound (58 mg, 58%) as a yellow solid:
¹H NMR (300 MHz, DMSO-d₆) δ 1.21-2.13 (8H, m), 2.39 (3H, br s), 2.99 (2H, s), 3.09 (1H, s), 4.77-5.02 (0.6H, m), 5.02-5.27 (0.4H, m), 6.91 (0.6H, s), 6.93 (0.4H, s), 7.40 (0.6H, s), 7.46 (0.4H, s), 7.79 (0.6H, br s), 8.11 (0.4H, br s), 12.86 (1H, br s).

Example 119

Preparation of 2,2-dimethyl-6-(5-methyl-1H-pyrazol-4-yl)-1-(3-nitrobenzyl)-2,3-dihydrothieno[3,2-d]pyrimidin-4(1H)-one

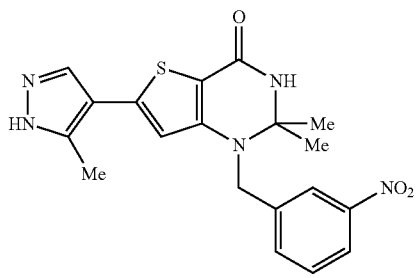 [SMILES: Cc1[nH]ncc1-c1cc2c(s1)C(=O)NC(C)(C)N2Cc1cccc([N+](=O)[O-])c1]

Step 1

Preparation of methyl 5-bromo-3-[(3-nitrobenzyl)amino]thiophene-2-carboxylate

A mixture of methyl 5-bromo-3-[(trifluoroacetyl)amino]thiophene-2-carboxylate (500 mg, 1.51 mmol), 1-(bromomethyl)-3-nitrobenzene (490 mg, 2.27 mmol), cesium carbonate (1.23 g, 3.78 mmol) and DMF (10 mL) was stirred at 70° C. for 1 h. Then, water was added to quench the reaction. The organic materials were extracted with EtOAc. The combined extracts were washed with water and brine, dried over Na₂SO₄ and filtered. After removal of the solvent at reduced pressure, the residue was purified by column chromatography (Purif, silica gel, hexane to 80:20 hexane/EtOAc) to give a yellow oil. A mixture of this oil, MeOH (5 mL), potassium carbonate (500 mg) and water (2.5 mL) was stirred at room temperature for 0.5 h. After removal of the solvent at reduced pressure, the organic materials were extracted with EtOAc. The combined extracts were washed with brine, dried over Na₂SO₄ and filtered. After removal of the solvent at reduced pressure, the title compound (495 mg, 88%) was obtained as a yellow oil:
¹H NMR (300 MHz, CDCl₃) δ 3.82 (3H, s), 4.55 (2H, d, J=6.2 Hz), 6.50 (1H, s), 7.36 (1H, br s), 7.49-7.60 (1H, m), 7.61-7.76 (1H, m), 8.01-8.25 (2H, m).

Step 2

Preparation of 5-bromo-3-[(3-nitrobenzyl)amino]thiophene-2-carboxamide

To a solution of methyl 5-bromo-3-[(3-nitrobenzyl)amino]thiophene-2-carboxylate (495 mg, 1.33 mmol) in MeOH (4 mL) was added a solution of sodium hydroxide (160 mg, 3.99 mmol) in water (2 mL). After stirring at 60° C. for 4 h, 6 M aqueous HCl (0.42 mL) was added to the mixture to adjust the pH to 10. After removal of the solvent at reduced pressure, the residue was diluted with DMF (6 mL). Then, triethylamine (3.7 mL, 27 mmol) and ammonium chloride (1.4 g, 27 mmol) were added. After stirring at room temperature for 5 min, 1-ethyl-3-(3-dimethylaminopropyl)carbodiimide hydrochloride (1.5 g, 8.0 mmol) and 1-hydroxybenzotriazole (1.1 g, 8.0 mmol) were added to the mixture, and stirring was continued for 17 h. Then, water was added to quench the reaction. The organic materials were extracted with EtOAc. The combined extracts were washed with water and brine, dried over Na₂SO₄ and filtered. After removal of the solvent at reduced pressure, the residue was purified by column chromatography (Purif, silica gel, hexane to 50:50 hexane/EtOAc) to give the title compound (269 mg, 57%) as a yellow solid:
¹H NMR (300 MHz, CDCl₃) δ 4.53 (2H, d, J=6.4 Hz), 5.12 (2H, br s), 6.52 (1H, s), 7.47-7.57 (1H, m), 7.66 (1H, d, J=7.7 Hz), 7.98-8.08 (1H, m), 8.14 (1H, d, J=8.1 Hz), 8.18 (1H, s).

Step 3

Preparation of 2,2-dimethyl-6-(5-methyl-1H-pyrazol-4-yl)-1-(3-nitrobenzyl)-2,3-dihydrothieno[3,2-d]pyrimidin-4(1H)-one A mixture of 5-bromo-3-[(3-nitrobenzyl)amino]thiophene-2-carboxamide (260 mg, 0.730 mmol), 2,2-dimethoxypropane (2.0 mL), CSA (17 mg, 0.073 mmol), MgSO₄ (200 mg) and DMA (2 mL) was microwave-irradiated at 120° C. for 1 h. Then, saturated aqueous sodium hydrogen carbonate was added to quench the reaction. The organic materials were extracted with EtOAc. The combined extracts were washed with water and brine, dried over Na₂SO₄ and filtered. After removal of the solvent at reduced pressure, a yellow crystalline solid was obtained. A flask was charged with this solid, 1,2-dimethoxyethane (4 mL), tert-butyl 3-methyl-4-(4,4,5,5-tetramethyl-1,3,2-dioxaborolan-2-yl)-1H-pyrazole-1-carboxylate (675 mg, 2.19 mmol), sodium carbonate (219 mg, 3.65 mmol) and water (2 mL). The flask was purged with argon. Then, 1,1'-bis(diphenylphosphino) ferrocenepalladium (II) dichloride dichloromethane adduct (60 mg, 0.073 mmol) was added to the mixture. The flask was purged with argon again. After stirring at 100° C. for 2 h, 8 M aqueous NaOH (1.0 mL) was added. After stirring at 100° C. for 1 h, the organic materials were extracted with EtOAc. The combined extracts were washed with brine, dried over Na₂SO₄ and filtered. After removal of the solvent at reduced pressure, the residue was purified by column chromatography (Purif, silica gel, 80:20 hexane/EtOAc to EtOAc), then crystallized from MeOH/EtOAo/hexane to give the title compound (124 mg, 43%) as a yellow solid:

$^1$H NMR (300 MHz, DMSO-d$_6$) δ 1.45 (6H, s), 2.30 (3H, br s), 4.74 (2H, s), 6.70 (1H, s), 7.54-7.77 (2.6H, m), 7.81 (1H, d, J=7.9 Hz), 8.01 (0.4H, br s), 8.13 (1H, d, J=7.9 Hz), 8.20 (1H, s), 12.85 (1H, br s).

Example 120

Preparation of 1-(3-aminobenzyl)-2,2-dimethyl-6-(5-methyl-1H-pyrazol-4-yl)-2,3-dihydrothieno[3,2-d]pyrimidin-4(1H)-one

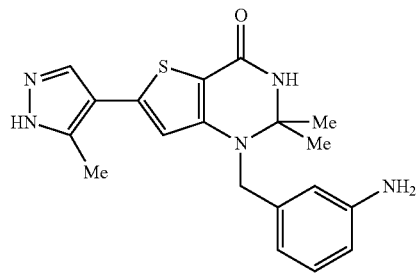 [SMILES: Cc1[nH]ncc1-c1cc2c(s1)C(=O)NC(C)(C)N2Cc1cccc(N)c1]

A mixture of 2,2-dimethyl-6-(5-methyl-1H-pyrazol-4-yl)-1-(3-nitrobenzyl)-2,3-dihydrothieno[3,2-d]pyrimidin-4(1H)-one (147 mg, 0.37 mmol), platinum(IV) oxide (15 mg) and ethanol (20 mL) was stirred at room temperature for 3 h under hydrogen atmosphere (1 atm). Then, the catalyst was removed by filtration. After removal of the solvent at reduced pressure, the residue was purified by column chromatography (Purif, silica gel, EtOAc to 90:10 EtOAc/MeOH), then crystallized from MeOH/EtOAc/hexane to give the title compound (52 mg, 38%) as a yellow solid:

$^1$H NMR (300 MHz, DMSO-d$_6$) δ 1.43 (6H, s), 2.31 (3H, br s), 4.39 (2H, s), 5.07 (2H, s), 6.41 (1H, d, J=7.7 Hz), 6.49 (1H, d, J=7.7 Hz), 6.57 (1H, s), 6.63 (1H, s), 6.91-7.02 (1H, m), 7.50 (1H, s), 7.66 (0.6H, br s), 8.03 (0.4H, br s), 12.83 (1H, br s).

Example 121

Preparation of 1-ethyl-6'-(5-methyl-1H-pyrazol-4-yl)-1'H-spiro[piperidine-4,2'-thieno[3,2-d]pyrimidin]-4'(3'H)-one

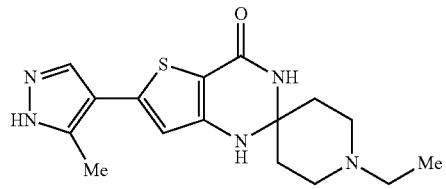 [SMILES: CCN1CCC2(CC1)NC(=O)c1sc(-c3cn[nH]c3C)cc1N2]

Step 1

Preparation of methyl 5-bromo-3-[(trifluoroacetyl)amino]thiophene-2-carboxylate

To a stirred mixture of N-(1-methylethyl)propan-2-amine (40.0 mL, 285 mmol) and THF (400 mL) at −78° C. was added slowly 1.6 M n-butyllithium in hexane (165 mL, 264 mmol). The mixture was allowed to 0° C. over 2 h. Then, the mixture was cooled to −78° C. again. Then, a solution of methyl 3-[(trifluoroacetyl)amino]thiophene-2-carboxylate (20.3 g, 80 mmol) in THF (80 mL) was added to the mixture slowly. After 1 h, 1,2-dibromoethane (41.2 mL, 476 mmol) was added at once. The stirring was continued at −78° C. for 1 h, and the dry ice-acetone bath was removed. After further stirring for 30 min, the mixture was poured into saturated aqueous NaHCO$_3$ (1 L) and EtOAc (1 L). After shaking well, the organic layer was collected, washed with brine, dried over MgSO$_4$, filtered and concentrated under reduced pressure to give an orange oil. This residue was purified by column chromatography (Purif, silica gel, hexane to 90:10 hexane/EtOAc) to afford the title compound (10.4 g, 39%) as a beige solid:

$^1$H NMR (300 MHz, DMSO-d$_6$) δ 3.84 (3H, s), 7.79 (1H, s), 11.21 (1H, br s).

Step 2

Preparation of methyl 3-amino-5-bromothiophene-2-carboxylate

A mixture of methyl 5-bromo-3-[(trifluoroacetyl)amino]thiophene-2-carboxylate (8.15 g, 24.5 mmol), potassium carbonate (4.15 g, 30 mmol), MeOH (200 mL) and water (100 mL) was stirred at room temperature for 2 h. The mixture was concentrated to about a half volume and poured into saturated aqueous NaHCO$_3$ (300 mL). Extraction with EtOAc (300 mL), washing with brine, drying over MgSO$_4$, filtration and concentration under reduced pressure gave the title compound as a yellow solid (5.67 g, 98%):

$^1$H NMR (300 MHz, DMSO-d$_6$) δ 3.70 (3H, s), 6.69 (2H, br s), 6.75 (1H, s).

Step 3

Preparation of 3-amino-5-bromothiophene-2-carboxamide

A mixture of methyl 3-amino-5-bromothiophene-2-carboxylate (5.67 g, 24.0 mmol) was mixed with sodium hydroxide (2.94 g, 73.6 mmol), MeOH (100 mL) and water (25 mL) was stirred at 70° C. overnight. After cooling to 0° C., 6 M HCl (8.17 mL, 49.0 mmol) was added. This mixture was concentrated under reduced pressure to give a yellow solid. Co-evaporation was carried out with toluene and the resulting solid was dried under reduced pressure well. This residue was mixed with ammonium chloride (26.3 g, 491 mmol), triethylamine (49.7 g, 491 mmol) and DMF (230 mL). After stirred at room temperature for 5 min, 1-hydroxybenzotriazole (19.9 g, 144 mmol) and 1-ethyl-3-(3-dimethylaminopropyl)carbodiimide hydrochloride (28.2 g, 147 mmol) were added. The stirring was continued for 2 days. The reaction mixture was poured into saturated aqueous NaHCO$_3$ (700 mL) and extracted with EtOAc (700 mL), and the extract was washed with saturated aqueous NaHCO$_3$, dried over MgSO$_4$, filtered and concentrated under reduced pressure. The residual brown oil was purified by column chromatography (Purif, silica gel, hexane to EtOAc) to afford the title compound (4.05 g, 75%) as yellow solid:
$^1$H NMR (300 MHz, DMSO-d$_6$) δ 6.56 (2H, br s), 6.70 (1H, s), 6.91 (2H, br s).

Step 4

Preparation of 2,2-dimethyl-6-(5-methyl-1H-pyrazol-4-yl)-2,3-dihydrothieno[3,2-d]pyrimidin-4(1H)-one A mixture of 3-amino-5-bromothiophene-2-carboxamide (1.99 g, 9.0 mmol), 2,2-dimethoxypropane (10 mL), CSA (209 mg, 0.90 mmol), MgSO$_4$ (2.17 g, 18 mmol) and DMA (10 mL) was stirred at 90° C. for 2 h. After removal of MgSO$_4$ by filtration, saturated aqueous NaHCO$_3$ was added to the filtrate. The organic materials were extracted with EtOAc. The combined extracts were washed with water and brine, dried over Na$_2$SO$_4$ and filtered. After removal of the solvent at reduced pressure, a brown crystalline solid was obtained. A flask was charged with this solid, tert-butyl 3-methyl-4-(4,4,5,5-tetramethyl-1,3,2-dioxaborolan-2-yl)-1H-pyrazole-1-carboxylate (6.0 g, 19.5 mmol), sodium carbonate (2.3 g, 38.3 mmol), 1,2-dimethoxyethane (30 mL) and water (15 mL). The flask was purged with argon. Then, 1,1'-bis(diphenylphosphino)ferrocenepalladium (II) dichloride dichloromethane adduct (626 mg, 0.766 mmol) was added to the mixture. The flask was purged with argon again. After stirring at 100° C. for 3.5 h, 8 M aqueous NaOH (2.0 mL) was added. After stirring at 100° C. for 1 h, the organic materials were extracted with EtOAc/THF. The combined extracts were dried over Na$_2$SO$_4$ and filtered. After removal of the solvent at reduced pressure, the residue was purified by column chromatography (Purif, silica gel, EtOAc to 90:10 EtOAc/MeOH) to give the title compound (1.97 g, 86%) as a brown solid:
$^1$H NMR (300 MHz, DMSO-d$_6$) δ 1.40 (6H, s), 2.37 (3H, br s), 6.53 (1H, s), 6.95 (1H, s), 7.34 (1H, s), 7.71 (0.6H, br s), 8.06 (0.4H, br s), 12.84 (1H, br s).

Step 5

Preparation of 3-amino-5-(5-methyl-1H-pyrazol-4-yl)thiophene-2-carboxamide

A mixture of 2,2-dimethyl-6-(5-methyl-1H-pyrazol-4-yl)-2,3-dihydrothieno[3,2-d]pyrimidin-4(1H)-one (1.97 g, 7.51 mmol), 1 M aqueous HCl. (38 mL) and MeOH (38 mL) was stirred at 50° C. for 4 h. After removal of the solvent at reduced pressure, the organic materials were extracted with EtOAc/THF. The combined extracts were dried over Na$_2$SO$_4$ and filtered. After removal of the solvent at reduced pressure, the residue was purified by column chromatography (Purif, silica gel, EtOAc to 90:10 EtOAc/MeOH) to give the title compound (1.20 g, 72%) as a green solid:
$^1$H NMR (300 MHz, DMSO-d$_6$) δ 2.37 (3H, br s), 6.44 (2H, br s), 6.59 (1H, s), 6.75 (2H, br s), 7.63 (0.6H, br s), 7.95 (0.4H, br s), 12.83 (1H, br s).

Step 6

Preparation of 1-ethyl-6'-(5-methyl-1H-pyrazol-4-yl)-1'H-spiro [piperidine-4,2'-thieno[3,2-d]pyrimidin]-4'(3'H)-one A mixture of 3-amino-5-(5-methyl-1H-pyrazol-4-yl) thiophene -2-carboxamide (100 mg, 0.45 mmol), 1-ethylpiperidin-4-one (0.067 mL, 0.50 mmol), CSA (125 mg, 0.54 mmol), MgSO$_4$ (108 mg, 0.90 mmol) and DMA (2.0 mL) was stirred at 100° C. for 4 h. Then, the mixture was poured into saturated aqueous NaHCO$_3$. The organic materials were extracted with EtOAc. To the aqueous layer, NaCl was added. The organic materials were extracted again with EtOAc/THF. The combined organic layers were concentrated under reduced pressure. The residue was purified by column chromatography (Purif, NH, 80:20 hexane/EtOAc to EtOAc then to 90:10 EtOAc/MeOH), then crystallized from MeOH/EtOAc/hexane to give the title compound (89 mg, 64%) as yellow solid:
$^1$H NMR (300 MHz, DMSO-d$_6$) δ 0.99 (3H, t, J=7.1 Hz), 1.65-1.98 (4H, m), 2.21-2.44 (7H, m), 2.53-2.65 (2H, m), 6.62 (1H, s), 7.00 (1H, s), 7.35 (1H, s), 7.69 (0.6H, br s), 8.04 (0.4H, br s), 12.87 (1H, br s).

Example 122

Preparation of 2-fluoro-6'-(5-methyl-1H-pyrazol-4-yl)-1'H-spiro [cyclohexane-1,2'-thieno[3,2-d]pyrimidin]-4'(3'H)-one

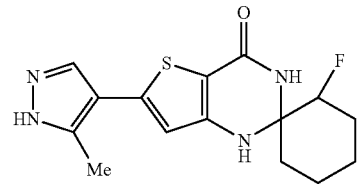 [SMILES: Cc1[nH]ncc1-c1cc2c(s1)C(=O)NC1(CCCCC1F)N2]

A mixture of 3-amino-5-(5-methyl-1H-pyrazol-4-yl) thiophene -2-carboxamide (66 mg, 0.30 mmol), 2-fluorocyclohexanone (0.10 mL, 0.90 mmol), CSA (7.0 mg, 0.030 mmol), MgSO$_4$ (72 mg, 0.60 mmol) and DMA (1 mL) was stirred at 80° C. for 2 h. Then, saturated aqueous NaHCO$_3$ and EtOAc were added to quench the reaction. The organic materials were extracted with EtOAc. The combined extracts were washed with water and brine, dried over Na$_2$SO$_4$. After removal of the solvent at reduced pressure, the residue was purified by column chromatography (Purif, silica gel 85:15 hexane/EtOAc to EtOAc), then crystallized from MeOH/EtOAc/hexane) to give the title compound (53 mg, 55%) as a pale yellow solid:
$^1$H NMR (300 MHz, DMSO-d$_6$) δ 1.22-1.99 (8H, m), 2.38 (3H, br s), 4.49-4.79 (1H, m), 6.60 (1H, d, J=2.1 Hz), 7.02-7.22 (1H, m), 7.48 (1H, d, J=3.0 Hz), 7.70 (0.6H, br s), 8.05 (0.4H, br s), 12.87 (1H, br s).

Example 123

Preparation of 1-(2-hydroxyethyl)-2,2-dimethyl-6-(5-methyl-1H-pyrazol-4-yl)-2,3-dihydrothieno[3,2-d]pyrimidin-4(1H)-one

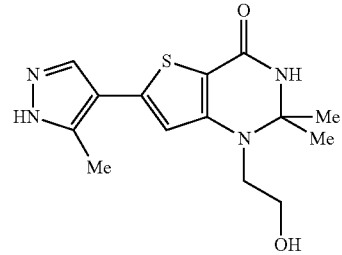 [SMILES: Cc1[nH]ncc1-c1cc2c(s1)C(=O)NC(C)(C)N2CCO]

Step 1

Preparation of 5-bromo-3-[(2-hydroxyethyl)amino] thiophene-2-carboxamide

A mixture of methyl 5-bromo-3-[(trifluoroacetyl)amino] thiophene-2-carboxylate (500 mg, 1.55 mmol), (2-bromoethoxy) (tert-butyl)dimethylsilane (0.99 mL, 4.66 mmol), cesium carbonate (1.52 g, 4.66 mmol), sodium iodide (24 mg, 0.16 mmol) and DMF (3 mL) was microwave-irradiated at 130° C. for 1.5 h. Then, water was added to quench the reaction. The organic materials were extracted with EtOAc. The combined extracts were washed with water and brine, dried over $Na_2SO_4$ and filtered. After removal of the solvent at reduced pressure, the residue was dissolved in MeOH (20 mL). To the solution were added potassium carbonate (1.86 g) and water (5 mL). The mixture was stirred at room temperature for 2 h. After removal of the solvent at reduced pressure, the organic materials were extracted with EtOAc. The combined extracts were washed with brine, dried over $Na_2SO_4$ and filtered. After removal of the solvent at reduced pressure, the residue was purified by column chromatography (Purif, silica gel, hexane to 80:20 hexane/EtOAc) to give a yellow oil. The oil was mixed with MeOH (4 mL), water (2 mL) and sodium hydroxide (147 mg, 3.68 mmol). The mixture was stirred at 70° C. for 6 h. Then, 6 M aqueous HCl (0.39 mL) was added to the mixture to adjust the pH to 10. After removal of the solvent at reduced pressure, the residue was mixed with ammonium chloride (1.32 g, 24.6 mmol), triethylamine (3.4 mL, 24.6 mmol) and DMF (6.0 mL). After stirring at room temperature for 5 min, 1-hydroxybenzotriazole (997 mg, 7.38 mmol) and 1-ethyl-3-(3-dimethylaminopropyl) carbodiimide hydrochloride (1.41 g, 7.38 mmol) were added. After stirring at room temperature for 18 h, water and EtOAc were added to quench the reaction. The organic materials were extracted with EtOAc. The combined extracts were washed with water and brine, dried over $Na_2SO_4$ sulfate and filtered. After removal of the solvent at reduced pressure, the residue was purified by column chromatography (Purif, silica gel, hexane to EtOAc) to give the title compound (108 mg, 26%) as a pale brown solid:

$^1$H NMR (300 MHz, CDCl$_3$) δ 3.15 (1H, s), 3.34-3.46 (2H, m), 3.70-3.85 (2H, m), 5.10 (2H, br s), 6.76 (1H, s), 7.58 (1H, br s).

Step 2

Preparation of 1-(2-hydroxyethyl)-2,2-dimethyl-6-(5-methyl-1H-pyrazol-4-yl)-2,3-dihydrothieno[3,2-d]pyrimidin-4(1H)-one A mixture of 5-bromo-3-[(2-hydroxyethyl)amino] thiophene-2-carboxamide (100 mg, 0.377 mmol), acetone (1.0 mL), PTSA (6.5 mg, 0.038 mmol) and acetic acid (1.0 mL) was stirred at 70° C. for 1 h. The mixture was poured into saturated aqueous NaHCO$_3$. The organic materials were extracted with EtOAc. The combined extracts were washed with brine, dried over Na$_2$SO$_4$ and filtered. After removal of the solvent at reduced pressure, a pale brown amorphous solid was obtained. A flask was charged with the amorphous, 1,2-dimethoxyethane (3.0 mL), tert-butyl 3-methyl-4-(4,4,5,5-tetramethyl-1,3,2-dioxaborolan-2-yl)-1H-pyrazole-1-carboxylate (349 mg, 1.13 mmol), sodium carbonate (113 mg, 1.89 mmol) and water (1.5 mL). The flask was purged with argon. Then, 1,1'-bis(diphenylphosphino)ferrocenepalladium (II) dichloride dichloromethane adduct (31 mg, 0.038 mmol) was added to the mixture. The flask was purged with argon. After stirring at 100° C. for 1 h, 8 M aqueous NaOH (1.0 mL) was added. After stirring at 100° C. for 1.5 h, the organic materials were extracted with EtOAc/THF. The combined extracts were washed with brine, dried over Na$_2$SO$_4$ and filtered. After removal of the solvent at reduced pressure, the residue was purified by column chromatography (Purif, silica gel, 90:10 hexane/EtOAc to EtOAc then to 90:10 EtOAc/MeOH), then crystallized from MeOH/EtOAc/hexane) to give the title compound (40 mg, 35%) as a pale brown solid:

$^1$H NMR (300 MHz, DMSO-d$_6$) δ 1.43 (6H, s), 2.29-2.45 (3H, m), 3.24-3.40 (2H, m), 3.45-3.62 (2H, m), 4.80 (1H, t, J=5.6 Hz), 6.79 (1H, s), 7.40 (1H, s), 7.75 (0.6H, br s), 8.09 (0.4H, br s), 12.55-13.06 (1H, m).

Example 124

Preparation of 1'-(2,2-difluoroethyl)-6'-(5-methyl-1H-pyrazol-4-yl)-1'H-spiro[cyclopentane-1,2'-thieno[3,2-d]pyrimidin]-4'(3'H)-one

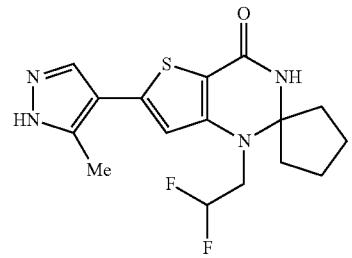 [SMILES: Cc1[nH]ncc1-c1cc2c(s1)C(=O)NC1(CCCC1)N2CC(F)F]

A mixture of 5-bromo-3-[(2,2-difluoroethyl)amino] thiophene-2-carboxamide (150 mg, 0.53 mmol), cyclopentanone (2.0 mL), CSA (12 mg, 0.053 mmol), MgSO$_4$ (100 mg) and DMA (1 mL) was stirred at 110° C. for 20 h. The mixture was poured into saturated aqueous NaHCO$_3$. The organic materials were extracted with EtOAc. The combined extracts were washed with water and brine, dried over Na$_2$SO$_4$ and filtered. After removal of the solvent at reduced pressure, the residue was purified by column chromatography (Purif, silica gel, hexane to 80:20 hexane/EtOAc) to give a brown crystalline solid. A flask was charged with this solid, 1,2-dimethoxyethane (4 mL), tert-butyl 3-methyl-4-(4,4,5,5-tetramethyl-1,3,2-dioxaborolan-2-yl)-1H-pyrazole-1-carboxylate (370 mg, 1.20 mmol), sodium carbonate (120 mg, 2.00 mmol) and water (2 mL). The flask was purged with argon. Then, 1,1'-bis(diphenylphosphino) ferrocenepalladium (II) dichloride dichloromethane adduct (33 mg, 0.040 mmol) was added to the mixture. The flask was purged with argon. After stirring at 100° C. for 2 h, 8 M aqueous NaOH (1.0 mL) was added. After stirring at 100° C. for 30 min, organic materials were extracted with EtOAc. The combined extracts were washed with brine, dried over Na$_2$SO$_4$ and filtered. After removal of the solvent at reduced pressure, the residue was purified by column chromatography (Purif, silica gel, 80:20 hexane/EtOAc to EtOAc), then crystallized from heptanes/EtOAc to give the title compound (29 mg, 16%) as a yellow solid:

$^1$H NMR (300 MHz, DMSO-d$_6$) δ 1.54-2.06 (8H, m), 2.41 (3H, br s), 3.63-3.84 (2H, m), 5.91-6.41 (1H, m), 6.93 (1H, s), 7.68-7.89 (1.6H, m), 8.11 (0.4H, br s), 12.88 (1H, br s).

Example 125

Preparation of benzyl [6'-(5-methyl-1H-pyrazol-4-yl)-4'-oxo-3',4'-dihydro-1'H-spiro[cyclohexane-1,2'-thieno[3,2-d]pyrimidin]-4-yl]carbamate

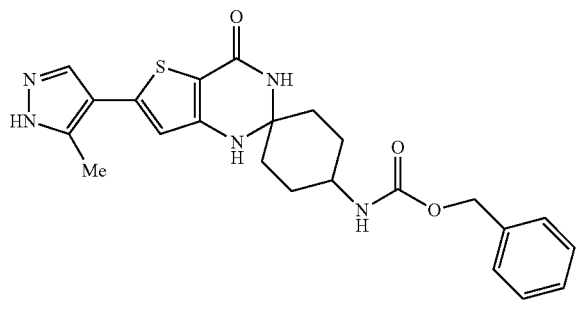 [SMILES: Cc1[nH]ncc1-c1cc2c(s1)C(=O)NC1(CCC(NC(=O)OCc3ccccc3)CC1)N2]

Step 1

Preparation of 3-amino-5-(5-methyl-1H-pyrazol-4-yl)thiophene-2-carboxamide

A mixture of 2,2-dimethyl-6-(5-methyl-1H-pyrazol-4-yl)-2,3-dihydrothieno[3,2-d]pyrimidin-4(1H)-one (660 mg, 2.52 mmol), 1 M HCl (8.81 mL) and MeOH (27 mL) was stirred at 50° C. for 2 h. Then, the reaction mixture was poured into excess saturated aqueous NaHCO$_3$ and extracted with EtOAc/THF, and the extract was dried over MgSO$_4$, filtered and concentrated under reduced pressure to afford the title compound (531 mg, 95%) as a yellow solid.

Step 2

Preparation of benzyl [6'-(5-methyl-1H-pyrazol-4-yl)-4'-oxo-3',4'-dihydro-1'H-spiro[cyclohexane-1,2'-thieno[3,2-d]pyrimidin]-4-yl]carbamate A mixture of 3-amino-5-(3-methyl-1H-pyrazol-4-yl)thiophene-2-carboxamide (111 mg, 0.50 mmol), benzyl (4-oxocyclohexyl)carbamate (495 mg, 2.00 mmol), MgSO$_4$ (120 mg, 1.00 mmol), CSA (11.61 mg, 0.050 mmol) and DMA (3 mL) was stirred at 100° C. for 1 h. The mixture was poured into saturated aqueous NaHCO$_3$ and extracted with EtOAc, and the extract was dried over MgSO$_4$, filtered and concentrated under reduced pressure. The residue was purified by column chromatography (Purif, silica gel, hexane to EtOAc then to 80:20 EtOAc/MeOH). The obtained residue was triturated with 2-propanol-EtOAc, and the precipitate was collected by filtration to afford the title compound (58.4 mg, 26%, a mixture of 4:1 cis/trans isomers, absolute structure not determined) as a yellow solid:
$^1$H NMR (300 MHz, DMSO-d$_6$) δ 1.51-1.73 (6H, m), 1.99-2.09 (2H, m), 2.33-2.38 (3H, m), 3.24 (1H, m), 5.01 (2H, s), 6.56 (0.2H, s), 6.62 (0.8H, s), 6.93 (0.8H, br s), 6.97 (0.2H, s), 7.21-7.38 (7H, m), 7.69 (0.67H, br s), 8.05 (0.33H, br s), 12.77 (0.33H, br s), 12.87 (0.67H, br s).

The filtrate was concentrated under reduced pressure to give yellow oil (about 120 mg). This residue was dissolved with small amount of 2-propanol and poured into a stirred hexane (50 mL). The precipitate was collected by filtration to afford the title compound (94 mg, 42%, a mixture of cis/trans isomers with the ratio as 1:1) as a yellow solid:
$^1$H NMR (300 MHz, DMSO-d$_6$) δ 1.51-1.73 (6H, m), 1.99-2.09 (2H, m), 2.33-2.38 (3H, m), 3.24 (1H, m), 5.01 (2H, s), 6.56 (0.5H, s), 6.62 (0.5H, s), 6.93 (0.5H, br s), 6.97 (0.5H, s), 7.21-7.38 (7H, m), 7.69 (0.6H, br s), 8.05 (0.4H, br s), 12.77 (0.4H, br s), 12.87 (0.6H, br s).

Example 126

Preparation of 4-amino-6'-(5-methyl-1H-pyrazol-4-yl)-1'H-spiro[cyclohexane-1,2'-thieno[3,2-d]pyrimidin]-4'(3'H)-one

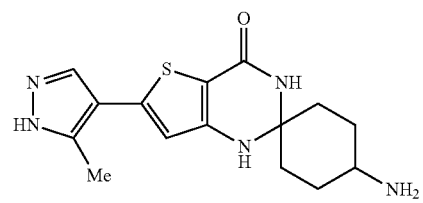 [SMILES: Cc1[nH]ncc1-c1cc2c(s1)C(=O)NC1(CCC(N)CC1)N2]

A mixture of benzyl [6'-(5-methyl-1H-pyrazol-4-yl)-4'-oxo-3',4'-dihydro-1'H-spiro[cyclohexane-1,2'-thieno[3,2-d]pyrimidin]-4-yl]carbamate (the isomer ratio was 1:1, 78 mg, 0.173 mmol), 10% Pd/C (20 mg, 50% wet) and MeOH (5 mL) was stirred for 1 h at room temperature under H$_2$ atmosphere. Then, 20% palladium hydroxide on carbon (200 mg, 50% wet) was added. After 1 h, the mixture was filtered through a pad of celite, and the celite was washed with MeOH well. The filtrate was concentrated under reduced pressure, and the residue was triturated with MeOH/EtOAc. The precipitate was collected by filtration to afford the title compound (35.3 mg, 64%, a mixture of 1:1 cis/trans isomers) as a white solid:
$^1$H NMR (300 MHz, DMSO-d$_6$) δ 1.29-1.68 (8H, m), 1.99-2.07 (2H, m), 2.32-2.36 (3H, m), 2.55-2.73 (1H, m), 6.55 (0.5H, s), 6.63 (0.5H, s), 6.92 (0.5H, br s), 7.01 (0.5H, br s), 7.24-7.25 (1H, m), 7.81 (0.9H, m), 8.10 (0.1H, m), 12.85 (1H, m).

Example 127

Preparation of 2,2-dimethyl-6-(5-methyl-1H-pyrazol-4-yl)-1-(pyridin-2-ylmethyl)-2,3-dihydrothieno[3,2-d]pyrimidin-4(1H)-one

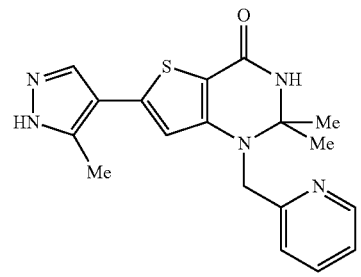 [SMILES: Cc1[nH]ncc1-c1cc2c(s1)C(=O)NC(C)(C)N2Cc1ccccn1]

Step 1

Preparation of methyl 5-bromo-3-[(pyridin-2-ylmethyl)amino]thiophene-2-carboxylate A mixture of methyl 5-bromo-3-[(trifluoroacetyl)amino]thiophene-2-carboxylate (500 mg, 1.51 mmol), 2-(bromomethyl)pyridine hydrobromide (457 mg, 1.81 mmol), cesium carbonate (1.72 g, 5.29 mmol) and DMA (15 mL) was stirred at 80° C. for 2 h. Then, water was added to quench the reaction. The organic materials were extracted with EtOAc. The combined extracts were washed with water and brine, dried over Na$_2$SO$_4$ and filtered. After removal of the solvent at reduced pressure, the residue was dissolved in MeOH (5 mL). To the solution were added potassium carbonate (500 mg) and water (2.5 mL). The mixture was stirred at room temperature for 1 h. After removal of the solvent at reduced pressure, the organic materials were extracted with EtOAc. The combined extracts were washed with brine, dried over Na$_2$SO$_4$ and filtered. After removal of the solvent at reduced pressure, the residue was purified by column chromatography (Purif, silica gel, hexane to 70:30 hexane/EtOAc) to give the title compound (336 mg, 68%) as a yellow solid:

$^1$H NMR (300 MHz, CDCl$_3$) δ 3.82 (3H, s), 4.57 (2H, d, J=6.0 Hz), 6.60 (1H, s), 7.16-7.24 (1H, m), 7.30 (1H, d, J=7.9 Hz), 7.56 (1H, br s), 7.63-7.73 (1H, m), 8.44-8.72 (1H, m).

Step 2

Preparation of 5-bromo-3-[(pyridin-2-ylmethyl)amino]thiophene-2-carboxamide

To a solution of methyl 5-bromo-3-[(pyridin-2-ylmethyl)amino]thiophene-2-carboxylate (336 mg, 1.03 mmol) in MeOH (3 mL) and ethanol (10 mL) was added a solution of sodium hydroxide (124 mg, 3.09 mmol) in water (1.5 mL). After stirring at 100° C. for 5 h, 6 M aqueous HCl (0.33 mL) was added to the mixture to adjust the pH to 10. After removal of the solvent at reduced pressure, the residue was diluted with DMF (5 mL). Then, triethylamine (2.9 mL, 21 mmol) and ammonium chloride (1.1 g, 21 mmol) were added. After stirring at room temperature for 5 min, 1-ethyl-3-(3-dimethylaminopropyl) carbodiimide hydrochloride (1.2 g, 6.2 mmol) and 1-hydroxybenzotriazole (835 mg, 6.2 mmol) were added to the mixture, and stirring was continued for 18 h. Then, water was added to quench the reaction. The organic materials were extracted with EtOAc. The combined extracts were washed with water and brine, dried over Na$_2$SO$_4$ and filtered. After removal of the solvent at reduced pressure, the residue was purified by column chromatography (Purif, silica gel, 95:5 hexane/EtOAc to EtOAc) to give the title compound (160 mg, 50%) as a yellow solid:

$^1$H NMR (300 MHz, DMSO-d$_6$) δ 4.52 (2H, d, J=6.2 Hz), 6.97 (1H, s), 7.00 (2H, br s), 7.24-7.35 (2H, m), 7.73-7.83 (1H, m), 8.13 (1H, t, J=6.2 Hz), 8.45-8.64 (1H, m).

Step 3

Preparation of 2,2-dimethyl-6-(5-methyl-1H-pyrazol-4-yl)-1-(pyridin-2-ylmethyl)-2,3-dihydrothieno[3,2-d]pyrimidin-4(1H)-one A mixture of 5-bromo-3-[(pyridin-2-ylmethyl)amino]thiophene-2-carboxamide (160 mg, 0.51 mmol), 2,2-dimethoxypropane (1.5 mL), CSA (12 mg, 0.051 mmol), MgSO$_4$ (150 mg) and DMA (1.5 mL) was microwave-irradiated at 120° C. for 1 h. The mixture was poured into saturated aqueous NaHCO$_3$. The organic materials were extracted with EtOAc. The combined extracts were washed with water and brine, dried over Na$_2$SO$_4$ and filtered. After removal of the solvent at reduced pressure, a brown solid was obtained. A flask was charged with this solid, 1,2-dimethoxyethane (5 mL), tert-butyl 3-methyl-4-(4,4,5,5-tetramethyl-1,3,2-dioxaborolan-2-yl)-1H-pyrazole-1-carboxylate (472 mg, 1.53 mmol), sodium carbonate (153 mg, 2.55 mmol) and water (2.5 mL). The flask was purged with argon. Then, 1,1'-bis(diphenylphosphino)ferrocenepalladium (II) dichloride dichloromethane adduct (42 mg, 0.051 mmol) was added to the mixture. The flask was purged with argon. After stirring at 100° C. for 0.5 h, 8 M aqueous NaOH (1.0 mL) was added. After stirring at 100° C. for 1 h, the organic materials were extracted with EtOAc/THF. The combined extracts were washed with brine, dried over Na$_2$SO$_4$ and filtered. After removal of the solvent at reduced pressure, the residue was purified by column chromatography (Purif, silica gel, 80:20 hexane/EtOAc to EtOAc then to 90:10 EtOAc/MeOH), then crystallized from MeOH/EtOAc) to give the title compound (59 mg, 33%) as a pale yellow solid:

$^1$H NMR (300 MHz, DMSO-d$_6$) δ 1.44 (6H, s), 2.31 (3H, br s), 4.64 (2H, s), 6.72 (1H, br s), 7.23-7.33 (1H, m), 7.39 (1H, d, J=7.7 Hz), 7.56 (1H, s), 7.67 (0.6H, br s), 7.73-7.83 (1H, m), 8.03 (0.4H, br s), 8.50-8.61 (1H, m), 12.59-13.16 (1H, m).

Example 128

Preparation of 2,2-dimethyl-6-(5-methyl-1H-pyrazol-4-yl)-1-(pyridin-3-ylmethyl)-2,3-dihydrothieno[3,2-d]pyrimidin-4(1H)-one

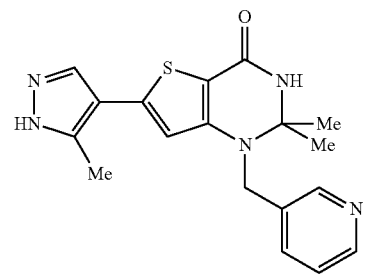 [SMILES: Cc1[nH]ncc1-c1cc2c(s1)C(=O)NC(C)(C)N2Cc1cccnc1]

Step 1

Preparation of methyl 5-bromo-3-[(pyridin-3-ylmethyl)amino]thiophene-2-carboxylate A mixture of methyl 5-bromo-3-[(trifluoroacetyl)amino]thiophene-2-carboxylate (100 mg, 1.51 mmol), 3-(bromomethyl)pyridine hydrobromide (457 mg, 1.81 mmol), cesium carbonate (1.72 g, 5.29 mmol) and DMA (15 mL) was stirred at 80° C. for 2 h. Then, water was added to quench the reaction. The organic materials were extracted with EtOAc. The combined extracts were washed with water and brine, dried over Na$_2$SO$_4$ and filtered. After removal of the solvent at reduced pressure, the residue was dissolved in MeOH (5 mL). To the solution were added potassium carbonate (500 mg) and water (2.5 mL). The mixture was stirred at room temperature for 2 h. After removal of the solvent at reduced pressure, the organic materials were extracted with EtOAc. The combined extracts were washed with brine, dried over Na$_2$SO$_4$ and filtered. After removal of the solvent at reduced pressure, the residue was purified by column chromatography (Purif, silica gel, hexane to 50:50 hexane/EtOAc) to give the title compound (260 mg, 53%) as a yellow solid:

$^1$H NMR (300 MHz, CDCl$_3$) δ 3.81 (3H, s), 4.47 (2H, d, J=6.2 Hz), 6.56 (1H, s), 7.27-7.33 (2H, m), 7.58-7.71 (1H, m), 8.49-8.65 (2H, m).

Step 2

Preparation of 5-bromo-3-[(pyridin-3-ylmethyl)amino]thiophene-2-carboxamide

To a solution of methyl 5-bromo-3-[(pyridin-3-ylmethyl)amino]thiophene-2-carboxylate (260 mg, 0.795 mmol) in MeOH (3 mL) was added a solution of sodium hydroxide (96 mg, 2.39 mmol) in water (1.5 mL). After stirring at 80° C. for 5 h, 6 M aqueous HCl (0.25 mL) was added to the mixture to adjust the pH to 10. After removal of the solvent at reduced pressure, the residue was suspended with DMF (5 mL). Then, triethylamine (2.2 mL, 16 mmol) and ammonium chloride (850 mg, 16 mmol) were added. After stirring at room temperature for 5 min, 1-ethyl-3-(3-dimethylaminopropyl)carbodiimide hydrochloride (914 mg, 4.8 mmol) and 1-hydroxybenzotriazole (645 mg, 4.8 mmol) were added to the mixture, and the stirring was continued for 18 h. Then, water and EtOAc were added to quench the reaction. The organic materials were extracted with EtOAc. The combined extracts were washed with water and brine, dried over $Na_2SO_4$ and filtered. After removal of the solvent at reduced pressure, the residue was purified by column chromatography (Purif, silica gel, 90:10 hexane/EtOAc to EtOAc) to give the title compound (175 mg, 71%) as a yellow solid:

$^1$H NMR (300 MHz, DMSO-$d_6$) δ 4.47 (2H, d, J=6.6 Hz), 6.96-7.12 (3H, m), 7.33-7.41 (1H, m), 7.70 (1H, d, J=7.6 Hz), 8.00 (1H, t, J=6.6 Hz), 8.43-8.49 (1H, m), 8.54 (1H, s).

Step 3

Preparation of 2,2-dimethyl-6-(5-methyl-1H-pyrazol-4-yl)-1-(pyridin-3-ylmethyl)-2,3-dihydrothieno[3,2-d]pyrimidin-4(1H)-one A mixture of 5-bromo-3-[(pyridin-3-ylmethyl)amino]thiophene-2-carboxamide (175 mg, 0.56 mmol), 2,2-dimethoxypropane (1.5 mL), CSA (13 mg, 0.056 mmol), $MgSO_4$ (150 mg) and DMA (1.5 mL) was microwave-irradiated at 120° C. for 1 h. The mixture was poured into saturated aqueous $NaHCO_3$. The organic materials were extracted with EtOAc. The combined extracts were washed with water and brine, dried over $Na_2SO_4$ and filtered. After removal of the solvent at reduced pressure, a brown solid was obtained. A flask was charged with this solid, 1,2-dimethoxyethane (5.0 mL), tert-butyl 3-methyl-4-(4,4,5,5-tetramethyl-1,3,2-dioxaborolan-2-yl)-1H-pyrazole-1-carboxylate (518 mg, 1.68 mmol), sodium carbonate (168 mg, 2.80 mmol) and water (2.5 mL). The flask was purged with argon. Then, 1,1'-bis(diphenylphosphino)ferrocenepalladium (II) dichloride dichloromethane adduct (41 mg, 0.056 mmol) was added to the mixture. The flask was purged with argon. After stirring at 100° C. for 1 h, 8 M aqueous NaOH (1.0 mL) was added. After stirring at 100° C. for 1 h, the organic materials were extracted with EtOAc/THF. The combined extracts were washed with brine, dried over $Na_2SO_4$ and filtered. After removal of the solvent at reduced pressure, the residue was purified by column chromatography (Purif, silica gel, 80:20 hexane/EtOAc to EtOAc then to 90:10 EtOAc/MeOH), then crystallized from MeOH/EtOAc) to give the title compound (64 mg, 32%, 3 steps) as a pale yellow solid:

$^1$H NMR (300 MHz, DMSO-$d_6$) δ 1.44 (6H, s), 2.31 (3H, br s), 4.63 (2H, s), 6.72 (1H, br s), 7.33-7.43 (1H, m), 7.58 (1H, s), 7.63-7.78 (1.6H, m), 8.04 (0.4H, br s), 8.41-8.51 (1H, m), 8.58 (1H, d, J=2.1 Hz), 12.85 (1H, br s).

Example 129

Preparation of 2,2-dimethyl-6-(5-methyl-1H-pyrazol-4-yl)-1-(pyridin-4-ylmethyl)-2,3-dihydrothieno[3,2-d]pyrimidin-4(1H)-one

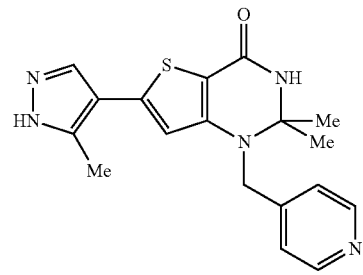 [SMILES: Cc1[nH]ncc1-c1cc2c(s1)C(=O)NC(C)(C)N2Cc1ccncc1]

Step 1

Preparation of methyl 5-bromo-3-[(pyridin-4-ylmethyl)amino]thiophene-2-carboxylate A mixture of methyl 5-bromo-3-[(trifluoroacetyl)amino]thiophene-2-carboxylate (500 mg, 1.51 mmol), 4-(bromomethyl)pyridine hydrobromide (457 mg, 1.81 mmol), cesium carbonate (1.72 g, 5.29 mmol) and DMA (15 mL) was stirred at 80° C. for 2 h. Then, water was added to quench the reaction. The organic materials were extracted with EtOAc. The combined extracts were washed with water and brine, dried over $Na_2SO_4$ and filtered. After removal of the solvent at reduced pressure, the residue was dissolved in MeOH (5 mL). To the solution were added potassium carbonate (500 mg) and water (2.5 mL). The mixture was stirred at room temperature for 2 h. After removal of the solvent at reduced pressure, the organic materials were extracted with EtOAc. The combined extracts were washed with brine, dried over $Na_2SO_4$ and filtered. After removal of the solvent at reduced pressure, the residue was purified by column chromatography (Purif, silica gel, hexane to 50:50 hexane/EtOAc) to give the title compound (238 mg, 48%) as a yellow solid:

$^1$H NMR (300 MHz, $CDCl_3$) δ 3.82 (3H, s), 4.47 (2H, d, J=6.2 Hz), 6.46 (1H, s), 7.23 (2H, d, J=5.9 Hz), 7.34 (1H, br s), 8.53-8.63 (2H, m).

Step 2

Preparation of 5-bromo-3-[(pyridin-4-ylmethyl)amino]thiophene-2-carboxamide

To a solution of methyl 5-bromo-3-[(pyridin-4-ylmethyl)amino]thiophene-2-carboxylate (238 mg, 0.727 mmol) in MeOH (2 mL) and ethanol (10 mL) was added a solution of sodium hydroxide (87 mg, 2.18 mmol) in water (1 mL). After stirring at 100° C. for 5 h, 6 M aqueous HCl (0.23 mL) was added to the mixture to adjust the pH to 10. After removal of the solvent at reduced pressure, the residue was diluted with DMF (4 mL). Then, triethylamine (2.0 mL, 15 mmol) and ammonium chloride (777 mg, 15 mmol) were added. After stirring at room temperature for 5 min, 1-ethyl-3-(3-dimethylaminopropyl) carbodiimide hydrochloride (836 mg, 4.4 mmol) and 1-hydroxybenzotriazole (589 mg, 4.4 mmol) were added to the mixture, and stirring was continued for 18 h. Then, water and EtOAc were added to quench the reaction.

The organic materials were extracted with EtOAc. The combined extracts were washed with water and brine, dried over $Na_2SO_4$ and filtered. After removal of the solvent at reduced pressure, the residue was purified by column chromatography (Purif, silica gel, 90:10 hexane/EtOAc to EtOAc) to give the title compound (167 mg, 74%) as a brown solid:

$^1$H NMR (300 MHz, DMSO-$d_6$) δ 4.49 (2H, d, J=6.8 Hz), 6.90 (1H, s), 7.06 (2H, br s), 7.27 (2H, d, J=6.0 Hz), 8.02-8.12 (1H, m), 8.50 (2H, d, J=6.0 Hz).

Step 3

Preparation of 2,2-dimethyl-6-(5-methyl-1H-pyrazol-4-yl)-1-(pyridin-4-ylmethyl)-2,3-dihydrothieno[3,2-d]pyrimidin-4(1H)-one A mixture of 5-bromo-3-[(pyridin-4-ylmethyl)amino]thiophene-2-carboxamide (167 mg, 0.53 mmol), 2,2-dimethoxypropane (1.5 mL), CSA (12 mg, 0.053 mmol), $MgSO_4$ (150 mg) and DMA (1.5 mL) was microwave-irradiated at 120° C. for 1 h. The mixture was poured into saturated aqueous $NaHCO_3$. The organic materials were extracted with EtOAc. The combined extracts were washed with water and brine, dried over $Na_2SO_4$ and filtered. After removal of the solvent at reduced pressure, a brown solid was obtained. A flask was charged with the solid, 1,2-dimethoxyethane (5 mL), tert-butyl 3-methyl-4-(4,4,5,5-tetramethyl-1,3,2-dioxaborolan-2-yl)-1H-pyrazole-1-carboxylate (490 mg, 1.59 mmol), sodium carbonate (159 mg, 2.65 mmol) and water (2.5 mL). The flask was purged with argon. Then, 1,1'-bis(diphenylphosphino)ferrocenepalladium (II) dichloride dichloromethane adduct (43 mg, 0.053 mmol) was added to the mixture. The flask was purged with argon again. After stirring at 100° C. for 0.5 h, 8 M aqueous NaOH (1.0 mL) was added. After stirring at 100° C. for 1 h, the organic materials were extracted with EtOAc/THF. The combined extracts were washed with brine, dried over $Na_2SO_4$ and filtered. After removal of the solvent at reduced pressure, the residue was purified by column chromatography (Purif, silica gel, 80:20 hexane/EtOAc to EtOAc then to 90:10 EtOAc/MeOH), then crystallized from MeOH/EtOAc) to give the title compound (38 mg, 20%) as a pale yellow solid:

$^1$H NMR (300 MHz, DMSO-$d_6$) δ 1.43 (6H, s), 2.16-2.38 (3H, m), 4.62 (2H, br s), 6.56-6.71 (1H, m), 7.34 (2H, d, J=5.9 Hz), 7.60 (1H, s), 7.66 (0.6H, br s), 8.02 (0.4H, br s), 8.52 (2H, d, J=5.9 Hz), 12.71-12.93 (1H, m).

Example 130

Preparation of ethyl 6'-(5-methyl-1H-pyrazol-4-yl)-4'-oxo-3',4'-dihydro-1'H-spiro[cyclohexane-1,2'-thieno[3,2-d]pyrimidine]-4-carboxylate

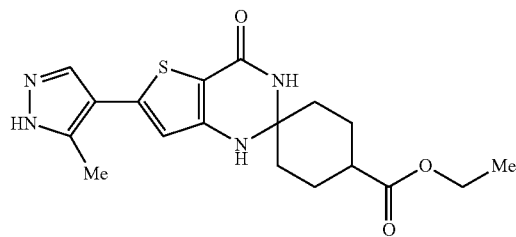 [SMILES: CCOC(=O)C1CCC2(CC1)NC(=O)c1sc(-c3cn[nH]c3C)cc1N2]

A mixture of 3-amino-5-(5-methyl-1H-pyrazol-4-yl)thiophene-2-carboxamide (0.111 g, 0.50 mmol), ethyl 4-oxocyclohexanecarboxylate (0.34 g, 2.00 mmol), $MgSO_4$ (0.120 g, 1.00 mmol), CSA (0.012 g, 0.05 mmol) and DMA (3 mL) was stirred at 100° C. for 1 h. The mixture was poured into saturated aqueous $NaHCO_3$ and extracted with EtOAc, and the extract was dried over $MgSO_4$, filtered and concentrated under reduced pressure. The residue was purified by column chromatography (Purif, silica gel, hexane to EtOAc then to 80:20 EtOAc/MeOH). The obtained residue was triturated with EtOAc, and the precipitate was collected by filtration to afford the title compound (96 mg, 51%, a mixture of 3:2 cis/trans isomers, absolute structure not determined) as yellow solid:

$^1$H NMR (300 MHz, DMSO-$d_6$) δ 1.16-1.22 (3H, m), 1.51-2.39 (12H, m), 4.03-4.11 (2H, m), 6.56 (0.4H, s), 6.63 (0.6H, s), 7.00 (0.4H, br s), 7.09 (0.6H, br s), 7.33 (0.6H, br s), 7.42 (0.4H, br s), 7.69 (0.6H, m), 8.04 (0.4H, m), 12.78 (0.4H, br s), 12.87 (0.6H, br s).

Example 131

Preparation of 6'-(5-methyl-1H-pyrazol-4-yl)-4-phenyl-1'H-spiro[cyclohexane-1,2'-thieno[3,2-d]pyrimidin]-4'(3'H)-one

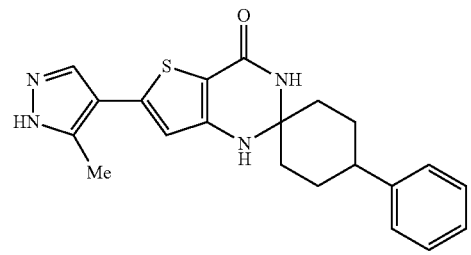 [SMILES: Cc1[nH]ncc1-c1cc2c(s1)C(=O)NC1(CCC(c3ccccc3)CC1)N2]

A mixture of 3-amino-5-(5-methyl-1H-pyrazol-4-yl)thiophene-2-carboxamide (111 mg, 0.50 mmol), 4-phenylcyclohexanone (261 mg, 1.50 mmol), $MgSO_4$ (120 mg, 1.00 mmol), CSA (11.61 mg, 0.050 mmol) and DMA (3 mL) was stirred at 80° C. for 1 h. The mixture was poured into saturated aqueous $NaHCO_3$ and 2:1 EtOAc/THF. The precipitate was collected by filtration and washed with water and EtOAc to give the title compound (28.7 mg, 15%, single isomer on cyclohexane, absolute structure not determined) as gray solid:

$^1$H NMR (300 MHz, DMSO-$d_6$) δ 1.48-1.64 (4H, m), 1.90-2.02 (2H, m), 2.22-2.27 (2H, m), 2.38 (3H, m), 2.45-2.55 (1H, m), 6.56 (1H, s), 6.98 (1H, br s), 7.15-7.37 (5H, m), 7.68-7.73 (1.6H, m), 8.07 (0.4H, br s), 12.78 (0.4H, br s), 12.87 (0.6H, br s).

From the filtrate, the organic layer was collected, dried over $MgSO_4$, filtered and concentrated under reduced pressure. The residue was purified by column chromatography (Purif, silica gel, hexane to EtOAc then to 80:20 EtOAc/MeOH). The residue was triturated with EtOAc, and the precipitate was collected by filtration to afford the title compound (70 mg, 37%, a mixture of 85:15 cis/trans isomers, absolute structure not determined, major isomer different from above one) as a yellow solid:

$^1$H NMR (300 MHz, DMSO-$d_6$) δ 1.54-1.68 (4H, m), 1.73-1.88 (2H, m), 2.18-2.27 (2H, m), 2.35-2.41 (3H, m), 2.45-2.53 (1H, m), 6.56 (0.15H, s), 6.67 (0.85H, s), 6.98 (0.15H, br s), 7.16-7.23 (1.85H, br s), 7.27-7.37 (5H, m), 7.68 (0.7H, br s), 8.04 (0.3H, br s), 12.79 (0.3H, br s), 12.87 (0.7H, br s).

Example 132

Preparation of tert-butyl [6'-(5-methyl-1H-pyrazol-4-yl)-4'-oxo-3',4'-dihydro-1'H-spiro[cyclohexane-1,2'-thieno[3,2-d]pyrimidin]-4-yl]carbamate

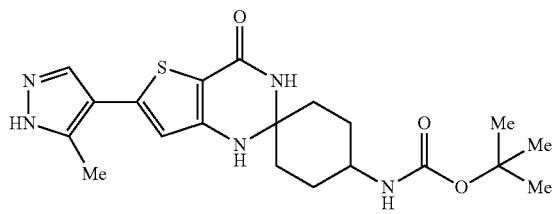 [SMILES: Cc1[nH]ncc1-c1cc2c(s1)C(=O)NC1(CCC(NC(=O)OC(C)(C)C)CC1)N2]

A mixture of 3-amino-5-(5-methyl-1H-pyrazol-4-yl)thiophene-2-carboxamide (111 mg, 0.50 mmol), tert-butyl (4-oxocyclohexyl)carbamate (320 mg, 1.50 mmol), MgSO$_4$ (120 mg, 1.00 mmol), CSA (11.6 mg, 0.05 mmol) and DMA (3 mL) was stirred at 100° C. for 1 h. The mixture was poured into saturated aqueous NaHCO$_3$ and extracted with EtOAc, and the extract was dried over MgSO$_4$, filtered and concentrated under reduced pressure. The residue was purified by column chromatography (Purif, silica gel, hexane to EtOAc then to 80:20 EtOAc/MeOH). The residue obtained was dissolved with small amount of MeOH/EtOAc and added dropwise to a stirred solution of hexane (100 mL). The precipitate was collected by filtration to afford the title compound (122 mg, 58%, a mixture of 11:9 cis/trans isomers, absolute structure not determined) as yellow solid:
$^1$H NMR (300 MHz, DMSO-d$_6$) δ 1.38-1.59 (15H, m), 1.99-2.09 (2H, m), 2.32-2.39 (3H, m), 3.15-3.30 (1H, m), 6.56 (0.45H, s), 6.62 (0.55H, s), 6.67-6.76 (1H, m), 6.89 (0.55H, br s), 6.96 (0.45H, br s), 7.21 (0.45H, br s), 7.28 (0.55H, br s), 7.70 (0.67H, br s), 8.05 (0.33H, br s), 12.77-12.87 (1H, m).

Example 133

Preparation of 6'-(5-methyl-1H-pyrazol-4-yl)-1'H,3H-spiro [cyclopentane-1,2'-thieno[3,2-d]pyrimidine]-3,4'(3'H)-dione

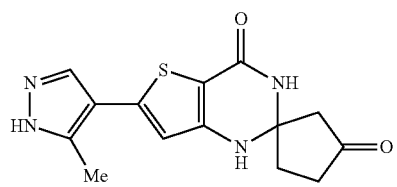 [SMILES: Cc1[nH]ncc1-c1cc2c(s1)C(=O)NC1(CCC(=O)C1)N2]

A mixture of 3-amino-5-(5-methyl-1H-pyrazol-4-yl)thiophene-2-carboxamide (111 mg, 0.50 mmol), 1,3-cyclopentanedione (490 mg, 5.00 mmol), MgSO$_4$ (120 mg, 1.00 mmol), CSA (11.6 mg, 0.050 mmol) and DMA (3 mL) was stirred at 80° C. for 1 h. The mixture was poured into saturated aqueous NaHCO$_3$ and 2:1 EtOAc/THF. The organic layer was collected, dried over MgSO$_4$, filtered and concentrated under reduced pressure. The residue was purified by column chromatography (Purif, silica gel, hexane to EtOAc then to 70:30 EtOAc/MeOH). The obtained solid was triturated with EtOAc and collected by filtration to afford the title compound (21.2 mg, 14%) as a beige solid:
$^1$H NMR (300 MHz, DMSO-d$_6$) δ 2.25-2.29 (2H, m), 2.42 (3H, m), 2.76-2.80 (2H, m), 5.66 (1H, s), 7.32 (1H, s), 7.56 (2H, br s), 7.94 (0.6H, br s), 8.35 (0.4H, br s), 10.66 (1H, s), 12.90 (1H, br s).

Example 134

Preparation of 4,4-difluoro-6'-(5-methyl-1H-pyrazol-4-yl)-1'H-spiro[cyclohexane-1,2'-thieno[3,2-d]pyrimidin]-4'(3'H)-one

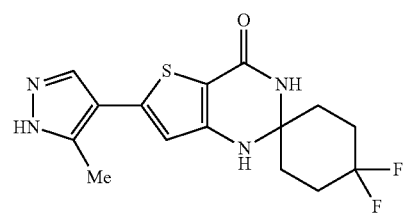 [SMILES: Cc1[nH]ncc1-c1cc2c(s1)C(=O)NC1(CCC(F)(F)CC1)N2]

A mixture of 3-amino-5-(5-methyl-1H-pyrazol-4-yl)thiophene-2-carboxamide (100 mg, 0.45 mmol), 4,4-difluorocyclohexanone (181 mg, 1.35 mmol), CSA (10 mg, 0.045 mmol), MgSO$_4$ (108 mg, 0.90 mmol) and DMA (1 mL) was stirred at 80° C. for 2 h. The mixture was poured into saturated aqueous NaHCO$_3$. The organic materials were extracted with EtOAc. The combined extracts were washed with water and brine, dried over Na$_2$SO$_4$ and filtered. After removal of the solvent at reduced pressure, the residue was purified by column chromatography (Purif, silica gel, 90:10 hexane/EtOAc to EtOAc), then crystallized from MeOH/EtOAc to give the title compound (59 mg, 39%) as a pale yellow solid:
$^1$H NMR (300 MHz, DMSO-d$_6$) δ 1.78-2.20 (8H, m), 2.39 (3H, br s), 6.60 (1H, s), 7.20 (1H, s), 7.58 (1H, s), 7.71 (0.6H, br s), 8.07 (0.4H, br s), 12.88 (1H, br s).

Example 135

Preparation of 1-benzyl-6'-(5-methyl-1H-pyrazol-4-yl)-1'H-spiro [piperidine-4,2'-thieno[3,2-d]pyrimidin]-4'(3'H)-one

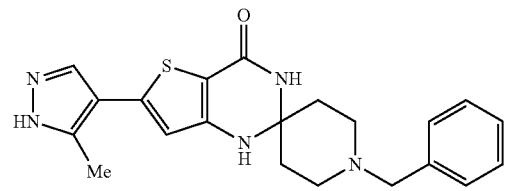 [SMILES: Cc1[nH]ncc1-c1cc2c(s1)C(=O)NC1(CCN(Cc3ccccc3)CC1)N2]

A mixture of 3-amino-5-(5-methyl-1H-pyrazol-4-yl)thiophene-2-carboxamide (100 mg, 0.45 mmol), 1-benzylpiperidin-4-one (0.093 mL, 0.50 mmol), CSA (125 mg, 0.54 mmol), MgSO$_4$ (108 mg, 0.90 mmol) and DMA (1 mL) was stirred at 100° C. for 3 h. The mixture was poured into saturated aqueous NaHCO$_3$. The organic materials were extracted with EtOAc. The combined extracts were washed with water and brine, and then dried over Na$_2$SO$_4$. After removal of the solvent at reduced pressure, the residue was purified by column chromatography (Purif, NH, 90:10 hexane/EtOAc to EtOAc then to 90:10 EtOAc/MeOH), then crystallized from MeOH/EtOAc/hexane to give the title compound (45 mg, 25%) as a yellow solid:

$^1$H NMR (300 MHz, DMSO-d$_6$) δ 1.71-1.99 (4H, m), 2.27-2.44 (5H, m), 2.53-2.61 (2H, m), 3.49 (2H, s), 6.63 (1H, s), 7.02 (1H, s), 7.20-7.43 (6H, m), 7.69 (0.6H, br s), 8.06 (0.4H, br s), 12.73-12.93 (1H, m).

Example 136

Preparation of 6'-(5-methyl-1H-pyrazol-4-yl)-1,3-dihydro-1'H-spiro[indene-2,2'-thieno[3,2-d]pyrimidin]-4'(3'H)-one

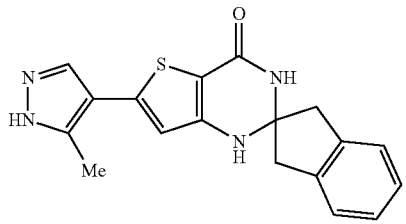 [SMILES: Cc1[nH]ncc1-c1cc2c(s1)C(=O)NC1(Cc3ccccc3C1)N2]

A mixture of 3-amino-5-(5-methyl-1H-pyrazol-4-yl) thiophene-2-carboxamide (111 mg, 0.50 mmol), 2-indanone (330 mg, 2.50 mmol), MgSO$_4$ (120 mg, 1.00 mmol), CSA (11.6 mg, 0.050 mmol) and DMA (3 mL) was stirred at 80° C. for 1 h. The mixture was poured into saturated aqueous NaHCO$_3$ and 2:1 EtOAc/THF. The organic layer was collected, dried over MgSO$_4$, filtered and concentrated under reduced pressure. The residue was purified by column chromatography (Purif, silica gel, hexane to EtOAc, then to 90:10 EtOAc/MeOH), then triturated with EtOAc, and the precipitate was collected by filtration to afford the title compound (21 mg, 12%) as a beige solid:

$^1$H NMR (300 MHz, DMSO-d$_6$) δ 2.31-2.38 (3H, m), 3.25 (4H, s), 6.56 (1H, s), 7.16-7.24 (4H, m), 7.38 (1H, br s), 7.68 (0.6H, br s), 7.79 (1H, br s), 8.06 (0.4H, br s), 12.78 (0.4H, br s), 12.87 (0.6H, br s).

Example 137

Preparation of 1-(4-fluorophenyl)-6'-(5-methyl-1H-pyrazol-4-yl)-1'H-spiro[piperidine-4,2'-thieno[3,2-d]pyrimidin]-4'(3'H)-one

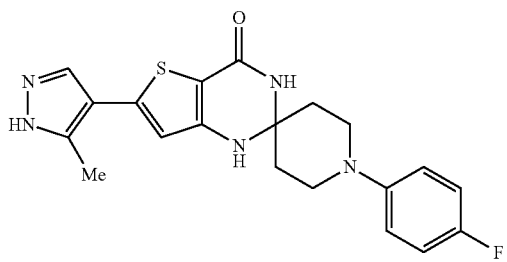 [SMILES: Cc1[nH]ncc1-c1cc2c(s1)C(=O)NC1(CCN(c3ccc(F)cc3)CC1)N2]

A mixture of 3-amino-5-(5-methyl-1H-pyrazol-4-yl) thiophene-2-carboxamide (111 mg, 0.50 mmol), N-(4-fluorophenyl)-piperidin-4-one (290 mg, 1.50 mmol), MgSO$_4$ (120 mg, 1.00 mmol), CSA (11.6 mg, 0.05 mmol) and DMA (4 mL) was stirred at 100° C. for 1 h. The mixture was poured into saturated aqueous NaHCO$_3$ and extracted with 3:1 EtOAc/THF, and the extract was dried over MgSO$_4$ and concentrated under reduced pressure. The residue was purified by column chromatography (Purif, silica gel, EtOAc to 80:20 EtOAc/MeOH). The obtained residue was triturated with EtOAc, and the precipitates were collected by filtration to afford the title compound (102 mg, 51%) as a light yellow solid:

$^1$H NMR (300 MHz, DMSO-d$_6$) δ 1.84-2.02 (4H, m), 2.37 (3H, br s), 3.06-3.15 (2H, m), 3.30-3.39 (2H, m), 6.62 (1H, s), 6.94-7.07 (4H, m), 7.16 (1H, br s), 7.51 (1H, br s), 7.71 (0.66H, br s), 8.05 (0.34H, br s), 12.86 (1H, br s).

Example 138

Preparation of 4-hydroxy-6'-(5-methyl-1H-pyrazol-4-yl)-1'H-spiro[cyclohexane-1,2'-thieno[3,2-d]pyrimidin]-4'(3'H)-one

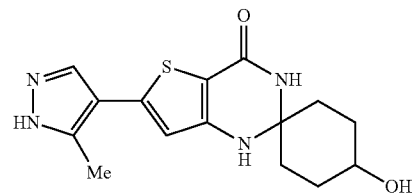 [SMILES: Cc1[nH]ncc1-c1cc2c(s1)C(=O)NC1(CCC(O)CC1)N2]

A mixture of 3-amino-5-(5-methyl-1H-pyrazol-4-yl) thiophene-2-carboxamide (100 mg, 0.450 mmol), 4-{[tert-butyl(dimethyl) silyl]oxy}cyclohexanone (0.339 mL, 1.35 mmol), CSA (10.5 mg, 0.0450 mmol), MgSO$_4$ (108 mg, 0.900 mmol) in anhydrous DMA (1.5 mL) was stirred at 90° C. for 1 h. The mixture was partitioned between EtOAc (20 mL) and aqueous NaHCO$_3$ (10 mL). The aqueous layer was extracted with EtOAc (5 mL). The combined organic layers were washed with brine (5 mL), dried over Na$_2$SO$_4$ and concentrated under reduced pressure. The residue was purified by column chromatography (Purif, silica gel, 30:70 hexane/EtOAc to EtOAc) to give 4-{[tert-butyl(dimethyl)silyl]oxy}-6'-(5-methyl-1H-pyrazol-4-yl)-1'H-spiro[cyclohexane-1,2'-thieno[3,2-d]pyrimidin]-4'(3'H)-one as a pale yellow oil.

To a solution of 4-{[tert-butyl(dimethyl)silyl]oxy}-6'-(5-methyl-1H-pyrazol-4-yl)-1'H-spiro[cyclohexane-1,2'-thieno[3,2-d]pyrimidin]-4'(3'H)-one (<0.450 mmol) in THF (4 mL) was added N,N,N,N-tetrabutylammonium fluoride (1.0 M in THF, 1.08 mL, 1.08 mmol). The mixture was stirred at room temperature for 16 h and at 50° C. for 1 h. The mixture was partitioned between EtOAc (20 mL) and aqueous NaHCO$_3$ (10 mL). The aqueous layer was extracted with EtOAc (5 mL×2). The combined organic layers were washed with brine (5 mL), dried over Na$_2$SO$_4$ and concentrated under reduced pressure. The residue was purified by column chromatography (Purif, silica gel, EtOAc to 85:15 EtOAc/MeOH) followed by trituration with EtOAc (5 mL) to give the title compound (32.1 mg, 22%) as a pale yellow solid:

$^1$H NMR (300 MHz, DMSO-d$_6$) δ 1.42-1.75 (6H, m), 1.86-2.07 (2H, m), 2.36 (3H, s), 3.48 (0.5H, br s), 3.65 (0.5H, br s), 4.44 (0.5H, d, J=2.8 Hz), 4.61 (0.5H, d, J=3.2 Hz), 6.58 (0.5H, s), 6.62 (0.5H, s), 6.95 (0.5H, s), 7.06 (0.5H, s), 7.26 (0.5H, s), 7.35 (0.5H, s), 7.74 (1H, br s), 12.83 (1H, br s).

Example 139

Preparation of 6'-(5-methyl-1H-pyrazol-4-yl)-1-phenyl-1'H-spiro [piperidine-4,2'-thieno[3,2-d]pyrimidin]-4'(3'H)-one

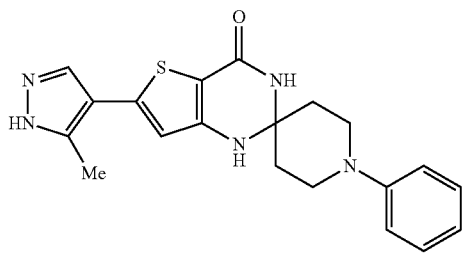 [SMILES: Cc1[nH]ncc1-c1cc2c(s1)C(=O)NC1(CCN(c3ccccc3)CC1)N2]

Step 1

Preparation of 8-phenyl-1,4-dioxa-8-azaspiro[4.5]decane

A mixture of 1,4-dioxa-8-azaspiro[4.5]decane (0.65 mL, 5.0 mmol), 1,1'-binaphthalene-2,2'-diylbis(diphenylphosphane) (255 mg, 0.375 mmol), sodium 2-methylpropan-2-olate (1.44 g, 15 mmol), bromobenzene (0.684 mL, 6.5 mmol), tris(dibenzylideneacetone) dipalladium(0) (114 mg, 0.125 mmol) and toluene (15 mL) was stirred at 110° C. for 5 h under Ar atmosphere. Water was added to quench the reaction. The organic materials were extracted with EtOAc. The combined extracts were washed with brine, dried over $Na_2SO_4$ and filtered. After removal of the solvent at reduced pressure, the residue was purified by column chromatography (Purif, silica gel, 90:10 hexane/EtOAc to 50:50 hexane/EtOAc) to give the title compound (1.09 g, 99%) as an orange oil:

$^1$H NMR (300 MHz, DMSO-$d_6$) δ 1.64-1.77 (4H, m), 3.20-3.30 (4H, m), 3.91 (4H, s), 6.70-6.80 (1H, m), 6.94 (2H, d, J=8.7 Hz), 7.10-7.36 (2H, m).

Step 2

Preparation of 6'-(5-methyl-1H-pyrazol-4-yl)-1-phenyl-1'H-spiro[piperidine-4,2'-thieno[3,2-d]pyrimidin]-4'(3'H)-one A mixture of 3-amino-5-(5-methyl-1H-pyrazol-4-yl) thiophene -2-carboxamide (100 mg, 0.45 mmol), 8-phenyl-1,4-dioxa-8-azaspiro[4.5]decane (109 mg, 0.50 mmol), CSA (125 mg, 0.54 mmol), $MgSO_4$ (108 mg, 0.90 mmol) and DMA (1 mL) was stirred at 100° C. for 1 h. Then, saturated aqueous $NaHCO_3$ was added to quench the reaction. The organic materials were extracted with EtOAc/THF. The combined extracts were dried over $Na_2SO_4$ and filtered. After removal of the solvent at reduced pressure, the residue was purified by column chromatography (Purif, NH, 80:20 hexane/EtOAc to EtOAc then to 95:5 EtOAc/MeOH), then crystallized from MeOH/EtOAc/heptane to give the title compound (46 mg, 27%) as a yellow solid:

$^1$H NMR (300 MHz, DMSO-$d_6$) δ 1.67-2.07 (4H, m), 2.38 (3H, br s), 3.06-3.26 (2H, m), 3.38-3.55 (2H, m), 6.62 (1H, s), 6.75 (1H, t, J=8.0 Hz), 6.95 (2H, d, J=8.0 Hz), 7.13-7.28 (3H, m), 7.52 (1H, br s), 7.70 (0.6H, br s), 8.06 (0.4H, br s), 12.88 (1H, br s).

Example 140

Preparation of (1r,4r)-4-(4-fluorophenyl)-4-hydroxy-6'-(5-methyl-1H-pyrazol-4-yl)-1'H-spiro[cyclohexane-1,2'-thieno[3,2-d]pyrimidin]-4'(3'H)-one and (1s,4s)-4-(4-fluorophenyl)-4-hydroxy-6'-(5-methyl-1H-pyrazol-4-yl)-1'H-spiro[cyclohexane-1,2'-thieno[3,2-d]pyrimidin]-4'(3'H)-one

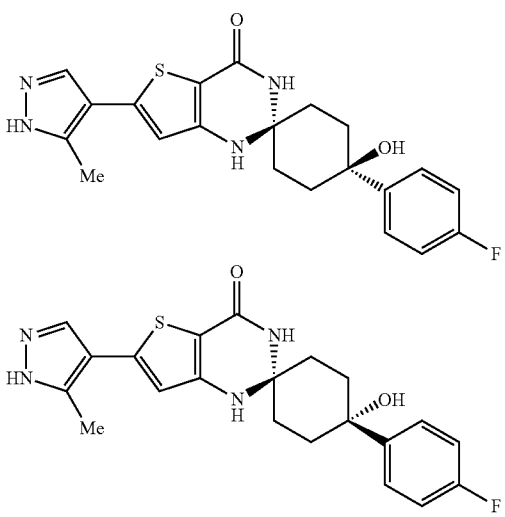

Step 1

Preparation of 8-(4-fluorophenyl)-1,4-dioxaspiro[4.5]decan-8-ol

To a solution of 1,4-dioxaspiro[4.5]decan-8-one (3.00 g, 19.2 mmol) in THF (80 mL) was dropwise added (4-fluorophenyl) magnesium bromide (1.0 M in THF, 28.8 mL, 28.8 mmol) at 0° C. over 15 min. The mixture was stirred at 0° C. for 30 min, and then quenched with aqueous $NH_4Cl$ (100 mL). The layers were separated and the aqueous layer was extracted with EtOAc (30 mL). The combined organic layers were washed with brine (15 mL), dried over $Na_2SO_4$ and concentrated under reduced pressure. The residue was purified by column chromatography (Purif, silica gel, 80:20 hexane/EtOAc to 50:50 hexane/EtOAc) to give title compound (1.96 g, 40%) as a colorless solid:

$^1$H NMR (300 MHz, DMSO-$d_6$) δ 1.46-1.72 (4H, m), 1.84-2.01 (4H, m), 3.33 (4H, s), 4.96 (1H, s), 7.06-7.16 (2H, m), 7.42-7.52 (2H, m).

Step 2

Preparation of 4-(4-fluorophenyl)-4-hydroxycyclohexanone

To a solution of 8-(4-fluorophenyl)-1,4-dioxaspiro[4.5]decan-8-ol (1.95 g, 7.73 mmol) in THF (30 mL) was added 3 M HCl (10 mL). The mixture was stirred at 50° C. for 1.5 h, and then poured into EtOAc (50 mL) and aqueous $NaHCO_3$ (50 mL). The aqueous layer was extracted with EtOAc (20 mL). The combined organic layers were washed with brine (15 mL), dried over $Na_2SO_4$ and concentrated under reduced pressure. The residue was purified by column chromatography (Purif, silica gel, hexane to 60:40 hexane/EtOAc) to give the title compound (1.34 g, 83%) as a colorless solid:

$^1$H NMR (300 MHz, DMSO-d$_6$) δ 1.86-1.97 (2H, m), 2.07-2.30 (4H, m), 2.76 (2H, td, J=13.5, 6.3 Hz), 5.44 (1H, s), 7.09-7.19 (2H, m), 7.53-7.63 (2H, m).

Step 3

Preparation of (1r,4r)-4-(4-fluorophenyl)-4-hydroxy-6'-(5-methyl-1H-pyrazol-4-yl)-1'H-spiro[cyclohexane-1,2'-thieno[3,2-d]pyrimidin]-4'(3'H)-one and (1s,4s)-4-(4-fluorophenyl)-4-hydroxy-6'-(5-methyl-1H-pyrazol-4-yl)-1'H-spiro[cyclohexane-1,2'-thieno[3,2-d]pyrimidin]-4'(3'H)-one A mixture of 3-amino-5-(5-methyl-1H-pyrazol-4-yl)thiophene-2-carboxamide (100 mg, 0.450 mmol), 4-(4-fluorophenyl)-4-hydroxycyclohexanone (281 mg, 1.35 mmol), CSA (10.5 mg, 0.0450 mmol), MgSO$_4$ (108 mg, 0.900 mmol) in DMA (2 mL) was stirred at 80° C. for 45 min. The mixture was partitioned between EtOAc (20 mL) and aqueous NaHCO$_3$ (10 mL). The aqueous layer was extracted with EtOAc (5 mL×2). The combined organic layers were washed with brine (5 mL), dried over Na$_2$SO$_4$ and concentrated under reduced pressure. The residue was purified by column chromatography (Purif, silica gel, EtOAc to 95:5 EtOAc/MeOH), followed by crystallization with MeOH/EtOAc to give the (1r,4r)-title compound (less polar isomer, 51.8 mg, 28%) as a yellow solid:

$^1$H NMR (300 MHz, DMSO-d$_6$) δ (ppm) 1.44-1.55 (2H, m), 1.85-2.06 (4H, m), 2.09-2.23 (2H, br s), 2.37 (3H, s), 4.94 (1H, s), 6.55 (1H, s), 7.04 (1H, s), 7.13 (2H, t, J=8.9 Hz), 7.70 (1H, br s), 7.65 (2H, dd, J=8.9, 5.7 Hz), 7.78 (1H, s), 12.82 (1H, br s).

The (1s,4s)-title compound (more polar isomer, 35.4 mg, 19%) was obtained by crystallization with EtOH/water of corresponding fractions as a pale yellow solid:

$^1$H NMR (300 MHz, DMSO-d$_6$) δ 1.48-1.58 (2H, m), 1.93-2.06 (6H, m), 2.38 (3H, s), 4.93 (1H, s), 6.65 (1H, s), 7.14 (2H, t, J=8.9 Hz), 7.27 (1H, s), 7.40 (1H, s), 7.61 (2H, dd, J=8.9, 5.7 Hz), 7.71 (1H, br s), 12.84 (1H, br s).

The stereochemistry was determined by X-ray crystallographic analysis of (1r,4r)-isomer.

Example 141

Preparation of (1r,4r)-4-cyclohexyl-4-hydroxy-6'-(5-methyl-1H-pyrazol-4-yl)-1'H-spiro[cyclohexane-1,2'-thieno[3,2-d]pyrimidin]-4'(3'H)-one and (1s,4s)-4-cyclohexyl-4-hydroxy-6'-(5-methyl-1H-pyrazol-4-yl)-1'H-spiro[cyclohexane-1,2'-thieno[3,2-d]pyrimidin]-4'(3'H)-one

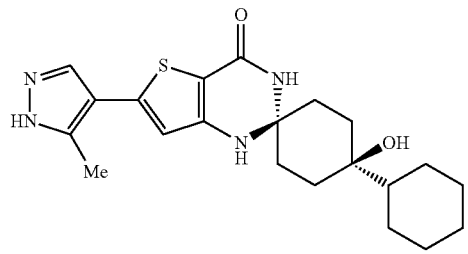

-continued

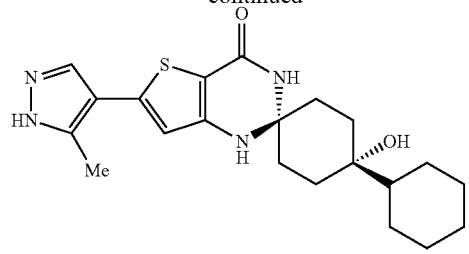

Step 1

Preparation of 4-cyclohexyl-4-hydroxycyclohexanone

To a solution of 1,4-dioxaspiro[4.5]decan-8-one (5.00 g, 24.0 mmol) in THF (100 mL) was dropwise added cyclohexylmagnesium chloride (2.0 M in diethyl ether, 24.0 mL, 48.0 mmol) at −78° C. over 10 min. The mixture was stirred at 0° C. for 1.5 h, and then quenched with aqueous NH$_4$Cl (100 mL). The layers were separated, and the aqueous layer was extracted with EtOAc (50 mL). The combined organic layers were washed with brine (20 mL), dried over Na$_2$SO$_4$ and concentrated under reduced pressure. The residue was purified by column chromatography (Purif, silica gel, hexane to 70:30 hexane/EtOAc) to give crude 8-cyclohexyl-1,4-dioxaspiro[4.5]decan-8-ol as a colorless solid. To a solution of crude 8-cyclohexyl-1,4-dioxaspiro[4.5]decan-8-ol (<24.0 mmol) in THF (45 mL) was added 3 M HCl (15 mL). The mixture was stirred at room temperature for 4 h, and then poured into EtOAc (50 mL) and aqueous NaHCO$_3$ (50 mL). The aqueous layer was extracted with EtOAc (20 mL×2). The combined organic layers were washed with brine (15 mL), dried over Na$_2$SO$_4$ and concentrated under reduced pressure. The residue was purified by column chromatography (Purif, silica gel hexane to 70:30 hexane/EtOAc) to give the title compound (2.34 g, 37%) as a colorless solid:

$^1$H NMR (300 MHz, DMSO-d$_6$) δ 0.90-1.34 (6H, m), 1.55-1.86 (9H, m), 2.02 (2H, dt, J=14.4, 2.1 Hz), 2.50-2.67 (2H, m), 4.30 (1H, s).

Step 2

Preparation of (1r,4r)-4-cyclohexyl-4-hydroxy-6'-(5-methyl-1H-pyrazol-4-yl)-1'H-spiro[cyclohexane-1,2'-thieno[3,2-d]pyrimidin]-4'(3'H)-one and (1s,4s)-4-cyclohexyl-4-hydroxy-6'-(5-methyl-1H-pyrazol-4-yl)-1'H-spiro[cyclohexane-1,2'-thieno[3,2-d]pyrimidin]-4'(3'H)-one A mixture of 3-Amino-5-(5-methyl-1H-pyrazol-4-yl)thiophene-2-carboxamide (150 mg, 0.675 mmol), 4-cyclohexyl-4-hydroxycyclohexanone (397 mg, 2.02 mmol), CSA (15.7 mg, 0.0675 mmol), MgSO$_4$ (162 mg, 1.35 mmol) in DMA (3 mL) was stirred at 80° C. for 2 h. The mixture was partitioned between EtOAc (20 mL) and aqueous NaHCO$_3$ (10 mL). The aqueous layer was extracted with EtOAc (5 mL×2). The combined organic layers were washed with brine (5 mL), dried over Na$_2$SO$_4$ and concentrated under reduced pressure. The residue was purified by column chromatography (Purif, silica gel, EtOAc to 97:3 EtOAc/MeOH) followed by crystallization with MeOH/EtOAc to give the (1r,4r)-title compound (less polar isomer, 64.8 mg, 24%) as a pale yellow solid:

$^1$H NMR (300 MHz, DMSO-d$_6$) δ (ppm) 0.90-1.27 (6H, m), 1.29-1.41 (2H, m), 1.53-1.94 (11H, m), 2.36 (3H, s), 3.78 (1H, s), 6.53 (1H, s), 6.98 (1H, s), 7.39 (1H, s), 7.82 (1H, br s), 12.83 (1 H, br s).

The (1s,4s)-title compound (more polar isomer, 91.2 mg, 34%) was obtained by crystallization with EtOH/water of corresponding fractions as a pale yellow solid:

$^1$H NMR (300 MHz, DMSO-d$_6$) δ 0.90-1.25 (6H, m), 1.31-1.44 (2H, m), 1.45-1.67 (3H, m), 1.68-1.92 (8H, m), 2.37 (3H, s), 3.74 (1H, s), 6.62 (1H, s), 6.93 (1H, s), 7.30 (1H, s), 7.80 (1H, br s), 12.83 (1H, br s).

The stereochemistry was determined by X-ray crystallographic analysis of (1s,4s)-isomer.

Example 142

Preparation of 6'-(5-methyl-1H-pyrazol-4-yl)-1-(pyrimidin-2-yl)-1'H-spiro[piperidine-4,2'-thieno[3,2-d]pyrimidin]-4'(3'H)-one

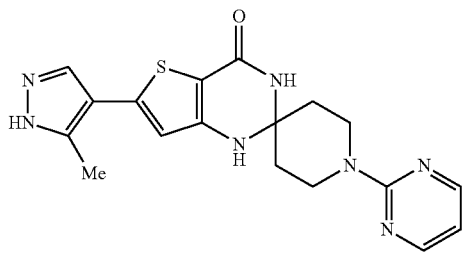 [SMILES: Cc1[nH]ncc1-c1cc2c(s1)C(=O)NC1(CCN(c3ncccn3)CC1)N2]

A mixture of 3-amino-5-(5-methyl-1H-pyrazol-4-yl)thiophene-2-carboxamide (111 mg, 0.50 mmol), 1-(2-pyrimidinyl)-piperidin-4-one (266 mg, 1.50 mmol), CSA (11.6 mg, 0.05 mmol), MgSO$_4$ (120 mg, 1.00 mmol) and DMA (4 mL) was stirred at 100° C. for 1 h. The mixture was poured into saturated aqueous NaHCO$_3$ and extracted with 3:1 EtOAc/THF, and the extract was dried over MgSO$_4$, filtered and concentrated under reduced pressure. The residue was purified by column chromatography (Purif, silica gel, EtOAc to 80:20 EtOAc/MeOH). The obtained yellow solid was triturated with MeOH/EtOAc and collected by filtration to afford the title compound (141 mg, 74%) as a pale yellow solid:

$^1$H NMR (300 MHz, DMSO-d$_6$) δ 1.74-1.98 (4H, m), 2.34-2.40 (3H, m), 3.55-3.64 (2H, m), 4.12-4.20 (2H, m), 6.60-6.63 (2H, m), 7.24 (1H, br s), 7.52 (1H, br s), 7.71 (0.67H, br s), 8.08 (0.33H, br s), 8.35-8.37 (2H, m), 12.79 (0.33H, br s), 12.87 (0.67H, br s).

Example 143

Preparation of 6'-(5-methyl-1H-pyrazol-4-yl)-4-(phenylamino)-1'H-spiro[cyclohexane-1,2'-thieno[3,2-d]pyrimidin]-4'(3'H)-one

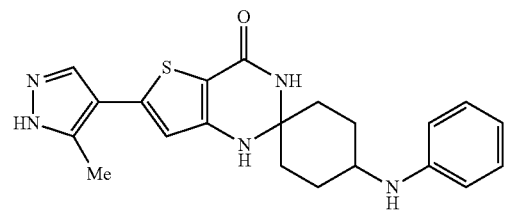 [SMILES: Cc1[nH]ncc1-c1cc2c(s1)C(=O)NC1(CCC(Nc3ccccc3)CC1)N2]

Step 1

Preparation of N-phenyl-1,4-dioxaspiro[4.5]decan-8-amine

To a solution of aniline (0.58 mL, 6.4 mmol) and acetic acid (0.73 mL, 12.8 mmol) in MeOH (6 mL) was added 1,4-dioxaspiro[4.5]decan-8-one (1.0 g, 6.4 mmol). The mixture was stirred at 50° C. for 2 h. Then, NaCNBH$_3$ (402 mg, 6.4 mmol) was added at 0° C. The mixture was stirred at room temperature for 2 h. Then, 2 M aqueous NaOH was added to quench the reaction. The organic materials were extracted with EtOAc. The combined extracts were washed with brine, dried over Na$_2$SO$_4$ and filtered. After removal of the solvent at reduced pressure, the residue was purified by column chromatography (Purif, silica gel, 95:5 hexane/EtOAc to 70:30 hexane/EtOAc) to give the crude title compound (1.39 g, 93%) as a pale yellow solid:

$^1$H NMR (300 MHz, DMSO-d$_6$) δ 1.34-1.93 (8H, m), 3.23-3.35 (1H, m), 3.88 (4H, br s), 5.41 (1H, d, J=8.1 Hz), 6.46 (1H, t, J=7.3 Hz), 6.56 (2H, d, J=7.3 Hz), 7.00-7.07 (2H, m). This material was used for the next reaction without further purification.

Step 2

Preparation of 6'-(5-methyl-1H-pyrazol-4-yl)-4-(phenylamino)-1'H-spiro[cyclohexane-1,2'-thieno[3,2-d]pyrimidin]-4'(3'H)-one A mixture of 3-amino-5-(5-methyl-1H-pyrazol-4-yl)thiophene-2-carboxamide (146 mg, 0.66 mmol), N-phenyl-1,4-dioxaspiro [4.5]decan-8-amine (169 mg, 0.723 mmol), CSA (183 mg, 0.788 mmol), MgSO$_4$ (158 mg, 1.31 mmol) and DMA (1 mL) was stirred at 100° C. for 1 h. EtOAc and saturated aqueous NaHCO$_3$ were added to quench the reaction. The organic materials were extracted with EtOAc/THF. The combined extracts were dried over Na$_2$SO$_4$ and filtered. After removal of the solvent at reduced pressure, the residue was purified by column chromatography (Purif, NH, 95:5 hexane/EtOAc to EtOAc then to 95:5 EtOAc/MeOH), then crystallized from 2-propanol/heptane to give the title compound (41 mg, 16%) as a yellow solid:

$^1$H NMR (300 MHz, DMSO-d$_6$) δ 1.39-1.71 (4H, m), 1.77-1.95 (2H, m), 2.03-2.21 (2H, m), 2.29-2.43 (3H, m), 3.08-3.24 (1H, m), 5.26-5.36 (1H, m), 6.44-6.54 (1H, m), 6.54-6.61 (2H, m), 6.62 (1H, s), 6.99-7.09 (3H, m), 7.38 (1H, s), 7.69 (0.6H, br s), 8.04 (0.4H, br s), 12.64-13.02 (1H, m).

Example 144

Preparation of 6'-(5-methyl-1H-pyrazol-4-yl)-1-(pyridin-2-yl)-1'H-spiro[piperidine-4,2'-thieno[3,2-d]pyrimidin]-4'(3'H)-one

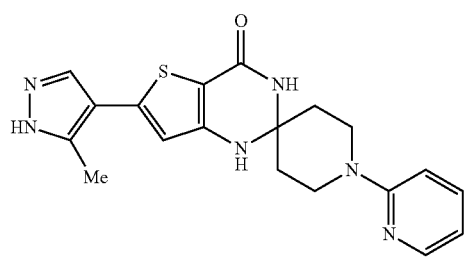 [SMILES: Cc1[nH]ncc1-c1cc2c(s1)C(=O)NC1(CCN(c3ccccn3)CC1)N2]

A mixture of 3-amino-5-(5-methyl-1H-pyrazol-4-yl)thiophene-2-carboxamide (111 mg, 0.50 mmol), 1-(2-pyridyl)-piperidin-4-one (264 mg, 1.50 mmol), CSA (11.6 mg, 0.05 mmol), MgSO$_4$ (120 mg, 1.00 mmol) and DMA (4 mL) was stirred at 100° C. for 1 h. The mixture was poured into saturated aqueous NaHCO$_3$ and extracted with 3:1 EtOAc/THF, and the extract was dried over MgSO$_4$, filtered and concentrated under reduced pressure. The residue was purified by column chromatography (Purif, silica gel, EtOAc to 80:20 EtOAc/MeOH). The obtained yellow solid (190 mg) was triturated with MeOH/EtOAc and collected by filtration to afford the title compound (147 mg, 77%) as a pale yellow solid:

$^1$H NMR (300 MHz, DMSO-d$_6$) δ 1.74-1.96 (4H, m), 2.34-2.39 (3H, m), 3.38-3.47 (2H, m), 3.85-3.93 (2H, m), 6.59-6.63 (2H, m), 6.86 (1H, d, J=8.7 Hz), 7.23 (1H, br s), 7.49-7.55 (2H, m), 7.71 (0.5H, br s), 8.05-8.12 (1.5H, m), 12.80-12.88 (1H, m).

Experimental Example 1A

Preparation of Human MCM2 Proteins

The genetic manipulation described below was performed according to the method described in a book (Maniatis et al., Molecular•cloning, ColdSpring Harbor Laboratory, 1989) or the method described in the protocol attached to the reagent.

Recombinant human N-terminal His6-tagged MCM2 protein corresponding to residues 10-294 was cloned into the bacterial expression vector pET-21.

Vector pET21-HH was prepared by inserting the following 6×His-tagged synthetic DNA 5'-TATGCATCATCATCATCATCACGGATCCCATCATCATCATCATCACTGAGC-3' (SEQ ID NO: 1); and 5'-GGCCGCTCAGTGATGATGATGATGATGGGATCCGTGATGATGATGATGATGCA-3' (SEQ ID NO: 2) into the Nde I-Not I site of pET-21a(+) (Novagen).

The gene "Mcm2(10-294 a.a.) gene" encoding the 10th to 294th amino acids from the N terminal side of human MCM2 protein was cloned by PCR method using synthetic DNA prepared by reference to the base sequence described in "GenBank accession No.: NM_004526, 5'-CGCGGATCCATGGCATCCAGCCCGGCCCA-3' (SEQ ID NO: 3); and 5'-ATTCTTATGCGGCCGCtcacagctcctccaccagaggca-3' (SEQ ID NO: 4) as a primer set and Human testis cDNA library (Takara Bio) as a template. The PCR reaction was performed using Pyrobest (Takara Bio) and according to the attached protocol.

The obtained 883 bp fragment was digested with restriction enzymes BamHI and NotI and inserted into BamHI-NotI site of pET21-HH. The base sequence insert was confirmed to obtain Plasmid pET21-HHhMcm2(10-294).

Plasmid pET21-HHhMcm2(10-294) was expressed in *E. coli* BL21 (DE3) cells (American Type Culture Collection). Transformants were cultured in LB broth (1% trypton, 0.5% yeast extract, and 0.5% NaCl) with 50 mg/L ampicillin at 37° C. and MCM2 expression was induced with 1 mM IPTG for 6 hr. The MCM2 expressing cells were collected by centrifugation (6000 rpm, 10 min.) and washed with a phosphate buffered saline (Invitrogen, CA, USA), and the cells were preserved at −80° C. The cryopreserved cells were thawed on ice, and suspended in buffer A (25 mM Tris-HCl (pH 7.4), 2.7 mM KCl, 137 mM NaCl, 10% Glycerol, 10 mM imidazole) supplemented with Complete, EDTA-free (Roche Diagnostics GmbH, Mannheim, Germany). The cells were disrupted by treatment with 1 mg/mL lysozyme for 1 hr, followed by sonication for 30 sec, four times at 170W with an Insonator 201M (Kubota, Tokyo, Japan). The cell lysate was clarified by centrifugation at 15000 rpm for 20 min. and filtered with a 0.22 μm filter. The filtrate was passed through a Ni-NTA Superflow resin (QIAGEN Inc., CA, U.S.A.). The resin was washed with buffer A, and eluted with buffer B (25 mM Tris-HCl (pH 7.4), 2.7 mM KCl, 137 mM NaCl, 10% Glycerol, 200 mM imidazole). The eluate was concentrated with Amicon Ultra 4 (5K MWCO, Millipore, Mass., U.S.A.). The concentrate was purified by gel filtration using HiLoad 16/60 Superdex 200 pg (GE Healthcare, Chalfont St. Giles, UK) equilibrated with buffer C (25 mM Tris-HCl (pH 7.4), 2.7 mM KCl, 137 mM NaCl, 10% Glycerol). The fractions containing MCM2 protein were concentrated, and cryopreserved at −80° C.

Experimental Example 1B

Determination of cdc7 Kinase Inhibitory Activity

Full-length cdc7 co-expressed with full-length Dbf4 was purchased from Carna Bioscience, Inc. (Kobe, Japan). Homogeneous time-resolved fluorescence (HTRF) Tran-screener ADP assay (Cisbio Inc., MA., U.S.A.) was used for detecting cdc7/Dbf4 kinase activity. Reactions were performed in kinase buffer (20 mM HEPES, pH 7.5, 10 mM magnesium acetate, 1 mM dithiothreitol) containing 1.0 μM ATP, 10 μg/ml MCM2, 0.1 μg/ml cdc7/Dbf4 for 90 min at room temperature. Free ADP from the ATP hydrolysis reaction was detected by the monoclonal ADP antibody labeled with Eu$^{3+}$-Cryptate, which competes with both native ADP and d2-coupled ADP. The TR-FRET signal was detected by EnVision (PerkinElmer Inc., MA, U.S.A.). Cdc7 kinase inhibitory rate (%) of the test compound was calculated by the following formula:

Inhibitory rate(%)=(1−(count of test compound−blank)÷(control−blank))×100

The count of the solution reacted without addition of the compound was used as a "control", and the count of the solution without the compound and cdc7/Dbf4 was used as a "blank".

TABLE 1

| Test compound | Inhibitory rate (%) at 1 μM |
|---|---|
| Example 6 | 98.5 |
| Example 9 | 102.8 |

TABLE 1-continued

| Test compound | Inhibitory rate (%) at 1 μM |
|---|---|
| Example 15 | 97.6 |
| Example 22 | 97.1 |
| Example 34 | 104.2 |
| Example 27 | 100.7 |
| Example 104 | 100.8 |
| Example 122 | 91.8 |

Experimental Example 1C

Determination of Cell Proliferation Inhibitory Activity

Cell proliferation was measured by using Cell Titer-Glo Luminescent Cell Viability Assay (Promega, Wis., USA,). The CellTiter-Glo Luminescent Cell Viability Assay is a homogeneous method of determining the number of viable cells in culture based on quantitation of the ATP present, which signals the presence of metabolically active cells. Colo205 cells (American Type Culture Collection) were sown at $3.0 \times 10^3$ cells/well to a 96 well microplate and cultured in an incubator (37° C., 5% carbon dioxide). On the following day, 100 μl of a solution of each test compound, which was previously diluted, was added. According to the instruction manual from vender, cellular ATP content of final treatment day was measured. After incubation for 3 days, solution of Cell Titer-Glo Luminescent Cell Viability Assay was added to each well and incubated for approximately 15 min at room temperature. Luminescence of each well was measured by ARVO Light (PerkinElmer Inc., MA, USA). Taking as 100% the ATP content for the none compound treatment control group, the ratio of the residual ATP content for each treatment group was determined.

TABLE 2

| Test compound | Inhibitory rate (%) at 1 μM |
|---|---|
| Example 27 | 59.6 |
| Example 104 | 62.9 |
| Example 114 | 67.4 |
| Example 115 | 66.1 |
| Example 122 | 48.9 |

Formulation Example 1

A medicament containing the compound of the present invention as an active ingredient can be produced according to, for example, the following formulation.

| 1. Capsule | | |
|---|---|---|
| (1) | compound obtained in Example 1 | 40 mg |
| (2) | lactose | 70 mg |
| (3) | microcrystalline cellulose | 9 mg |
| (4) | magnesium stearate | 1 mg |

1 capsule—120 mg (1), (2), (3) and ½ of (4) are blended and granulated. Thereto is added the rest of (4) and the whole amount is filled in a gelatin capsule.

| 2. Tablet | | |
|---|---|---|
| (1) | compound obtained in Example 1 | 40 mg |
| (2) | lactose | 58 mg |
| (3) | cornstarch | 18 mg |
| (4) | microcrystalline cellulose | 3.5 mg |
| (5) | magnesium stearate | 0.5 mg |

1 tablet—120 mg (1), (2), (3), ⅔ of (4) and ½ of (5) are blended and granulated. The rest of (4) and (5) is added to the granules and the mixture is compression molded into a tablet.

Formulation Example 2

The compound (50 mg) obtained in Example 1 is dissolved in Japanese Pharmacopoeia distilled water for injection (50 ml), to which Japanese Pharmacopoeia distilled water for injection is added to make the volume 100 ml. Thus obtained solution is filtered under sterile conditions. The solution (1 ml) is taken, filled in a vial for injection under sterile conditions and freeze-dried, and the vial is sealed.

INDUSTRIAL APPLICABILITY

Since the compound of the present invention has a superior cdc7 inhibitory action, it is clinically useful as an agent for the prophylaxis or treatment of cdc7-associated diseases (e.g., cancer etc.). In addition, since the compound of the present invention is superior in the efficacy expression, pharmacokinetics, solubility, interaction with other pharmaceutical products, safety and stability, it is useful as a pharmaceutical product.

The invention claimed is:

1. A compound represented by the formula

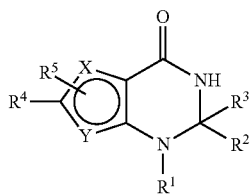

(I)

wherein
as X and Y,
(1) X is a sulfur atom, and Y is a carbon atom, or
(2) X is a carbon atom, and Y is a sulfur atom;
$R^1$ is a hydrogen atom, a hydrocarbon group optionally having substituent(s) or a heterocyclic group optionally having substituent(s),
$R^2$ is a hydrogen atom, a halogen atom, a hydrocarbon group optionally having substituent(s), a heterocyclic group optionally having substituent(s), or acyl,
$R^3$ is a hydrogen atom, a halogen atom, a hydrocarbon group optionally having substituent(s), a heterocyclic group optionally having substituent(s), or acyl, or
$R^1$ and $R^2$ are optionally bonded to form a nitrogen-containing heterocycle optionally having substituent(s), or
$R^2$ and $R^3$ are optionally bonded to form a ring optionally having substituent(s);
$R^4$ is a heterocyclic group optionally having substituent(s); and
$R^5$ is a hydrogen atom, a halogen atom or a hydrocarbon group optionally having substituent(s),
or a salt thereof.

2. The compound of claim 1, wherein X is a sulfur atom, and Y is a carbon atom.

3. The compound of claim 1, wherein $R^1$ is a hydrogen atom or a $C_{1-6}$ alkyl group optionally having substituent(s).

4. The compound of claim 1, wherein $R^2$ is a $C_{1-6}$ alkyl group optionally having substituent(s) or a $C_{6-14}$ aryl group optionally having substituent(s).

5. The compound of claim 1, wherein $R^3$ is a hydrogen atom or a $C_{1-6}$ alkyl group optionally having substituent(s).

6. The compound of claim 1, wherein $R^2$ and $R^3$ are optionally bonded to form a $C_{3-8}$ cycloalkane optionally condensed with a benzene ring, which optionally has substituent(s), or a 5- or 6-membered non-aromatic heterocycle optionally crosslinked, which optionally has substituent(s).

7. The compound of claim 1, wherein $R^4$ is an aromatic heterocyclic group optionally having substituent(s).

8. The compound of claim 1, wherein $R^5$ is a hydrogen atom.

9. The compound of claim 1, wherein
X is a sulfur atom;
Y is a carbon atom;
$R^1$ is
  (1) a hydrogen atom; or
  (2) a $C_{1-6}$ alkyl group optionally substituted by 1 to 3 substituents selected from
    (a) a halogen atom,
    (b) a hydroxy group,
    (c) a $C_{1-6}$ alkoxy-carbonyl group,
    (d) a $C_{6-14}$ aryl group optionally substituted by 1 to 3 substituents selected from
      (i) an amino group, and
      (ii) a nitro group,
    (e) an aromatic heterocyclic group, and
    (f) a non-aromatic heterocyclylcarbonyl group;
$R^2$ is
  (1) a $C_{1-6}$ alkyl group optionally substituted by 1 to 3 substituents selected from
    (a) a halogen atom,
    (b) a $C_{1-6}$ alkoxy-carbonyl group, and (c) a carbamoyl group optionally mono- or di-substituted by $C_{1-6}$ alkyl group(s); or
(2) a $C_{6-14}$ aryl group;
$R^3$ is
(1) a hydrogen atom;
(2) a $C_{1-6}$ alkyl group optionally substituted by 1 to 3 substituents selected from
  (a) a halogen atom,
  (b) a $C_{1-6}$ alkoxy-carbonyl group, and
  (c) a carbamoyl group optionally mono- or di-substituted by $C_{1-6}$ alkyl group(s); or
(3) —CO—OR$^{41}$ (wherein R$^{41}$ is a hydrogen atom or a $C_{1-6}$ alkyl group); or
$R^2$ and $R^3$ are optionally bonded to form
(1) a $C_{3-8}$ cycloalkane optionally condensed with a benzene ring, which is optionally substituted by 1 to 3 substituents selected from
  (a) a halogen atom,
  (b) a hydroxy group,
  (c) an oxo group,
  (d) a $C_{1-6}$ alkoxy-carbonyl group,
  (e) a $C_{6-14}$ aryl group optionally substituted by 1 to 3 halogen atoms,
  (f) a $C_{3-10}$ cycloalkyl group, and
  (g) an amino group optionally mono- or di-substituted by substituent(s) selected from
    (i) a $C_{6-14}$ aryl group, and
    (ii) a $C_{1-6}$ alkoxy-carbonyl group optionally substituted by 1 to 3 $C_{6-14}$ aryl groups; or
(2) a 5- or 6-membered non-aromatic heterocycle optionally crosslinked, which is optionally substituted by 1 to 3 substituents selected from
  (a) a $C_{1-6}$ alkyl group optionally substituted by 1 to 3 substituents selected from
    (i) a $C_{6-14}$ aryl group,
    (ii) a $C_{1-6}$ alkoxy-carbonyl group,
    (iii) a $C_{3-10}$ cycloalkyl-carbonyl group,
    (iv) an aromatic heterocyclic group optionally substituted by 1 to 3 $C_{1-6}$ alkyl groups,
  (b) a $C_{6-14}$ aryl group optionally substituted by 1 to 3 halogen atoms,
  (c) an aromatic heterocyclic group,
  (d) a $C_{1-6}$ alkyl-carbonyl group optionally substituted by 1 to 3 substituents selected from
    (i) a halogen atom,
    (ii) a $C_{1-6}$ alkoxy group,
    (ii) a $C_{1-6}$ alkoxy-carbonyl group,
    (iii) a $C_{6-14}$ aryl group,
    (iv) an aromatic heterocyclic group, and
    (v) an amino group optionally mono- or di-substituted by substituent(s) selected from a $C_{1-6}$ alkyl-carbonyl group and a $C_{1-6}$ alkoxy-carbonyl group,
  (e) a $C_{1-6}$ alkoxy-carbonyl group optionally substituted by 1 to 3 $C_{6-14}$ aryl groups,
  (f) a $C_{6-14}$ aryl-carbonyl group,
  (g) a $C_{6-14}$ aryloxy-carbonyl group,
  (h) a $C_{3-10}$ cycloalkyl-carbonyl group optionally substituted by 1 to 3 $C_{6-14}$ aryl groups,
  (i) an aromatic heterocyclylcarbonyl group,
  (j) a non-aromatic heterocyclylcarbonyl group, and
  (k) a carbamoyl group optionally mono- or di-substituted by $C_{1-6}$ alkyl group(s);
$R^4$ is a 5- or 6-membered aromatic heterocyclic group optionally condensed with a benzene ring or a 5- or 6-membered aromatic heterocycle, which is optionally substituted by 1 to 3 substituents selected from
  (a) a halogen atom,
  (b) an amino group,
  (c) a $C_{1-6}$ alkyl group optionally substituted by amino group(s) optionally mono- or di-substituted by $C_{7-13}$ aralkyl group(s), and
  (d) a sulfamoyl group optionally mono- or di-substituted by $C_{1-6}$ alkyl group(s); and
$R^5$ is a hydrogen atom, a halogen atom or a $C_{1-6}$ alkyl group.

10. The compound of claim 1 which is 1'-Ethyl-6'-(pyridin-4-yl)-1'H-spiro[cyclopentane-1,2'-thieno[3,2-d]pyrimidin]-4'(3'H)-one, or a salt thereof.

11. The compound of claim 1 which is 1,2-Dimethyl-6-(5-methyl-1H-pyrazol-4-yl)-2-(2,2,2-trifluoroethyl)-2,3-dihydrothieno[3,2-d]pyrimidin-4(1H)-one, or a salt thereof.

12. The compound of claim 1 which is 2-Fluoro-6'-(5-methyl-1H-pyrazol-4-yl)-1'H-spiro [cyclohexane-1,2'-thieno[3,2-d]pyrimidin]-4'(3'H)-one, or a salt thereof.

13. A medicament comprising the compound of claim 1.

14. A method of inhibiting a cell division cycle 7 in a mammal, which comprises administering an effective amount of the compound of claim 1 to the mammal.

15. A method for the treatment of cancer in a mammal, which comprises administering an effective amount of the compound of claim 1 to the mammal.

* * * * *